United States Patent
Canan-Koch et al.

(10) Patent No.: US 6,545,049 B1
(45) Date of Patent: Apr. 8, 2003

(54) DIMER-SELECTIVE RXR MODULATORS AND METHODS FOR THEIR USE

(75) Inventors: Stacie Canan-Koch, San Diego, CA (US); Chan K. Hwang, Boulder, CO (US); Marcus F. Boehm, San Diego, CA (US); Beth Ann Badea, San Diego, CA (US); Laura J. Dardashti, Santa Anna, CA (US); Lin Zhang, San Diego, CA (US); Alex M. Nadzan, San Diego, CA (US); Richard A. Heyman, Encinitas, CA (US); Ranjan Mukherjee, San Diego, CA (US); Deepak S. Lala, San Diego, CA (US); Luc J. Farmer, La Jolla, CA (US)

(73) Assignee: Ligand Pharmaceuticals Incorporated, San Diego, CA (US)

( * ) Notice: Subject to any disclaimer, the term of this patent is extended or adjusted under 35 U.S.C. 154(b) by 0 days.

(21) Appl. No.: 09/388,888

(22) Filed: Sep. 2, 1999

Related U.S. Application Data

(62) Division of application No. 08/710,427, filed on Sep. 17, 1996, now abandoned.
(60) Provisional application No. 60/004,897, filed on Oct. 6, 1995, provisional application No. 60/009,884, filed on Jan. 11, 1996, provisional application No. 60/018,318, filed on May 24, 1996, and provisional application No. 60/021,839, filed on Jul. 10, 1996.

(51) Int. Cl.[7] .................. A61K 31/19; C07D 333/00
(52) U.S. Cl. .................. 514/569; 514/725; 560/500
(58) Field of Search .................. 560/58; 546/152, 546/176; 514/569, 725

(56) References Cited

U.S. PATENT DOCUMENTS

| | | |
|---|---|---|
| 4,193,931 A | 3/1980 | Loeliger et al. |
| 4,534,979 A | 8/1985 | Loev et al. |
| 4,539,154 A | 9/1985 | Krebs |

(List continued on next page.)

FOREIGN PATENT DOCUMENTS

| | | |
|---|---|---|
| EP | 0718285 | 6/1996 |
| FR | 2390428 | 12/1978 |
| FR | 2719041 | 10/1995 |

(List continued on next page.)

OTHER PUBLICATIONS

Allegretto, et al., "Retinoid X Receptor Acts as a Hormone Receptor in Vivo to Induce a Key Metabolic Enzyme of 1,25–Dihydroxyvitamin $D_3$," *J. Biol. Chem.*, 270:23906 (1995).

Apfel, et al., "A retinoic acid receptor α antagonist selectivity counteracts retinoic acid effects," *Proc. Natl. Acad. Sci.*, 89:7129 (1992).

Aurell, et al., "Trienediolates of Hexadienoic Acids in Synthesis. Synthesis of Retinoic and nor–Retinoic Acids." *Tetrahedron Lett.*, 49:6089 (1993).

Beard, et al., "Synthesis and Structure–Activity Relationships of Stilbene Retinoid Analogs Substituted with Heteroaromatic Carboxylic Acids," *J. Med. Chem.*, 38:2820 (1995).

(List continued on next page.)

*Primary Examiner*—Sabiha Qazi
(74) *Attorney, Agent, or Firm*—Brobeck Phleger & Harrison LLP

(57) ABSTRACT

Dimer-selective RXR modulator compounds having agonist, partial agonist and/or antagonist activity in the context of an RXR homodimer and/or RXR heterodimers are provided. Also provided are pharmaceutical compositions incorporating such dimer-selective RXR modulator compounds and methods for their therapeutic use.

36 Claims, 3 Drawing Sheets

U.S. PATENT DOCUMENTS

| | | | |
|---|---|---|---|
| 4,788,213 | A | 11/1988 | Klaus et al. |
| 4,801,733 | A | 1/1989 | Wuest et al. |
| 4,831,052 | A | 5/1989 | Shudo et al. |
| 4,833,240 | A | 5/1989 | Maignan et al. |
| 4,874,747 | A | 10/1989 | Shroot et al. |
| 4,879,284 | A | 11/1989 | Lang et al. |
| 4,892,940 | A | 1/1990 | Maignan et al. |
| 4,898,864 | A | 2/1990 | Maignan et al. |
| 4,925,979 | A | 5/1990 | Shudo |
| RE33,533 | E | 2/1991 | Shroot et al. |
| 5,004,730 | A | 4/1991 | Philippe et al. |
| 5,124,473 | A | 6/1992 | Shroot et al. |
| 5,198,567 | A | 3/1993 | Lang et al. |
| 5,320,833 | A | 6/1994 | Deckers et al. |
| 5,391,569 | A | 2/1995 | Brion et al. |
| 5,391,766 | A | 2/1995 | Klaus et al. |
| 5,466,861 | A | 11/1995 | Dawson et al. |
| 5,552,271 | A | 9/1996 | Pfahl et al. |
| 5,668,175 | A | 9/1997 | Evans et al. |
| 5,705,167 | A | 1/1998 | Bernardon et al. |
| 5,712,093 | A | 1/1998 | Pfahl et al. |
| 5,728,739 | A | 3/1998 | Ailhaud et al. |
| 5,827,897 | A | 10/1998 | Ailhaud et al. |
| 5,968,908 | A | 10/1999 | Epstein et al. |
| 5,977,125 | A | 11/1999 | Hibi et al. .................. 514/277 |

FOREIGN PATENT DOCUMENTS

| | | |
|---|---|---|
| FR | 2729664 | 7/1996 |
| GB | 2197316 | 5/1988 |
| WO | 9303713 | 3/1993 |
| WO | 9321146 | 10/1993 |
| WO | 9412880 | 6/1994 |
| WO | 9415901 | 7/1994 |
| WO | 9415902 | 7/1994 |
| WO | WO 94/17796 A1 | 8/1994 |
| WO | WO 94/20093 A1 | 9/1994 |
| WO | 9504036 | 2/1995 |
| WO | 9605165 | 2/1996 |
| WO | 962091 | 7/1996 |
| WO | 9614876 | 1/1997 |
| WO | 9958486 | 11/1999 |

OTHER PUBLICATIONS

Bissonnette, et al., "9–cis Retinoic Acid Inhibition of Activation–Induced Apoptosis Is Mediated via Regulation of Fas Ligand and Requires Retinoic Acid Receptor and Retinoid X Receptor Activation," *Mol. & Cellular Biol.,* 15:5576 (1995).

Boehm, et al., "Synthesis and Structure–Activity Relationships of Novel Retinoid X Receptor Selective Retinoids," *J. Med Chem.,* 37:2930 (1994).

Boehm, et al., "Design and Synthesis of Potent Retinoid X Receptor Selective Ligands That Induce Apoptosis in Leukemia Cells," *J. Med Chem.,* 38:3146 (1995).

Danielian, et al., "Identification of Residues in the Estrogen receptor That confer Differential Sensitivity to Estrogen and Hydroxytamoxifen," *Mol. Endocrinol.,* 7:232–240 (1993).

Dawson, et al., "Effect of Structural Modifications in the C7–C11 Region of the Retinoid Skeleton on Biological Activity in a Series of Aromatic Retinoids," *J. Med. Chem.,* 32:1504(1989).

Evans, "The Steroid and Thyroid Hormone Receptor Superfamily," *Science,* 240:889–895 (1988).

Eyrolles, et al., "Retinobenzoic Acids. 6. Retoid Antagonists with a Heterocyclic Ring," *J. Med. Chem.*, 37:1508 (1994).

Eyrolles, et al., "Retinoid Antagonists: Molecular Design Based on the Ligand Superfamily in Concept," *Med. Chem. Res.,* 2:361 (1992).

Forman, et al., "Unique Response Pathways Are Established by Allosteric Interactions among Nuclear Hormone Receptors," *Cell* 81:541–550 (1995).

Giguere, et al., "Identification of a receptor for the morphogen retinoic acid," *Nature,* 330:624–529 (1987).

Heyman, et al., "9–Cis Retenoic Acid is a High Affinity Ligand for the Retinoid X Receptor," *Cell,* 68:397–406 (1992).

Jow and Mukherjee, "The Human Peroxisome Proliferator–activated Receptor (PPAR) Subtype NUC1 Prepresses the Activation of hPPARα and Thyroid Hormone Receptors," *J. Biol. Chem.,* 3836–3840 (1995).

Kagechika, et al., "Retinobenzoic Acids. 2. Structure–Activity Relationship of Chalcone–4–carboxylic Acids and Stilbene–4–carboxylic Acids," *J. Med. Chem.,* 32:834 (1989).

Kagechika, et al., "Retinobenzoic Acids. 3. Structure–Activity Relationships of Retinoidal Axobenzene–4–carboxylic Acids and Stilbene–4–carboxylic Acids," *J. Med. Chem.,* 32:1098 (1989).

Kagechika, et al., "Retinobenzoic Acids. 4. Conformation of Aromatic Amides with Retinoidal Activity. Importance of trans–Amide Structure for the Activity," *J. Med. Chem.,* 32:2292 (1989).

Kaneko, et al., "Retinoid Antagonists," *Med. Chem. Res.,* 1:220 (1991).

Keidel, et al., "Different Agonist– and Antagonist–Induced Conformational Changes in Retinoic Acid Receptors Analyzed by Protease Mapping," *Mol. Cell. Biol.,* 14:287 (1994).

Kliewer, et al., "Convergence of 9–cis retinoic acid and peroxisome proliferator signalling pathways through heterodimer formation of their receptors," *Nature,* 358:771–774 (1992).

Kurokawa, et al., "Regulation of retinoid signalling by receptor polarity and allosteric control of ligand binding," *Nature,* 371:528–531 (1995).

Lee, et al., "A synthetic retinoid antagonist inhibits the human immunodeficiency virus type 1 promoter," *Proc. Natl. Acad. Sci.,* 91:5632 (1994).

Levin, et al., "9–Cis retinoic acid steroisomer binds and activates the nuclear receptor RXRα," *Nature,* 355:359–361 (1992).

Mangelsdorf, et al., "The Retinoid Receptors" in *The Retinoids: Biology, Chemistry and Medicine,* M.B. Sporn, A.B. Roberts and D.S. Goodman, Eds., Raven Press, New York New York, Second Edition (1994).

Mangelsdorf, et al., "A Direct Repeat in the Cellular Retinol–Binding Protein Type II Gene Confers Differential Regulation by RXR and RAR," *Cell,* 66:555–561 (1991).

Mukherjee, et al. .., "Human and Rat Peroxisome Proliferator Activated Receptors (PPARS) Demonstrate Similar Tissue Distribution but Different Responsiveness to PPAR Activators," *J. Steriod Biochem., Molec., Biol.,* 157–166 (1994).

Petkovich, et al., "A human retinoic acid receptor which belongs to the family of nuclear receptors," *Nature,* 330:444–450 (1987).

Roy, et al., "Synergistic Activation of Retinoic Acid (RA)–Responsive Genes and Induction of Embryonal Carcinoma Cell Differentiation by an RA Receptor α (RARα)–, RARβ–, or RARγ–Selective Ligand in Combination with a Retinoid X Receptor–Specific Ligand," *Mol. C. Biol.*, 15:6481–6487 (1995).

Yoshimura, et al., "A Novel Type of Retinoic Acid Receptor Antagonist: Synthesis and Structure–Activity Relationships of Heterocyclic Ring Containing Benzoic Acid Derivatives," *J. Med. Chem.*, 38:3163 (1995).

Ampel, N.M. et al. "Persistent rectal ulcer associated with human papillomavirus type 33 in a patient with AIDS: successful treatment with isotretinoin," *Reviews of Infectious Diseases*, v. 12, 6:1004–7 (1990 Nov.–Dec.).

"The Evolving Role of Retinoids in the Management of Cutaneous Conditions," *Journal of the American Academy of Dermatology*, v. 39, 2:Table of Contents Only (1998 Aug.).

Anstead, G.M. "Steroids, retinoids, and wound healing," *Advances in Wound Care*, v. 11, 6:277–85 (1998 Oct.).

Bergfeld, W.F., et al. "Retinoids and hair growth," *Journal of the American Academy of Dermatology*, v. 39, 2:S86–9 (1998 Aug.).

Bershad, S. et al., "Topical retinoids in the treatment of acne vulgaris," *Cutis*, v. 64, 2:8–20 (1999 Aug.).

Boehm, M.F. et al., "Retinoids: biological function and use in the treatment of dermatological disease", *Exp. Opin. Invest. Drugs*, 4(7): 593–612 (1995).

Conant, M.A. "Immunomodulatory therapy in the management of viral infections in patients with HIV infection," *Journal of the American Academy of Dermatology*, v. 43, 1:S27–30 (2000 Jul.).

Conley, B.A., et al. "Current status of retinoids in chemoprevention of oral squamous cell carcinoma: an overview," *Journal of Cranio–Maxillo–Facial Surgery*, v. 24, 6:339–45 (1996 Dec.).

Dabon–Almirante, C.L. et al. "Related case report: in vivo suppression of thyrotropin by 9–cis retinoic acid," *Cancer Journal From Scientific American*, v. 5, 3:171–3 (1999 May–Jun.).

Edwards, K.R., et al. "Treatment of localized discold lupus erythematosus with tazarotene," *Journal of the Americal Academy of Dermatology*, v. 41, 6:1049–50 (1999 Dec.).

El–Metwally, T.H., "Optimization of treatment conditions for studying the anticancer effects of retinoids using pancreatic adenocarcinoma as a model," *Biochemical and Biophysical Research Communications*, v. 257, 2:596–603 (1999 Apr. 13).

Federman, D.G. et al., "Topical psoriasis therapy," *American Family Physician*, v. 59, 4:957–62, 964 (1999 Feb. 15).

Georgouras, K.E., et al. "Systemic treatment of severe psoriasis," *Australian Journal of Dermatology*, v. 38, 4:171–80 (1997 Nov.).

Gergely, P. et al. "Immunological effects of retinoids," *Tokai Journal of Experimental and Clinical Medicine*, v. 15, 2–3:235–9 (*1990 May*).

Gross, G. et al. "Effect of oral aromatic retinoid (Ro 10–9359) on human papilloma virus–2–induced common warts," *Dermatologica*, v. 166, 1:48–53 (1983).

Hill, D.L. et al. "Retinoids and cancer prevention," *Annual Review of Nutrition*, pp. 12161–81 (1992)/

Hinds, T.S. "Carotenoids and retinoids: a review of research, clinical, and public health applications," *Journal of Clinical Pharmacology*, v. 37, 7:551–8 (1997 Jul.).

Hofmann, S.L. "Retinoids–'differentiation agents' for cancer treatment and prevention," *American Journal of the Medical Sciences*, v. 304, 3:202–13 (1992 Sep.).

Katsambas, A.D. et al., "Topical retinoids in the treatment of aging of the skin," *Advances in Experimental Medicine and Biology*, pp. 455477–82 (1999).

Kligman, A.M. "The treatment of acne with topical retinoids: one man's opinions," *Journal of the American Acadmey of Dermatology*, v. 36, 6:S92–5 (1997 Jun.).

Kurie, J.M., "The biologic basis for the use of retinoids in cancer prevention and treatment," *Current Opinion in Oncology*, v. 11, 6:497–502 (1999 Nov.).

Lenhard, J.M. "The RXR agonist LG100268 causes hepatomegaly, improves glycaemic control and decreases cardiovascular risk and cachexia in diabetic mice suffering from pancreatic beat–cell dysfunction," *Diabetologia*, v. 42, 5:545–54 (1999 May).

Leyden, J.J. "Retinoids and acne," *Journal of the American Academy of Dermatology*, v. 19: 164–8 (1988 Jul.).

Lippman, S.M. "Retinoids in chemoprevention of head and neck carcinogenesis," *Preventive Medicine*, v. 22, 5:693–700 (1993 Sep.).

Lippman, S.M. et al. "Retinoids and chemoprevention: clinical and basic studies," *USA Journal of Cellular Biochemistry. Supplement*, pp. 221–210 (1995).

Lippman, S.M., et al. "Retinoid–interferon therapy of solid tumors," *USA International Journal of Cancer*, v. 70, 4:481–3 (1997 Feb. 7).

Lippman, S.M., et al. "Retinoids, neoplasia and differentiation therapy," *Cancer Chemotherapy and Biological Response Modifiers*, pp. 17349–62 (1997).

Lotan, R. "Retinoids in cancer chemoprevention," *Faseb Journal*, v. 10, 9:1031–9 (1996 Jul.).

Man, T. "Solid tumours–chemoprevention with retinoids," *Leukemia*, v. 8, 3:3587–92 (1994).

Miller, W.H. Jr., "The emerging role of retinoids and reintoic acid metabolism blocking agents in the treatment of cancer," *Cancer*, v. 83, 8:1471–82 (1998 Oct. 15).

Minton, S.E., "Chemoprevention of breast cancer in the older patient," *Hematology/Oncology Clinics of North America*, vol. 14, 1:113–30 (2000 Feb.).

Moon, R.C. et al. "Retinoids as chemopreventative agents for breast cancer," *Cancer Detection and Prevention*, v. 16, 1:73–9 (1992).

Ney, U.M. "Anti–inflammatory effects of synthetic retinoids may be related to their immunomodulatory action," *Dermatologica*, 175:193–9 (1987).

Oridate, N. et al. "Inhibition of proliferation and induction of apoptosis in cervial carcinoma cells by retinoids: implications for chemoprevention," *Journal of Cellular Biochemistry. Supplement*, 23:80–86 (1995).

Papadimitrakopoulou, V.A., et al. "Retinoids in head and neck chemoprevention," *Proceedings of the Society for Experimental Biology and Medicine*, v. 216, 2:283–90 (1997 Nov.).

Paquette R.L. et al. "Differentiation therapy," *Hematology/Oncology Clinics of North America*, v. 6, 3:687–706 (1992 Jun.).

Pereira, M.A., "Prevention of colon cancer and modulation of aberrant crypt foci, cell proliferation, and apoptosis by retinoids and NSAIDs," *Advances in Experimental Medicine and Biology*, pp. 47055–63 (1999).

Personett, D. et al. "Retinoic acid–mediated enhancement of the cholinergic/neuronal nitric oxide synthase phenotype of the medial septal SN56 clone: establishment of a nitric oxide–sensitive proapoptotoic state," *CODEN*, v. 74, 6:2412–2424 (2000).

Recchia F. et al., "Beta–interferon, retinoids and tamoxifen combination in advanced breast cancer," *Clinica Terapeutica*, v. 149, 3:203–8 (1998 May–Jun.).

Roy, B. et. al. "Stimulatory effects of retinoic acid on tumor growth and serum insulin–like growth factor–1 in rats bearing estrogen–responsive pituitary tumor MtT/Se," *Japanese Journal of Cancer Research*, v. 82, 7:815–9 (1991 Jul.).

Saurat, J. "Systemic retinoids: what's new?," *CODEN: DRMCDJ*, v. 16, 2:331–340 (1998).

Singh, D. et al., "Cancer chemoprevention. Part 1: Retinoids and carotenoids and other classic antioxidants," *Oncology*, v. 12, 11:1643–53, 1657–8 (1998 Nov.).

Terezakis, N.K. et al. "Retinoids: compounds important to hair growth," *Clinics in Dermatology*, v. 6, 4:129–31 (1988 Oct.–Dec.).

Thacher, S.M. "Therapeutic applications for ligands of retinoid receptors," *USA*, v. 6, 1:25–58 (2000 Jan.).

Torras, H. "Retinoids in aging," *Clinics in Dermatology*, v. 14, 2:207–15 (1996 Mar.–Apr.).

Tseng, S.C. "Topical retinoid treatment for dry eye disorders," *Transactions of the Ophthalmological Societies of the United Kingdom*, 104:489–94 (1985).

Tseng, S.C. "Topical retinoid treatment for various dry–eye disorders," *Ophthalmology*, v. 92, 6:717–27 (1985 Jun.).

Wieder, J.M. et al. "Systemic retinoids for psoriasis," *Dermatologic Clinics*, v. 13, 4:891–6 (1995 Oct.).

Zhang, L. et al. "Retinoids and apoptosis," *CODEN:AOB-IFW Journal*, pp. 161–196 (1997).

DIMER-SELECTIVE RXR MODULATORS AND METHODS FOR THEIR USE

RELATED APPLICATIONS

This is a divisional of application(s) Ser. No. 08/710,427, filed on Sep. 17, 1996, now abandoned which claims the benefit of prior provisional applications under 35 USC 119(e), provisional applications Ser. No. 60/004,897, filed Oct. 6, 1995; Ser. No. 60/009,884, filed Jan. 11, 1996; Ser. No. 60/018,318, filed on May 24, 1996; Ser. No. 60/021,839, filed Jul. 10, 1996.

FIELD OF THE INVENTION

The present invention relates to compounds having agonist, partial agonist and antagonist activity for retinoid X receptors, and to methods for the production and therapeutic use of such compounds.

BACKGROUND OF THE INVENTION

The vitamin A metabolite, retinoic acid, has long been recognized to induce a broad spectrum of biological effects. For example, retinoic acid-containing products, such as Retin-A® and Accutane®, have found utility as therapeutic agents for the treatment of various pathological conditions. In addition, a variety of structural analogues of retinoic acid have been synthesized that also have been found to be bioactive. Many of these synthetic retinoids have been found to mimic many of the pharmacological actions of retinoic acid, and thus have therapeutic potential for the treatment of number disease states.

Medical professionals have become very interested in the therapeutic applications of retinoids. Among their uses approved by the FDA is the treatment of severe forms of acne and psoriasis. A large body of evidence also exists that these compounds can be used to arrest and, to an extent, reverse the effects of skin damage arising from prolonged exposure to the sun. Other evidence exists that these compounds have clear effects on cellular proliferation, differentiation and programmed cell death (apoptosis), and thus, may be useful in the treatment and prevention of a variety of cancerous and pre-cancerous conditions, such as acute promyleocytic leukemia (APL), epthelial cancers, squamous cell carcinomas, including cervical and skin cancers and renal cell carcinoma. Furthermore, retinoids may have beneficial activity in treating and preventing diseases of the eye, cardiovascular disease and other skin disorders.

Major insight into the molecular mechanism of retinoic acid signal transduction was gained in 1988, when a member of the steriod/thyroid hormone intracellular receptor superfamily was shown to transduce a retinoic acid signal. Giguere et al., *Nature*, 330:624–29 (1987); Petkovich et al., *Nature*, 330: 444–50 (1987); for review. See Evans, *Science*, 240:889–95 (1988). It is now known that retinoids regulate the activity of two distinct intracellular receptor subfamilies; the Retinoic Acid Receptors (RARs) and the Retinoid X Receptors (RXRs), including their subtypes, RARα, β, γ and RXRα, β, γ. All-trans-retinoic acid (ATRA) is an endogenous low-molecular-weight ligand which modulates the transcriptional activity of the RARs, while 9-cis retinoic acid (9-cis) is the endogenous ligand for the RXRs. Heyman et al., *Cell*, 68:397–406 (1992) and Levin et al. *Nature*, 355:359–61 (1992).

Although both the RARs and RXRs respond to ATRA in vivo, due to the in vivo conversion of some of the ATRA to 9-cis, the receptors differ in several important aspects. First, the RARs and RXRs are significantly divergent in primary structure (e.g., the ligand binding domains of RARα and RXRα have only approximately 30% amino acid identity). These structural differences are reflected in the different relative degrees of responsiveness of RARs and RXRs to various vitamin A metabolites and synthetic retinoids. In addition, distinctly different patterns of tissue distribution are seen for RARs and RXRs. For example, RXRα mRNA is expressed at high levels in the visceral tissues, e.g., liver, kidney, lung, muscle and intestine, while RARα mRNA is not. Finally, the RARs and RXRs have different target gene specificity. In this regard, RARs and RXRs regulate transcription by binding to response elements in target genes that generally consist of two direct repeat half-sites of the consensus sequence AGGTCA. RAR:RXR heterodimers activate transcription ligand by binding to direct repeats spaced by five base pairs (a DR5) or by two base pairs (a DR2). However, RXR:RXR homodimers bind to a direct repeat with a spacing of one nucleotide (a DR1). See Mangelsdorf et al., "The Retinoid Receptors" in *The Retinoids: Biology, Chemistry and Medicine*, M. B. Sporn, A. B. Roberts and D. S. Goodman, Eds,. Raven Press, New York, N.Y., Second Addition (1994). For example, response elements have been identified in the cellular retinal binding protein type II (CRBPII), which consists of a DR1, and Apolipoprotein AI genes which confer responsiveness to RXR, but not RAR. Further, RAR has also been recently shown to repress RXR-mediated activation through the CRBPII RXR response element (Manglesdorf et al., *Cell*, 66:555–61 (1991)). Also, RAR specific target genes have recently been identified, including target genes specific for RARβ (e.g., βRE), which consists of a DR5. These data indicate that two retinoic acid responsive pathways are not simply redundant, but instead manifest a complex interplay.

RXR agonists in the context of an RXR:RXR homodimer display unique transcriptional activity in contrast to the activity of the same compounds through an RXR heterodimer. Activation of a RXR homodimer is a ligand dependent event, i.e., the RXR agonist must be present to bring about the activation of the RXR homodimer. In contrast, RXR working through a heterodimer (e.g., RXR:RAR, RXR:VDR) is often the silent partner, i.e., no RXR agonist will activate the RXR-containing heterodimer without the corresponding ligand for the heterodimeric partner. However, for other heterodimers, (.e., PPAR:RXR) a ligand for either or both of the heterodimeric partners can activate the heterodimeric complex. Furthermore, in some instances, the presence of both an RXR agonist and the agonist for the other heterodimeric partner (e.g., gemfibrizol for PPARα and TTNPB for RARα) leads to at least an additive, and often a synergistic enhancement of the activation pathway of the other IR of the heterodimer pair (e.g., the PPARα pathway). See, e.g., PCT Aplication No. PCT/US93/10204, filed Oct. 22, 1993, published as PCT Publication No. WO 94/15902 on Jul. 21, 1994; R. Mukherjee et al., 51 *J. Steroid Biochem. Molec. Biol.*, 157–166 (1994) and L. Jow and R. Mukherjee, 270 *Journ. Biol. Chem.*, 3836–3840 (1995).

RAR and RXR retinoid agonists, including both RAR specific and RXR specific agonists have been previously identified. See e.g., PCT Publication Nos. WO 94/15902 WO93/21146, WO94/15901, WO94/12880, WO94/17796, WO94/20093, WO96/05165 and PCT Application No. PCT/US93/10166; EPO Patent Application Nos. 87110303.2, 87309681.2 and EP 0718285; U.S. Pat. Nos. 4,193,931, 4,539,134, 4,801,733, 4,831,052, 4,833,240, 4,874,747, 4,879,284, 4,898,864, 4,925,979, 5,004,730, 5,124,473, 5,198,567, 5,391,569 and Re 33,533; and H. Kagechika et al., "Retinobenzoic Acids. 2. Structure-Activity Relationship of Chalcone-4-carboxylic Acids and Flavone-4'-carboxylic Acids", 32 *J. Med. Chem.,* 834 (1989); H. Kagechika et al., "Retinobenzoic Acids. 3. Structure-Activity Relationships of Retinoidal Azobenzene-4-carboxylic Acids and Stilbene-4-carboxylic Acids", 32 *J. Med. Chem.,* 1098 (1989); H. Kagechika et al., "Retinobenzoic Acids. 4. Conformation of Aromatic Amides with Retinoidal Activity. Importance of trans-Amide Structure for the Activity", 32 *J. Med. Chem.,* 2292 (1989); M. Boehm et al., 37 *J. Med. Chem.,* 2930 (1994); M. Boehm et al., 38 *J. Med. Chem.,* 3146 (1995); E. Allegretto et al., 270 *Journal of Biol. Chem.,* 23906 (1995); R. Bissonnette et al., 15 *Mol. & Cellular Biol.* 5576 (1995); R. Beard et al., 38 *J. Med. Chem.,* 2820 (1995) and M. I. Dawson et al., "Effect of Structural Modifications in the C7–C11 Region of the Retinoid Skeleton on Biological Activity in a Series of Aromatic Retinoids", 32 *J. Med. Chem.,* 1504 (1989). Further, antagonists to the RAR subfamily of receptors have recently been identified. See e.g., C. Apfel et al., 89 *Proc. Natl. Acad. Sci.,* 7129 (1992); S. Keidel et al., 14 *Mol. Cell Biol.,* 287 (1994); S. Kaneko et al., 1 *Med. Chem. Res.* 220 (1991); L. Eyrolles et al., 2 *Med. Chem. Res.* 361 (1992); J. Eyrolles et al., 37 *J. Med. Chem.,* 1508 (1994); M-O Lee et al., 91 *Proc. Natl. Acad. Sci.,* 5632 (1994); Yoshimura et al., 38 *J. Med. Chem.,* 3163 (1995) and U.S. Pat. No. 5,391,766. In addition, various polyene compounds have been disclosed to be useful in the treatment of inflammatory conditions, psoriasis, allergic reactions, and for use in sunscreens in cosmetic preparations. See e.g., U.S. Pat. Nos. 4,534,979 and 5,320,833. Also, trienediolates of hexadienoic acids have proved useful in the synthesis of retinoic and nor-retinoic acids. See M. J. Aurell, et al., 49 *Tetrahedron,* 6089 (1993). However, to date, compounds that are RXR antagonist (e.g., that bind to RXR and do not activate, but antagonize transcription) and/or RXR selective compounds that have distinct heterodimer selective properties, such that they are capable of manifesting agonist, partial agonist and antagonist properties, have not been identified or characterized.

SUMMARY OF THE INVENTION

The present invention provides novel RXR modulators that selectively bind to RXR receptors in preference to RAR receptors and that, depending upon the receptor and/or cellular context, display activity as full agonists, partial agonists and/or full antagonists on RXR homodimers and/or RXR heterodimers. Thus, these compounds display unique selectivity for RXR heterodimers, and a referred to herein as dimer-selective RXR modulators. The present invention also provides pharmaceutical compositions incorporating these novel compounds and methods for the therapeutic use of such compounds and pharmaceutical compositions.

These and various other advantages and features of novelty which characterize the invention are pointed out with particularity in the claims annexed hereto and forming a part hereof. However, for a better understanding of the invention, its advantages, and objects obtained by its use, reference should be had to the accompanying drawings and descriptive matter, in which there is illustrated and described preferred embodiments of the invention.

DEFINITIONS

In accordance with the present invention and as used herein, the following terms are defined with the following meanings, unless explicitly stated otherwise.

The term alkyl refers a straight-chain, branched-chain, cyclic and combination alkyls, including optional unsaturation (thereby resulting in alkenyls and alkynyls).

The term heteroalkyl refers to an optionally substituted straight-chain, branched-chain, cyclic and combination $C_1$ to $C_{10}$ alkyls containing one or more heteroatoms selected from the group consisting of halogen (i.e., F, Cl, Br, I) (including perfluoro alkyls), oxygen, nitrogen and sulfur, including optional unsaturation.

The term cycloalkyl refers to an optionally substituted $C_3$ to $C_6$ group which forms a ring, including optional unsaturation and optional heteroatom (e.g., O, N or S) substitution in or on the cyclalkyl ring.

The term aryl refers to optionally substituted phenyl, biphenyl, naphthyl or anthracenyl ring systems.

The term heteroaryl refers to an optionally substituted five-membered or six-membered heterocyclic or other aryl ring containing one or more heteroatoms selected from the group consisting of oxygen, nitrogen and sulfur, including, without limitation, furyl, pyrrolyl, pyrrolidinyl, thienyl, pyridyl, piperidyl, indolyl, quinolyl, thiazole, benzthiazole and triazole.

The term arylalkyl or heteroarylalkyl refers to optionally substituted alkyls containing one or more aryl and/or heteroaryl groups.

The term acyl refers to alkyl, aryl or arylalkyl or heteroarylalkyl substitutes attached to a compound via a carbonyl functionality (e.g., —CO-alyl, —CO-aryl, —CO-arylalkyl or heteroarylalkyl etc. . .).

The term dimer-selective RXR modulator refers to a compound that binds to one or more Retinoid X Receptors and modulates (i.e., increases or decreases the transcriptional activity and/or biological properties of the given receptor dimer) the transcriptional activity of an RXR homodimer (i.e., RXR:RXR) and/or RXR in the context of a heterodimer, including but not limited to heterodimer formation with peroxisome proliferator activated receptors (e.g., RXR:PPARα,β,γ1 or γ2), thyroid receptors (e.g., RXR:TRα or β), vitamin D receptors (e.g., RXR:VDR), retinoic acid receptors (e.g., RXR:RARα,β or γ), NGFID receptors (e.g., RAR:NGFIB), NURR1 receptors (e.g., RXR:NURR1) LXR receptors (e.g., RXR:LZRα,β), DAX receptors (e.g., RXR:DAX), as well as other orphan receptors that form heterodimers with RXR, as either an agonist, partial agonist and/or antagonist. The particular effect of a dimer-selective RXR modulator as an agonist, partial agonist and/or antagonist will depend upon the cellular context as well as the heterodimer partner in which the modulator compounds acts. In this regard, the present invention describes dimer-selective RXR modulators, i.e., modulators that are selective activators and/or repressors through Retinoid X Receptors (i.e., RXRα, RXRβ, and/or RXRγ) rather than Retinoic Acid Receptors (i.e., RARα, RARβ, and/or RARγ).

BRIEF DESCRIPTION OF THE DRAWING

The invention may be further illustrated by reference to the accompanying Drawings wherein.

DETAILED DESCRIPTION OF EMBODIMENTS OF THE INVENTION

Figure 1A:
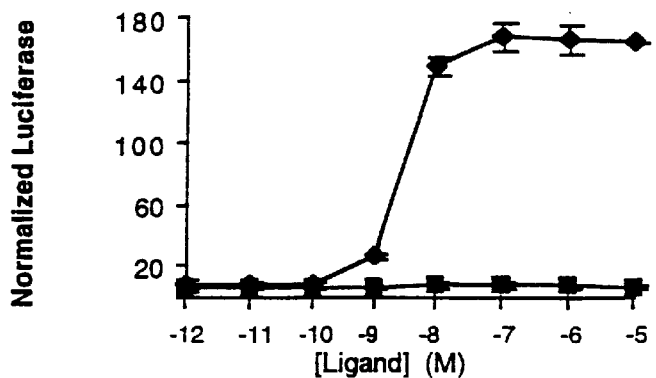
FIG. 1A, is a dose response curve showing that Compound 122 of the present invention (■) fails to activate RXR:RXR homodimers, while the known RXR agonist, LG100268 (♦) (Ligand Pharmaceuticals, Inc.), does activate the RXR:RXR homodimer.

In accordance with a first aspect of the present invention, we have developed compounds of the formula:

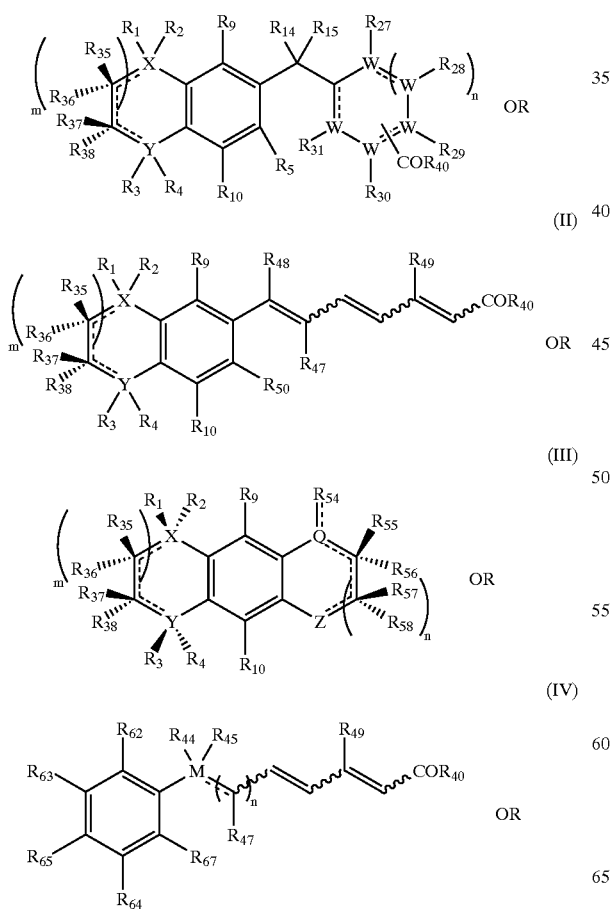

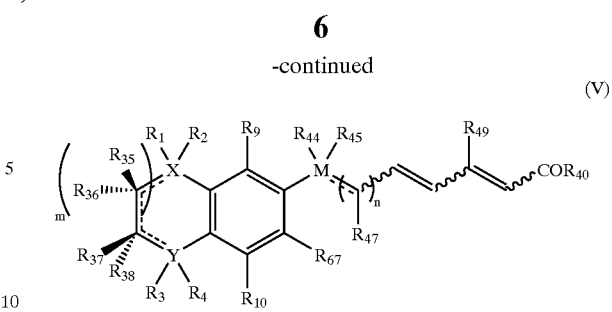

wherein, $R_1$ through $R_4$ each independently are hydrogen, a $C_1$–$C_6$ alkyl or a $C_7$–$C_{15}$ arylalkyl or heteroarylalkyl;

$R_5$ is a $C_5$–$C_{10}$ alkyl, heteroalkyl, aryl, heteroaryl, a $C_7$–$C_{15}$ arylalkyl or heteroarylalkyl, $NR_6R_7$, or $OR_8$, where $R_6$ and $R_7$ each independently are a $C_7$–$C_{10}$ alkyl, heteroalkyl, a $C_7$–$C_{15}$ arylalkyl or heteroarylalkyl, a $C_3$–$C_{10}$ acyl, provided that only one of $R_6$ or $R_7$ can be acyl, or $R_6$ and $R_7$ taken together are $C_3$–$C_6$ cycloalkyl, and where $R_8$ is a $C_7$–$C_{10}$ alkyl, heteroalkyl, aryl, heteroaryl, or a $C_7$–$C_{15}$ arylalkyl or heteroarylalkyl;

$R_9$ and $R_{10}$ each independently are hydrogen, a $C_1$–$C_{10}$ alkyl, halogen, heteroarylalkyl, $NR_{11}R_{12}$, $NO_2$ or $OR_{13}$, where $R_{11}$ and $R_{12}$ each independently are hydrogen, a $C_1$–$C_{10}$ alkyl, heteroalkyl, a $C_7$–$C_{15}$ arylalkyl or heteroarylalkyl, a $C_1$–$C_8$ acyl, provided that only one of $R_{11}$ or $R_{12}$ can be acyl, or $R_{11}$ and $R_{12}$ taken together are a $C_3$–$C_6$ cycloalkyl, and where $R_{13}$ is hydrogen or a $C_1$–$C_{10}$ alkyl, heteroalkyl or a $C_7$–$C_{15}$ arylalkyl or heteroarylalkyl;

$R_{14}$ and $R_{15}$ each independently are hydrogen, a $C_1$–$C_{10}$ alkyl, a $C_1$–$C_8$ acyl, or $OR_{16}$ where $R_{16}$ is hydrogen or a $C_1$–$C_{10}$ alkyl; or $R_{14}$ and $R_{15}$ taken together are keto, methano, optionally substituted oxime, optionally substituted hydrazine, optionally substituted epoxy, 1,3-dioxolane, 1,3-dioxane, 1,3-dithiolane, 1,3-dithiane, oxazolidine or:

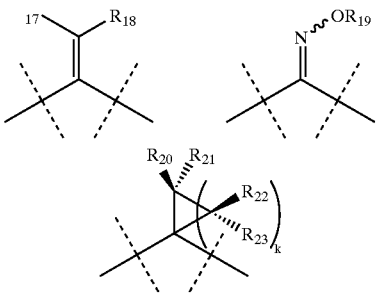

where $R_{17}$ through $R_{23}$ have the definitions given below and the dashed lines crossing the bonds indicate the attachment bonds to the rings adjacent to $R_{14}$ and $R_{15}$;

$R_{17}$ and $R_{18}$ each independently are hydrogen, a $C_1$–$C_{10}$ alkyl, heteroalkyl, aryl, a $C_7$–$C_{15}$ arylalkyl or heteroarylalkyl or $R_{17}$ and $R_{18}$ taken together are a $C_3$–$C_6$ cycloalkyl;

$R_{19}$ is hydrogen, a $C_1$–$C_{10}$ alkyl, heteroalkyl, aryl, heteroaryl, a $C_7$–$C_{15}$ arylalkyl or heteroarylalkyl;

$R_{20}$ through $R_{23}$ each independently are hydrogen, halogen, a $C_1$–$C_{10}$ alkyl, heteroalkyl, aryl, heteroaryl, a $C_7$–$C_{15}$ arylalkyl or heteroarylalkyl, $NR_{24}R_{25}$, $NO_2$, or $OR_{26}$, where $R_{24}$ and $R_{25}$ each independently are hydrogen, a $C_1$–$C_{10}$ alkyl, heteroalkyl, a $C_7$–$C_{15}$ arylalkyl or heteroarylalkyl or a $C_1$–$C_8$ acyl, provided that only one of $R_{24}$ or $R_{25}$ can be acyl, and where $R_{26}$ is hydrogen or a $C_1$–$C_{10}$ alkyl, heteroalkyl, aryl, heteroaryl, or a $C_7$–$C_{15}$ arylalkyl or heteroarylalkyl;

$R_{27}$ through $R_{31}$ each independently are hydrogen, a $C_1$–$C_{10}$ alkyl, heteroalkyl, halogen, $NR_{32}R_{33}$, $NO_2$ or $OR_{34}$, where $R_{32}$ and $R_{33}$ each independently are hydrogen, a $C_1$–$C_{10}$ alkyl, a $C_7$–$C_{15}$ arylalkyl or heteroarylalkyl, a $C_1$–$C_8$ acyl, provided that only one of $R_{32}$ or $R_{33}$ can be acyl, or $R_{32}$ and $R_{33}$ taken together are a $C_3$–$C_6$ cycloalkyl, and where $R_{34}$ is hydrogen or a $C_1$–$C_{10}$ alkyl, heteroalkyl or a $C_7$–$C_{15}$ arylalkyl or heteroarylalkyl and can only exist when W is C;

$R_{35}$ through $R_{38}$ each independently are hydrogen, a $C_1$–$C_2$ alkyl or $OR_{39}$ where $R_{39}$ is hydrogen or a $C_1$–$C_{10}$ alkyl, or $R_{35}$ and $R_{36}$ or $R_{37}$ and $R_{38}$ taken together are keto, or $R_{35}$ and $R_{36}$, $R_{37}$ and $R_{38}$, $R_{35}$ and $R_{37}$ or $R_{36}$ and $R_{38}$ taken together are epoxy;

$COR_{40}$ can originate from any W, when the originating W is C, and $R_{40}$ is $OR_{41}$ or $NR_{24}R_{43}$, with $R_{41}$ being hydrogen, a $C_1$–$C_6$ alkyl or a $C_7$–$C_{15}$ arylalkyl or heteroarylalkyl, and with $R_{42}$ and $R_{43}$ each independently being hydrogen, a $C_1$–$C_6$ alkyl, a $C_7$–$C_{15}$ arylalkyl or heteroarylalkyl, aryl, ortho-, meta-, or para-substituted hydroxyarl, or taken together are a $C_3$–$C_6$ cycloalkyl;

$R_{44}$ and $R_{45}$ each independently are hydrogen, a $C_1$–$C_4$ alkyl or $CH_2OR_{46}$, where $R_{46}$ is hydrogen or a $C_1$–$C_6$ alkyl, or $R_{44}$ and $R_{45}$ taken together are a $C_3$–$C_6$ cycloalkyl or cycloheteroalkyl;

$R_{47}$ is hydrogen, a $C_1$–$C_4$ alkyl, or when n=1, $R_{47}$ taken together with $R_{44}$ or $R_{45}$ are a $C_3$–$C_6$ cycloalkyl or cycloheteroalkyl;

$R_{48}$ and $R_{49}$ each independently are $C_1$–$C_4$ alkyl;

$R_{50}$ is a $C_4$–$C_{10}$ alkyl, keteroalkyl, aryl, heteroaryl, a $C_7$–$C_{15}$ arylalkyl or heteroarylalkyl, $NR_{51}R_{52}$, or $OR_{53}$, where $R_{51}$ and $R_{52}$ each independently are a $C_2$–$C_{10}$ alkyl, heteroalkyl, a $C_7$–$C_{15}$ arylalkyl or heteroarylalkyl, a $C_3$–$C_{10}$ acyl, provided that only one of $R_{51}$ or $R_{52}$ can be acyl, or $R_{51}$ and $R_{52}$ taken together are $C_3$–$C_6$ cycloalkyl, and where $R_{53}$ is a $C_7$–$C_{10}$ alkyl, heteroalkyl, aryl, heteroaryl, a $C_3$–$C_6$ alkyl, heteroalkyl, aryl or heteroalkyl or a $C_7$–$c_{15}$ arylalkyl or heteroarylalkyl;

$R_{54}$ represents:

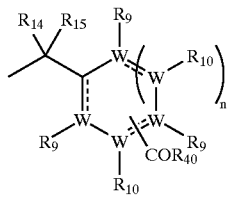

where $R_9$, $R_{10}$, $R_{14}$, $R_{15}$ and $R_{40}$ have the definitions given above;

$R_{55}$ through $R_{58}$ each independently are hydrogen, halogen, a $C_1$–$C_{10}$ alkyl, heteroalkyl, aryl, heteroaryl, a $C_7$–$C_{15}$ arylalkyl or heteroarylalkyl, $NR_{59}R_{60}$ or $OR_{61}$, where $R_{59}$ and $R_{60}$ each independently are hydrogen, a $C_1$–$C_{10}$ alkyl or heteroalkyl, a $C_7$–$C_{15}$ arylalkyl or heteroarylalkyl, a $C_1$–$C_8$ acyl, provided that only one of $R_{59}$ or $R_{60}$ can be acyl, or $R_{59}$ and $R_{60}$ taken together are $C_3$–$C_6$ cycloalkyl, and where $R_{61}$ is hydrogen or a $C_1$–$C_{10}$ alkyl, heteroalkyl, aryl, heteroaryl, or a $C_7$–$C_{15}$ arylalkyl or heteroarylalkyl, or where $R_{55}$ and $R_{56}$ or $R_{57}$ and $R_{58}$ taken together are keto, methano, a $C_1$–$C_{10}$ alkyl methylene, a $C_1$–$C_{10}$ dialkylmethylene, $C_7$–$C_{15}$ arylalkyl or heteroarylalkylmethylene, oxime, O-alkyl oxime, hydrazone, 1,3-dioxolane, 1,3-dioxane, 1,3-dithiolane, 1,3-dithiane, oxazolidine, or $R_{55}$ and $R_{57}$ or $R_{56}$ and $R_{58}$ taken together are epoxy;

$R_{62}$ through $R_{64}$ each independently are hydrogen, aryl, heteroaryl, $CF_3$, a $C_2$–$C_6$ alkyl, $C_2$–$C_6$ heteroalkyl or $NR_{51}R_{52}$, where $R_{51}$ and $R_{52}$ have the definitions given above;

$R_{65}$ is hydrogen, a $C_1$–$C_2$ alkyl or $OR_{66}$, where $R_{66}$ is a $C_1$–$C_2$ alkyl;

$R_{67}$ is a $C_4$–$C_{10}$ alkyl, heteroalkyl, aryl, heteroaryl, a $C_7$–$C_{15}$ arylalkyl or heteroarylalkyl, $NR_{51}R_{52}$, or $OR_{68}$, where $R_{51}$ and $R_{52}$ have the definitions described above, and where $R_{68}$ is a $C_3$–$C_{10}$ alkyl, heteroalkyl, aryl, heteroaryl, or a $C_7$–$C_{15}$ arylalkyl or heteroarylalkyl;

X and Y each independently represent C, O, S, N, SO or $SO_2$, provided, however, that when X or Y are O, S, SO or $SO_2$, then either $R_1$ and $R_2$ or $R_3$ and $R_4$ respectively do not exist, and further provided, that when X or Y is N, then one each of $R_1$ and $R_2$ or $R_3$ and $R_4$ respectively, do not exist;

M is N or C;

Q is N or C;

Z is O, S, SO, $SO_2$, $CR_{69}R_{70}$ or $NR_{71}$, where $R_{69}$ through $R_{71}$ each independently are hydrogen or a $C_1$–$C_{10}$ alkyl, heteroalkyl, aryl, heteroaryl, a $C_7$–$C_{15}$ arylalkyl or heteroarylalkyl, or $R_{69}$ and $R_{70}$ each independently are $OR_{71}$, or $R_{69}$ and $R_{70}$ taken together are a cycloalkyl;

each W is independently C, N, S or O, or a pharmaceutically acceptable salt, but is not O or S if attached by a double bond to another W or if attached to another shuch W which is O or S, and is not N if attached by a single bond to another such W which is N;

m is 0, 1 or 2 carbon atoms;

n is 0 or 1 carbon atoms;

k is 1 to 5 carbon atoms;

the dashed lines in the structures, other than at $R_{14}$ and $R_{15}$, represent optional double bonds, provided, however, that the double bonds cannot be contiguous, and further provided that when such optional double bonds exist then the substitution patterns around such bonds cannot violate double bond valency; and the wavy lines represent olefin geometry that is either cis (Z) or trans (E), and unless otherwise indicated, for substituents $R_1$ through $R_{71}$, all olefin geometric isomers (i.e., cis (Z) or trans (E)) of the above compounds are included.

The compounds of the present invention will find particular application as RXR modulators, and in particular, as dimer-selective RXR modulators, including, but not limited to RXR homodimer antagonists and agonist, partial agonist and antagonists of RXRs in the context of a heterodimer.

In a second aspect, the present invention provides a method of modulating processes mediated by RXR homodimers and/or RXR heterodimers comprising administering to a patient an effective amount a dimer-selective RXR modulator compound of the formula:

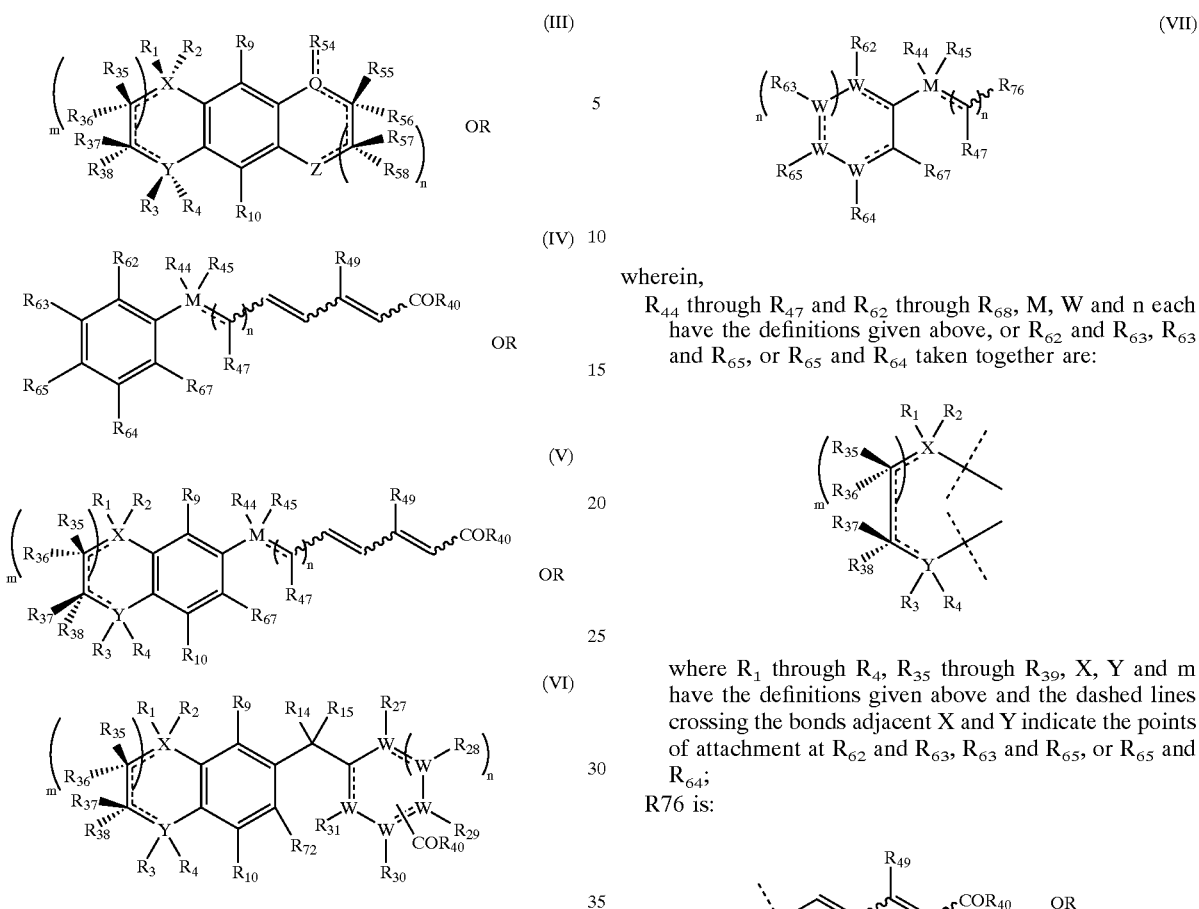

(III) OR (IV) OR (V) OR (VI)

wherein
- $R_1$ through $R_{71}$, M, Q, W, X, Y, Z, k, m and n each have the definitions given above;
- $R_{72}$ is a $C_3$–$C_{10}$ alkyl, heteroalkyl, aryl, heteroaryl, a $C_7$–$C_{15}$ arylalkyl or heteroarylalkyl, $NR_{73}R_{74}$, or $OR_{75}$, where $R_{73}$ and $R_{74}$ each independently are a $C_7$–$C_{10}$ alkyl, heteroalkyl, a $C_7$–$C_{15}$ arylalkyl or heteroarylalkyl, a $C_3$–$C_{10}$ acyl, provided that only one of $R_{73}$ or $R_{74}$ can be acyl, or $R_{73}$ and $R_{74}$ taken together are $C_3$–$C_6$ cycloalkyl, and where $R_{75}$ is a $C_2$–$C_{10}$ alkyl, heteroalkyl, aryl, heteroaryl, or a $C_7$–$C_{15}$ arylalkyl or heteroarylalkyl;
- the dashed lines in the structures, other than at $R_{14}$ and $R_{15}$, represent optional double bonds, provided, however, that the double bons cannot be contiguous, and further provided that when such optional double bonds exist then the substitution patterns around such bonds cannot violate double bond valency; and
- the wavy lines represent olefin geometry that is either cis (Z) or trans (E), and unless otherwise indicated, for substituents $R_1$ through $R_{75}$, all olefin geometric isomers (i.e., cis (Z) or trans (E)) of the above compounds are included.

In a third aspect, the present invention further provides a method of modulating processes mediated by RXR homodimers and/or RXR heterodimers comprising administering to a patient an effective amount a dimer-selective RXR modulator compound of the formula:

(VII)

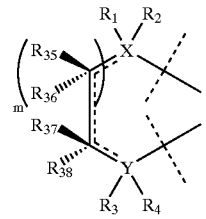

wherein,
$R_{44}$ through $R_{47}$ and $R_{62}$ through $R_{68}$, M, W and n each have the definitions given above, or $R_{62}$ and $R_{63}$, $R_{63}$ and $R_{65}$, or $R_{65}$ and $R_{64}$ taken together are:

where $R_1$ through $R_4$, $R_{35}$ through $R_{39}$, X, Y and m have the definitions given above and the dashed lines crossing the bonds adjacent X and Y indicate the points of attachment at $R_{62}$ and $R_{63}$, $R_{63}$ and $R_{65}$, or $R_{65}$ and $R_{64}$;

R76 is:

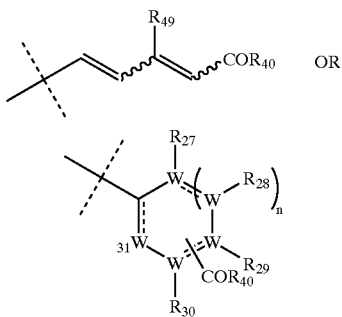

where $R_{27}$ through $R_{34}$, $R_{40}$ through $R_{43}$, $R_{49}$, W and n have the same definitions given above and the dashed lines crossing the bonds adjacent $R_{49}$ and $R_{27}/R_{31}$ indicate the points of attachment at $R_{76}$;

other than as inicated above for points of attachment, the dashed lines in the structures represent optional double bonds, provided, however, that the double bonds cannot be contiguous, and further provided that when such optional double bonds exist then the substitution patterns around such bonds cannot violate double bond valency; and the wavy lines represent olefin geometry that is either cis (Z) or trans (E), and unless otherwise indicated, for substituents $R_1$ through $R_{76}$, all olefin geometric isomers (i.e., cis (Z) or trans (E)) of the above compounds are included.

In a fourth aspect, the present invention provides antagonists of a RXR homodimer and/or a RXR heterodimer. Preferably, the anagonists are selective RXR homodimer antagonists, i.e., the compounds antagonize a RXR homodimer, but do not antagonize RXR in the context of a heterodimer (e.g., an RXR:RAR or RXR:PPAR heterodimer). More preferably, the present invention provides RXR homodimer and and/or heterodimer antagonists of the formula:

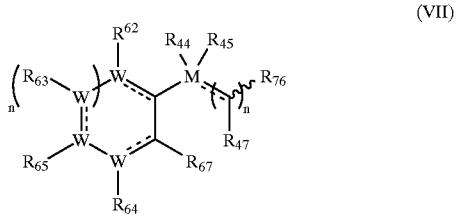

(VII)

wherein, $R_{44}$ through $R_{47}$ and $R_{62}$ through $R_{68}$. M, W and n each have the definitions given above, or $R_{62}$ and $R_{63}$, $R_{63}$ and $R_{65}$, or $R_{65}$ and $R_{64}$ taken together are:

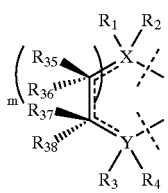

where $R_1$ through $R_4$, $R_{35}$ through $R_{39}$, X, Y and m have the definitions given above and the dashed lines crossing the bonds adjacent X and Y indicate the points of attachment at $R_{62}$ and $R_{63}$, $R_{63}$ and $R_{65}$, or $R_{65}$ and $R_{64}$;

R76 is:

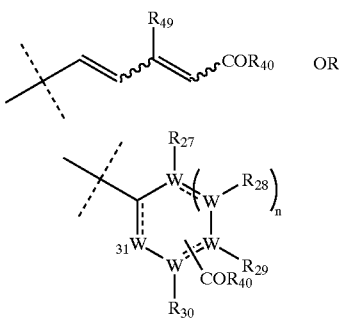

where $R_{27}$ through $R_{34}$, $R_{40}$ through $R_{43}$, $R_{49}$, W and n have the same definitions given above and the dashed lines crossing the bonds adjacent $R_{49}$ and $R_{27}/R_{31}$ indicate the points of attachment at $R_{76}$;

other than as inicated above for points of attachment, the dashed lines in the structures represent optional double bonds, provided, however, that the double bonds cannot be contiguous, and further provided that when such optional double bonds exist then the substitution patterns around such bonds cannot violate double bond valency; and the wavy lines represent olefin geometry that is either cis (Z) or trans (E), and unless otherwise indicated, for substituents $R_1$ through $R_{76}$, all olefin geometric isomers (i.e., cis (Z) or trans (E)) of the above compounds are included.

The compounds of the present invention, as well as the compounds utilized in the methods of the present invention, also include all pharmaceutically acceptable salts, as well as esters and amides. As used in this disclosure, pharmaceutically acceptable salts include, but are not limited to: pyridine, ammonium, piperazine, diethylamine, nicotinamide, formic, urea, sodium, potassium, calcium, magnesium, zinc, lithium, cinnamic, methylamino, methanesulfonic, picric, tartaric, triethylamino, dimethylamino, and tris(hydroxymethyl) aminomethane. Additional pharmaceutically acceptable salts are known to those skilled in the art.

The compounds of the present invention are useful in the modulation of transcriptional activity through an RXR homodimer (i.e., RXR:RXR), as well as through RXR in the context of a heterodimer (e.g., RXR:PPARα,β,γ; RXR:TR; RXR:VDR; RXR:RARα,β,γ; RXR:NGFID; RXR:NURR1; RXR:LXRα,β, RXR:DAX), including any other intracellular receptors (IRs) which form a heterodimer with RXR. For example, application of the compounds of the present invention to modulate a RXRα:PPARα heterodimer is useful to modulate, i.e. increase HDL cholesterol levels and reduce triglyceride levels. Yet, application of many of the same compounds of the present invention to a RXRα:PPARγ heterodimer modulates a distinct activity, i.e., modulation of adipocyte biology, including effects on the differentiation and apoptosis of adipocytes which will have implications in the treatment and/or prevention of diabetes and obesity. In addition, use of the modulator compounds of the present invention with activators of the other heterodimer partner (e.g., fibrates for PPARα and thiazolidinediones for PPARγ) can lead to a synergistic enhancement of the desired response. Likewise, application of the modulator compounds of the present invention in the contexts of a RXRα:RARα and/or RXRα:VDR heterodimers will be useful to modulate skin related processes (e.g., photoaging, acne, psoriasis), malignant and pre-malignant conditions and programmed cell death (apoptosis). Further, it will be understood by those skilled in the art that the modulator compounds of the present invention will also prove useful in the modulation of other heterometer interactions that include RXR, e.g., trimers, tetramers and the like.

Thus, the present inventors have discovered novel dimer-selective RXR modulators with multifunctional activity, that selectively bind to RXRs in preference to RARs and that, depending upon the cellular and/or receptor context, can modulate processes as full agonists, partial agonists and/or full antagonists. For example, in the context of an RXR homodimer, the compounds of the present invention function as RXR antagonists, the first demonstration of such RXR antagonism to date. In addition, many of these same compounds show a surprisingly different biology when exerting their effects through an RXR heterodimer. For example, in the context of a RXR:RAR or RXR-PPAR heterodimer, many of the same RXR homodimer antagonist compounds will serve as partial or full agonists, both alone, and in the presence of a corresponding RAR modulator (e.g., all-trans retinoic acid (ATRA or TTNPB) or PPAR modulator (e.g., gemfibrizol). In other instances, the compounds of the present invention will also antagonize RXR in the context of a heterodimer.

Importantly, the dimer-selective RXR modulators of the present invention activate the transcriptional activity of RXRs in the context of heterodimers without the presence of a corresponding modulator of the other heterodimeric partner (e.g., clofibric acid or gemfibrizol for PPARα; ATRA or TTNPB for RARα). In fact, and in contrast to heterodimers with PPAR, RAR suppresses RXR ligand binding and transactivation for typical RXR agonists (e.g., LGD1069) in the absence of a RAR ligand. However, many of the modulator compounds of the present invention escape suppression by RAR on RXR (e.g., Compounds 122 and 130), and as such, can activate and RAR:RXR heterodimer alone or in the presence of a RAR ligand. While not being bound to a theory of operation, one possible explanation arises from the fact that these unique modulator compounds mechanistically interact with an RXR:RAR heterodimer in a different manner than pure RXR agonists (e.g., LGD1069). Unlike typical RXR agonists, which require an intact activation domain of an RXR receptor in the context of a RAR:RXR heterodimer, the modulator compounds of the present invention require an intact activation domain for the heterodimeric partner (e.g., RAR), but not for the RXR receptor. Accordingly, the modulator compounds of the present invention will, in certain contexts, serve as RAR mimics, activating a subset of the genes activated by typical RAR compounds (e.g., ATRA or TTNPB) and/or activating distinct genes from those activated by typical RAR compounds. In this regard, the modulator compounds of the present invention display many of the benefits of RAR compounds in animals without the typical RAR retinoid-associated toxicities.

Further, when the modulator compounds of the present invention are combined with a corresponding modulator of the other heterodimeric partner, a surprising synergistic enhancement of the activation of the heterodimer pathway can occur. For example, with respect to a RXRα:PPARα heterodimer, the combination of a compound of the present invention with clofibric acid or gemfibrozil unexpectedly leads to a greater than additive (i.e. synergistic) activation of PPARα responsive genes, which in turn is useful to modulate serum cholesterol and triglyceride levels and other conditions associated with lipid metabolism.

Whether acting on an RXR heterodimer pathway, or the RXR homodimer pathway, it will also be understood by those skilled in the art that the dimer-selective RXR modulator compounds of the present invention will prove useful in any therapy in which agonists, partial agonists and/or full antagonists of such pathways will find application. Importantly, because the compounds of the present invention can differentially activate RXR homodimers and RXR heterodimers, their effects will be tissue and/or cell type specific, depending upon the cellular context of the different tissue types in a given patient. For example, compounds of the present invention will exert and RXR antagonists effect in tissues where RXR homodimers prevail, and partial agonist of full agonist activity on the PPAR pathway where RXRα:PPARα heterodimers prevail (e.g., in liver tissue). Thus, the compounds of the present invention will exert a differential effect in various tissues in an analogous fashion to the manner in which various classes of estrogens and antiestrogens (e.g., Estrogen, Tamoxifen, Raloxifen) exert differential effects in different tissue and/or cell types (e.g., bone, breast, uterus). See e.g., Maty T. Tzukerman et al., 8 Mol. Endo. 21–30 (1994); Donald P. McDonnell et al., 9 Mol. Endo. 659–669 (1995). However, in the present case, it is believed that the differential effects of the compounds of the present invention is based upon the particular dimer pair through which the compound acts, rather than through different transactivating regions of the estrogen receptor in the case of estrogens and antiestrogens.

The particular conditions that may be treated with the compounds of the present invention include, skin-related diseases, such as actinic keratoses, arsenic keratoses, inflammatory and non-inflammatory acne psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical antimicrobial, as skin pigmentation agents and to treat and reverse the effects of age and photo damage to the skin. With respect to the modulation of malignant and pre-malignant conditions, the compounds may also provide useful for the prevention and treatment of cancerous and pre-cancerous conditions, including, premalignant and malignant hyperproliferative diseases and cancers of epithelial origin such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposis sarcoma. In addition, the present compounds may be used as agents to treat and prevent various cardiovascular diseases, including, without limitation, diseases associated with lipid metabolism such as dyslipidemias, prevention of restenosis and as an agent to increase the level of circulating tissue plasminogen activator (TPA), metabolic diseases such as obesity and diabetes (i.e., non-insulin dependent diabetes mellitus and insulin dependent diabetes mellitus), the modulation of differentiation and proliferation disorders, as well as the prevention and treatment of neurodegenerative diseases such as Alzheimer's disease, Parkinson's disease and Amyotrophic Lateral Sclerosis (ALS), and in the modulation of apoptosis, including both the induction of apoptosis and inhibition of T-Cell activated apoptosis.

Furthermore, it will be understood by those skilled in the art that the compounds of the present invention, including pharmaceutical compositions and formulations containing these compounds, can be used in a wide variety of combination therapies to treat the conditions and diseases described above. Thus, the compounds of the present invention can be used in combination with modulators of the other heterodimeric partner with RXR (i.e., in combination with the PPARα modulators, such as fibrates, in the treatment of cardiovascular disease, and in combination with PPARγ modulators, such thiazolidinediones, in the treatment of diabetes, including non-insulin dependent diabetes mellitus and insulin dependent diabetes mellitus, and with agents used to treat obesity) and with other therapies, including, without limitation, chemotherapeutic agents such as cytostatic and cytotoxic agents, immunological modifiers such as interferons, interleukins, growth hormones and other cytokines, hormone therapies, surgery and radiation therapy. By utilizing the compounds of the present invention with modulators of the other heterodimeric partner one is able to utilize lower dosages of either or both modulators, thereby leading to a significant decrease is the side-effects associated with such modulators when employed alone at the strengths required to achieve the desired effect. Thus, the modulator compounds of the present invention, when utilized in combination therapies, provide an enhanced therapeutic index (i.e., significantly enhanced efficacy and/or decrease side-effect profiles) over utilization of the compounds by themselves.

Representative modulator compounds of the present invention include, without limitation, 4-[(3-n-propyl-5,6,7,8-tetrahydro-5,5,8,8-tetramethyl-2-naphthyl)carbonyl] benzoic acid (Compound 101); 4-[(3-n-propyl-5,6,7,8-tetrahydro-5,5,8,8-tetramethyl-2-naphthyl)ethenyl]benzoic acid (Compound 102); 4-[(3-n-propyl-5,6,7,8-tetrahydro-5,5,8,8-tetramethyl-2-naphthyl)cyclopropyl]benzoic acid (Compound 103); 4-[(3-n-propyl-5,6,7,8-tetrahydro-5,5,8,8-tetramethyl-2-naphthyl)carbonyl]benzoic acid oxime (Compound 104); 4-[(3,5,5,8,8-pentamethyl-5,6,7,8-tetrahydro-2-naphthyl)carbonyl]benzoic acid O-benzyloxime (Compound 105); 4-[(3,5,5,8,8-pentamethyl-5,6,7,8-tetrahydro-2-naphthyl)carbonyl] benzoic acid O-hexyloxime (Compound 106); 4-[(3-ethoxy-5,6,7,8-tetrahydro-5,5,8,8-tetramethyl-2-naphthyl)ethenyl] benzoic acid (Compound 107); 4-[(3-ethoxy-5,6,7,8-tetrahydro-5,5,8,8-tetramethyl-2-naphthyl) carbonyl] benzoic acid O-methyloxime (Compound 108); 4-[(3-propoxy-5,6,7,8-tetrahydro-5,5,8,8-tetramethyl-2-naphthyl) carbonyl]benzoic acid oxime (Compound 109); 4-[(3-propoxy-5,6,7,8-tetrahydro-5,5,8,8-tetramethyl-2-naphthyl) carbonyl]benzoic acid O-methyloxime (Compound 110); 4-[(3-butyloxy-5,6,7,8-tetrahydro-5,5,8,8-tetramethyl-2-naphthyl)carbonyl]benzoic acid (Compound 111); 4-[(3-butyloxy-5,6,7,8-tetrahydro-5,5,8,8-tetramethyl-2-naphthyl)ethenyl]benzoic acid (Compound 112); 4-[(3- butyloxy-5,6,7,8-tetrahydro-5,5,8,8-tetramethyl-2-naphthyl)carbonyl]benzoic acid O-methyloxime (Compound 113); 4-[(3-hexyloxy-5,6,7,8-tetrahydro-5,5,8,8-tetramethyl-2-naphthyl)carbonyl]benzoic acid oxime (Compound 114); 4-[(3-heptyloxy-5,6,7,8-tetrahydro-5,5,8,8-tetramethyl-2-naphthyl)carbonyl]benzoic acid oxime (Compound 115); 4-[(3-heptyloxy-5,6,7,8-tetrahydro-5,5,8,8-tetramethyl-2-naphthyl)ethenyl]benzoic acid (Compound 116); cis-4-[(3-benzyloxy-5,6,7,8-tetrahydro-5,5,8,8-tetramethyl-2-naphthyl)carbonyl]benzoic acid oxime (Compound 117); trans-4-[(3-benzyloxy-5,6,7,8-tetrahydro-5,5,8,8-tetramethyl-2-naphthyl)carbonyl]benzoic acid oxime (Compound 118); (2E, 4E, 6E)-7-[3-butyl-5,6,7,8-tetrahydro-5,5,8,8-tetramethyl-2-naphthalen-2-yl]-3-methylocta-2,4,6-trienoic acid (Compound 119); (2Z, 3E, 6E)-7-[3-(butyl)-5,6,7,8-tetrahydro-5,5,8,8-tetramethyl-2-naphthalen-2-yl]-3-methylocta-2,4,6-trienoic acid (Compound 120); (2E, 4E, 6E)-7-[3-propoxy-5,5,8,8-tetramethyl-5,6,7,8-tetrahydro-2-naphthalen-2-yl]-3-methylocta-2,4,6-trienoic acid (Compound 121); (2E, 4E, 6Z)-7-[3-propoxy-5,5,8,8-tetramethyl-5,6,7,8-tetrahydro-2-naphthalen-2-yl]-3-methylocta-2,4,6-trienoic acid (Compound 122); (2Z, 4E, 6E)-7-(3-ethoxy-5,6,7,8-tetrahydro-5,5,8,8-tetramethyl-2-naphthalen-2-yl)-3-methylocta-2,4,6-trienoic acid (Compound 123); (2E, 4E, 6Z)-7-[3-hexyloxy-5,6,7,8-tetrahydro-5,5,8,8-tetramethyl-2-naphthalen-2-yl]-3-methylocta-2,4,6-trienoic acid (Compound 124); (2E, 4E, 6E)-7-[3-hexyloxy-5,6,7,8-tetrahydro-5,5,8,8-tetramethyl-2-naphthalen-2-yl]-3-methylocta-2,4,6-trienoic acid (Compound 125); (2E, 4E, 6E)-7-[3-(3-methylbut-2-enyloxy)-5,6,7,8-tetrahydro-5,5,8,8-tetramethyl-2-naphthalen-2-yl]-3-methylocta-2,4,6-trienoic acid (Compound 126); (2E, 4E, 6E)-7-[3-benzyloxy-5,6,7,8-tetrahydro-5,5,8,8-tetramethyl-2-naphthalen-2-yl]-3-methylocta-2,4,6-trienoic acid (Compound 127); (2E, 4E, 6Z)-7-[3-benzyloxy-5,6,7,8-tetrahydro-5,5,8,8-tetramethyl-2-naphthalen-2-yl]-3-methylocta-2,4,6-trienoic acid (Compound 128); (2E, 4E, 6E)-7-[3-(4-methylbenzyloxy)-5,6,7,8-tetrahydro-5,5,8,8-tetramethyl-2-naphthalen-2-yl]-3-methylocta-2,4,6-trienoic acid (Compound 129); (2E, 4E, 6Z)-7-[3-(4-methylbenzyloxy)-5,6,7,8-tetrahydro-5,5,8,8-tetramethyl-2-naphthalen-2-yl]-3-methylocta-2,4,6-trienoic acid (Compound 130); 4-(3,4,5,6,7,8-hexahydro-5,5,8,8-tetramethyl-anthracen-1-ylmethyl)benzoic acid (Compound 131); 4-(5,6,7,8-tetrahydro-5,5,8,8-tetramethyl-3H-cyclopenta[b]naphthalen-1-ylmethyl)benzoic acid (Compound 132); 4-(6,7,8,9-tetrahydro-6,6,9,9-tetramethyl-2H-benzo[g]chromen-4-ylmethyl)benzoic acid (Compound 133); 4-(3,4,6,7,8,9-hexahydro-2-oxo-6,6,9,9-tetramethyl-2H-benzo[g]quinolin-1-ylmethyl)benzoic acid (Compound 134); 4-(3,4,6,7,8,9-hexahydro-6,6,9,9-tetramethyl-2H-benzo[g]quinolin-1-ylmethyl)benzoic acid (Compound 135); 4-(2,3,6,7,8,9-hexahydro-6,6,9,9-tetramethyl-naphtho[2,3-b][1,4]oxazin-4-ylmethyl)benzoic acid (Compound 136); 4-(3-hydroxy-5,6,7,8-tetrahydro-5,5,8,8-tetramethyl-anthracene-1-carbonyl)benzoic acid (Compound 137); 4-[(5,6,7,8-tetrahydro-5,5,8,8-tetramethyl-anthracen-1-yl)-hydroxymethyl]benzoic acid (Compound 138); 4-(5,6,7,8-tetrahydro-5,5,8,8-tetramethyl-anthracen-1-ylmethyl)benzoic acid (Compound 139); 4-[1-hydroxy-1-(5,6,7,8-tetrahydro-5,5,8,8-tetramethyl-anthracen-1-yl)ethyl]benzoic acid (Compound 140); 4-[1-methoxy-1-(5,6,7,8-tetrahydro-5,5,8,8-tetramethyl-anthracen-1-yl)ethyl]benzoic acid (Compound 141); 4-[1-(5,6,7,8-tetrahydro-5,5,8,8-tetramethyl-anthracen-1-yl)vinyl]benzoic acid (Compound 142); trans-4-(5,6,7,8-tetrahydro-5,5,8,8-tetramethyl-anthracene-1-carbonyl oxime)benzoic acid (Compound 143); cis-4-(5,6,7,8-tetrahydro-5,5,8,8-tetramethyl-anthracene-1-carbonyl oxime)benzoic acid (Compound 144); trans-4-(5,6,7,8-tetrahydro-5,5,8,8-tetramethyl-anthracene-1-carbonyl O-methyloxime)benzoic acid (Compound 145); (2E, 4E, 6E)-7-(3,5-diisopropyl-2-n-heptyloxyphenyl)-3-methylocta-2,4,6-trienoic acid (Compound 146); (2E, 4E, 6Z)-7-(3,5-diisopropyl-2-n-heptyloxyphenyl)-3-methylocta-2,4,6-trienoic acid (Compound 147); (2E, 4E)-7-(3,5-diisopropyl-2-n-heptyloxyphenyl)-3-methylocta-2,4-dienoic acid (Compound 148); (2Z, 4E)-7-(3,5-diisopropyl-2-n-heptyloxyphenyl)-3-methylocta-2,4-dienoic acid (Compound 149); (2E, 4E, 6E)-7-(3,5-diisopropyl-2-benzyloxyphenyl)-3-methylocta-2,4,6-trienoic acid (Compound 150); (2E, 4E, 6E)-7-(3,5-diisopropyl-2-n-butyloxyphenyl)-3-methylocta-2,4,6-trienoic acid (Compound 151); (2E, 4E)-6-[2-(5,5,8,8-tetramethyl-3-propyloxy-5,6,7,8-tetrahydronaphthalen-2-yl)cyclopropan-1-yl]-3-methyl hexadienoic acid (Compound 152); (2E, 4E)-6-[2-(5,5,8,8-tetramethyl-3-heptyloxy-5,6,7,8-tetrahydronaphthalen-2-yl)cyclopropan-1-yl]-3-methyl hexadienoic acid (Compound 153); (2E, 4E)-6-[2-(5,5,8,8-tetramethyl-3-benzyloxy-5,6,7,8-tetrahydronaphthalen-2-yl)cyclopropan-1-yl]-3-methyl hexadienoic acid (Compound 154); (2E, 4E)-7-[(5,5,8,8-tetramethyl-3-propyloxy-5,6,7,8-tetrahydronaphthalen-2-yl)cyclopropan-1-yl]-3-methyl heptadienoic acid (Compound 155); (2E, 4E)-7-[(5,5,8,8-tetramethyl-3-heptyloxy-5,6,7,8-tetrahydronaphthalen-2-yl)cyclopropan-1-yl]-3-methyl heptadienoic acid (Compound 156); (2E, 4E)-7-[(5,5,8,8-tetramethyl-3-benzyloxy-5,6,7,8-tetrahydronaphthalen-2-yl)cyclopropan-1-yl]-3-methyl heptadienoic acid (Compound 157); (2E, 4E)-5-[2-(5,5,8,8-tetramethyl-3-propyloxy-5,6,7,8-tetrahydronaphthalen-2yl)cyclopent-1-en-1-yl]-3-methyl pentadienoic cid (Compound 158); cis-(2E, 4E)-5-[2-(5,5,8,8-tetramethyl-3-propyloxy-5,6,7,8-tetrahydro-2-naphthyl)cyclopentan-1-yl]-3-methyl pentadienoic acid (Compound 159); 4-[(3-(4-t-butylbenzyloxy)-5,6,7,8-tetrahydro-5,5,8,8-tetramethyl-2-naphthyl)carbonyl]benzoic acid oxime (Compound 160); 4-[(3-(4-bromobenzyloxy)-5,6,7,8-tetrahydro-5,5,8,8-tetramethyl-2-naphthyl)carbonyl]benzoic acid oxime (Compound 161); cis-4-[(3-benzyloxy-5,6,7,8-tetrahydro-5,5,8,8-tetramethyl-2-naphthyl)carbonyl]benzoic acid O-methyloxime (Compound 162); trans-4-[(3-benzyloxy-5,6,7,8-tetrahydro-5,5,8,8-tetramethyl-2-naphthyl)carbonyl]benzoic acid O-methyloxime (Compound 163); 4-[2-(3-benzyloxy-5,6,7,8-tetrahydro-5,5,8,8-tetramethyl-2-naphthyl)-[1,3]dioxolan-2-yl]benzoic acid (Compound 164); 4-[2-methyl-1-(3-benzyloxy-5,6,7,8-tetrahydro-5,5,8,8-tetramethyl-2-naphthyl)propenyl]benzoic acid (Compound 165); (2E, 4E, 6E)-7-[3-(4-tert-butylbenzyloxy)-5,6,7,8-tetrahydro-5,5,8,8-tetramethyl-2-naphthalen-2-yl]-3-methyl-octa-2,4,6-trienoic acid. (Compound 166); (2E, 4E, 6Z)-7-[3-(4-tert-butylbenzyloxy)-5,6,7,8-tetrahydro-5,5,8,8-tetramethyl-2-naphthalen-2-yl]-3-methyl-octa-2,4,6-trienoic acid. (Compound 167); (2E, 4E, 6E)-7-[3-isobutyloxy-5,6,7,8-tetrahydro-5,5,8,8-tetramethyl-2-naphthalen-2-yl]-3-methyl-octa-2,4,6-trienoic acid. (Compound 168); (2E, 4E, 6Z)-7-[3-isobutyloxy-5,6,7,8-tetrahydro-5,5,8,8-tetramethyl-2-naphthalen-2-yl]-3-methyl-octa-2,4,6-trienoic acid. (Compound 169); (2E, 4E, 6E)-7-[3-pentyloxy-5,6,7,8-tetrahydro-5,5,8,8-tetramethyl-2-naphthalen-2-yl]-3-methyl-octa-2,4,6-trienoic acid. (Compound 170), (2E, 4E, 6Z)-7-[3-pentyloxy-5,6,7,8-tetrahydro-5,5,8,8-tetramethyl-2-naphthalen-2-yl]-3-methyl-octa-2,4,6-trienoic acid. (Compound 171); (2E, 4E, 6E)-7-[3-heptyloxy-5,6,7,8-tetrahydro-5,5,8,8-tetramethyl-2-naphthalen-2-yl]-3-methyl-octa-2,4,6-trienoic acid. (Compound 172); (2E, 4E, 6Z)-7-[3-heptyloxy-5,6,7,8-tetrahydro-5,5,8,8-tetramethyl-2-naphthalen-2-yl]-3-methyl-octa-2,4,6-trienoic acid. (Compound 173); (2E, 4E, 6E)-7-[3-(4-methoybenzyloxy)-5,6,7,8-tetrahydro-5,5,8,8- tetramethyl-2-naphthalen-2-yl]-3-methyl-octa-2,4,6-trienoic acid. (Compound 174) and (2E, 4E)-7-[3-propoxy-5,6,7,8-tetrahydro-5,5,8,8-tetramethyl-2-naphthalen-2-yl]-3-methyl-octa-2,4-dienoic acid. (Compound 175).

The compounds of the present invention can be obtained by modification of the compounds disclosed or by a total synthesis approach, by techniques known to those skilled in the art. In this regard, the synthesis of the dimer-specific RXR modulator compounds of the present invention follow established retinoid synthesis schemes and techniques as described in M. I. Dawson and W. H. Okamura, "Chemistry and Biology of Synthesis Retinoids", Chapters 3, 8, 14 and 16, CRC Press, Inc., Fla. (1990); M. I. Dawson and P. D. Hobbs, *The Synthetic Chemistry of Retinoids,* In chapter 2: "The Retinoids, Biology, Chemistry and Medicine", M. B. Sporn et al., Eds. (2nd en.), Raven Press, New York, N.Y., pp. 5–178 (1994); R. S. H. Liu and A. E. Asato, "Photochemistry and Synthesis of Stereoisomers of Vitamin A," 40 *Tetrahedron,* 1931 (1984), 43 *Cancer Res.,* 5268 (1983); 15 *Eur. J. Med. Chem.,* 9 (1980); M. Boehm et al., 37 *J. Med. Chem.,* 2930 (1994); M. Boehm et al., 38 *J. Med. Chem.,* 3146 (1995); E. Allegretto et al., 270 *Journal of Biol. Chem.,* 23906 (1995); R. Bissonette et al., 15 *Mol. & Cellular Bio.,* 5576 (1995); R Beard et al., 38 *J. Med. Chem.* 2820 (1995), S. Canan Koch et al., 39 *J. Med. Chem.,* 3229 (1996) and U.S. Pat. Nos. 4,326,055 and 4,578,498, the disclosures of which are herein incorporated by reference. The sequence of steps of the general schemes of synthesizing the compounds of the present invention are shown below. In addition, more detailed and illustrative synthetic schemes for specific compounds of the present invention will be found in the Examples included herein.

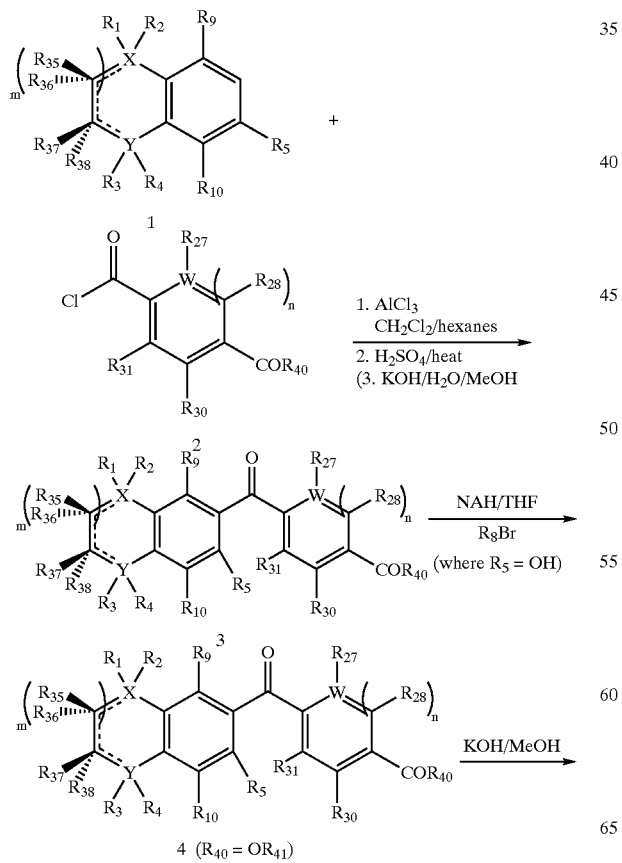

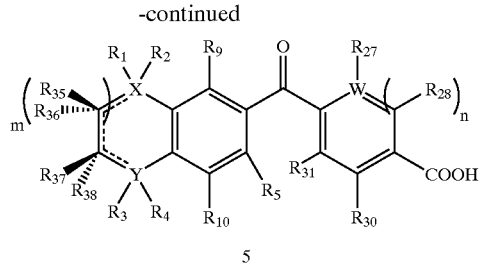

In Scheme 1, the compound 3, a common precursor to the compounds of the present invention, 5–12, may be prepared by Friedel-Crafts acylation of an appropriately substituted tetrahydrotetramethylnaphthalene 1 with an acid chloride 2, such as monomethyl teraphthalate acid chloride, under Lewis acid (such as aluminum trichloride) and/or protic acid (such as $H_2SO_4$) catalyzed conditions in solvents such as dichloromethane or dichloroethane. In cases such that the naphthalene has a hydroxy functionality, an O-alkylation of the naphthol may be achieved by treatment with a base, such as NaH or $K_2CO_3$, and an alkyl halide to provide the keto ether 4. The acid 5 is readily obtainable from the corresponding ester by hydrolysis in an alkanol solvent at ambient temperature with about a three molar excess of base, for example, potassium hydroxide. Alternatively, the ester 4 may be hydrolyzed in THF/water or acetone/water at ambient temperature with, for example, excess lithium hydroxide. The hydrolysis solution is acidified and the hydrolysate recovered by conventional means to provide the keto acid 5.

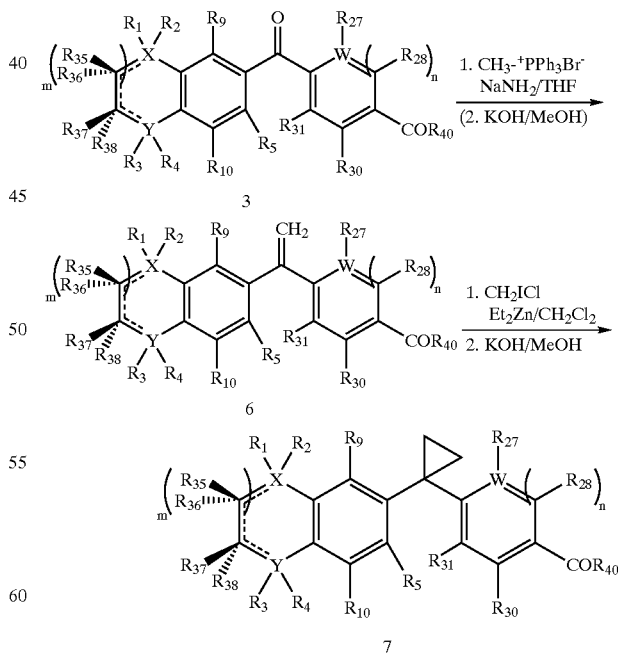

In accordance with reaction Scheme 2, treatment of the ketone 3 with a phosphonium ylide, such as methyl triphenylphosphonium bromide-sodium amide in solvents such as THF or ether at room temperature or at elevated temperatures affords the ethenyl compound 6 where $R_{38}$ is $OCH_3$. Hydrolysis to afford the olefin acid is conducted in the same fashion as described in Scheme 1 above. The cyclopropyl derivatives such as 7 can be prepared in a Simmons-Smith reaction as shown in Scheme 2 by treatment of the ethenyl compound 6 ($R38=OCH_3$) with $CH_2ClI$, $Et_2Zn$, and CuCl in solvents such as dichloromethane at reflux temperature, followed by the same standard hydrolysis processes as employed in the preparation process of Scheme 1.

In accordance with reaction Scheme 3, the ketone 3 may also be treated with hydroxylamine hydrochloride in ethanol and pyridine and heated at reflux to afford, after standard hydrolysis, the oxime acid 8. Other O-substituted oximes may also be prepared as shown in Scheme 3. These compounds are synthesized from the corresponding free oxime 8 by treatment of the oxime with a base, such as sodium hydride, in solvents such as THF or ether or DMF at ambient temperature, followed by alkylation with the appropriate alkylhalide (R-Br or R-I), and standard hydrolysis by the same processes as employed in the preparation process of Scheme 1 to provide the O-alkylated oxime 9.

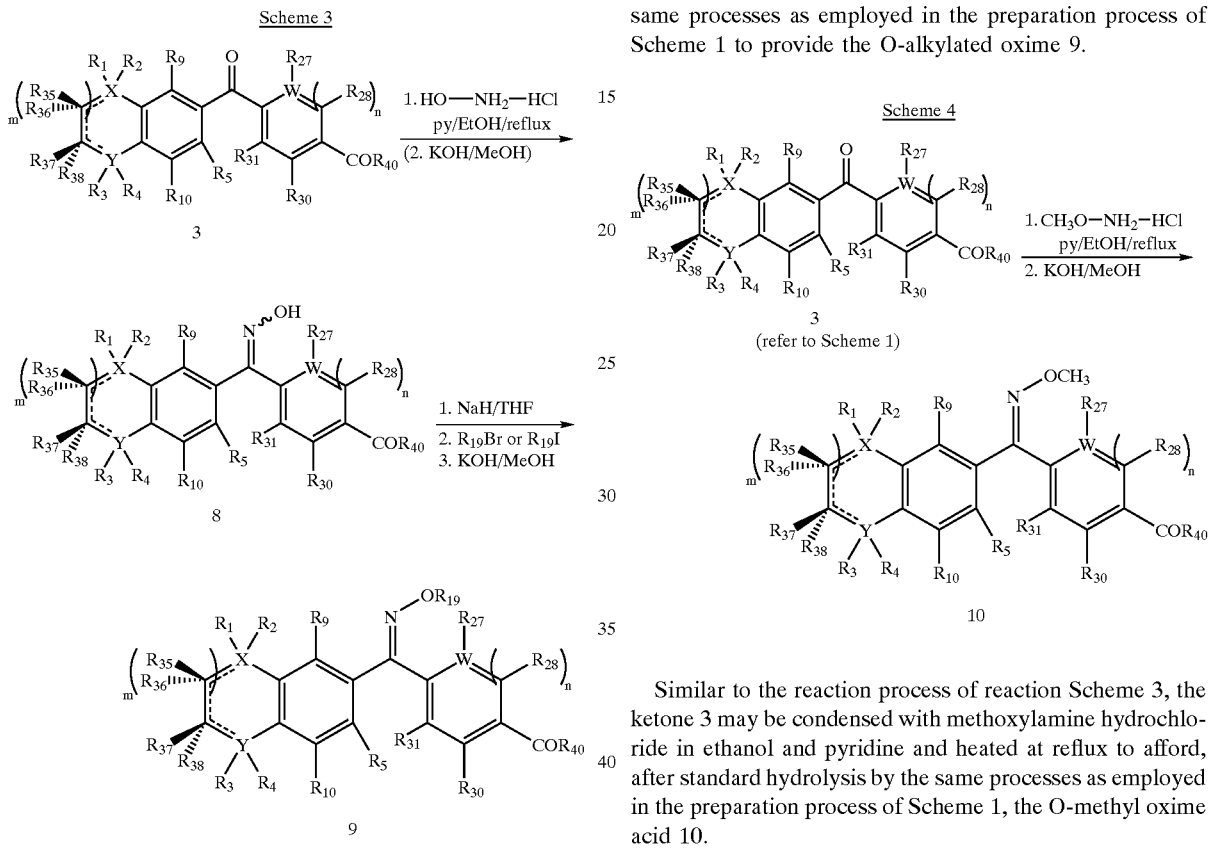

Similar to the reaction process of reaction Scheme 3, the ketone 3 may be condensed with methoxylamine hydrochloride in ethanol and pyridine and heated at reflux to afford, after standard hydrolysis by the same processes as employed in the preparation process of Scheme 1, the O-methyl oxime acid 10.

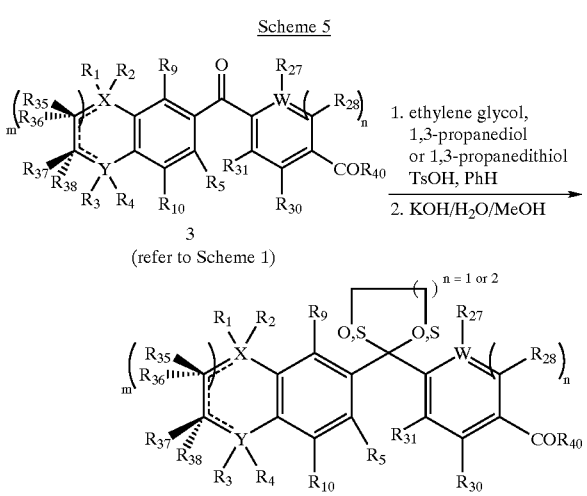

In accordance with reaction Scheme 5, ketal and dithioketal derivatives such as compound 11 can be obtained by condensation of the ketone 3 with ethylene glycol, 1,3-propanediol, or 1,3-propanedithiol in solvents such as benzene and acid catalysis with acids such as p-toluenesulfonic acid, followed by standard hydrolysis by the same processes as employed in the preparation process of Scheme 1, to afford the ketal or dithioketal 11.

Scheme 6

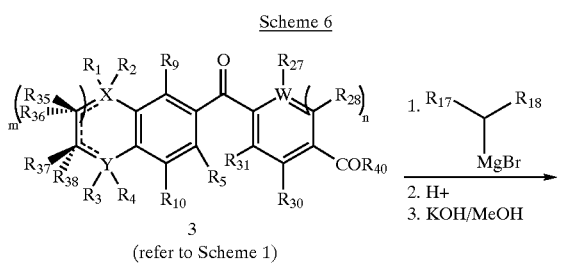

3
(refer to Scheme 1)

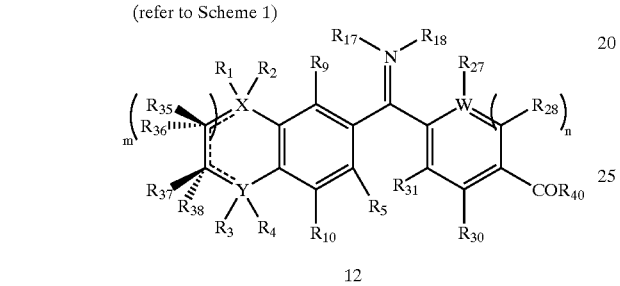

12

In accordance with reaction Scheme 6, other substituted olefin derivatives such as compound 12 may be derived by Grignard addition of alkyl magnesium halides, such as isopropyl magnesium bromide, with ketone 3, followed by dehydration with acid catalysis, such as p-toluenesulfonic acid or sulfuric acid, and standard hydrolysis by the same processes as employed in the preparation process of Scheme 1 to afford the olefin analogues 12.

Scheme 7

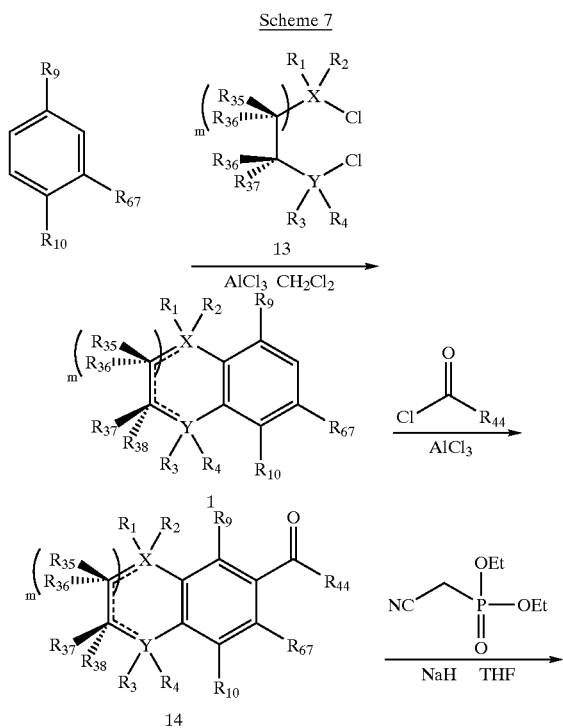

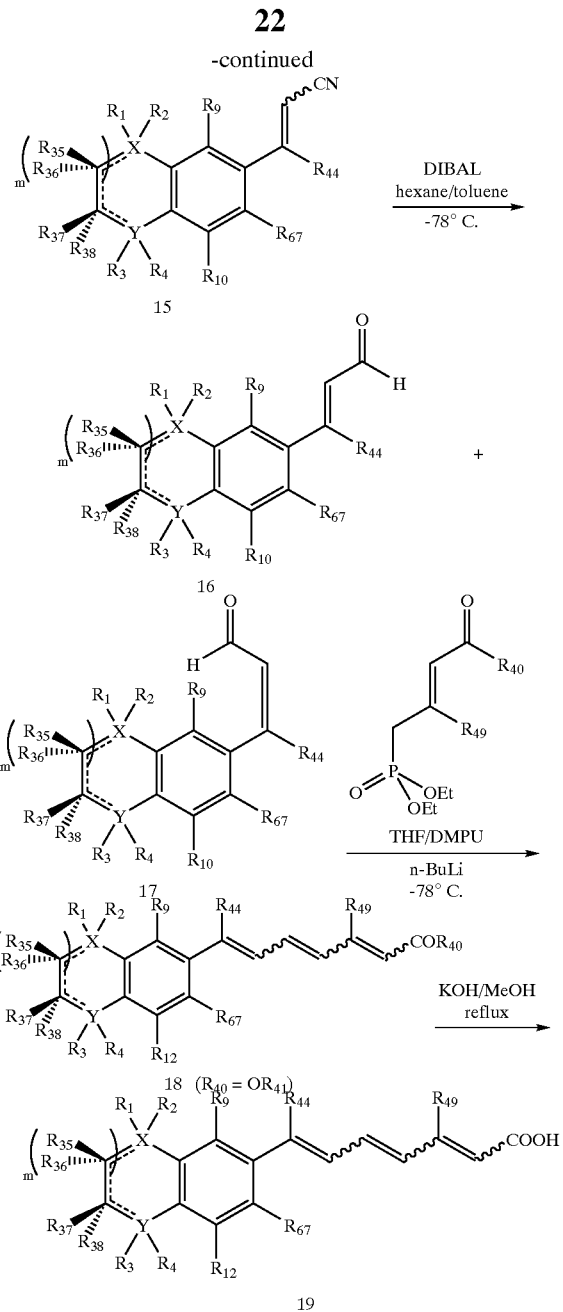

The bicyclic derivatives of the present invention, that is compounds of general structures 19, may be prepared in accordance with reaction Scheme 7. The starting materials for this sequence, substituted tetrahydrotetramethylnaphthalenes of general structure 1, may be prepared by Friedel-Crafts alkylation/cyclization of an appropriately substituted benzene with a dichloroalkane 13, such as 2,5-dimethyl-2,5-dichlorohexane, under Lewis acid catalyzed conditions in solvents such as dichloromethane or dichloroethane. Treatment of 1 with an acid chloride, such as acetyl chloride, and a Lewis acid, such as aluminum trichloride, provides the acylated naphthalene 14. In cases such that the naphthalene has a hydroxy functionality, an O-alkylation of the naphthol may be achieved by treatment with a base, such as KOH, and an alkyl halide to provide the keto ether 14 (where $R_{47}=OR_{50}$). Further, in accordance with this sequence of reactions aryl ketones of general structure 14 are condensed with a phosphonate, such as the sodium or lithium salt of diethyl cyanomethylphosphonate, in THF at ambient or reduced temperatures in a Horner-Wadsworth-Emmons olefination reaction to provide cyano olefin 15. The cyano olefin 15 is reduced with DIBAL at −78° C. to provide the intermediate enals 16 and 17. The solvent to be used in the reduction includes methylene chloride, hexanes, and THF. The trans and cis isomers 16 and 17 may be separated at this stage via thin-layer chromatography (TLC), or other recognized procedures known to those skilled in the art. These separated aldehydes 16 and 17 are then treated with a phosphonate, such as the lithium salt of diethyl 3-ethoxycarbonyl-2-methylprop-2-enylphosphonate (mixture of double bond isomers), in THF at reduced temperatures in a Horner-Wadsworth-Emmons olefination reaction to provide the trienoate esters 18 where $R_{38}$ is OEt. The olefination reaction is preferably conducted in the presence of 1,3-dimethyl-3,4,5,6-tetrahydro-2(1H)-pyrimidinone (DMPU). The acids and salts 19 are readily obtainable from the corresponding esters by hydrolysis in an alkanol solvent at ambient temperature with about a three molar excess of base, for example, potassium hydroxide. Alternatively, the ethyl esters may be hydrolyzed in THF/water or acetone/water at ambient temperature with, for example, excess lithium hydroxide. The hydrolysis solution is acidified and the hydrolysate recovered by conventional means to give as the major product the (2E, 4E, 6E)-bicyclic triene carboxylic acid derivatives of structure 19 where $R_{38}$ is OH. The minor (2E, 4E, 6Z)-bicyclic triene and (2Z, 4E, 6E)-bicyclic triene geometric isomers, by-products of the olefination reaction, are readily isolated by silica gel chromatography or HPLC purification of the hydrolysate mixture.

An alternative means for making the (2E, 4E, 6Z)-bicyclic triene derivatives of general structure 23 is in accordance with reaction Scheme 8. The aryl ketone 14 is treated with phosphorous oxychloride in solvents such as DMF and the intermediate chloroenal is treated with a strong base, such as sodium hydroxide, to provide the aryl alkyne 20. The aryl alkyne is then treated with a suitable nitrile source, such as PhOCN, in the presence of a base, such as ethylmagnesium bromide, to give alkyne nitrile 21, which is then subjected to reductive methylation to provide as the major product the cis isomer, nitrile 22. Nitrile 22 is then reduced to the corresponding aldehyde 17 and homologated in the same fashion as described in Scheme 7 to yield the (2E, 4E, 6Z)-bicyclic triene 23.

Scheme 9

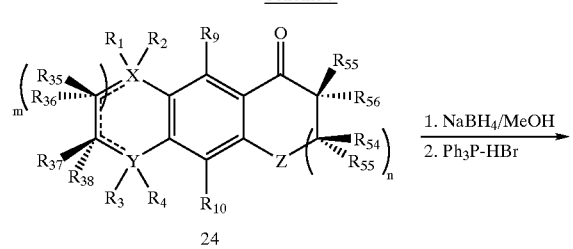

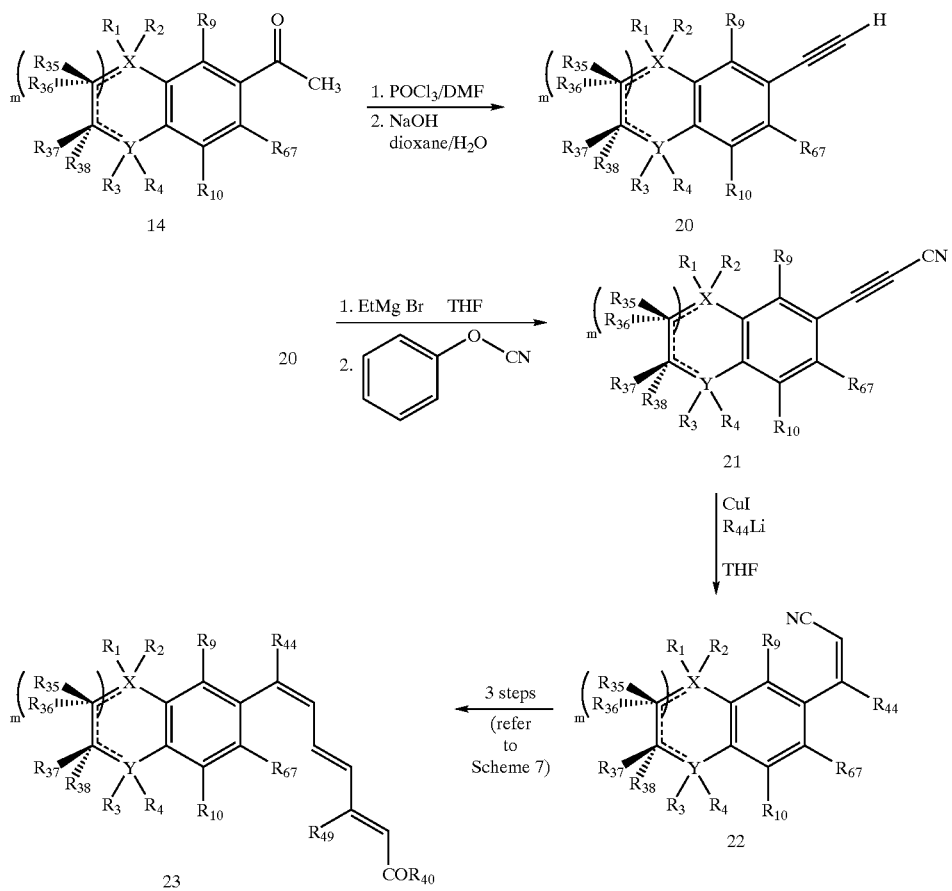

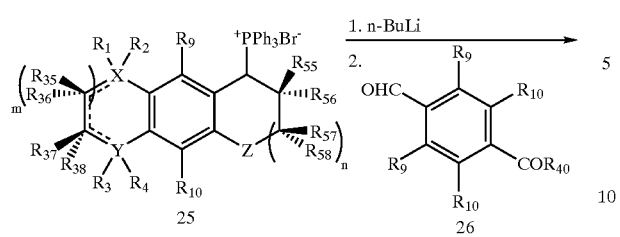

25

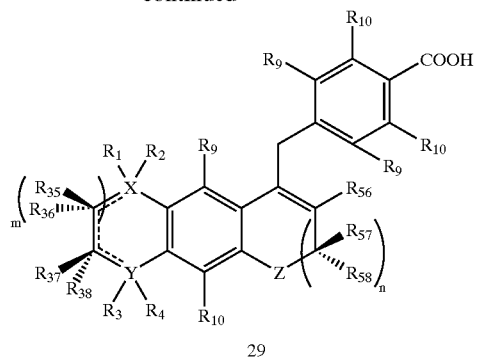

26

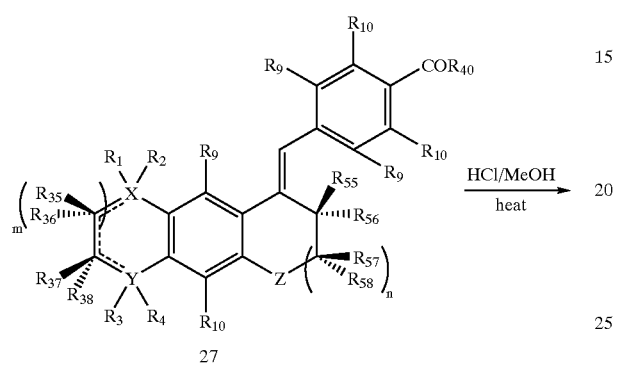

27

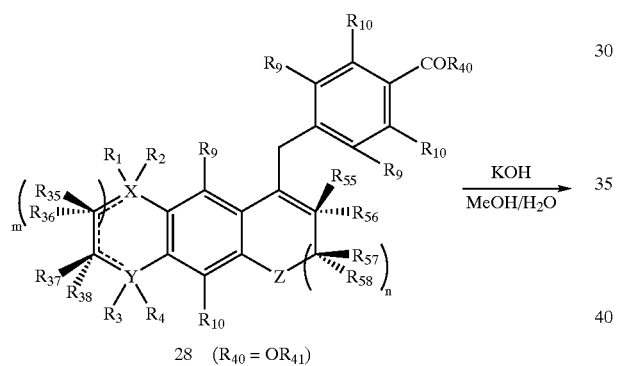

28 (R$_{40}$ = OR$_{41}$)

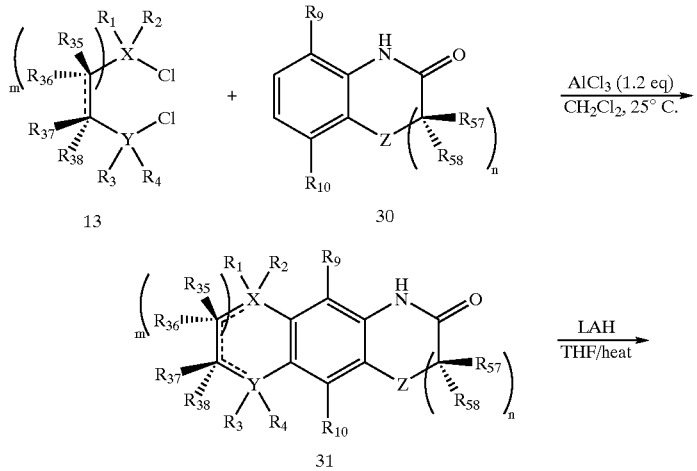

29

The tricyclic derivatives of the present invention, that is compounds of general structure 29, may be prepared in accordance with reaction Scheme 9. The starting materials for this sequence, ketones of general structure 24, may be prepared from the appropriately substituted octahydroanthracene by oxidation with chromium trioxide in acetic acid at ambient temperature or with chromium trioxide in methylene chloride/pyridine at 0° C. The tricyclic ketones are reduced with sodium borohydride in methanol at low temperature and the resultant benzylic alcohols are reacted with triphenylphosphine hydrobromide in methanol at elevated temperature to provide phosphonium salts of general structure 25. Compounds of general structure 27 may be prepared from the lithium salt of the phosphonium bromide of general structure 25 and aldehyde of general structure 26 by a Horner-Wadsworth-Emmons olefination reaction in THF at reduced temperatures. The olefination reaction is preferably conducted in the presence of 1,3-dimethyl-3,4,5,6-tetrahydro-2(1H)-pyrimidinone (DMPU). The exocyclic olefin product 27 may be isomerized to the endocyclic olefin analogue of general structure 28 by treatment with methanolic HCl at elevated temperatures. The acids and salts 29 are readily obtainable from the corresponding esters by hydrolysis in an alkanol solvent at ambient temperature with about a three molar excess of base, for example, potassium hydroxide. Alternatively, the ethyl esters may be hydrolyzed in THF/water or acetone/water at ambient temperature with, for example, excess lithium hydroxide. The hydrolysis solution is acidified and the hydrolysate recovered by conventional means to give the tricyclic carboxylic acid derivatives of structure 29.

Scheme 10

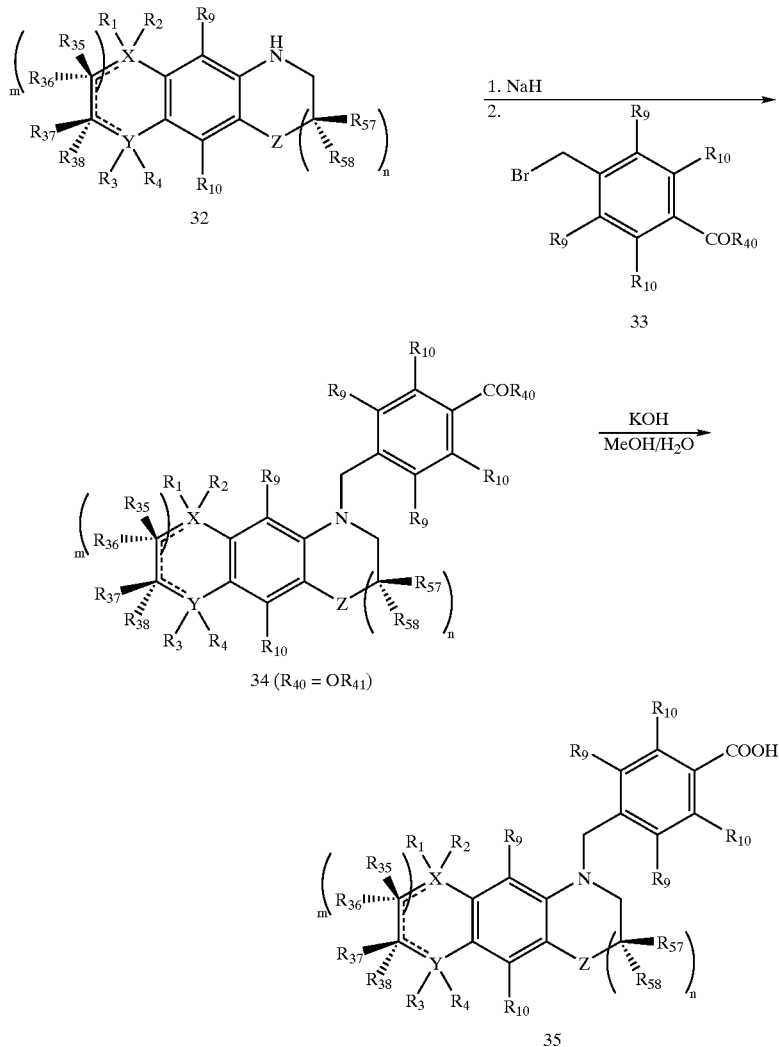

34 (R₄₀ = OR₄₁)

35

The tricyclic derivatives of general structure 35 can be prepared in accordance with reaction Scheme 10. The tricyclic amides 31 can be prepared from quinolone of general structure 30 and 2,5-dichloro-2,5-dialkylhexanes of general structure 13 by aluminum trichloride catalyzed Friedel-Crafts alkylation/cyclization in dichloromethane at ambient temperature. Amides of general structure 31 can be reduced with agents such as LAH or DIBAL in solvents such as THF or methylene chloride at 25° C. to provide the corresponding amines 32. The amines of general structure 32 are deprotonated with NaH at reduced temperatures in THF and alkylated at ambient temperature with alkyl or benzylhalides, such as methyl bromomethylbenzoate 33, to give substituted amines of general structure 34. The acids and salts derived from general structure 34 are readily obtainable from the corresponding esters by the same processes as those employed in the preparation process of Scheme 9 to give the acid analogues 35.

Scheme 11

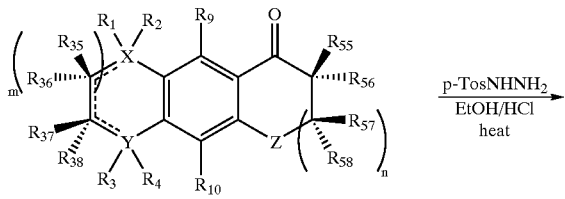

24

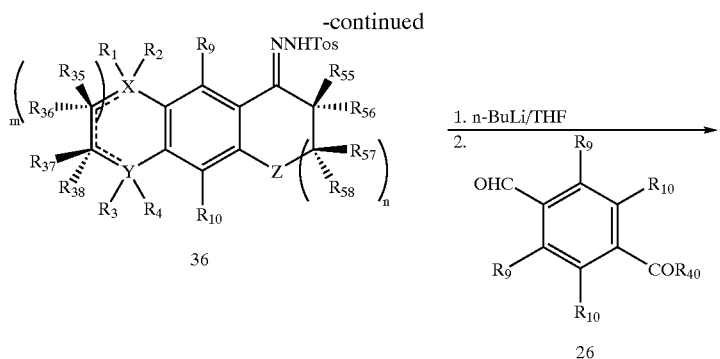

36

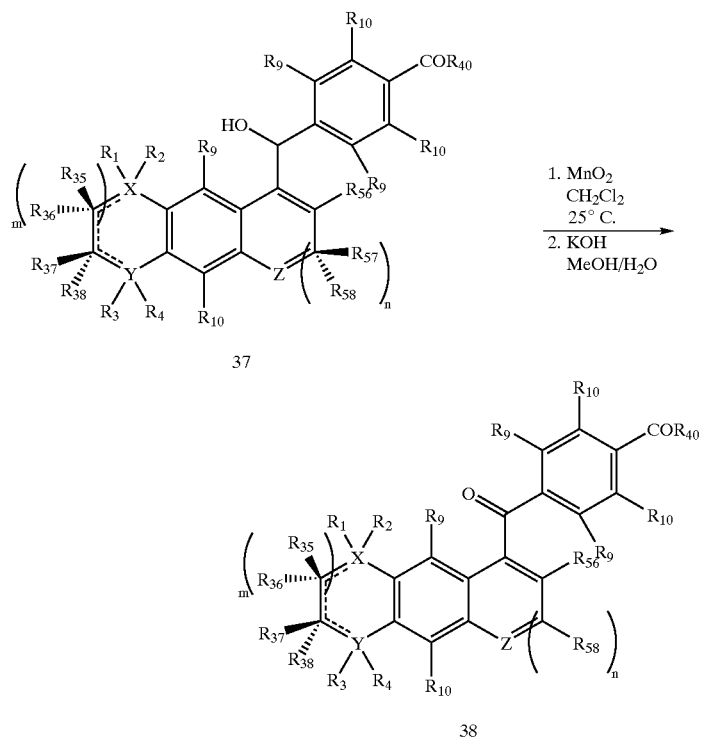

37

38

The tricyclic derivatives of general structure 37 and 38 can be prepared in accordance with reaction Scheme 11. The tricyclic ketone 24 (from Scheme 9) can be condensed with p-toluenesulfonhydrazide in alcoholic solvents, such as ethanol or methanol, with catalysis by acids such as hydrochloric acid or sulfuric acid at elevated temperatures to provide the hydrazones of general structure 36. The hydrazones can undergo a Shapiro-type reaction in the presence of two equivalents of a strong base, such as n-butyl lithium, in solvents such as THF or ether at reduced temperatures, and the vinyl anion thus generated can be reacted with carbonyl compounds, such as 4-formyl benzoates 26, to provide the anthracenylhydroxymethyl benzoic acid derivatives of general structure 37. The hydroxy functionality in compound 37 can be oxidized by agents such as manganese dioxide in dichloromethane to provide the keto derivatives of general structure 38. The acids and salts 37 and 38 are readily obtainable from the corresponding esters by hydrolysis in an alkanol solvent at ambient temperature with about a three molar excess of base, for example, potassium hydroxide. Alternatively, the ethyl esters may be hydrolyzed in THF/water or acetone/water at ambient temperature with, for example, excess lithium hydroxide. The hydrolysis solution is acidified and the hydrolysate recovered by conventional means to give as the major product the tricyclic-carbonyl benzoic acid derivatives of general structure 37 and 38 where $R_{38}$ is OH.

Scheme 12

38
(refer to Scheme 11)

1. $NaBH_4$/MeOH
(2. KOH/MeOH/$H_2O$)

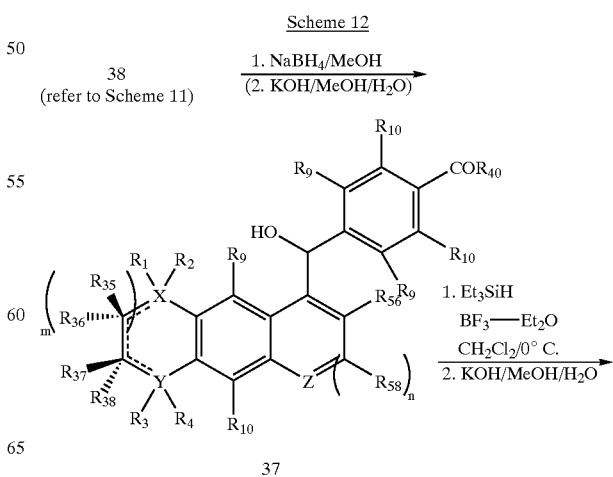

37

1. $Et_3SiH$
   $BF_3$—$Et_2O$
   $CH_2Cl_2$/0° C.
2. KOH/MeOH/$H_2O$

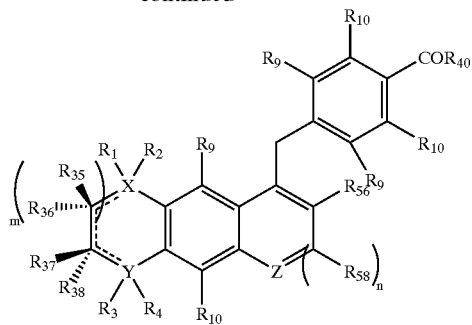

39

Additional tricyclic derivatives of general structure 39 can be prepared in accordance with reaction Scheme 12. The tricyclic-carbonyl derivatives 38 (from Scheme 11) can be reduced to the hydroxy functionalized derivatives of general structure 37 with agents such as sodium borohydride in alcoholic solvents such as methanol, and further reduced to the methylene derivatives of general structure 39 with agents such as triethylsilane and boron triflouride-etherate in dichloromethane at reduced temperatures. The acids and salts 39 are readily obtainable from the corresponding esters by the same processes as those employed in the preparation process of Scheme 9 to give the acid analogues of general structure 39 where $R_{38}$ is OH.

Other substituted tricyclic derivatives of general structures 40–42 can be prepared in accordance with reaction Scheme 13. Addition of trimethylaluminum to the keto compound 38 and treatment of the intermediate tertiary alcohol 40 with acids such as hydrochloric acid in solvents such as methanol or ethanol at elevated temperatures provides the alkoxy substituted and methylene-linked tricyclic derivatives of general structures 41 and 42. The acids and salts are readily obtainable from the corresponding esters by hydrolysis following the standard conditions outlined in Scheme 9 to give the acid analogues where $R_{38}$ is OH.

Scheme 14

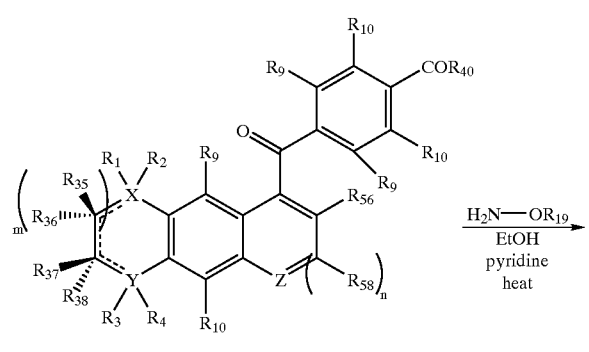

P
(refer to Scheme 11)

Scheme 13

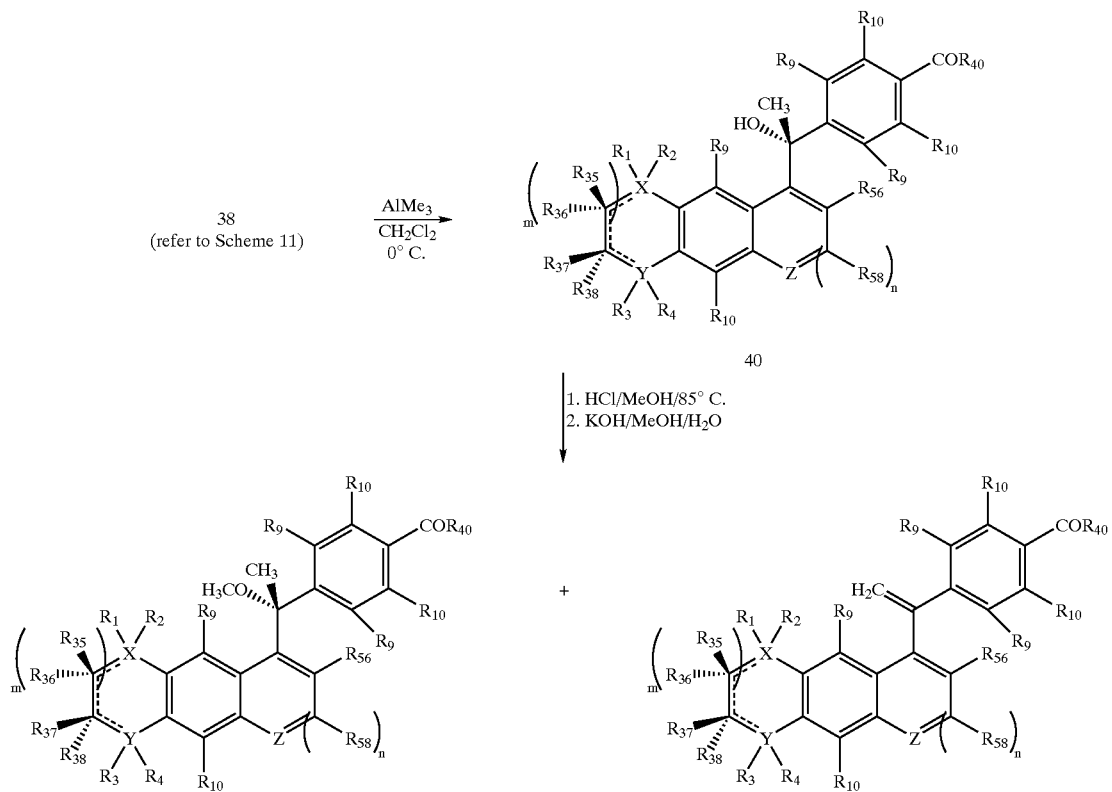

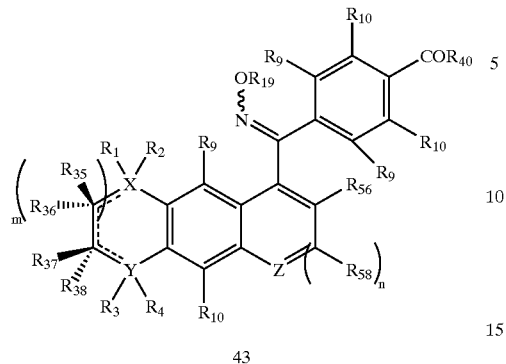

43

The keto tricyclic derivatives of general structure 38 may also be treated with hydroxylamine hydrochloride or alkoxyamines in alcoholic solvents, such as ethanol, with pyridine and heated at reflux to afford the oxime acids of general structure 43 in accordance with reaction Scheme 14. Other O-substituted oximes may also be synthesized from the corresponding free oxime 43 (where $R_{19}$ is H) by treatment of the oxime with a base, such as sodium hydride, in solvents such as THF or ether or DMF at ambient temperature, followed by alkylation with the appropriate alkylhalide or arylalkylhalide (R-Br or R-I). The acids and salts are readily obtainable from the corresponding esters by hydrolysis following the standard conditions provided in Scheme 9 to give the acid analogues where $R_{38}$ is OH.

Scheme 15

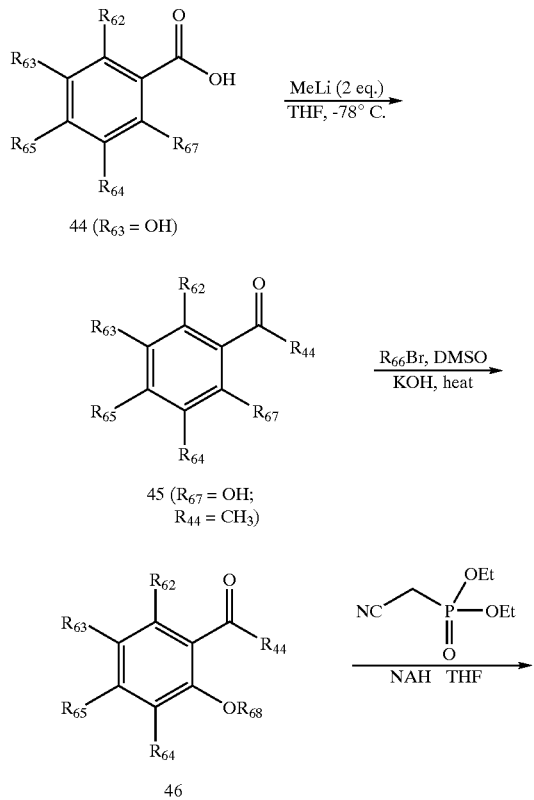

44 ($R_{63}$ = OH)

45 ($R_{67}$ = OH; $R_{44}$ = $CH_3$)

46

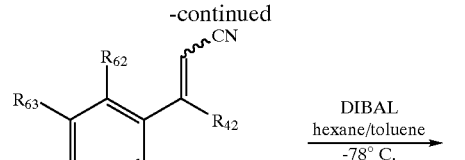

47

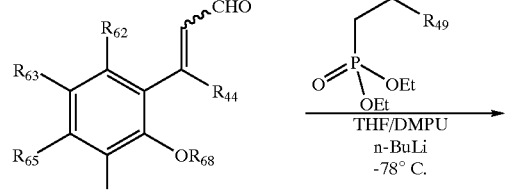

48

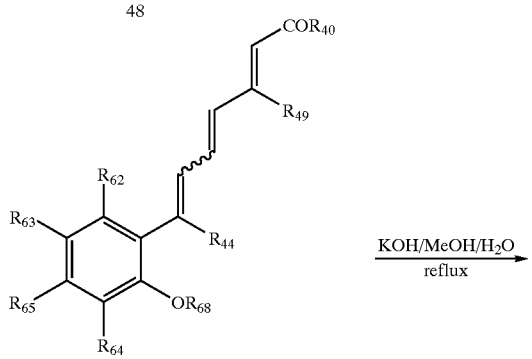

49 ($R_{40}$ = $OR_{41}$)

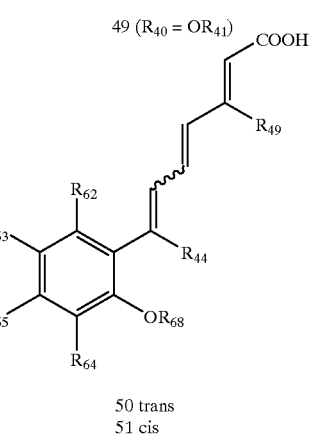

50 trans
51 cis

The aromatic trienes of the present invention, that is compounds of general structures 50 and 51, may be prepared in accordance with reaction Scheme 15. The starting materials for this sequence, substituted benzoic acids of general structure 44, may be treated with alkyl lithiums, such as methyllithium, at low temperatures in solvents such as THF or ether to produce alkyl aryl ketones of general structure 45. In cases where the aryl group contains a hydroxy functionality, the phenol may be alkylated by treatment with a base, such as KOH, and an alkyl or benzyl halide in a solvent such as DMSO to provide the keto ether 46. Further, in accordance with this sequence of reactions aryl ketones of general structure 46 are condensed with a phosphonate, such as the sodium or lithium salt of diethyl cyanomethylphosphonate, in THF at ambient or reduced temperatures in a Horner-Wadsworth-Emmons olefination reaction to provide cyano olefin 47. The cyano olefin 47 is reduced with DIBAL at −78° C. to provide the intermediate enal 48. The solvent to be used in the reduction includes methylene chloride, hexanes, and THF. The trans and cis isomers may be separated at this stage via thin-layer chromatography (TLC), or other recognized procedures known to those skilled in the art. The aldehyde intermediate is then treated with a phosphonate, such as the lithium salt of diethyl 3-ethoxycarbonyl-2-methylprop-2-enylphosphonate (mixture of double bond isomers) in THF at reduced temperatures in a Horner-Wadsworth-Emmons olefination reaction to provide the trienoate esters 49 where $R_{38}$ is $OR_{39}$. The olefination reaction is preferably conducted in the presence of 1,3-dimethyl-3,4,5,6-tetrahydro-2(1H)-pyrimidinone (DMPU). The acids and salts 50 and 51 are readily obtainable from the corresponding esters by hydrolysis in an alkanol solvent at ambient temperature with about a three molar excess of base, for example, potassium hydroxide. Alternatively, the ethyl esters may be hydrolyzed in THF/water or acetone/water at ambient temperature with, for example, excess lithium hydroxide. The hydrolysis solution is acidified and the hydrolysate recovered by conventional means to give as the major product the (2E, 4E, 6E)-aromatic triene carboxylic acid derivatives of structure 50. The minor (2E, 4E, 6Z)-aromatic triene geometric isomer, 51, a by-product of the first olefination reaction, is readily isolated by silica gel chromatography or HPLC purification of the hydrolysate mixture.

Scheme 16

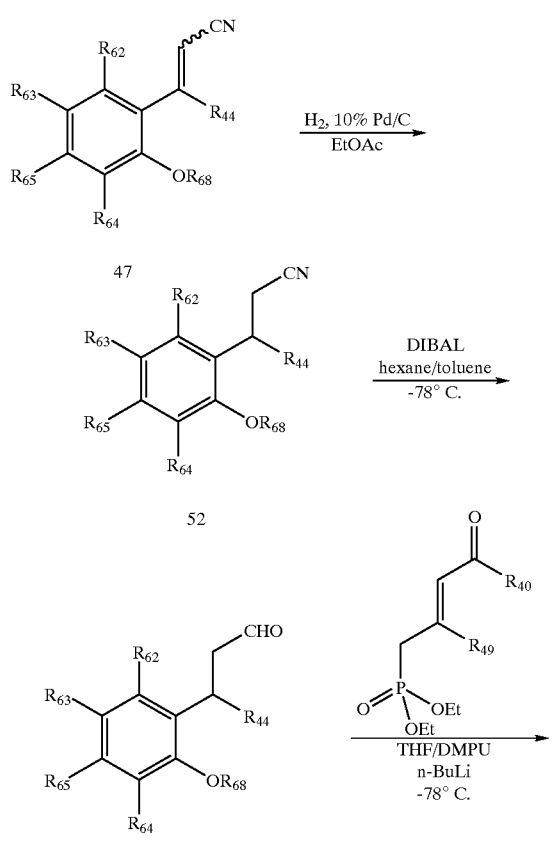

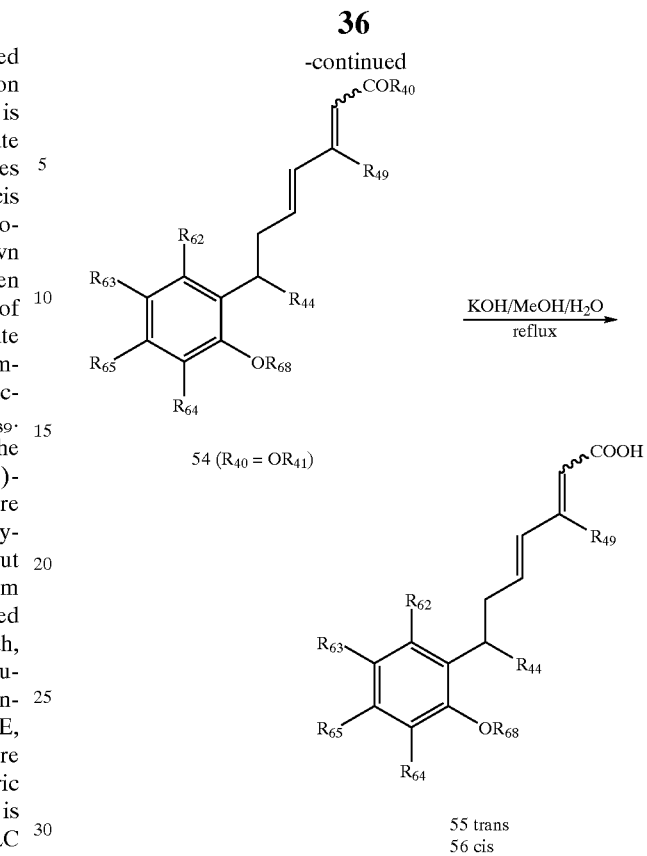

54 ($R_{40} = OR_{41}$)

55 trans
56 cis

In accordance with reaction Scheme 16, reduction of the intermediate cyano olefin 47 under an atmosphere of hydrogen gas and in the presence of a catalyst, such as 10% palladium on carbon, provides the saturated nitrile 52. The nitrile can be reduced in the same fashion as described in reaction Scheme 15 to yield the saturated aldehyde intermediate 53. The aldehyde 53 is then homologated in the same fashion as described in Scheme 15 to yield as the major product the (2E, 4E)-aromatic diene of general structure 55 and as the minor geometric isomer, the (2Z, 4E)-aromatic diene of general structure 56.

Scheme 17

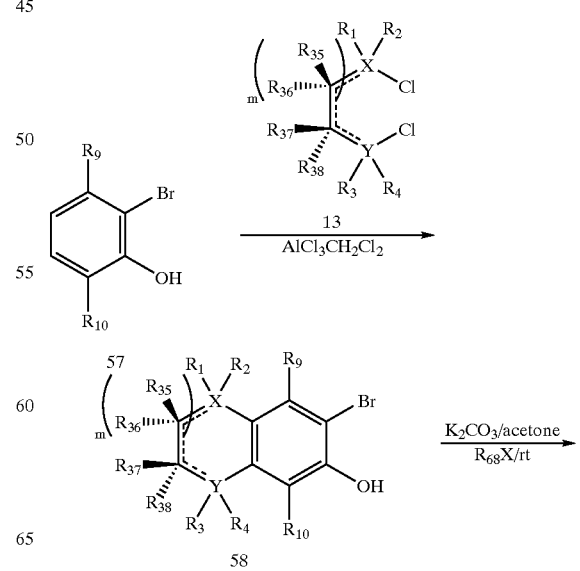

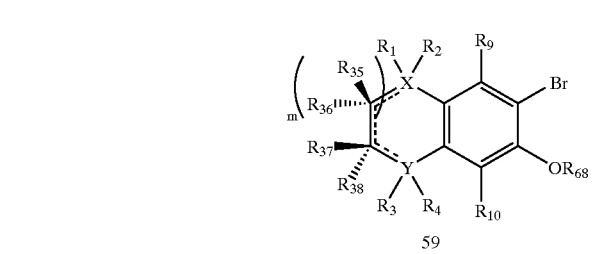

59

1) n-BuLi/THF
   -78° C.
59  ────────────────→
    2) (MeO)₃B
    3) HCl

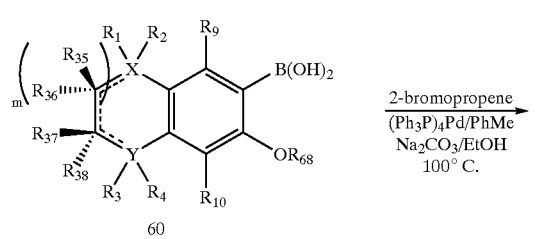

60

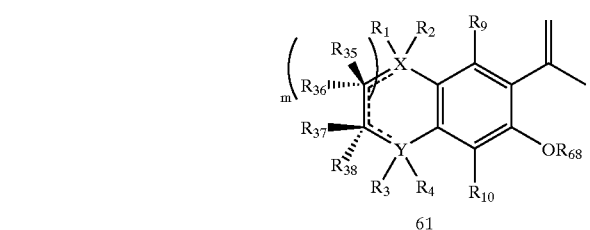

61

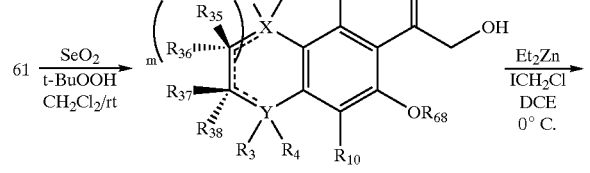

62

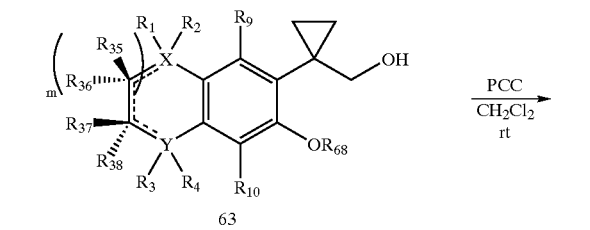

63

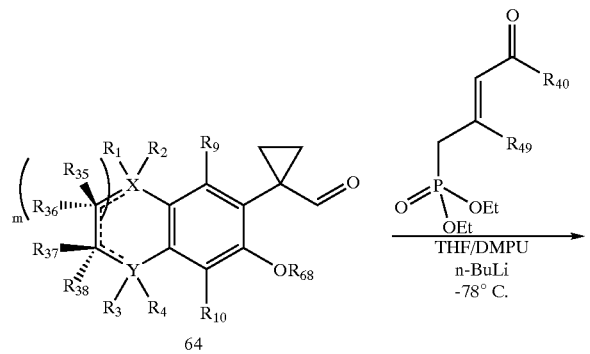

64

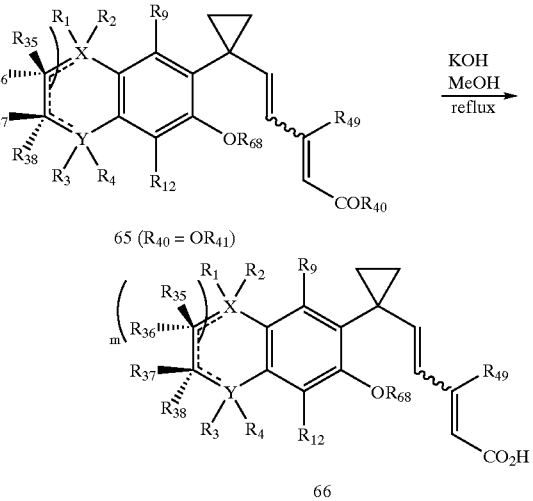

65 (R₄₀ = OR₄₁)

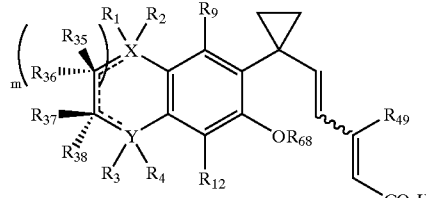

66

The bicyclic derivatives of the present invention, that is compounds of general structures 66, may be prepared in accordance with Scheme 17. The starting materials for this sequence, substituted tetrahydrotetramethylnaphthalenes of general structure 58, may be prepared by Friedel-Crafts alkylation/cyclization of an appropriately substituted benzene with a dichloroalkane 13, such as 2,5-dimethyl-2,5-dichlorohexane, under Lewis acid catalyzed conditions in solvents such as dichloromethane or dichloroethane. Treatment of 58 with potassium carbonate and an alkyl halide, such as iodopropane, in refluxing acetone provides the ether 59. Halogen-metal exchange of the bromonaphthol 59 with a base, such as n-BuLi, followed by treatment with trimethyl borate and acidification with aqueous 10% hydrochloric acid provides the boronic acid precursor 60. The dienoic acid side chain precursor was introduced by the Suzuki coupling of boronic acid 60 with 2-bromo-1-propene in the presence of tetrakis triphenylphosphine palladium (0) and a base, such as sodium carbonate, in toluene at 100° C. to provide compound 61. Allylic oxidation with catalytic selenium dioxide and t-butyl hydroperoxide in dichloromethane at room temperature, known as the Sharpless conditions, provides allylic alcohol 62. Cyclopropanation of allylic alcohol 62 with reagents such as diethyl zinc and chloroiodomethane in dichloroethane provides the cyclopropane compound 63. Oxidation of alcohol 63 with a reagent such as PCC in dichloromethane, provides aldehyde 64. This aldehyde 64 can be treated with a phosphonate, such as the lithium salt of diethyl 3-ethoxycarbonyl-2-methylprop-2-enylphosphonate (mixture of double bond isomers) in THF at reduced temperatures in a Horner-Wadsworth-Emmons olefination reaction to provide the dienoate esters 65 where R₃₈ is OEt. The olefination reaction is preferably conducted in the presence of 1,3-dimethyl-3,4,5,6-tetrahydro-2(1H)-pyrimidinone (DMPU). The acids and salts 66 are readily obtainable from the corresponding esters by hydrolysis in an alkanol solvent at ambient temperature with about a three molar excess of base, for example, potassium hydroxide. Alternatively, the ethyl esters may be hydrolyzed in THF/water or acetone/water at ambient temperature with, for example, excess lithium hydroxide. The hydrolysis solution is acidified and the hydrolysate recovered by conventional means to give as the major product the (2E, 4E)-bicyclic diene carboxylic acid derivatives of structure 66 where R₃₈ is OH. The minor (2E, 4Z)-bicyclic diene and (2Z, 4E)-bicyclic diene geometric isomers, by-products of the olefination reaction, are readily isolated by silica gel chromatography or HPLC purification of the hydrolysate mixture.

Scheme 18

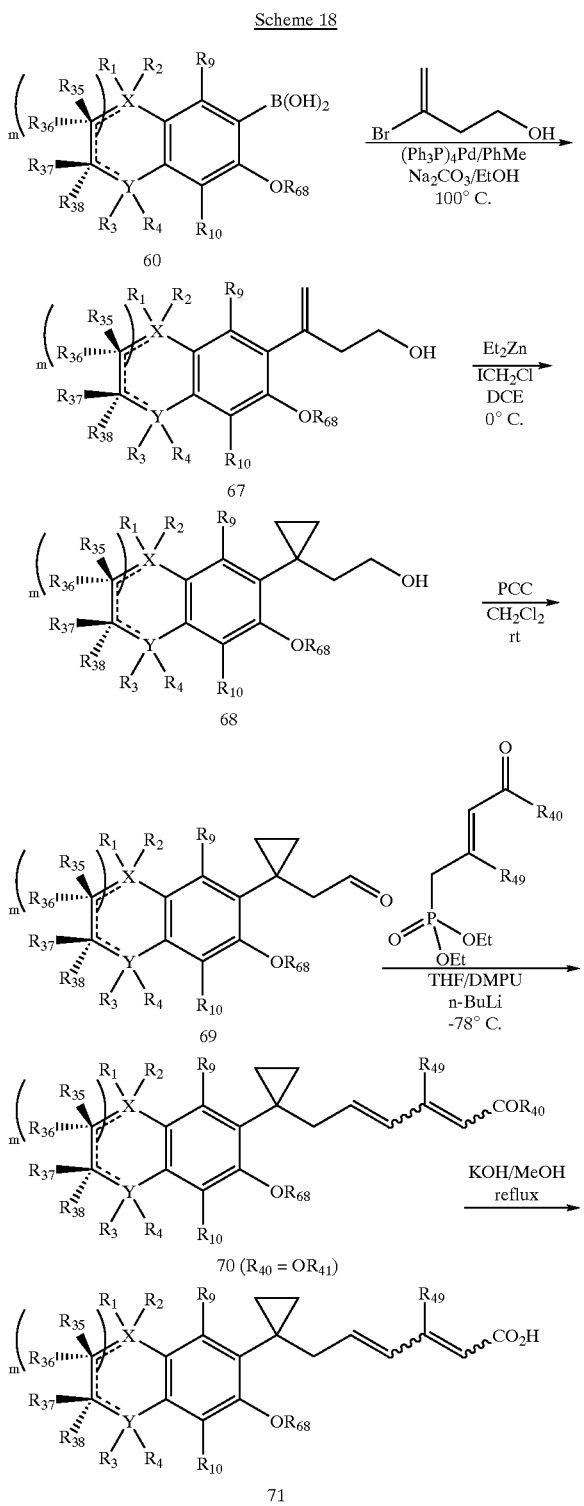

The bicyclic derivatives of the present invention, that is compounds of general structures 71, may be prepared in accordance with Scheme 18. The dienoic acid side chain of 71 was introduced by the Suzuki coupling of boronic acid 60 with 3-bromo-3-buten-1-ol in the presence of tetrakis triphenylphosphine palladium (0) and a base such as sodium carbonate in toluene at 100° C. to provide compound 67. Cyclopropanation of homoallylic alcohol 67 with reagents such as diethyl zinc and chloroiodomethane in dichloroethane provides the cyclopropane compound 68. Oxidation of alcohol 68 with reagent such as PCC in dichloromethane, provides aldehyde 69. The aldehyde 69 can be treated with a phosphonate, such as the lithium salt of diethyl 3-ethoxycarbonyl-2-methylprop-2-enylphosphonate (mixture of double bond isomers) in THF at reduced temperatures in a Horner-Wadsworth-Emmons olefination reaction to provide the dienoate esters 70 where $R_{38}$ is OEt. The olefination reaction is preferably conducted in the presence of 1,3-dimethyl-3,4,5,6-tetrahydro-2(1H)-pyrimidinone (DMPU). The acids and salts 71 are readily obtainable from the corresponding esters by hydrolysis in an alkanol solvent at ambient temperature with about a three molar excess of base, for example, potassium hydroxide. Alternatively, the ethyl esters may be hydrolyzed in THF/water or acetone/water at ambient temperature with, for example, excess lithium hydroxide. The hydrolysis solution is acidified and the hydrolysate recovered by conventional means to give as the major product the (2E, 4E)-bicyclic diene carboxylic acid derivatives of structure 71 where $R_{38}$ is OH. The minor (2Z, 4E)-bicyclic diene geometric isomer, by-product of the olefination reaction, is readily isolated by silica gel chromatography or HPLC purification of the hydrolysate mixture.

Scheme 19

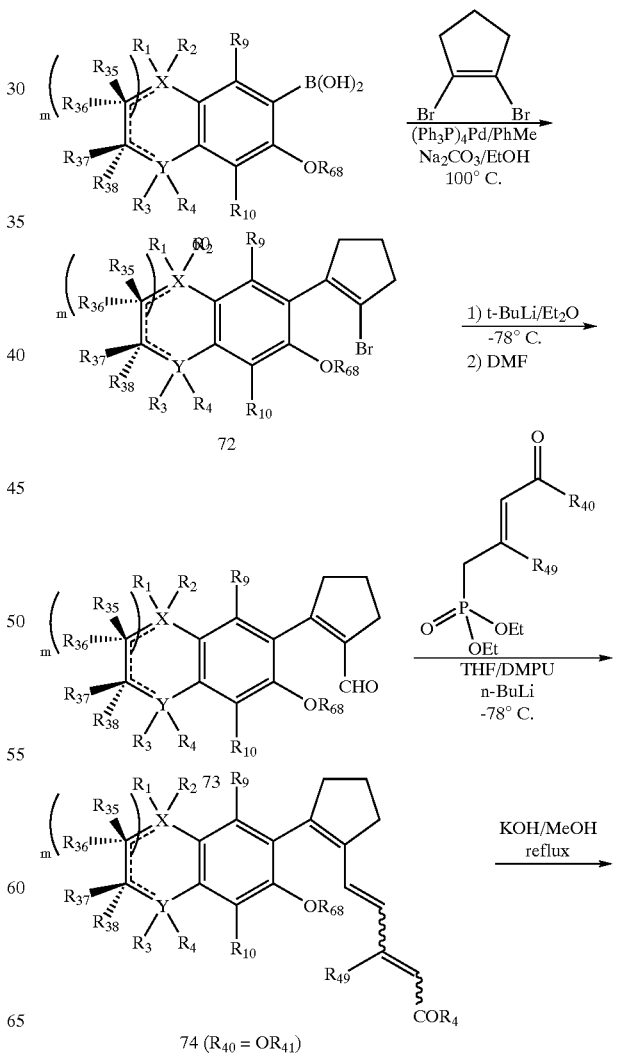

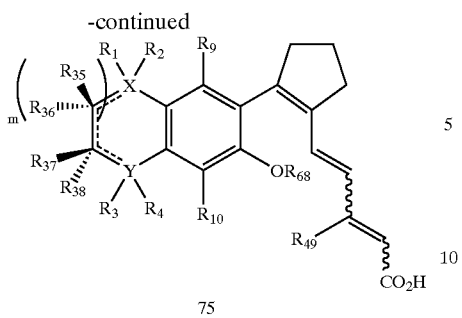

75

The bicyclic derivatives of the present invention, that is compounds of general structures 75, may be prepared in accordance with Scheme 19. The side chain of 75 was introduced by the Suzuki coupling of boronic acid 60 with 1,2-dibromocyclopentene in the presence of tetrakis triphenylphosphine palladium (0) and a base such as sodium carbonate in toluene at 100° C. to provide compound 72. Halogen-metal exchange with a base such as t-BuLi in ether at −78° C. followed by a treatment with dimethyl formamide (DMF), provides aldehyde 73. The aldehyde 73 can be treated with a phosphonate, such as the lithium salt of diethyl 3-ethoxycarbonyl-2-methylprop-2-enylphosphonate (mixture of double bond isomers) in THF at reduced temperature in a Horner-Wadsworth-Emmons olefination reaction to provide the dienoate esters 74 where $R_{38}$ is OEt. The olefination reaction is preferably conducted in the presence of 1,3-dimethyl-3,4,5,6-tetrahydro-2(1H)-pyrimidinone (DMPU). The acids and salts 75 are readily obtainable from the corresponding esters by hydrolysis in an alkanol solvent at ambient temperature with about a three molar excess of base, for example, potassium hydroxide. Alternatively, the ethyl esters may be hydrolyzed in THF/water or acetone/water at ambient temperature with, for example, excess lithium hydroxide. The hydrolysis solution is acidified and the hydrolysate recovered by conventional means to give as the major product the 2E, 4E)-bicyclic diene carboxylic acid derivatives of structure 75 where $R_{38}$ is OH. The minor (2Z, 4E)-bicyclic diene geometric isomer, by-product of the olefination reaction, is readily isolated by silica gel chromatography or HPLC purification of the hydrolysate mixture.

Scheme 20

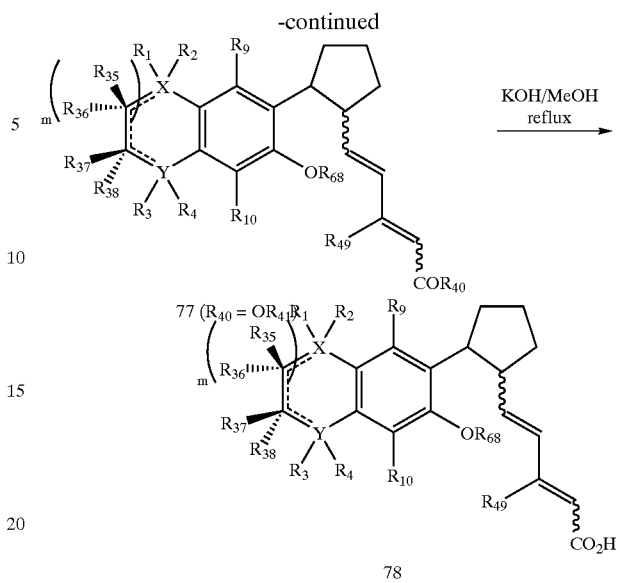

The bicyclic derivatives of the present invention, that is compounds of general structures 78, may be prepared in accordance with Scheme 20. The α,β-unsaturated aldehyde 73 was hydrogenated under an atmosphere of hydrogen with palladium on charcoal in ethyl acetate to provide aldehyde 76. The aldehyde 76 can be treated with a phosphonate, such as the lithium salt of diethyl 3-ethoxycarbonyl-2-methylprop-2-enylphosphonate (mixture of double bond isomers) in THF at reduced temperature in a Horner-Wadsworth-Emmons olefination reaction to provide the dienoate esters 77 where $R_{38}$ is OEt. The olefination reaction is preferably conducted in the presence of 1,3-dimethyl-3,4,5,6-tetrahydro-2(1H)-pyrimidinone (DMPU). The acids and salts 78 are readily obtainable from the corresponding esters by hydrolysis in an alkanol solvent at ambient temperature with about a three molar excess of base, for example, potassium hydroxide. Alternatively, the ethyl esters may be hydrolyzed in THF/water or acetone/water at ambient temperature with, for example, excess lithium hydroxide. The hydrolysis solution is acidified and the hydrolysate recovered by conventional means to give as the major product the (2E, 4E)-bicyclic diene carboxylic acid derivatives of structure 78 where $R_{38}$ is OH. The minor (2Z, 4E)-bicyclic diene geometric isomer, by-product of the olefination reaction, is readily isolated by silica gel chromatography or HPLC purification of the hydrolysate mixture.

It will be understood by those skilled in the art that certain modifications can be made to the above-described methods that remain within the scope of the present invention. For example, the modulator compounds of the present invention may also be produced in the form of the corresponding amides or esters, or pharmaceutically acceptable salts.

In another aspect, the dimer-selective RXR modulator compounds of the present invention are combined in a mixture with a pharmaceutically acceptable carrier to provide pharmaceutical compositions useful for treating the biological conditions or disorders noted herein in mammalian, and more preferably, in human patients. The particular carrier employed in these pharmaceutical compositions may take a wide variety of forms depending upon the type of administration desired, e.g., intravenous, oral, topical, suppository, parenteral or in a liposomal formulation.

In preparing the compositions in oral liquid dosage forms (e.g., suspensions, elixirs and solutions), typical pharmaceutical media, such as water, glycols, oils, alcohols, flavoring agents, preservatives, coloring agents and the like can be employed. Similarly, when preparing oral solid dosage forms (e.g., powders, tablets and capsules), carriers such as starches, sugars, diluents, granulating agents, lubricants, binders, disintegrating agents and the like will be employed. Due to their ease of administration, tablets and capsules represent the most advantageous oral dosage form for the pharmaceutical compositions of the present invention.

For parenteral administration, the carrier will typically comprise sterile water, although other ingredients that aid in solubility or serve as preservatives, may also be included. Furthermore, injectable suspensions may also be prepared, in which case appropriate liquid carriers, suspending agents and the like will be employed.

For topical administration, the compounds of the present invention may be formulated using bland, moisturizing bases, such as ointments or creams. Examples of suitable ointment bases are petrolatum, petrolatum plus volatile silicones, lanolin, and water in oil emulsions such as Eucerin™ (Beiersdorf). Examples of suitable cream bases are Nivea™ Cream (Beiersdorf), cold cream (USP), Purpose Cream™ (Johnson & Johnson), hydrophilic ointment (USP), and Lubriderm™ (Warner-Lambert).

The pharmaceutical compositions and compounds of the present invention will generally be administered in the form of a dosage unit (e.g., tablet, capsule, etc.) at from about 1 µg/kg of body weight to about 500 mg/kg of body weight, more preferably from about 10 µg/kg to about 250 mg/kg, and most preferably from about 20 µg/kg to about 100 mg/kg. As recognized by those skilled in the art, the particular quantity of pharmaecutical composition according to the present invention administered to a patient will depend upon a number of factors, including, without limitation, the biological activity desired, the condition of the patient, and tolerance for the drug.

The compounds of this invention also have utility when labeled, either with a radio or stable isotope label, and used in assays to determine the presence of RXRs. They are particularly useful due to their ability to selectively bind to members of the RXR subfamily and can therefore be used to determine the presence of RXR isoforms in the presence of other retinoid receptors or related intracellular receptors.

Due to the selectively specificity of the compounds of this invention for binding to retinoid X receptors, these compounds can also be used to purify samples of RXRs in vitro. Such purification can be carried out by mixing samples containing retinoid receptors with one of more of the compounds of the present invention, so that the modulator compound (ligand) binds to the receptor, and then separating out the bound ligand/receptor combination by separation techniques which are known to those of skill in the art. These techniques include column separation, filtration, centrifugation, tagging and physical separation, and antibody complexing, among others.

The compounds of the present invention also include racemate, individual stereoisomers, including enantiomers and mixtures thereof. These isomers are then isolated by standard resolution techniques, including fractional crystallization and reverse phase and chiral column chromatography.

The compounds and pharmaceutical compositions of the present invention can advantageously be used in the treatment of the disease and conditions described herein. In this regard, the dimer-selective modulator compounds and compositions will prove particularly useful in the modulation of process controlled by RXR homodimers and/or RXR heterodimers, such as apolipoprotein metabolism, either alone, or in combination with PPARs and/or TR modulators such as gemfibrozil or thyroid hormone, as well as modulation of skin-related processes, malignant and pre-malignant conditions and apoptosis, including combinations with RAR and VDR modulators. Likewise, the compounds and compositions will also prove useful in the modulation of processes mediated by RXR homodimers, including selective modulation of programmed cell death (apoptosis). Further, all of these treatment pathways can be triggered without activating the RXR agonist homodimer pathway.

Furthermore, the modulator compounds and pharmaceutical compositions of the present invention are extremely potent antagonists of a RXR homodimer, typically displaying 50% inhibition of activation of one or more of the retinoid X receptors at a concentration of less than 500 nM, preferably at a concentration of less than 100 nM, more preferably at a concentration of less than 50 nM, more preferably yet at a concentration of less than 20 nM, and most preferably at a concentration of less than 10 nM. Concurrently, the modulator compounds of the present invention are also extremely potent agonists in the contest of a RXR heterodimer, typically displaying 50% activation of retinoid X receptors heterodimers at a concentration of less than 500 nM, preferably at a concentration of less than 100 nM, more preferably at a concentration of less than 50 nM, more preferably yet at a concentration of less than 20 nM, and most preferably at a concentration of less than 10 nM. Also, the dimer-selective RXR modulator compounds of the present invention preferentially bind to and inhibit transactivation of one or more of the RXR subfamily of retinoid receptors at a level at least 2 times greater, preferably at least 5 times greater, more preferably at least 10 times greater, and most preferably at least 100 times greater than one the RAR subfamily of retinoid receptors.

The invention will be further illustrated by reference to the following non-limiting Examples.

EXAMPLE 1

4-[(3-n-Propyl-5,6,7,8-tetrahydro-5,5,8,8-tetramethyl-2-naphthyl)carbonyl]benzoic acid (Compound 101, prepared as illustrated and described in Scheme 1)

3-n-Propyl-5,6,7,8-tetrahydro-5,5,8,8-tetramethylnaphthalene (prepared from Friedel-Crafts alkylation/cyclization of n-propylbenzene with 2,5-dichloro-2,5-dimethylhexane) was combined with monomethylterephthalate acid chloride in dichloromethane and treated portionwise at ambient temperature with aluminum chloride until the spontaneous reflux had subsided and the solution become dark red/brown in color. After stirring at room temperature for 10–15 min, the reaction was poured into ice water and the layers were separated. The aqueous layer was extracted with EtOAc. The combined organic extracts were washed with water and brine, dried (MgSO$_4$), filtered, and concentrated to give a yellow oil. The crude product was crystallized (CH$_2$Cl$_2$/hexanes) to give 4-[(3-n-propyl-5,5,8,8-tetramethyl-5,6,7,8-tetrahydro-2-naphthyl) carbonyl]benzoic acid methyl ester as white crystals (95%): TLC (20% ethyl acetate: 80% hexanes) R$_f$ 0.7; mp 112–114° C.; $^1$H-NMR (400 MHz, CDCl$_3$) δ8.19 (½ABq, J=8.0 Hz, 2H, ArH); 7.89 (½ABq, J=8.0 Hz, 2H, ArH), 7.22 (s, 1H, ArH), 7.20 (s, 1H, ArH), 3.95 (s, 3H, OCH$_3$), 2.64 (t, J=8.0 Hz, 2H, CH$_2$), 1.69 (s, 4H, 2CH$_2$), 1.55 (m, 2H, CH$_2$), 1.31 (s, 6H, 2CH$_3$), 1.20 (s, 6H, 2CH$_3$), 0.89 (t, J=7.5 Hz, 3H, CH$_3$), Anal. (C$_{23}$H$_{32}$O$_3$) C, H. The ester was hydrolyzed in excess KOH/MeOH at ambient temperature for 24 h. The methanol was removed in vacuo. The residue was taken-up in water and the aqueous layer was adjusted to pH=4–5 with 1 M aqueous HCl. The aqueous solution was extracted 3 times with EtOAc; the organic layers were combined, and washed with water (2×) and brine. The organic solution was dried ($Na_2SO_4$), filtered, and concentrated to give 4-[(3-n-propyl-5,6,7,8-tetrahydro-5,5,8,8-tetramethyl-2-naphthyl)carbonyl]benzoic acid (101). Crystallization gave a white powder (93%): TLC (10% MeOH: 90% $CHCl_3$) $R_f$ 0.3; mp 252–254° C.; $^1$H-NMR (400 MHz, $CDCl_3$) δ8.20 (½ABq, J=8.0 Hz, 2H, ArH), 7.90 (½Abq, J=8.0 Hz, 2H, ArH), 7.20 (s, 1H, ArH), 7.25 (s, 1H, ArH), 2.64 (t, J=8.0 Hz, 2H, $CH_2$), 1.69 (s, 4H, 2$CH_2$), 1.55 (m, 2H, $CH_2$), 1.31 (s, 6H, 2$CH_3$), 1.20 (s, 6H, 2$CH_3$), 0.89 (t, J=7.5 Hz, 3H, $CH_3$), Anal. ($C_{25}H_{30}O_3$) C, H.

EXAMPLE 2

4-[(3-n-Propyl-5,6,7,8-tetrahydro-5,5,8,8-tetramethyl-2-naphthyl)ethenyl]benzoic acid (Compound 102, prepared as illustrated and described in Scheme 2)

4-[(3-n-Propyl-5,5,8,8-tetramethyl-5,6,7,8-tetrahydro-2-naphthyl)carbonyl]benzoic acid methyl ester (2.7 mmol) in THF (25 mL) was treated with methyltriphenylphosphonium bromide/sodium azide (1.2 g, 3.1 mmol) and the solution was allowed to stir at ambient temperature for 3 h. The reaction was quenched with saturated aqueous $NH_4Cl$ and diluted with EtOAc. The organic solution was separated and washed with water and brine, dried ($MgSO_4$), filtered, and concentrated to give a yellow oil. The crude product was crystallized ($CH_2Cl_2$/hexanes) to give 4-[(3-n-propyl-5,5,8, 8-tetramethyl-5,6,7,8-tetrahydro-2-naphthyl)ethenyl] benzoic acid methyl ester as white crystal (78%): TLC (20% ethyl acetate: 80% hexanes) $R_f$ 0.8; mp 120–121° C.; $^1$H-NMR (400 MHz, $CDCl_3$) δ7.94 (½ABq, J=8.0 Hz, 2H, ArH), 7.33 (½ABq, J=8.0 Hz, 2H, ArH), 7.09 (s, 1H, ArH), 7.08 (s, 1H, ArH), 5.80 (s, 1H, olefinic), 5.30 (s, 1H, olefinic), 3.90 (s, 3H, $OCH_3$), 2.24 (t, J=8.0 Hz, 2H, $CH_2$), 1.70 (s, 4H, 2$CH_2$), 1.39 (m, 2H, $CH_2$), 1.30 (s, 6H, 2$CH_3$), 1.26 (s, 6H, 2$CH_3$), 0.73 (t, J=7.5 Hz, 3H, $CH_3$), Anal. ($C_{27}H_{34}O_2$) C, H. The ester was hydrolized using the standard conditions of Example 1 to yield 4-[(3-n-propyl-5,6,7,8-tetrahydro-5,5,8,8-tetramethyl-2-naphthyl)ethyl] benzoic acid (102). Crystallization gave white crystals (83%): TLC (10% MeOH-90% $CHCl_3$) $R_f$ 0.5; mp 263–265° C. $^1$H-NMR (400 MHz, $CDCl_3$) δ8.00 (½ABq, J=8.0 Hz, 2H, ArH), 7.09 (s, 1H, ArH), 7.08 (s, 1H, ArH), 5.81 (s, 1H, olefinic), 5.31 (s, 1H, olefinic), 2.23 (t, J=8.0 Hz, 2H, $CH_2$), 1.70 (s, 4H, 2$CH_2$), 1.39 (m, 2H, $CH_2$), 1.30 (s, 6H, 2$CH_3$), 1.26 (s, 6H, 2$CH_3$), 0.73 (t, J=7.5 Hz, 3H, $CH_3$), FAB-MS m/z 377 (MH+); Anal. ($C_{26}H_{32}O_2$) C, H.

EXAMPLE 3

4[(3n-Propyl-5,6,7,8-tetrahydro-5,5,8,8-tetramethyl-2-naphthyl)cyclopropyl]benzoic acid (Compound 103, prepared as illustrated and described in Scheme 2)

4-[3-n-Propyl -5,5,8,8-tetramethyl-5,6,7,8-tetrahydro-2-naphthyl)ethenyl]benzoic acid methyl ester (0.573 mmol) in dichloromethane (10 mL) under a nitrogen atomspheric at 0° C. was combined with $Et_2Zn$ (0.29 mL, 2.87 mM). To this solution was added $CH_2ClI$ (0.8 mmol) dropwise via a syringe and the reaction mixture was stirred at 0° C. for 10 min. The solution was then heated at 55° C. for 6 h. The solution was cooled to ambient temperature, water was added, and the mixture was extracted with EtOAc. The organic solution was washed with water and brine, dried ($MgSO_4$), filtered, and concentrated to give a yellow oil. The crude product was purified by $SiO_2$ flash chromatography to give 4-[(3-n-propyl-5,5,8,8-tetramethyl-5,6,7,8-tetrahydro-2-naphthyl)cyclopropyl]benzoic acid methyl ester (14%) as a white solid: $^1$H-NMR (400 MHz, $CDCl_3$) δ7.94 (½ABq, J=8.0 Hz, 2H, ArH), 7.33 (½ABq, J=8.0 Hz, 2H, ArH), 7.09 (s, 1H, ArH), 7.08 (s, 1H, ArH), 3.90 (s, 3H, $OCH_3$), 2.24 (t, J=8.0 Hz, 2H, $CH_2$), 1.70 (s, 4H, 2$CH_2$), 1.39 (s, 4H, 2$CH_2$), 1.35 (m, 2H, $CH_2$), 1.30 (s, 6H, 2$CH_3$), 1.26 (s, 6H, 2$CH_3$), 0.73 (t, J=7.5 Hz, 3H, $CH_3$). The ester was hydrolyzed using the standard conditions of Example 1 to yield 4-[(3-n-propyl-5,6,7,8-tetrahydro-5,5,8,8-tetramethyl-2-naphthyl) cyclopropyl] benzoic acid (103). Crystallization gave white crystals (88%): $^1$H-NMR (400 MHz, $CDCl_3$) δ8.00 (½ABq, J=8.0 Hz, 2H, ArH), 7.36 (½ABq, J=8.0 Hz, 2H, ArH), 7.09 (s, 1H, ArH), 7.08 (s, 1H, ArH), 2.23 (t, J=8.0 Hz, 2H, $CH_2$), 1.69 (s, 4H, 2$CH_2$) 1.39 (s, 4H, 2$CH_2$), 1.35 (m, 2H, $CH_2$), 1.30 (s, 6H, 2$CH_3$), 1.26 (s, 6H, 2$CH_3$), 0.73 (t, J=7.5 Hz, 3H, $CH_3$).

EXAMPLE 4

4[(3-n-Propyl-5,6,7,8-tetrahydro-5,5,8,8-tetramethyl-2-naphthyl)carbonyl]benzoic acid oxime (Compound 104, prepared as illustrated and described in Scheme 3)

4-[(3-n-propyl-5,6,7,8-tetrahydro-5,5,8,8-tetramethyl-2-napthyl)carbonyl]benzoic acid (101) (12.6 mmol) in EtOH (10 mL) and pyridine (15.3 mL) was treated with hydroxylamine hydrochloride (4.38 g, 63 mmol), and the mixture was heated at reflux. After 6 h, the mixture was cooled to room temperature and the ethanol was removed in vacuo. The residue was taken-up in water and the aqueous layer was adjusted to pH=4–5 with 1 M aqueous HCl. The aqueous solution was extracted with EtOAc, 3×. The organic layers were combined and washed with water (2×) and brine. The organic solution was dried ($NaSO_4$), filtered, and concentrated to give a foamy white solid. Recrystallization ($CH_2Cl_2$/ether/hexanes) gave 4-[(3-n-propyl,5,6,7,8-tetrahydro-5,5,8,8-tetramethyl-2-naphthyl)carbonyl] benzoic acid oxime (104), as white crystals (85%): mp 255–257°C.; $^1$H-NMR (400 MHz, $CDCl_3$) δ8.19 (½ABq, J=8.3 Hz, 2H, ArH), 7.89 (½ABq, J=8.3 Hz, 2H, ArH), 7.23 (s, 1H, ArH), 7.20 (s, 1H, ArH), 2.65 (m, 2H, $CH_2$), 1.70 (m, 4H, 2$CH_2$), 1.56 (m, 2H, $CH_2$), 1.32 (s, 6H, 2$CH_3$) 1.20 (s, 6H, 2$CH_3$), 0.88 (t, J=7.3 Hz, 3H, $CH_3$).

EXAMPLE 5

4-[(3,5,5,8,8-Pentamethyl-5,6,7,8-tetrahydro-2-naphthyl)carbonyl]benzoic acid O-benzyloxime (Compound 105, prepared as illustrated and described in Scheme 3)

4-[(3,5,5,8,8-Pentamethyl-5,6,7,8-tetrahydro-2-naphthyl) carbonyl]benzoic acid (4.41 g, 12.6 mmol) in EtOH (10 mL) and pyridine (15.3 mL) was treated with hydroxylamine hydrochloride (4.38 g, 63 mmol), and the mixture was heated at reflux. After 6 h, the mixture was cooled to room temperature and the ethanol was removed in vacuo. The residue was taken-up in water and the aqueous layer was adjusted to pH=4.5 with 1 M aqueous HCl. The aqueous solution was extracted with EtOAc, 3×. The organic layer were combined and washed with water (2×) and brine. The organic solution was dried (NaSO$_4$), filtered, and concentrated. Recrystallization (CH$_2$Cl$_2$/hexanes) gave 4-[(3,5,5,8,8-pentamethyl-5,6,7,8-tetrahydro-2-naphthyl)carbonyl] benzoic acid oximate 4.05 g (88%) as a white solid: mp 204–209° C. (d); $^1$H NMR (CDCl$_3$/d-4MeOH) δ7.99 (½ABq, J=8.4 Hz, 2H, ArH), 7.53 (½ABq, J=8.4 Hz, 2H, ArH), 7.20 (s, 1H, ArH), 6.99 (s, 1H, ArH), 2.11 (s, 3H, CH$_3$), 1.69 (s, 4H, 2CH$_2$), 1.32 (s, 6H, 2CH$_3$), 1.22 (s, 6H, 2CH$_3$); HRMS: 366.2060 (MH$^+$). A solution of 4-[(3,5,5,8,8-pentamethyl-5,6,7,8-tetrahydro-2-naphthyl)carbonyl] benzoic acid oxime (100 mg, 0.27 mmol) in THF (0.3 mL) and DMPU (0.3 mL) was added at 0° C. to a suspension of NaH (20 mg, 0.82 mmol) in THF (1.0 mL). The suspension was allowed to warm to room temperature was stirring over 30 minutes, then a solution of benzyl bromide (71 mL, 0.82 mmol) was added. The solution was allowed to warm to room temperature and stirred for 12 h. Aqueous, saturated NH$_4$Cl (5.0 mL) was added and the aqueous layer was adjusted to pH=4–5 with 1 M aqueous HCl. The aqueous solution was extracted with EtOAc, 3×. The organic layers were combined and washed with water (2×) and brine. The organic solution was dried (Na$_2$SO$_4$), filtered, and concentrated to give a white solid. Purification by radial chromatography (10:1=hexanes: EtOAc) gave 4-[3,5,5,8,8-pentamethyl-5,6,7,8-tetrahydro-2-naphthyl)carbonyl] benzoic acid O-benzyloxime (105) 154 mg (61%) as a white solid: mp 169–172° C.; IR (neat) 2961 m, 2926 m 1691 s, 1420 w, 1285 w, 1016 w cm$^{-1}$; $^1$H NMR (400 MHz, CDCl$_3$) δ8.03 (½ABq, J=8.5 Hz, 2H, ArH), 7.55 (½ABq, J=8.5 Hz, 2H, ArH), 7.31 (m, 5H, ArH), 7.15 (s, 1H, ArH), 6.96 (s, 1H, ArH), 5.25 (s, 2H, OCH$_2$) 2.00 (s, 3H, Ar—CH$_3$), 1.69 (s, 4H, 2CH$_2$), 1.31 (s, 6H, 2CH$_3$), 1.22 (s, 6H, 2CH$_3$); $^{13}$C NMR (100.8 MHz, CDCl$_3$) δ171.7, 156.6, 145.3, 142.2, 141.4, 138.2, 132.5, 130.2, 130.1, 129.4, 128.2, 128.1, 127.9, 127.6, 127.0, 126.2, 35.2, 35.1, 34.1, 33.9, 31.9, 19.4; MS (FAB) m/e 4.56 (MH$^+$); HRMS (FAB, MH$^+$) Calcd for C$_{30}$H$_{33}$NO$_3$: 456.2539 Found: 456.2526.

EXAMPLE 6

4-[(3,5,5,8,8-Pentamethyl-5,6,7,8-tetrahydro-2-naphthyl)carbonyl]benzoic acid O-hexyloxime (Compound 106, prepared as illustrated and described in Scheme 3)

4-[(3,5,5,8,8-Pentamethyl-5,6,7,8-tetrahydro-2-naphthyl) carbonyl]benzoic acid methyl ester (5 mmol) in MeOH (10 mL) was treated with hydroxylamine hydrochloride (2eq) and pyridine (2.1 eq) and the mixture was heated at reflux for 5 h. The reaction was worked-up in a manner identical to that described for Example 5. The ester oxime was alkylated with 1-bromohexane in a manner similar to that described in Example 5 to give 4-[(3,5,5,8,8-pentamethyl-5,6,7,8-tetrahydro-2-naphthyl)carbonyl]benzoic acid O-hexyloxime methyl ester (80%): IR (neat) 2957 s, 2930 s, 2862 m, 1726 s, 1589 m, 1435 w, 1363 w, 1275 s, 1107 m, 1018 m, 864 cm$^{-1}$; $^1$H NMR (400 MHz, CDCl$_3$) δ7.96 (½ABq, J=8.5 Hz, 2H, ArH), 7.53 (½ABq, J=8.5 Hz, 2H, ArH), 7.15 (s, 1H, Ar—H), 6.96 (s, 1H, Ar—H), 4.18 (t, J=6.7 Hz, 2H, OCH$_2$), 3.97 (s, 3H, OCH$_3$), 2.04 (s, 3H, Ar—CH$_3$), 1.68 (m, 6H, 3CH$_2$), 1.31 (s, 6H, 2CH$_3$), 1.28 (m, 6H, 3CH$_2$), 1.21 (s, 6H, 2CH$_3$), 0.86 (t, J=6.8 Hz, 3H, CH$_3$). The ester was hydrolyzed using the standard conditions of Example 1 to yield, after recrystallization (THF/hexanes) 4-[(3,5,5,8,8-pentamethyl-5,6,7,8-tetrahydro-2-naphthyl)carbonyl] benzoic acid O-hexyloxime (106) (85%): mp 91–95° C., $^1$H NMR (400 MHz, CDCl$_3$) δ8.03 (½ABq, J=8.5 Hz, 2H, ArH), 7.57 (½ABq, J=8.5 Hz, 2H, ArH), 7.16 (s, 1H, Ar—H), 6.97 (s, 1H, Ar—H), 4.20 (t, J=6.7 Hz, 2H, OCH$_2$), 2.05 (s, 3H, Ar—CH$_3$), 1.69 (m, 6H, 3CH$_2$), 1.31 (s, 6H, 2CH$_3$), 1.29 (m, 6H, 3CH$_2$) 1.22 (s, 6H, 2CH$_3$), 0.86 (t, J=6.8 Hz, 3H, CH$_3$).

EXAMPLE 7

4[(3-Ethoxy-5,6,7,8-tetrahydro-5,5,8,8-tetramethyl-2-naphthyl)ethenyl]benzoic acid (Compound 107, prepared as illustrated and described in Scheme 1 and Scheme 3)

A solution of 5,6,7,8-tetrahydro-5,5,8,8-tetramethylnaphth-2-ol (5.09 g, 25.00 mmol; prepared by Friedel-Crafts alkylation/cyclization of phenol with 2,5-dichloro-2,5-dimethylhexane) and monomethyl terephthalate acid chloride (5.95 g, 29.9 mmol) in CH$_2$Cl$_2$ (10 mL) and hexanes (60 mL) was treated portionwise with aluminum trichloride (10.0 g, 75 mmol) over 30 minutes at ambient temperature. After the addition was complete, sulfuric acid (concentrated, 0.5 mL) was added and the orange solution was heated at reflux for 1 h. The solution was allowed to cool to ambient temperature and the reaction was quenched by slowly pouring the solution into ice/water accompanied by vigorous stirring. The mixture was stirred for an additional 30 min. The aqueous solution was extracted with EtOAc, 3×. The organic layers were combined and washed with water (2×) and brine. The organic solution was dried (NaSO$_4$), filtered, and concentrated to give a red oil. Purification by silica gel flash chromatography (20:1= hexanes:EtOAc) gave 4-[(3-hydroxy-5,6,7,8-tetrahydro-5,5,8,8-tetramethyl-2-naphthyl)carbonyl]benzoic acid methyl ester 3.24 g (35%) as a yellow solid: mp 155–159° C. (d); $^1$H NMR (400 MHz, CDCl$_3$) δ8.18 (½ABq, J=8.3 Hz, 2H, ArH), 7.72 (½ABq, J=8.3 Hz, 2H, ArH), 7.43 (s, 1H, ArH), 7.01 (s, 1H, ArH), 3.98 (s, 3H, OCH$_3$), 1.70 (m, 4H, 2CH$_2$), 1.31 (s, 6H, 2CH$_3$), 1.16(s, 6H, 2CH$_3$). A solution of the 4-[(3-hydroxy-5,6,7,8-tetrahydro-5,5,8,8-tetramethyl-2-naphthyl)carbonyl]benzoic acid methyl ester (433 mg, 1.18 mmol) in DMF (2mL) was treated with NaH (1.5 mmol) at 0° C. and allowed to warm to ambient temperature over 1 h. The yellow solution was cooled again to 0° C. and treated with a solution of bromoethane (83 mL, 1.30 mmol) in DMF (1 mL) and allowed to warm to ambient temperature and stirred for 10 h. The reaction was quenched with saturated aqueous NH$_4$Cl. The aqueous solution was extracted with EtOAc, 3×. The organic layers were combined and washed with water (2×) and brine. The organic solution was dried (NaSO$_4$), filtered, and concentrated to give a colorless oil. Purification by silica gel flash chromatography (20:1= hexanes:Et$_2$O) gave 4-[3-ethoxy-5,6,7,8-tetrahydro-5,5,8,8-tetramethyl-2-naphthyl)carbonyl]benzoic acid methyl ester 436 mg (97%) as a white solid: $^1$H NMR (400 MHz, CDCl$_3$) δ8.07 (½ABq, J=8.4 Hz, 2H, ArH), 7.82 (½ABq, J=8.4 Hz, 2H, ArH), 7.43 (s, 1H, ArH), 6.82 (s, 1H, ArH), 3.95 (s, 3H, OCH3), 3.88 (q, J=6.9 Hz, 2H, OCH$_2$), 1.70 (m, 4H, 2CH$_2$), 1.31 (s, 6H, 2CH$_3$), 1.27 (s, 6H, 2CH$_3$), 0.98 (t, J=6.9 Hz, 3H, CH$_3$); HRMS calcd. for C$_{25}$H$_{30}$O$_4$395.2222 (MH$^+$), found 395.2219. The ethoxy keto ester was converted to the ethenyl compound by the method described in Example 2 to give, after preparative silica gel TLC (1:1:1= hexanes:EtOAc:CH$_2$Cl$_2$+5% MeOH), 4-[(3-ethoxy-5,6,7,8-tetrahydro-5,5,8,8-tetramethyl-2-naphthyl)ethenyl]benzoic acid (107) (17%) as a white solid: mp 195–200° C. (d); $^1$H NMR (400 MHz, CDCl$_3$) δ8.01 (½ABq, J=8.3 Hz, 2H, ArH), 7.39 (½ABq, J=8.3 Hz, 2H, ArH), 7.19 (s, 1H, ArH), 6.74 (s, 1H, ArH), 5,67 (appp s, 1H, methylene), 5.45 (d, J=0.8 Hz, 1H, methylene), 3.78 (q, J=6.9 Hz, 2H, OCH$_2$), 1.70 (m, 4H, 2CH$_2$) 1.30 (s, 6H, 2CH$_3$), 1.28 (S, 6H, 2CH$_3$), 0.91 (t, J=6.9 Hz, 3H, CH$_3$); HRMS calcd. for C$_{25}$H$_{30}$O$_3$ 378.2195 (M$^+$), found 378.2210.

EXAMPLE 8

4[(3-Ethoxy-5,6,7,8-tetrahydro-5,5,8,8-tetramethyl-2-naphthyl)carbonyl]benzoic acid O-methyloxime (Compound 108, prepared as illustrated and described in Scheme 4)

The ethoxy keto ester from Example 7 was hydrolized as described in Example 1 to give 4-[(3-ethoxy-5,6,7,8-tetrahydro-5,5,8,8-tetramethyl-2-naphthyl)carbonyl] benzoic acid: $^1$H NMR (400 MHz, CDCl$_3$) δ8.15 (½ABq, J=8.3 Hz, 2H, ArH), 7.85 (½ABq, J=8.3 Hz, 2H, ArH), 7.46 (s, 1H, ArH), 6.83 (s, 1H, ArH), 3.89 (q, J=6.9 Hz, 2H, OCH$_2$), 1.70 (m, 4H, 2CH$_2$), 1.32 (s, 6H, 2CH$_3$), 1.28 (s, 6H, 2CH$_3$), 1.98 (t, J=6.9 Hz, 3H, CH$_3$), HRMS calcd. for C$_{24}$H$_{28}$O$_4$381.2066 (MH$^+$), found 381.2098. 4-[(3-Ethoxy-5,6,7,8-tetrahydro-5,5,8,8-tetramethyl-2-naphthyl)carbonyl] benzoic acid (0.41 mmol) in EtOH (1 mL) was treated with methoxylamine hydrochloride (52 mg, 0.62 mmol) and pyridine (70 mL, 0.82 mmol), and the mixture was heated at reflux for 5 h. The reaction was worked-up in a manner identical to that described for Example 5 to give, after recrystallization (THF/hexanes) 4-[(3-ethoxy-5,6,7,8-tetrahydro-5,5,8,8-tetramethyl-2-naphthyl)carbonyl] benzoic acid O-methyloxime, (108) (90%) as a colorless film: $^1$H NMR (400 MHz, CDCl$_3$) δ8.02 (½ABq, J=8.4 Hz, 2H, ArH), 7.59 (½ABq, J=8.4 Hz, 2H, ArH), 7.08 (s, 1H, ArH), 6.84 (s, 1H, ArH), 4.00 (s, 3H, OCH3), 3.90 (q, J=7.0 Hz, 2H, OCH$_2$), 1.69 (m, 4H, 2CH$_2$), 1.31 (s, 6H, 2CH$_3$), 1.23 (s, 6H, 2CH$_3$), 1.08 (t, J=7.0 Hz, 3H, CH$_3$).

EXAMPLE 9

4-[(3-Propoxy-5,6,7,8-tetrahydro-5,5,8,8-tetramethyl-2-naphthyl)carbonyl]benzoic acid oxime (Compound 109, prepared as illustrated and described in Scheme 1 and Scheme 3)

A solution of the 4-[(3-hydroxy,5,6,7,8-tetrahydro-5,5,8, 8-tetramethyl-2-naphthyl)carbonyl]benzoic acid methyl ester (from Example 7, 433 mg, 1.18 mmol) in DMSO (2 mL) was treated with KOH (1.5 mmol) at 0° C. and allowed to warm to ambient temperature over 1 h. The yellow solution was cooled again to 0° C., and treated with a solution of bromopropane (118 mL, 1.30 mmol) in DMSO (1mL) and allowed to warm to ambient temperature and stirred for 10 h. The reaction was quenched with saturated aqueous NH$_4$Cl. The aqueous solution was adjusted to pH=3 with 1M HCl and extracted with EtOAc, 3×. The organic layers were combined and washed with water (2×) and brine. The organic solution was dried (NaSO$_4$), filtered, and concentrated. Purification by silica gel radial chromatography (20:1=hexanes:Et$_2$O) gave 4-[2-propoxy-5,6,7,8-tetrahydro-5,5,8,8-tetramethyl-2-naphthyl)carbonyl]benzoic acid 337 mg (75%) as a coloreless oil: $^1$H NMR (400 MHz, CDCl$_3$) δ8.15 (½ABq, J=8.2 Hz, 2H, ArH), 7.85 (½ABq, J=8.2 Hz, 2H, ArH), 7.46 (s, 1H, ArH), 6.82 (s, 1H, ArH), 3.78 (t, J=6.3 Hz, 2H, OCH$_2$), 1.70 (m, 4H, 2CH$_2$), 1.36 (m, 2H, CH$_2$), 1.32 (s, 6H, 2CH$_3$), 1.28 (s, 6H, 2CH$_3$), 0.62 (t, J=7.4 Hz, 3H, CH$_3$). The propoxyketo acid (1.34 mg, 0.33 mmol) in EtOH (2mL) was converted to the oxime derivative as described in Example 4 to provide, after recrystallization (CH$_2$Cl$_2$/hexanes (4-[(3-propoxy-5,6,7,8-tetrahydro-5,5,8, 8-tetramethyl-2-naphthyl)carbonyl]benzoic acid oxime (109) (97%) as a white solid: mp 251–255° C. (d); $^1$H NMR (400 MHz, CDCl$_3$) δ7.98 (½ABq, J=8.4 Hz, 2H, ArH), 7.54 (½ABq, J=8.4 Hz, 2H, ArH), 7.13 (s, 1H, ArH), 6.86 (s, 1H, ArH), 3.81 (t, J=6.2 Hz, 2H, OCH$_2$), 1.70 (m, 4H, 2CH$_2$), 1.51 (m, 2H, CH$_2$), 1.32 (s, 6H, 2CH$_3$), 1.24 (s, 6H, 2CH$_3$), 0.72 (t, J=7.4 Hz, 3H, CH$_3$).

EXAMPLE 10

4-[(3-Propoxy-5,6,7,8-tetrahydro-5,5,8,8-tetramethyl-2-naphthyl)carbonyl]benzoic acid O-methyloxime (Compound 110, prepared as illustrated and described in Scheme 1 and Scheme 4)

p-[2-Propoxy-5,6,7,8-tetrahydro-5,5,8,8-tertramethyl-2-naphthyl)carbonyl]benzoic acid (from Example 9, 28 mg, 0.07 mmol) was converted to the O-methyloxime derivative as described in Example 8. Crystallization (CH$_2$Cl$_2$/Et$_2$O/ hexanes) gave 4-[(3-propoxy-5,6,7,8-tetramethyl-2-naphthyl)carbonyl]benzoic acid O-methyloxime (110) 21 mg (70%) as a white solid: mp 202–204° C., $^1$H NMR (400 MHz, CDCl$_3$) δ7.98 (½ABq, J=8.4 Hz, 2H, ArH), 7.54 (½ABq, J=8.4 Hz, 2H, ArH), 7.13 (s, 1H, ArH), 6.86 (s, 1H, ArH), 4.00 (s, 3H, OCH3), 3.81 (t, J=6.2 Hz, 2H, OCH$_2$), 1.70 (m, 4H, 2CH$_2$), 1.51 (m, 2H, CH$_2$), 1.32 (s, 6H, 2CH$_3$), 1.24 (s, 6H, 2CH$_3$), 0.72 (t, J=7.4 Hz, 3H, CH$_3$).

EXAMPLE 11

4-[(3-Butyloxy-5,6,7,8-tetrahydro-5,5,8,8-tetramethyl-2-naphthyl)carbonyl]benzoic acid (Compound 111, prepared as illustrated and described in Scheme 1)

A solution of the 4-[(3-hydroxy-5,6,7,8-tetrahydro-5,5,8, 8-tetramethyl-2-naphthyl)carbonyl]benzoic acid methyl ester (433 mg, 1.18 mmol) in DMF (2 mL) was treated with NaH (1.5 mmol) at 0° C. and allowed to warm to ambient temperature over 1 h. The yellow solution was cooled again to 0° C., and treated with a solution of bromobutane (119 mL, 1.30 mmol) in DMF (1 mL) and allowed to warm to ambient temperature and stirred for 10 h. The reaction was quenched with saturated aqueous NH$_4$Cl. The aqueous solution was extracted with EtOAc, 3×. The organic layers were combined and washed with water (2×) and brine. The organic solution was dried (NaSO$_4$), filtered, and concentrated to give a colorless oil. Purification by silica gel flash chromatography (20:1=hexanes:Et$_2$O) gave 4-[3-butyloxy-5,6,7,8-tetrahydro-5,5,8,8-tetramethyl-2-naphthyl)carbonyl] benzoic acid methyl ester 275 mg (55%) as a white solid: $^1$H NMR (400 MHz, CDCl$_3$) δ8.07 (½ABq, J=8.2 Hz, 2H, ArH), 7.81 (½ABq, J=8.2 Hz, 2H, ArH), 7.44 (s, 1H, ArH), 6.82 (s, 1H, ArH), 3.95 (s, 3H, OCH3), 3.81 (t, J=6.2 Hz, 2H, OCH$_2$), 1.70 (m, 4H, 2CH$_2$), 1.34 (m, 2H, CH$_2$), 1.32 (s, 6H, 2CH$_3$), 1.27 (s, 6H, 2CH$_3$), 1.02 (m, 2H, CH$_2$), 0.71 (t, J=7.2 Hz, 3H, CH$_3$); HRMS calcd. for C$_{27}$H$_{34}$O$_4$ 423.2535 (MH$^+$), found 423.2505. The butyloxy keto ester (150 mg, 0.36 mmol) was hydrolyzed with excess KOH in MeOH as described in Example 1 to give 4-[(3-butyloxy-5,6,7,8- tetrahydro-5,5,8,8-tetramethyl-2-naphthyl)carbonyl]benzoic acid (111) 82 mg (59%) as a white solid: mp 207–210° C.; $^1$H NMR (400 MHz, CDCl$_3$) δ8.14 (½ABq, J=8.2 Hz, 2H, ArH), 7.84 (½ABq, J=8.2 Hz, 2H, ArH), 7.46 (s, 1H, ArH), 6.82 (s, 1H, ArH), 3.81 (t, J=6.2 Hz, 2H, OCH$_2$), 1.71 (m, 4H, 2CH$_2$), 1.32 (s, 6H, 2CH$_3$), 1.29 (m, 2H, CH$_2$), 1.28 (s, 6H, 2CH$_3$), 1.00 (m, 2H, CH$_2$), 0.72 (t, J=7.3 Hz, 3H, CH$_3$); HRMS calcd. for C$_{26}$H$_{32}$O$_4$ 408.2301 (M$^+$), found 408.2300.

EXAMPLE 12

4-[(3-Butyloxy-5,6,7,8-tetrahydro-5,5,8,8-tetramethyl-2-naphthyl)ethenyl]benzoic acid (Compound 112, prepared as illustrated and described in Scheme 1 and Scheme 2)

4-[3-Butyloxy-5,6,7,8-tetrahydro-5,5,8,8-tetramethyl-2-naphthyl)carbonyl]benzoic acid methyl ester (from Example 11, 119 mg, 0.28 mmol) was converted to the ethenyl compound as described in Example 2 to afford, after recrystallization (CH$_2$Cl$_2$/hexanes) 4-[(3-butyloxy-5,6,7,8-tetrahydro-5,5,8,8-tetramethyl-2-naphthyl)ethenyl]benzoic acid methyl ester 43 mg (38%) as a pale yellow solid: $^1$H NMR (400 MHz, CDCl$_3$) δ7.94 (½ABq, J=8.4 Hz, 2H, ArH), 7.35 (½ABq, J=8.4 Hz, 2H, ArH), 7.18 (s, 1H, ArH), 6.72 (s, 1H, ArH), 5.64 (d, J=1.3 Hz, 1H, olefinic), 5.41 (d, J=1.3 Hz, 1H, olefinic), 3.90 (s, 3H, OCH3), 3.71 (t, J=6.2 Hz, 2H, OCH$_2$), 1.69 (m, 4H, 2CH$_2$), 1.30 (s, 6H, 2CH$_3$), 1.29 (m, 2H, CH$_2$), 1.27 (s, 6H, 2CH$_3$), 0.99 (m, 2H, CH$_2$), 0.71 (t, J=7.3 Hz, 3H, CH$_3$). The butyloxy ethenyl ester (43 mg, 0.10 mmol) was hydrolyzed with excess KOH in MeOH as described in Example 1 to give 4-[(3-butyloxy-5,6,7,8-tetrahydro-5,5,8,8-tetramethyl-2-naphthyl)ethenyl]benzoic acid (112) 32 mg (79%) as a white solid: mp 194–196° C.; $^1$H NMR (400 MHz, CDCl$_3$) δ8.01 (½ABq, J=8.4 Hz, 2H, ArH), 7.39 (½Abq, J=8.4 Hz, 2H, ArH), 7.20 (s, 1H, ArH), 6.73 (s, 1H, ArH), 5.66 (d, J=1.1 Hz, 1H, olefinic), 5.44 (d, J=1.1 Hz, 1H, olefinic), 3.72 (t, J=6.2 Hz, 2H, OCH$_2$), 1.70 (m, 4H, 2CH$_2$), 1.30 (s, 6H, 2CH$_3$), 1.28 (s, 6H, 2CH$_3$), 1.27 (m, 2H, CH$_2$), 0.97 (m, 2H, CH$_2$), 0.72 (t, J=7.4 Hz, 3H, CH$_3$); HRMS (EI$^+$, 70 ev) calcd. for C$_{27}$H$_{34}$O$_3$: 406.2508, found 406.2467.

EXAMPLE 13

4-[(3-Butyloxy-5,6,7,8-tetrahydro-5,5,8,8-tetramethyl-2-naphthyl)carbonyl]benzoic acid O-methyloxime (Compound 113, prepared as illustrated and described in Scheme 1 and Scheme 4)

4-[(3-butyloxy-5,6,7,8-tetrahydro-5,5,8,8-tetramethyl-2-naphthyl)carbonyl]benzoic acid (from Example 11) was converted to the O-methyloxime derivative as described in Example 8. Crystallization (hexanes/EtOAc) gave 4-[(3-butyloxy-5,6,7,8-tetrahydro-5,5,8,8-tetramethyl-2-naphthyl)carbonyl]benzoic acid O-methyloxime (113) 14 mg (100%) as a colorless film: $^1$H NMR (400 MHz, CDCl$_3$) δ8.06 and 7.55 (d of ABq, J=8.4 Hz, 4H, Ar—H), 7.40 (s, 1H, Ar—H), 6.98 (s, 1H, Ar—H), 3.99 (s, 3H, NOCH$_3$), 3.67 (t, J=6.1 Hz, 2H, OCH$_2$), 1.68 (s, 4H, 2CH$_2$), 1.31 (s, 6H, 2CH$_3$), 1.25 (s, 6H, 2CH$_3$), 1.24 (m, 2H, CH$_2$), 1.01 (m, 2H, CH$_2$), 0.90 (t, J=7.3 Hz, 3H, CH$_3$).

EXAMPLE 14

4-[(3-Hydroxy-5,6,7,8-tetrahydro-5,5,8,8-tetramethyl-2-naphthyl)carbonyl]benzoic acid oxime (Compound 114, prepared as illustrated and described in Scheme 1 and Scheme 3)

A solution of the 4-[(3-hydroxy-5,6,7,8-tetrahydro-5,5,8,8-tetramethyl-2-naphthyl)carbonyl]benzoic acid methyl ester (from Example 7, 433 mg, 1.18 mmol) in DMSO (2 mL) was treated with KOH (1.5 mmol) at 0° C. and allowed to warm to ambient temperature over 1 h. The yellow solution was cooled again to 0° C. and treated with a solution of bromohexane (156 mL, 1.30 mmol) in DMSO (1 mL) and allowed to warm to ambient temperature and stirred for 10 h. The reaction was quenched with saturated aqueous NH$_4$Cl. The aqueous solution was adjusted to pH=3 with 1M HCl and extracted with EtOAc, 3×. The organic layers were combined and washed with water (2×) and brine. The organic solution was dried (NaSO$_4$), filtered, and concentrated. Purification by silica gel radial chromatography (20:1=hexane:Et$_2$O) gave 4-[2-hexyloxy-5,6,7,8-tetrahydro-5,5,8,8-tetramethyl-2-naphthyl)carbonyl]benzoic acid, 317 mg (62%) as a colorless oil: $^1$H NMR (400 MHz, CDCl$_3$) δ8.14 (½ABq, J=8.4 Hz, 2H, ArH), 7.84 (½ABq, J=8.4 Hz, 2H, ArH), 7.47 (s, 1H, ArH), 6.81 (s, 1H, ArH), 3.80 (t, J=6.2 Hz, 2H, OCH$_2$), 1.17 (m, 4H, 2CH$_2$), 1.34 (m, 2H, CH$_2$), 1.32 (s, 6H, 2CH$_3$), 1.28 (s, 6H, 2CH$_3$), 1.11 (m, 4H, 2CH$_2$), 0.95 (m, 2H, CH$_2$), 0.80 (t, J=7.1 Hz, 3H, CH$_3$). The hexyloxyketo acid (87 mg, 0.19 mmol) in EtOH (2 mL) was converted into the oxime derivative as described in Example 4 to provide, after recrysallization (CH$_2$Cl$_2$/hexanes), 4-[(3-hexyloxy-5,6,7,8-tetrahydro-5,5,8,8-tetramethyl-2-naphthyl)carbonyl]benzoic acid oxime (114), 312 mg (60%) as a white solid: mp 197–199° C. (d); $^1$H NMR (400 MHz, CDCl$_3$) δ8.14 (½ABq, J=8.5 Hz, 2H, ArH), 7.57 (½ABq, J=8.5 Hz, 2H, ArH), 7.22 (s, 1H, ArH), 6.85 (s, 1H, ArH), 3.82 (t, J=6.3 Hz, 2H, OCH$_2$), 1.70 (m, 4H, 2CH$_2$), 1.45 (m, 2H, CH$_2$), 1.32 (s, 6H, 2CH$_3$), 1.25 (s, 6H, 2CH$_3$), 1.13 (m, 6H, 3CH$_2$), 0.80 (t, J=6.8 Hz, 3H, CH$_3$); 13C NMR (100 MHz, CDCl$_3$) δ155.7, 153.8, 147.8, 141.1, 137.0, 130.3, 129.9, 128.4, 127.0, 118.5, 110.0, 68.3, 35.3, 35.0, 34.8, 33.8, 31.9, 31.8, 31.4, 29.0, 25.4, 22.5, 13.9.

EXAMPLE 15

4[(3-Heptyloxy-5,6,7,8-tetrahydro-5,5,8,8-tetramethyl-2-naphthyl)carbonyl]benzoic acid oxime (Compound 115, prepared as illustrated and described in Scheme 1 and Scheme 3)

A solution of the 4-[(3-hydroxy-5,6,7,8-tetrahydro-5,5,8,8-tetramethyl-2-naphthyl)carbonyl]benzoic acid methyl acid methyl ester (from Example 7, 433 mg. 1.18 mmol) in DMSO (2 mL) was treated with KOH (1.5 mmol) at 0° C. and allowed to warm to ambient temperature over 1 h. The yellow solution was cooled again to 0° C., and treated with a solution of bromoheptane (174 mL, 1.30 mmol) in DMSO (1 mL) and allowed to warm to ambient temperature and stirred for 10 h. The reaction was quenched with saturated aqueous NH$_4$Cl. The aqueous solution was adjusted to pH=3 with 1M HCl and extracted with EtOAc, 3×. The organic layers were combined and washed with water (2×) and brine. The organic solution was dried (NaSO$_4$), filtered, and concentrated. Purification by silica gel radial chromatography (20:1 to 1:1=hexanes:Et$_2$O) gave 4-[(3-heptyloxy-5,6,7,8-tetrahydro-5,5,8,8-tetramethyl-2-naphthyl)carbonyl]benzoic acid 530 mg (99%) as a colorless solid: mp 154–158° C.; $^1$H NMR (400 MHz, CDCl$_3$) δ8.14 (½ABq, J=8.3 Hz, 2H, ArH), 7.84 (½ABq, J=8.3 Hz, 2H, ArH), 7.46 (s, 1H, ArH), 6.81 (s, 1H, ArH), 3.80 (t, J=6.2 Hz, 2H , OCH$_2$), 1.71 (m, 4H, 2CH$_2$), 1.35 (m, 2H, CH$_2$), 1.32 (s, 6H, 2CH$_3$), 1.28 (s, 6H, 2CH$_3$), 1.19 (m, 2H, CH$_2$), 1.08 (m, 4H, 2CH$_2$), 0.94 (m, 2H, CH$_2$), 0.83 (t, J=7.2 Hz, 3H, CH$_3$); HRMS calcd. for C$_{29}$H$_{38}$O$_4$ 451.2848 (MH$^+$), found 451.2818. The heptyloxyketo acid (30 mg, 0.07 mmol) in EtOH (1mL) was converted into the oxime derivative as described in Example 4 to provide, after recrystallization (CH$_2$Cl$_2$/hexanes), 4-[(3-heptyloxy-5,6,7,8-tetrahydro-5,5, 8,8-tetramethyl-2-naphthyl)carbonyl]benzoic acid oxime (115), 15 mg (46% as a white solid: mp 200–205°C.; $^1$H NMR (400 MHz, CDCl$_3$) δ7.97 (½ABq, J=7.7 Hz, 2H, ArH), 7.54 (½ABq, J=7.7 Hz, 2H, ArH), 7.16 (s, 1H, ArH), 6.87 (s, 1H, ArH), 3.83 (t, J=6.4 Hz, 2H, OCH$_2$), 1.71 (m, 4H, 2CH$_2$), 1.45 (m, 2H, CH$_2$), 1.32 (s, 6H, 2CH$_3$), 1.26 (s, 6H, 2CH$_3$), 1.20 (m, 2H, CH$_2$), 1.11 (m, 4H, 2CH$_2$), 0.89 (m, 2H, CH$_2$), 0.84 (t, J=7.0 Hz, 3H, CH$_3$); HRMS calcd. for C$_{29}$H$_{39}$NO$_4$ 466.2957 (MH$^+$), found 466.2930.

EXAMPLE 16

4-[(3-Heptyloxy-5,6,7,8-tetrahydro-5,5,8,8-tetramethyl-2-naphthyl)ethenyl]benzoic acid (Compound 116, prepared as illustrated and described in Scheme 1 and Scheme 2)

4-[3-Heptyloxy-5,6,7,8-tetrahydro-5,5,8,8-tetramethyl-2-naphthyl)carbonyl]benzoic acid (from Example 15, 150 mg, 0.32 mmol) was converted to the ethenyl compound as described in Example 2 to afford, after preparative silica gel TLC (1:1:1=hexanes:EtOAc:CH$_2$Cl$_2$+5% MeOH), 4-[(3-heptyloxy-5,6,7,8-tetrahydro-5,5,8,8-tetramethyl-2-naphthyl)ethenyl]benzoic acid (116), 45 mg (31%) as a white solid: mp 153–155° C.; $^1$H NMR (400 MHz, CDCl$_3$) δ8.01 (½ABq, J=8.3 Hz, 2H, ArH), 7.39 (½ABq, J=8.3 Hz, 2H, ArH), 7.20 (s, 1H, ArH), 6.72 (s, 1H, ArH), 5.67 (apparent s, 1H, olefinic), 5.43 (appparent s, 1H, olefinic), 3.71 (t, J=6.2 Hz, 2H, OCH$_2$), 1.70 (m, 4H, 2CH$_2$), 1.32 (m, 2H, CH$_2$), 1.30 (s, 6H, 2CH$_3$), 1.28 (s, 6H, 2CH$_3$), 1.22 (m, 2H, CH$_2$), 1.10 (m, 4H, 2CH$_2$), 0.93 (m, 2H, CH$_2$), 0.84 (t, J=7.2 Hz, 3H, CH$_3$); HRMS calcd. for C$_{30}$H$_{40}$O$_3$ 448.2978 (M$^+$), found 448.2948.

EXAMPLE 17 cis-4-[(3-Benzyloxy-5,6,7,8-tetrahydro-5,5,8,8-tetramethyl-2-naphthyl)carbonyl]benzoic acid oxime (Compound 117, prepared as illustrated and described in Scheme 1 and Scheme 3)

A solution of the 4-[(3-hydroxy-5,6,7,8-tetrahydro-5,5,8,8-tetramethyl-2-naphthyl)carbonyl]benzoic acid methyl ester (237 mg, 0.65 mmol) in DMF (1mL) was treated with NaH (0.68 mmol) at 0° C. and allowed to warm to ambient temperature over 1 h. The yellow solution was cooled again to 0° C., and treated with a solution of benzyl bromide (142 mg, 0.83 mmol) in DMF and allowed to warm to ambient temperature and stirred for 10 h. The reaction was quenched with saturated aqueous NH$_4$Cl. The aqueous solution was extracted with EtOAc, 3×. The organic layers were combined and washed with water (2×) and brine. The organic solution was dried (NaSO$_4$), filtered, and concentrated to give a colorless oil. Purification by silica gel flash chromatorgraphy (20:1=hexanes:EtOAc) gave 4-[3-benzyloxy-5,6,7,8-tetrahydro-5,5,8,8-tetramethyl-2-naphthyl)carbonyl] benzoic acid methyl ester 242 mg (82%) as a colorless oil: $^1$H NMR (400 MHz, CDCl$_3$) δ8.19 (½ABq, J=8.4 Hz, 2H, ArH), 7.81 (½ABq, J=8.4 Hz, 2H, ArH), 7.44 (s, 1H, ArH), 7.38 (m, 3H, ArH), 7.17 (m, 2H, ArH), 6.92 (s, 1H, ArH), 4.93 (s, 2H, OCH$_2$), 3.95 (s, 3H, OCH$_3$), 1.67 (m, 4H, 2CH$_2$), 1.29 (s, 6H, 2CH$_3$), 1.26(s, 6H, 2CH$_3$). The benzyloxy keto ester (204 mg, 0.46 mmol) in MeOH (2 mL) was treated with hydroxylamine hydrochloride (97 mg, 1.4 mmol) and KOH (156 mg, 2.8 mmol), and the mixture was heated at reflux for 3 h. After 6 h, the mixture was cooled to room temperature and the ethanol was removed in vacuo. The residue was taken-up in water and the aqueous layer was adjusted to pH=4–5 with 1 M aqueous HCl. The aqueous solution was extracted with EtOAc, 3×. The organic layers were combined and washed with water (2×) and brine. The organic solution was dried (Na$_2$SO$_4$), filtered, and concentrated to give a white foamy solid. Recrystallization (THF/hexanes) gave cis-4-[(3-benzyloxy-5,6,7,8-tetrahydro-5,5,8, 8-tetramethyl-2-naphthyl) carbonyl]benzoic acid oxime (117) 186 mg (88%) as a white solid: mp 199–205° C. (d); IR (neat) 3500–3100 (br) m, 2963 s, 2934 s, 1694 s, 1613 w, 1505 w, 1321 m, 1265 m, 1024 w cm$^{-1}$; $^1$H NMR (400 MHz, CDCl$_3$) δ8.00 (½ABq, J=8.4 Hz, 2H, ArH), 7.56 (½ABq, J=8.4 Hz, 2H, ArH), 7.20 (m, 3H, ArH), 7.15 (s, 1H, ArH), 7.08 (m, 2H, ArH), 6.91 (s, 1H, ArH), 4.96 (s, 2H, OCH$_2$), 1.69 (m, 4H, 2CH$_2$), 1.27 (s, 6H, 2CH$_3$), 1.24 (s, 6H, 2CH$_3$); HRMS (EI$^-$, 70 ev) calcd. for C$_{29}$H$_{31}$NO$_4$: 457.2253, found 457.2226; anal. calcd. for C$_{29}$H$_{31}$NO$_4$; C$_1$76.12; H$_1$ 6.83; N$_1$ 3.06, found C$_1$ 75.83; H$_1$ 6.95; N$_1$ 2.90.

EXAMPLE 18 trans-4-[(3-Benzyloxy-5,6,7,8-tetrahydro-5,5,8,8-tetramethyl-2-naphthyl)carbonyl]benzoic acid oxime (Compound 118, prepared as illustrated and described in Scheme 1 and Scheme 3)

The minor oxime isomer from the final product mixture of Example 17 was isolated by successive recrystallizations (CH$_2$Cl$_2$/hexanes) to give trans-4-[(3-benzyloxy-5,6,7,8-tetrahydro-5,5,8,8-tetramethyl-2-naphthyl)carbonyl] benzoic acid oxime (118) 21 mg (10%) as a white solid: mp220–222° C.(d); $^1$H NMR (400 MHz, CDCl$_3$) δ7.99 (½ABq, J=8.2 Hz, 2H, ArH), 7.56 (½ABq, J=8.2 Hz, 2H, ArH), 7.38 (s, 1H, ArH), 7.21 (m, 3H, ArH), 6.85 (m, 2H, ArH), 6.78 (s, 1H, ArH), 4.77 (s, 2H, OCH$_2$), 1.69 (m, 4H, 2CH$_2$), 1.30 (s, 6H, 2CH$_3$), 1.25 (s, 6H, 2CH$_3$).

EXAMPLE 19

(2E, 4E, 6E)-7-[3-Butyl-5,6,7,8-tetrahydro-5,5,8,8-tetramethyl-2-naphthalen-2-yl]-3-methylocta-2,4,6-trienoic acid (Compound 119, prepared as illustrated and described in Scheme 7)

A 200 mL round-bottomed flask equipped with stir bar and reflux condenser was charged with a solution of n-butylbenzene (14.7 g, 109 mmol, 17 mL) and 2,4-dichloro-2,4-dimethylhexane (10.0 g, 54.6 mmol) in dichloromethane (30 mL). Aluminum chloride (1.45 g, 10.9 mmol) was added slowly to the solution until the spontaneous reflux had subsided and the solution become dark red/brown in color. After stirring 10–15 min at room temperature, the reaction was poured into ice water (30 mL) and the layers were separated. The aqueous layer was extracted with EtOAc (5×20 mL). The combined organic extracts were washed with water and brine, dried (Na$_2$SO$_4$), filtered, and concentrated to give a yellow oil. Excess n-butylbenzene was removed by distillation at 1 mm Hg. The distillation residue corresponded to the product 6-butyl-1,2,3,4-tetrahydro-1,1,4,4-tetramethylnaphthalene 9.4 g (70%) as an opaque oil: $^1$H-NMR (400 MHz, CDCl$_3$) δ7.21 (d, J=8.6 Hz, 1H, Ar—H), 7.00 (d, J=2.0 Hz, 1H, Ar—H), 6.95 (dd, J=2.0, 8.6 Hz, 1H, Ar—H), 2.56 (t, 2H, CH$_2$), 1.67 (s, 4H, 2CH$_2$), 1.55 (m, 2H, CH$_2$), 1.35 (m, 2H, CH$_2$), 1.26 (s, 6H, 2CH$_3$), 1.25 (s, 6H, 2CH$_3$), 0.93 (t, 3H, CH$_3$).

A solution of the n-butyltetrahydronaphthalene adduct (2.09 g, 8.55 mmol) and acetylchloride (0.79 g, 9.40 mmol), 0.67 mL) in dichloromethane (10 mL) and hexanes (10 mL) was treated at room temperature with aluminum chloride (1.14 g, 8.55 mmol). The reaction solution was stirred at room temperature for 24 h and then poured into ice water (20 mL), and the layers were separated. The aqueous layer was extracted with EtOAc (3×20 mL) and the combined organic extracts were washed with water and brine, dried (Na$_2$SO$_4$), filtered, and concentrated to give the acylated product 1-(3-butyl-5,6,7,8-tetrahydro-5,5,8,8-tetramethylnaphthalen-2-yl)ethanone 2.46 g (100%) as an oil: $^1$H-NMR (400 MHz, CDCl$_3$) δ7.57 (s, 1H, Ar—H), 7.15 (s, 1H, Ar—H), 2.80 (t, 2H, CH$_2$), 2.56 (s, 3H, CH$_3$), 1.69 (s, 4H, 2CH$_2$), 1.55 (m, 2H, CH$_2$), 1.35 (m, 2H, CH$_2$), 1.26 (s, 6H, 2CH$_3$), 1.25 (s, 6H, 2CH$_3$), 0.93 (t, 3H, CH$_3$).

A flame-dried 50 mL round-bottomed flask equipped with N$_2$ bubbler, septa, and stir bar was charged with a 60% dispersion of NaH in mineral oil (0.515 g, 12.9 mmol). The NaH was rinsed free of mineral oil with hexanes (3×2 mL). THF (13 mL) was added, followed by the dropwise addition of diethyl cyanomethylphosphonate (3.04 g, 17.2 mmol, 2.82 mL) in THF (8 mL) at room temperature and the solution was stirred for 30 min. The acyl(N-butyl) naphthalene (2.46 g, 8.59 mmol) in THF (10 mL) was added dropwise via cannula to the yellow solution. The solution was stirred for 48 h and then concentrated. The residue was diluted with water (25 mL), and the mixture was extracted with EtOAc (3×20 mL). The combined organic extracts were washed with water and brine, dried (Na$_2$SO$_4$), filtered, and concentrated to give a dark brown/red oil which was purified by radial chromatography (9:1=hexanes:Et$_2$O) to give the product 3-(3-butyl-5,6,7,8-tetrahydro-5,5,8,8-tetramethylnaphthalen-2-yl) but-2-enenitrile 1.14 g (43%) as a yellow oil: $^1$H-NMR (400 MHz, CDCl$_3$) δ 7.12 (s, 1H, Ar-H), 6.92 (s, 1H, Ar-H), 5.23 (s, 1H, CH), 2.49 (t, 2H, CH$_2$), 2.37 (s, 3H, CH$_3$), 1.67 (s, 4H, 2CH$_2$), 1.53 (m, 2H, CH$_2$), 1.35 (m, 2H, CH$_2$), 1.27 (s, 6H, 2CH$_3$), 1.25 (s, 6H, 2CH$_3$), 0.93 (t, 3H, CH$_3$).

A round-bottomed flask equipped with N$_2$ bubbler, septa, and stir bar was charged with a solution of the cyano(n-butyl)naphthalene adduct (1:10 g, 3.71 mmol) in hexanes (5 mL) and toluene (5 mL). The solution was cooled to −78° C. and DIBAL (3.71 mL of a 1.0 M solution in toluene, 5.60 mmol) was added dropwise via syringe. After stirring for 1.5 h at −78° C., the solution was quenched with aqueous sodium-potassium tartrate solution (10 mL) and allowed to warm to room temperature over 30 min. The aqueous layer was acidified (1.0 M HCl to pH=4) and extracted with EtOAc (3×10 mL). The combined organic extracts were washed with water and brine, dried (Na$_2$SO$_4$), filtered, and concentrated to give the crude aldehyde. Purification by radial chromatography (5:1:0.5=hexanes:Et$_2$O:CH$_2$Cl$_2$) gave the aldehyde 3-(3-butyl-5,6,7,8-tetrahydro-5,5,8,8-tetramethylnaphthalen-2-yl) but-2-enal 0.911 g (82%) as a yellow solid as a mixture of trans:cis(5:1) isomers: $^1$H-NMR (trans isomer, CDCl$_3$) δ 10.23 (d, 1H, CHO), 7.13 (s, 1H, Ar-H) 6.96 (s, 1H, Ar-H), 5.98 (d, 1H, olefinic), 2.58 (t, 2H, CH$_2$), 2.50 (s, 3H, CH$_3$), 1.67 (s, 4H, 2CH$_2$), 1.53 (m, 2H, CH$_2$), 1.35 (m, 2H, CH$_2$), 1.27 (s, 6H, 2CH$_3$), 1.25 (s, 6H, 2CH$_3$), 0.93 (t, 3H, CH$_3$).

A flame-dried round-bottomed flask equipped with N$_2$ bubbler, septa, and stir bar was charged with a solution of diethyl 3-ethoxycarbonyl-2-methyl prop-2-enylphosphonate (0.417 g, 1.58 mmol, 0.39 mL) in THF (2.0 mL) and DMPU (0.7 mL). The solution was cooled to −78° C., and n-BuLi (0.96 mL of a 1.5 M solution in hexanes, 1.44 mmol) was added dropwise via syringe. The reaction mixture was warmed to 0° C. and stirred for 15 min. The red solution was then cooled to −78° C. and the above aldehyde (0.430 g, 1.31 mmol) was added dropwise via cannula. The solution was warmed to ambient temperature and gradually became a dark brown-reddish color. After stirring for 1.5 h, the reaction was quenched with water (15 mL), and the aqueous layer was extracted with EtOAc (3×10 mL). The combined organic extracts were washed with aqueous CuSO$_4$, water, and brine, dried (Na$_2$SO$_4$), filtered, and concentration to give the crude ester as an orange oil. The crude ester in MeOH (7 mL) was hydrolyzed with KOH (excess) at reflux temperature. After 4 h, the reaction was cooled to room temperature and quenched with 1M HCl (5 mL). The solution was concentrated, diluted with water (10 mL), and the aqueous layer was extracted with EtOAc (3×15 mL). The combined organic extracts were washed with water and brine, dried (Na$_2$SO$_4$), filtered, and concentrated to give the crude product as a mixture of geometric isomers (0.533 g, 94%) as a yellow oil. $^1$H-NMR indicated a 3:1 mixture of the trans to cis isomers. A sample of the product mixture was purified by radial chromatography (3:1:0.01= hexanes:Et$_2$O:MeOH) followed by preparative silica gel TLC (1% MeOH/CHCl$_3$) to give (2E, 4E, 6E)-7-[3-(butyl)- 5,6,7,8-tetrahydro-5,5,8,8-tetramethyl-2-naphthalen-2-yl]-3-methylocta-2,4,6-trienoic acid (119) as a yellow solid: $^1$H-NMR (400MHz, CDCl$_3$) δ 7.10 (s, 1H, Ar-H), 7.02 (dd, J=11.2, 15.2 Hz, 1H, olefinic), 6.97 (s, 1H, Ar-H), 6.28 (d, J=15.2 Hz, 1H, olefinic), 6.10 (d, J=11.2 Hz, 1H, olefinic), 5.82 (s, 1H, olefinic), 2.52 (t, J=7.9 Hz, 2H, CH$_2$), 2.40 (s, 3H, CH$_3$), 2.17 (s, 3H, CH$_3$), 1.67 (s, 4H, 2CH$_2$), 1.52 (m, 2H, CH$_2$), 1.34 (m, 2H, CH$_2$), 1.28 (s, 6H, 2CH$_3$), 1.26 (s, 6H, 2CH$_3$), 0.91 (t, J=7.3 Hz, 3H, CH$_3$).

EXAMPLE 20

(2Z, 4E, 6E)-7-[3-(Butyl)-5,6,7,8-Tetrahydro-5,5,8, 8-Tetramethyl-2-Naphthalen-2-yl]-3-Methylocta-2,4, 6-Trienoic Acid (Compound 120, Prepared as Illustrated and Described in Scheme 7)

The title compound was obtained from the final product mixture of Example 19 by radial chromatography (3:1:0.01= hexanes:Et$_2$O:MeOH) followed by preparative silica gel TLC (1% MeOH/CHCl$_3$) to give (2Z, 4E, 6E)-7-[3-(butyl)- 5,6,7,8-tetrahydro-5,5,8,8-tetramethyl-2-naphthalen-2-yl]-3-methylocta-2,4,6-trienoic acid (120) as a yellow solid: $^1$H-NMR (400MHz, CDCl$_3$) δ7.70 (d, J=15.4 Hz, 1H, olefinic), 7.08 (s, 1H, Ar-H), 7.00 (dd, J=11.3,15.4 Hz), 6.96 (s, 1H, Ar-H), 6.18 (d, J=11.3 Hz, 1H, olefinic), 5.30 (s, 1H, olefinic), 2.52 (t, J=8.0 Hz, 2H, CH$_2$), 2.16 (s, 3H, CH$_3$), 2.13 (s, 3H, CH$_3$), 1.66 (s, 4H, 2CH$_2$), 1.52 (m, 2H, CH$_2$), 1.33 (m, 2H, CH$_2$), 1.28 (s, 6H, 2CH$_3$), 1.25 (s, 6H, 2CH$_3$), 0.90 (t, J=7.3 Hz, 3H, CH$_3$).

EXAMPLE 21

(2E, 4E, 6E)-7-[3-Propoxy-5,5,8,8-Tetramethyl-5,6, 7,8-Tetrahydro-2-Naphthalen-2-yl]-3-Methylocta-2, 4,6-Trienoic Acid (Compound 121, Prepared as Illustrated and Described in Scheme 7)

A 200 mL round-bottomed flask equipped with stir bar was charged with a solution of phenol (10.2 g, 108 mmol)

and 2,4-dichloro-2,4-dimethylhexane (21.8 g, 119 mmol) in dichloromethane (50 mL) at 0° C. Aluminum chloride (1.44 g, 10.8 mmol) was added slowly to the solution until the spontaneous reflux had subsided and the solution became pale orange in color. After stirring 10–15 min at 0° C., the reaction was poured into ice water (30 mL) and the layers were separated. The aqueous layer was extracted with EtOAc (2×30 mL). The combined organic extracts were washed with water and brine, dried ($Na_2SO_4$), filtered, and concentrated to give a pale yellow/white solid. Recrystallization from hexanes gave the product 5,6,7,8-tetrahydro-5,5,8,8-tetramethylnaphthalen-2-ol 18.25 g (83%) as a white crystalline solid: $^1$H-NMR (400MHz, $CDCl_3$) δ 7.17 (d, J=8.5 Hz, 1H, Ar-H), 6.76 (d, J=3.0 Hz, 1Hz, Ar-H), 6.62 (dd, J=8.5 Hz, 3.0 Hz, 1H, Ar-H), 4.52 (s, 1H, OH), 1.65 (s, 4H, $2CH_2$), 1.26 (s, 6H, $2CH_3$), 1.24 (s, 6H, $2CH_3$).

A solution of the tetrahydronaphthol adduct (10.00 g, 49.0 mmol) and acetylchloride (4.62 g, 58.8 mmol, 4.18 mL) in dichloromethane (30 mL) was treated at room temperature with aluminum chloride (0.653 g, 4.90 mmol). The heterogenous reaction solution was stirred at room temperature for 15 min and because homogenous. Additional aluminum chloride (3.27 g, 25.0 mmol) was added portionwise and the reaction solution was heated to reflux; a final aliquot of aluminum chloride (3.27 g, 25.0 mmol) was added over 1 h until the solution became a dark red/brown. The solution was then poured into ice water and became yellow/orange. The aqueous layer was extracted with EtOAc (3×20 mL) and the combined organic extracts were washed with water and brine, dried ($Na_2SO_4$), filtered, and concentrated to give the acylated product 1-(3-hydroxy-5,6,7,8-tetrahydro-5,5,8,8-tetramethylnaphthalen-2-yl)ethanone 9.45 g (78%) as a white crystalline solid: $^1$H-NMR (400 MHz, $CDCl_3$) δ 7.66 (s, 1H, Ar-H), 6.89 (s, 1H, Ar-H), 2.61 (s, 3H, $CH_3$), 1.68 (s, 4H, $2CH_2$), 1.29 (s, 6H, $2CH_3$), 1.27 (s, 6H, $2CH_3$).

Potassium hydroxide (pellets, 0.036 g, 0.634 mmol) was added to a solution of the ketotetrahydronaphthol adduct (0.104 g, 0.423 mmol) in DMSO (5 mL) at room temperature. The reaction solution was stirred for 30 min and became brown. Bromopropane (0.073 g, 0.592 mmol, 0.054 mL) was added dropwise at room temperature. The solution was stirred for an additional 15 min and became orange. Water was added and the aqueous layer was extracted with EtOAc (3×20 mL). The combined organic extracts were washed with water and brine, dried ($Na_2SO_4$), filtered, and concentrated to give the crude ether. Crystallization from EtOAc/hexanes gave 1-(3-propoxy-5,6,7,8-tetrahydro-5,5,8,8-tetramethylnaphthalen-2-yl)ethanone 0.122 g, (100%) as a clear cyrstalline solid: $^1$H-NMR (400MHz, $CDCl_3$) δ 7.74 (s, 1H, Ar-H), 6.81 (s, 1H, Ar-H), 4.00 (t, J=6.3 Hz, 2H, $OCH_2$), 2.62 (s, 3H, $CH_3$), 1.86 (m, 2H, $CH_2$), 1.67 (s, 4H, $2CH_2$), 1.29 (s, 6H, $2CH_3$), 1.26 (s, 6H, $2CH_3$), 1.08 (t, J=7.5 Hz, 3H, $CH_3$).

The above propoxyketone (0.120 g, 0.416 mmol) and diethyl cyanomethylphosphonate (0.258 g, 1.46 mmol, 0.236 mL) were condensed as described for Example 19. Aqueous work-up afforded a dark brown/orange oil which was purified by flash chromatography (9:1=hexanes:EtOAc) to give the product 3-(3-propoxy-5,5,8,8-tetramethyl-5,6,7,8-tetrahydro-naphthalen-2-yl) but-2-enenitrile 0.106 g (78%) as a yellow oil: $^1$H-NMR (400 MHz, $CDCl_3$) δ 7.10 (s, 1H, Ar-H), 6.78 (s, 1H, Ar-H), 5.61 (s, 1H, olefinic) 3.92 (t, J=6.4 Hz, 2H, $OCH_2$), 2.44 (s, 3H, $CH_3$), 1.81 (m, 2H, $CH_2$), 1.67 (s, 4H, $2CH_2$), 1.28 (s, 6H, $2CH_3$), 1.25 (s, 6H, $2CH_3$), 1.04 (t, J=7.4 Hz, 3H, $CH_3$).

The cyano(n-propoxyl)naphthalene adduct (0.100 g, 0.307 mmol) was reduced with DIBAL (0.614 mL of a 1.0 M solution in hexanes. 0.641 mmol) ad described for Example 19. Aqueous work-up followed by radial chromatography (9:1=hexanes:$Et_2O$) gave the aldehyde of 3-(3-propoxy-5,5,8,8-tetramethyl-5,6,7,8-tetrahydro-naphthalen-2-yl) but-2-enal 0.093 g (92%) as a yellow solid as a mixture of trans:cis (5:1) isomers: $^1$H-NMR (trans isomer, 400 MHz, $CDCl_3$) δ 10.16 (d, 1H, CHO), 7.09 (s, 1H, Ar-H), 6.79 (s, 1H, Ar-H), 6.14 (d, J=7.9 Hz, 1H, olefinic), 3.93 (t, J=6.4 Hz, 2H, $CH_2$), 2.56 (s, 3H, $CH_3$), 1.81 (m, 2H, $CH_2$), 1.67 (s, 4H, $2CH_2$), 1.29 (s, 6H, $2CH_3$), 1.03 (t, J=7.4 Hz, 3H, $CH_3$).; $^1$H-NMR (cis isomer, 400 MHz, $CDCl_3$) δ 9.38 (d, 1H, CHO), 6.98 (s, 1H, Ar-H), 6.79 (s, 1H, Ar-H), 6.08 (d, 1H, olefinic), 3.91 (t, 2H, $CH_2$), 2.29 (s, 3H, $CH_3$), 1.81 (m, 2H, $CH_2$), 1.61 (s, 4H, $2CH_2$), 1.24 (s, 6H, $2CH_3$), 1.23 (s, 6H, $2CH_3$), 1.01 (t, 3H, $CH_3$).

The above aldehyde (0.090 g, 0.274 mmol) and diethyl 3-ethoxycarbonyl-2-methyl prop-2-enylphosphonate (0.181 g, 0.685 mmol, 0.168 mL) were condensed as described for Example 19. Aqueous work-up afforded the ester (0.121 g, 100%) as a yellow oil. Hydrolysis of the crude ester (0.121 g, 0.282 mmol) and aqueous work-up gave the acids as a mixture of geometric isomers (1.06 g, 94%) as a yellow solid. Recrystallization from EtOAc/hexanes gave (2E, 4E, 6E)-7-[3-propoxy-5,5,8,8-tetramethyl-5,6,7,8-tetrahydro-2-naphthalen-2-yl]-3-methylocta-2,4,6-trienoic acid (121) as a yellow solid: $^1$H-NMR (400 MHz, $CDCl_3$) δ 7.09 (s, 1H, Ar-H), 6.62 (dd, J=15.3, 10.9 Hz, 1H, olefinic), 6.75 (s, 1H, Ar-H), 6.32 (d, J=15.2 Hz, 2H olefinic), 6.32 (d, J=10.9 Hz, 2H, olefinic), 5,81 (s, 1H, olefinic), 3.90 (t, J=6.51 Hz, $OCH_2$), 2.40 (s, 3H, $CH_3$), 2.24 (s, 3H, $CH_3$), 1.79 (m, 2H, $CH_2$), 1.67 (s, 4H, $2CH_2$), 1.29 (s, 6H, $2CH_3$), 1.27 (s, 6H, $2CH_3$), 1.03 (t, J=7.5 Hz, 3H, $CH_3$).

EXAMPLE 22

(2E, 4E, 6Z)-7-[3-Propoxy-5,5,8,8-Tetramethyl-5,6,7,8-Tetrahydro-2-Naphthalen-2-yl]-3-Methylocta-2,4,6-Trienoic Acid (Compound 122, Prepared as Illustrated and Described in Scheme 8)

Phosphorous oxychloride (0.234 g, 0.142 mL, 1.52 mmol) was added dropwise to DMF (4 mL) at room temperature under a nitrogen atmosphere. The solution was stirred for 30 min. The 1-(3-propoxy-5,6,7,8-tetrahydro-5,5,8,8-tetramethylnaphthalen-2-yl)ethanone, (prepared as described in Example 21, 0.110 g, 0.381 mmol) was added quickly (in one portion) to the orange solution and the reaction solution was heated to 60° C. and stirred for 12 h. The dark brown solution was poured into ice water and the aqueous layer was adjusted to pH 7 with solid $NaHCO_3$. EtOAc extraction afforded the crude product, the chloro enal, 0.128 g, as an orange/brown oil. To a 80° C. solution of NaOH (0.061 g, 1.52 mmol) in dioxane: $H_2O$ (3:2; 20 mL) was added the crude chloro enal in a dioxane:water solution (3:2; 5 mL) in one portion and the yellow reaction solution was stirred at 80° C. for 2 h. The resulting orange reaction solution was cooled to room temperature and poured into brine and extracted with EtOAc. The organic solution was dried ($MgSO_4$), filtered, and concentrated to afford an orange oil which was purified by radial chromatography (10:1=Hex:EtOAc) to give the product 6-ethynyl-1,1,4,4-tetramethyl-7-propoxy-1,2,3,4-tetrahydronapthalene 0.040 g (39%) as a yellow oil: $^1$H-NMR (400 MHz, $CDCl_3$) δ 7.38 (s, 1H, Ar-H), 6.76 (s, 1Hz, Ar-H), 3.98 (t, J=6.6 Hz, 2H, $OCH_2$), 3.19 (s, 1H, CH), 1.83 (m, 2Hz, $CH_2$), 1.66 (m, 2H, $2CH_2$), 1.26 (s, 6H, $2CH_3$), 1.24 (s, 6H, $2CH_3$), 0.93 (t, J=7.4 Hz, 3H, $CH_3$).

Ethyl magnesium bromide (3.33 mL of a 1.0 M solution in THF, 3.32 mmol) was added dropwise to a room temperature solution of the acetylene ether (0.450 g, 1.66 mmol) in THF (10 mL). The solution was heated to reflux for 6 h and then cooled to room temperature. Phenyl cyanate (0.40 g, 0.50 mL, 3.33 mmol) was added neat to the reaction solution and reflux continued for an additional 2 h. The reaction solution was cooled to room temperature and quenched with a saturated ammonium chloride solution. Aqueous workup followed by radial chromatography (20:1= hexanes:EtOAc) afforded the product 3-(5,5,8,8-tetramethyl-3-propoxy-5,6,7,8-tetrahydronaphthalen-2-yl)-propynenitirle 0.393 g (80%) as a yellow solid: $^1$H-NMR (400 MHz, CDCl$_3$) δ 7.44 (s, 1H, Ar-H), 6.78 (s, 1H, Ar-H), 3.97 (t, J=6.5 Hz, 2H, OCH$_2$), 1.83 (m, 2H, CH$_2$), 1.67 (m, 2Hz, 2CH$_2$), 1.27 (s, 6H, 2CH$_3$), 1.24 (s, 6H, 2CH$_3$), 1.03 (t, J=7.3 Hz, 3H CH$_3$).

A flame dried flask was charged with a suspension of copper (I) iodide (0.057 g, 0.298 mmol) in THF (5 mL); the mixture was stirred at 0° C. under a nitrogen atmosphere. Methyl lithium (0.43 mL of a 1.4 M solution in ether, 0.596 mmol) was added dropwise and the solution colorless solution. The solution was cooled to −78° C. and became a yellow/brown color. The acetylene nitrile (0.040 g, 0.135 mmol) in THF (3.0 mL) was added dropwise and the solution was stirred at −78° C. for 45 min and then quenched with MeOH (5 mL). An aqueous workup afforded the cis-alkene nitrile 3-(3-propoxy-5,5,8,8-tetramethyl-5,6,7,8-tetrahydro-naphthalen-2-yl) but-2-enenitrile 0.040 g (97%) as a yellow oil: $^1$H-NMR (400 MHz, CDCl$_3$) δ 7.19 (s, 1H, Ar-H), 6.78 (s, 1H, Ar-H), 5.35 (s, 1H, olefinic), 3.92 (t, J=6.4 Hz, 2H, OCH$_2$), 2.27 (s, 3H, CH$_3$), 1.79 (m, 2H, CH$_2$), 1.67 (s, 2H, 2CH$_2$), 1.28 (s, 6H, 2CH$_3$), 1.27 (s, 6H, 2CH$_3$), 1.02 (t, J=7.4 Hz, 3H, CH$_3$).

The above cis-alkene was reduced with DIBAL as described in Example 19 to afford cis-3-(3-propoxy-5,5,8,8-tetramethyl-5,6,7,8-tetrahydro-naphthalen-2-yl)but-2-enal as a yellow oil: $^1$H-NMR (400 MHz, CDCl$_3$) δ 9.36 (d, J=8.4 Hz, 1H, CHO), 6.99 (s, 1H, Ar-H), 6.79 (s, 1H, Ar-H), 6.09 (s, J=8.4 Hz, 1H, olefinic), 3.90 (t, J=6.5 Hz, 2H, OCH$_2$), 2.29 (s, 3H, CH$_3$), 1.76 (m, 2H, CH$_2$), 1.68 (s, 2H, 2CH$_2$), 1.30 (s, 6Hz, 2CH$_3$), 1.24 (s, 6H, 2CH$_3$), 1.00 (t, J=7.4 Hz, 3H, CH$_3$).

The above cis-alkenal was converted into the title compound by the produce described in Example 19. The cis-triene acid was purified by recrystallization to give (2E, 4E, 6Z)-7-[5,5,8,8-tetramethyl-3-propoxy-5,6,7,8-tetrahydro-2-naphthalen-2-yl]-3-methylocta-2,4,6-trienoic acid (122) as a pale yellow solid: mp 177–179° C.; $^1$H-NMR (400 MHz, CDCl$_3$) δ 6.95 (s, 1H, Ar-H), 6.79 (s, 1H, Ar-H), 6.62 (dd, J=15.3, 11.0 Hz, 1H, oelfinic), 6.22 (appp br d, 2xolefinic), 5.76 (s, 1H, olefinic), 3.89 (t, J=6.5 Hz, 2H, OCH$_2$), 2.19 (s, 3H, CH$_3$), 2.13 (s, 3H, CH$_3$), 1.77 (m, 2H, CH$_2$), 1.68 (s, 4H, 2CH$_2$), 1.30 (s, 6Hz, 2CH$_3$), 1.23 (s, 6H, 2CH$_3$), 1.01 (t, J=7.4 Hz, 3H CH$_3$).

EXAMPLE 23

(2Z, 4E, 6E)-7-(3-Ethoxy-5,6,7,8-Tetrahydro-5,5,8,8-Tetramethyl-2-Naphthalen-2-yl)-3-Methylocta-2,4,6-Trienoic Acid (Compound 123, Prepared as Illustrated and Described in Scheme 7)

1-(3-hydroxy-5,6,7,8-tetrahydro-5,5,8,8-tetramethylnaphthalen-2-yl)ethanone (3.00 g, 12.3 mmol) in DMSO was alkylated with ethyl iodide (2.00 g, 12.9 mmol) as described in Example 21 to give 1-(3-ethoxy-5,6,7,8-tetrahydro-5,5,8,8-tetramethylnaphthalen-2-yl(ethanone 3.0 g (88%) as a yellow solid: $^1$H NMR (400 MHz, CDCl$_3$) δ 7.72 (s, 1H, ArH), 6.81 (s, 1H, ArH), 4.21 (q, 2H, OCH$_2$), 2.60 (s, 3H, CH$_3$), 1.67 (m, 4H, 2CH$_2$), 1.45 (t, 3H, CH$_3$), 1.28 (s, 6Hz, 2CH$_3$), 1.26 (s, 6H, 2CH$_3$).

The above ketone (3.0 g, 11.0 mmol) was condensed with diethyl cyanomethylphosphonate (2.9 g, 16.5 mmol) as described in Example 19 to give 3-(3-ethoxy-5,6,7,8-tetrahydro-5,5,8,8-tetramethylnaphthalen-2-yl)but-2-enenitrile 2.9 g (93%) as a yellow solid: $^1$H NMR (400 MHz, CDCl$_3$) δ 7.10 (s, 1H, ArH), 6.77 (s, 1H, ArH), 5.62 (s, 1H, olefinic), 4.05 (q, 2H, OCH$_2$), 2.45 (s, 3H, CH$_3$), 1.67 (m, 4H, 2CH$_2$), 1.42 (t, 3H, CH$_3$), 1.26 (s, 6H, 3CH$_3$), 1.24 (d, 6H, 3CH$_3$).

The nitrile olefin (2.8 g, 10.0 mmol) was readily reduced with DIBAL (15.0 mL of a 1.0 M solution in hexanes, 15.0 mmol) as described in Example 19 to yield the aldehyde 3-(3-ethoxy-5,6,7,8-tetrahydro-5,5,8,8-tetramethylnaphthalen-2-yl)but-2-enal 2.8 g (98%) as an orange solid: $^1$H NMR (400 MHz, CDCl$_3$) δ 10.15 (d, 1H, CHO), 7.10 (s, 1H, ArH), 6.80 (s, 1H, ArH), 6.15 (d, 1H, oelfinic), 4.05 (q, 2H, OCH), 2.55 (s, 3H, CH$_3$), 1.67 (m, 4H, 2CH$_2$) 1.42 (t, 3H, CH$_3$), 1.26 (s, 6H, 3CH$_3$), 1.24 (d, 6H, 3CH$_3$).

The above aldehyde (5.3 g, 20.00 mmol) was condensed with diethyl 3-ethoxycarbonyl-2-methyl prop-2-enylphosphonate as described in Example 19 to yield, after silica gel chromatography, the triene ester (2Z, 4E, 6E)-7-(3-ehtoxy-5,6,7,8-tetrahydro-5,5,8,8-tetramethyl-2-naphthalen-2-yl)-3-methylocta-2,4,6-trienoic acid ehtyl ester 3.3 g (83%) as an orange oil: $^1$H NMR (400 MHz, CDCl$_3$) δ 7.80 (s, 1H, olefinic), 7.10 (s, 1H, ArH), 6.83 (d, 1H, olefinic), 6.77 (s, 1H, ArH), 6.40 (d, 1H, olefinic), 5.67 (s, 1H, olefinic), 4.15 (q, 2H, OCH$_2$), 4.03 (q, 2H, OCH$_2$), 2.24 (s, 3H, CH$_3$), 2.10 (s, 3H, CH$_3$), 1.67 (br s, 4H, 2CH$_2$), 1.38 (t, 3H, CH$_3$), 1.28 (t, 3H, CH$_3$), 1.26 (s, 6H, 3CH$_3$), 1.24 (d, 6H, 3CH$_3$).

The ester (2.8 g, 7.0 mmol) was hydrolyzed using the standard conditions of Example 19 to yield after HPLC purification the title acid (2Z, 4E, 6E)-7-(3-ethoxy-5,6,7,8-tetrahydro-5,5,8,8-tetramethyl-2-naphthalen-2-yl)-3-methylocta-2,4,6-trienoic acid (123) 2.5 g (93%) as a light yellow solid: $^1$H NMR (400 MHz, CDCl$_3$) δ 7.75 (d, 1H, olefinic), 7.10 (s, 1H, ArH), 7.05 (dd, 1H, olefinic), 6.70 (s, 1H, ArH), 6.38 (d, 1H, olefinic), 5.67 (s, 1H, olefinic), 4.02 (q, 2H, OCH$_2$), 2.23 (s, 3H, CH$_3$), 2.13 (s, 3H, CH$_3$), 1.67 (br s, 4H, 2C$_2$), 1.40 (t, 3H, CH$_3$), 1.28 (s, 6H, 3CH$_3$), 1.25 (d, 6H, 3CH$_3$).

EXAMPLE 24

(2E, 4E, 6Z)-7-[3-Hexyloxy-5,6,7,8-Tetrahydro-5,5,8,8-Tetramethyl-2-Naphthalen-2-yl]-3-Methylocta-2,4,6-Trienoic Acid (Compound 124, Prepared as Illustrated and Described in Scheme 7)

1-(3-Hydroxy-5,6,7,8-tetrahydro-5,5,8,8-tetramethylnaphthalen-2-yl)ethanone (0.103 g, 0.418 mmol) in DMSO (1 mL) was alkylated with bromohexane (0.097 g, 0.585 mmol, 0.082 mL) as described in Example 21. Aqueous workup gave 1(3-hexyloxy-5,6,7,8-tetrahydro-5,5,8,8-tetramethylnaphthalen-2-yl)ethanone 0.161 g (100% crude) as an orange oil: $^1$H-NMR (400 MHz, CDCl$_3$) δ 7.74 (s, 1H, Ar-H), 6.82 (s, 1H, Ar-H), 4.02 (t, J=6.4 Hz, 2H, OCH$_2$), 2.61 (s, 3H, CH$_3$), 1.83 (m, 2H, CH$_2$), 1.67 (app br d, 4H, 2CH$_2$), 1.50 (m, 2H, CH$_2$), 1.36 (m, 4H, 2CH$_2$), 1.29 (s, 6H, 2CH$_3$), 1.26 (s, 6H, 2CH$_3$), 0.91 (t, J=7.0 Hz, 3H, CH$_3$).

The above heloxyketone (0.160 g, 0.484 mmol) was condensed with diethyl cyanomethylphosphonate (0.172 g, 0.968 mmol, 0.157 mL) as described for Example 19. Aqueous work-up afforded the crude product 3-(3-heloxy-5,6,7,8-tetrahydro-5,5,8,8-tetramethylnaphthalen-2yl)but-2-enenitrile 0.211 g (123%) as a dark brown oil: $^1$H-NMR (400 MHz, CDCl$_3$) δ 7.11 (s, 1H, Ar-H), 6.80 (s, 1H, Ar-H), 5.62 (s, 1H, olefinic), 3.96 (t, J=6.4 Hz, 2H, OCH$_2$), 2.45 (s, 3H, CH$_3$), 1.79 (m, 2H, CH$_2$), 1.68 (s, 4H, 2CH$_2$), 1.47 (m, 2H, CH$_2$), 1.35 (m, 4H, 2CH$_2$), 1.30 (s, 6H, 2CH$_3$), 1.26 (s, 6H, 2CH$_3$), 0.93 (t, J=6.87 Hz, 3H, CH$_3$).

The cyano(n-hexyloxy)naphthalene adduct (0.211 g, 0.597 mmol) was readily reduced with DIBAL (1.80 mL of a 1.0 M solution in hexanes, 1.80 mmol) as described for Example 19. Aqueous work-up gave the aldehyde 3-(3-hexyloxy-5,6,7,8-tetrahydro-5,5,8,8-tetramethylnaphthalen-2-yl)but-2-enal 0.162 g (76%) as a yellow oil (mixture of trans:cis=4:1) isomers: $^1$H-NMR (trans isomer, CDCl$_3$) δ 10.13 (d, J=8.2 Hz, 1H, CHO), 7.08 (s, 1H, Ar-H), 6.78 (s, 1H, Ar-H), 6.13 (d, J=8.0 Hz, 1H, olefinic), 3.96 (t, J=6.4 Hz, 2H, OCH$_2$), 2.55 (s, 3H, CH$_3$), 1.77 (m, 2H, CH$_2$), 1,67 (s, 4H, 2CH$_2$), 1.45 (m, 2H, CH$_2$), 1.33 (m, 4H, 2CH$_2$), 1.29 (s, 6H, 2CH$_3$), 1.25 (s, 6H, 2CH$_3$), 0.90 (m, 3H, CH$_3$); $^1$H-NMR (cis isomer, 400 MHz, CDCl$_3$) δ 9.34 (d, 1H, CHO), 6.98 (s, 1H, Ar-H), 6.78 (s, 1H, Ar-H), 6.08 (d, 1H, olefinic), 3.94 (t, 2H, OCH$_2$), 2.28 (s, 3H, CH$_3$), 1.65 (m, 2H, CH$_2$), 1.62 (s, 4H, 2CH$_2$), 1.42 (m, 2H, CH$_2$), 1.32 (m, 4H, 2CH$_2$), 1.29 (s, 6H, 2CH$_3$), 1.22 (s, 6H, 2CH$_3$), 0.90 (m, 3H, CH$_3$).

The above aldehyde (0.097 g, 0.272 mmol) and diethyl 3-ethoxycarbonyl-2-methyl prop-2-enylphosphonate (0.180 g, 0.680 mmol, 0.167 mL) were condensed as described for Example 19. Aqueous work-up afforded the ester (0.117 g, 94%) as a yellow oil. Standard hydrolysis of the crude ester (0.117 g, 0.256 mmol) followed by the typical aqueous work-up gave the acid as a mixture of geometric isomers (0.110 g, 100%) as an orange oil. A sample of the product mixture was purified by reverse phase HPLC (90% MeOH/10% 1 mM NH$_4$OAc with 0.5% AcOH) to give (2E, 4E, 6Z)-7-[3-hexyloxy-5,6,7,8-tetrahydro-5,5,8,8-tetramethyl-2-naphthalen-2-yl]-3-methylocta-2,4,6-trienoic acid (124) as a yellow oil: $^1$H-NMR (400MHz, CDCl$_3$) δ 6.95 (s, 1H, Ar-H), 6.79 (s, 1H, Ar-H), 6.63 (dd, J=10.9, 15.4 Hz, 1H, olefinic.), 6.23 (appp br d, 2H, 2×olefinic), 5.74 (s, 1H, olefinic), 3.92 (t, J=6.48, 2H, OCH$_2$), 2.19 (s, 3H, CH$_3$), 2.14 (s, 3H, CH$_3$), 1.74 (m, 2H, CH$_2$), 1.68 (s, 4H, 2CH$_2$), 1.42 (m, 2H, CH$_2$), 1.30 (s, 6H, 2CH$_3$), 1.29 (m, 4H, 2CH$_2$), 1.23 (s, 6H, 2CH$_3$), 0.88 (m, 3H, CH$_3$).

EXAMPLE 25

(2E, 4E, 6E)-7-[3-Hexyloxy-5,6,7,8-Tetrahydro-5,5,8,8-Tetramethyl-2-Naphthalen-2-yl]-3-Methylocta-2,4,6-Trienoic Acid (Compound 125, Prepared as Illustrated and Described in Scheme 7)

The final product mixture from Example 24 was purified by reverse phase HPLC (85% MeOH/15% 1 mM NH$_4$OAc with 0.5% AcOH) to give the title compound (2E, 4E, 6E)-7-[3-hexyloxy-5,6,7,8-tetrahydro-5,5,8,8-tetramethyl-2-naphthalen-2-yl]-3-methylocta-2,4,6-trienoic acid (125) as a yellow oil: $^1$H-NMR (400 MHz, CDCl$_3$) δ 7.08 (s, 1H, Ar-H), 7.06 (dd, J=11.4, 15.0 Hz, 1H, olefinic.), 6.75 (s, 1H, Ar-H), 6.32 (d, J=15.0 Hz, 1H, olefinic), 6.31 (d, J=11.4 Hz, 1H, olefinic), 5.83 (s, 1H, olefinic), 3.93 (t, J=6.4 Hz, 2H, OCH$_2$), 2.39 (s, 3H, CH$_3$), 2.24 (s, 3H, CH$_3$), 1.76 (m, 2H, CH$_2$), 1.67 (s, 4H, 2CH$_2$), 1.45 (m, 2H, CH$_2$), 1.32 (m, 4H, 2CH$_2$), 1.29 (s, 6H, 2CH$_3$), 1.27 (s, 6H, 2CH$_3$), 0.90 (m, 3H, CH$_3$).

EXAMPLE 26

(2E, 4E, 6E)-7-[3-(3-Hethylbut-2-enlay)-5,6,7,8-Tetrahydro-5,5,8,8-Tetramethyl-2-Naphthalen-2-yl]-3-Methylocta-2,4,6-Trienoic Acid (Compound 126, Prepared as Illustrated and Described in Scheme 7)

1-(3-Hydroxy-5,6,7,8-tetrahydro-5,5,8,8-tetramethylnaphthalen-2-yl)-ethanone (0.125 g, 0.507 mmol) in DMSO (1 mL) was alkylated with 4-bromo-2-methyl-2-butene (0.106 g, 0.710 mmol, 0.082 mL) as described in Example 21. Aqueous workup gave 1-[3-(3-methylbut-2-enyloxy)-5,6,7,8-tetrahydro-5,5,8,8-tetramethylnaphthalen-2-yl]ethanone 0.201 g (100% crude) as a clear yellow crystalline solid: $^1$H-NMR (400 MHz, CDCl$_3$) δ 7.72 (s, 1H, Ar-H), 6.83 (s, 1H, Ar-H), 5,48 (m, 1H, olefinic), 4.59 (d, J=6.6 Hz, 2H, OCH$_2$), 2.60 (s, 3H, CH$_3$), 1.79 (s, 3H, CH$_3$), 1.76 (s, 3H, CH$_3$), 1.67 (appp d, J=2.7 Hz, 4H, 2CH$_2$), 1.28 (s, 6H, 2CH$_3$), 1.26 (s, 6H, 2CH$_3$).

The above prenyloxyketone (0.160 g, 0.509 mmol) and diethyl cyanomethylphosphonate (0.315 g, 1.78 mmol, 0.288 mL) were condensed as described for Example 19. Aqueous work-up afforded the crude product 3-[3-(3-methylbut-2-enyloxy)-5,6,7,8-tetrahydro-5,5,8,8-tetramethylnaphthalen-2-yl]but-2-enenitrile 0.207 g as a yellow oil: $^1$H-NMR (400 MHz, CDCl$_3$) δ 7.10 (s, 1H, Ar-H), 6.80 (s, 1H, Ar-H), 5.62 (s, 1H, olefinic), 5.42 (m, 1H, olefinic), 4.51 (d, J=6.5 Hz, 2H, OCH$_2$), 2.43 (s, 3H, CH$_3$), 1.79 (s, 3H, CH$_3$), 1.74 (s, 3H, CH$_3$), 1.67 (s, 4H, 2CH$_2$), 1.28 (s, 6H, 2CH$_3$), 1.25 (s, 6H, 2CH$_3$).

The cyanoprenyloxynaphthalene adduct (0.207 g, 0.636 mmol) was readily reduced with DIBAL (1.91 mL of a 1.0 M solution in hexanes, 1.91 mmol) as described for Example 19. Aqueous work-up gave the aldehyde 3-[3-(3-methylbut-2-enyloxy)-5,6,7,8-tetrahydro-5,5,8,8-tetramethylnaphthalen-2-yl]but-2-enal 0.168 g as a crude yellow oil: $^1$H-NMR (trans isomer, CDCl$_3$) δ 10.14 (d, J=8.2 Hz, 1H, CHO), 7.09 (s, 1H, Ar-H), 6.80 (s, 1H, Ar-H), 6.13 (d, J=8.2 Hz, 1H, olefinic), 5.43 (m, 1H, olefinic), 4.52 (m, 2H, OCH$_2$), 2.54 (s, 3H, CH$_3$), 1.78 (s, 3H, CH$_3$), 1.74 (s, 3H, CH$_3$), 1.68 (s, 4H, 2CH$_2$), 1.29 (s, 6H, 2CH$_3$), 1.26 (s, 6H, 2CH$_3$).

The above aldehyde (0.168 g, 0.493 mmol) and diethyl 3-ethoxycarbonyl-2-methyl prop-2-enylphosphonate (0.326 g, 1.23 mmol, 0.302 mL) were condensed as described for Example 19. Aqueous work-up afforded the crude ester as a yellow oil. Standard hydrolysis of the ester (0.201 g, 0.467 mmol) and aqueous work-up gave the acid as a mixture of geometric isomers (0.172 g, 87%) as an orange oil. A sample of the product mixture was purfied by reverse phase HPLC (90% MeOH/10% 1 mM NH$_4$OAc with 0.5% AcOH) to give (2E, 4E, 6E)-7-[3-(3-methylbut-2-enyloxy)-5,6,7,8-tetrahydro-5,5,8,8-tetramethyl-2-naphthalen-2-yl]-3-methylocta-2,4,6-trienoic acid (126) as a yellow oil: $^1$H-NMR ((2E, 4E, 6E)-isomer, 400MHz, CDCl$_3$) δ 7.08 (s, 1H, Ar-H), 7.06 (dd, J=11.2, 15.1 Hz, 1H, olefinic.), 6.77 (s, 1H, Ar-H), 6.30 (dd, J=8.3, 15.1 Hz, 1H, olefinic), 5.81 (s, 1H, olefinic), 5.44 (m, 1H, olefinic), 4.50 (d, J=6.6 Hz, 2H, OCH$_2$), 2.39 (s, 3H, CH$_3$), 2.23 (s, 3H, CH$_3$), 1.77 (s, 3H, CH$_3$), 1.72 (s, 3H, CH$_3$), 1.67 (s, 4H, 2CH$_2$), 1.28 (s, 6H, 2CH$_3$), 1.27 (s, 6H, 2CH$_3$).

EXAMPLE 27

(2E, 4E, 6E)-7-[3-Benzyloxy-5,6,7,8-Tetrahydro-5,5,8,8-Tetramethyl-2-Naphthalen-2-yl]-3-Methylocta-2,4,6-Trienoic Acid (Compound 127, Prepared as Illustrated and Described in Scheme 7)

1-(3-Hydroxy-5,6,7,8-tetrahydro-5,5,8,8-tetramethylnaphthalen-2-yl)-ethanone (0.103 g, 0.418 mmol) in DMSO (1 mL) was alkylated with benzylbromide (0.100 g, 0.585 mmol, 0.070 mL) as described in Example 21. Aqueous workup gave 1-(3-benzyloxy-5,6,7,8-tetrahydro-5,5,8,8-tetramethylnaphthalen-2-yl)ethanone 0.106 g (75% crude) as a yellow oil: $^1$H-NMR (400 MHz, CDCl$_3$) δ 7.74 (s, 1H, ArH), 7.45 (m, 5H, ArH), 6.88 (s, 1H, ArH), 5.12 (s, 2H, OCH$_2$), 2.59 (s, 3H, CH$_3$), 1.66 (br s, 4H, 2CH$_2$), 1.28 (s, 6H, 2CH$_3$), 1.25 (s, 6H, 2CH$_3$).

The benzyloxyketone (0.106 g, 0.315 mmol) was condensed with diethyl cyanomethylphosphonate (0.195 g, 1.10 mmol, 0.18 mL) as described for Example 19. Aqueous work-up afforded the crude product 3-(3-benzyloxy-5,6,7,8-tetrahydro-5,5,8,8-tetramethylnaphthalen-2-yl)but-2-enenitrile 0.047 g (41%) as a yellow oil: $^1$H-NMR (400 MHz, CDCl$_3$) δ 7.36 (m, 5H, ArH), 7.11 (s, 1H, ArH), 6.85 (s, 1H, ArH), 5.58 (s, 1H, olefinic), 5.06 (s, 2H, OCH$_2$), 2.43 (s, 3H, CH$_3$), 1.66 (s, 4H, 2CH$_2$), 1.25 (s, 6H, 2CH$_3$), 1.24 (s, 6H, 2CH$_3$).

The cyanobenzyloxy naphthalene adduct (0.047 g, 0.131 mmol) was readily reduced with DIBAL (0.392 mL of a 1.0 M solution in hexanes, 0.392 mmol) as described for Example 19. Aqueous work-up gave the aldehyde E-3-(3-benzyloxy-5,6,7,8-tetrahydro-5,5,8,8-tetramethylnaphthalen-2-yl)but-2enal 0.020 g (42%) as a yellow oil: $^1$H-NMR (400 MHz, CDCl$_3$) δ 10.13 (d, J=8.0 Hz, 1H, CHO), 7.39 (m, 5H, ArH), 7.10 (s, 1H, ArH), 6.86 (s, 1H, ArH), 6.14 (d, J=8.0 Hz, 1H, olefinic), 5.06 (s, 2H, OCH$_2$), 2.54 (s, 3H, CH$_3$), 1.67 (s, 4H, 2CH$_2$), 1.25 (s, 12H, 4CH$_3$).

The above aldehyde (0.020 g, 0.0552 mmol) and diethyl 3-ethoxycarbonyl-2-methyl prop-2-enylphosphonate (0.31 g, 0.116 mmol, 0.029 mL) were condensed as described for Example 19. Aqueous work-up afforded the ester (0.026 g, 100%) as a yellow oil. Standard hydrolysis of the crude ester (0.026 g, 0.055 mmol) followed by the typical aqueous work-up gave the acid as a mixture of geometric isomers (0.022 g, 87%) as a yellow oil. A sample of the product mixture was purified by reverse phase HPLC (88% MeOH/12% 1 mM NH$_4$OAc with 0.5% AcOH) to give (2E, 4E, 6E)-7-[3-benzyloxy-5,6,7,8-tetrahydro-5,5,8,8-tetramethyl-2-naphthalen-2-yl]-3-methylocta-2,4,6-trienoic acid (127) as a yellow solid: $^1$H-NMR (400MHz, CDCl$_3$) δ 7.37 (m, 5H, ArH), 7.11 (s, 1H, ArH), 7.04 (dd, J=11.2, 15.2 Hz, 1H, olefinic), 6.83 (s, 1H, ArH), 6.33 (appp broad t, 2H, 2×olefinic), 5.84 (s, 1H, olefinic), 5.05 (s, 2H, OCH$_2$), 2.38 (s, 3H, CH$_3$), 2.25 (s, 3H, CH$_3$), 1.67 (s, 4H, 2CH$_2$), 1.27 (s, 6H, 2CH$_3$), 1.25 (s, 6H, 2CH$_3$).

EXAMPLE 28

(2E, 4E, 6Z)-7-[3-Benzyloxy-5,6,7,8-Tetrahydro-5,5,8,8-Tetramethyl-2-Naphthalen-2-yl]-3-Methylocta-2,4,6-Trienoic Acid (Compound 128, Prepared as Illustrated and Described in Scheme 7)

The final product mixture from Example 27 was purified by reverse phase HPLC (88% MeOH/12% 1 mM NH$_4$OAc with 0.5% AcOH) to give the title compound (2E, 4E, 6Z)-7-[3-benzyloxy-5,6,7,8-tetrahydro-5,5,8,8-tetramethyl-2-naphthalen-2-yl]-3-methylocta-2,4,6-trienoic acid (128) as a yellow solid: $^1$H-NMR (400 MHz, CDCl$_3$) δ 7.34 (m, 5H, ArH), 6.97 (s, 1H, ArH), 6.86 (s, 1H, ArH), 6.63 (dd, J=11.1, 15.0 Hz, 1H, olefinic), 6.23 (appp b t, 2H, 2×olefinic), 5.76 (s, 1H, olefinic), 5.05 (s, 2H, OCH$_2$), 2.21 (s, 3H, CH$_3$), 2.04 (s, 3H, CH$_3$), 1.67 (s, 4H, 2CH$_2$), 1.26 (s, 6H, 2CH$_3$), 1.23 (s, 6H, 2CH$_3$).

EXAMPLE 29

(2E, 4E, 6E)-7-[3(4-Methylbenzyloxy)-5,6,7,8-Tetrahydro-5,5,8,8-Tetramethyl-2-Naphthalen-2-yl]-3-Methylocta-2,4,6-Trienoic Acid (Compound 129, Prepared as Illustrated and Described in Scheme 7)

1-(3-Hydroxy-5,6,7,8-tetrahydro-5,5,8,8-tetramethylnaphthalen-2-yl)ethanone (0.116 g, 0.471 mmol) was alkylated with 4-methylbenzylchloride (0.93 g, 0.659 mmol, 0.087 mL) as described in Example 21. Aqueous workup gave 1-[3(4-Methylbenzyloxy)-5,6,7,8-tetrahydro-5,5,8,8-tetramethylnaphthalen-2-yl]ethanone 0.217 g (131% crude) as a pale orange solid: $^1$H-NMR (400 MHz, CDCl$_3$) δ 7.74 (s, 1H, ArH), 7.33 and 7.20 (d, of ABq, J=7.8 Hz, 4H, Ar-H), 6.91 (s, 1H, ArH), 5.08 (s, 2H, OCH$_2$), 2.56 (s, 3H, CH$_3$), 2.35 (s, 3H, ArCH$_3$), 1.66 (br s, 4H, 2CH$_2$), 1.28 (s, 6H, 2CH$_3$), 1.25 (s, 6H, 2CH$_3$).

The (4-methylbenzyloxy)ketone (0.217 g, 0.619 mmol) was condensed with diethyl cyanomethylphosphonate (0.329 g, 1.86 mmol, 0.300 mL) as described for Example 19. Aqueous work-up afforded the crude product 3(4-methylbenzyloxy)-5,6,7,8-tetrahydro-5,5,8,8-tetramethylnaphthalen-2-yl]but-2-enenitrile 0.173 g (75%) as an orange oil: $^1$H-NMR (400 MHz, CDCl$_3$) δ 7.27 and 7.20 (d of ABq, J=7.8 Hz, 4H, Ar-H), 7.10 (s, 1H, ArH), 6.87 (s, 1H, ArH), 5.58 (s, 1H, olefinic), 5.01 (s, 2H, OCH$_2$), 2.42 (s, 3H, CH$_3$), 2.37 (s, 3H, ArCH$_3$), 1.67 (s, 4H, 2CH$_2$), 1.26 (s, 6H, 2CH$_3$), 1.25 (s, 6H, 2CH$_3$).

The cyano(methylbenzyloxy)naphthalene adduct (0.173 g, 0.463 mmol) was readily reduced with DIBAL (1.39 mL of a 1.0 M solution in hexanes, 1.39 mmol) as described for Example 19. Aqeous work-up gave the aldehyde 3-(4-methylbenzyloxy)-5,6,7,8-tetrahydro-5,5,8,8-tetramethylnaphthalen-2-yl)but-2-enal 0.090 g (52%) as a yellow oil: $^1$H-NMR (400 MHz, CDCl$_3$) δ 10.12 (d, J=8.2 Hz, 1H, CHO), 7.28 and 7.18 (d of ABq, J=8.0 Hz, 4H, Ar-H), 7.10 (s, 1H, ArH), 6.87 (s, 1H, ArH), 6.11 (d, J=8.2 Hz, 1Hz, olefinic), 5.02 (s, 2H, OCH$_2$), 2.53 (s, 3H, CH$_3$), 2.36 (s, 3H, ArCH$_3$), 1.67 (s, 4H, 2CH$_2$), 1.26 (s, 6H, 2CH$_3$), 1.25 (s, 6H, 2CH$_3$).

The above aldhyde (0.090 g, 0.240 mmol) and diethyl 3-ethoxycarbonyl-2-methyl prop-2-enylphosphonate (0.0159 g, 0.601 mmol, 0.147 mL) were condensed as described for Example 19. Aqueous work-up afforded the ester (0.099 g, 85%) as a yellow oil. Standard hydrolysis of the crude ester (0.099 g, 0.203 mmol) followed by the typical aqueous work-up gave the acid as a crude mixture of geometric isomers (0.109 g, 117%) as a yellow oil. A sample of the product mixture was purified by reverse phase HPLC (90% MeOH/10% 1 mM NH$_4$OAc with 0.5% AcOH) to give (2E, 4E, 6E)-7-[3-(4-methylbenzyloxy)-5,6,7,8-tetrahydro-5,5,8,8-tetramethyl-2-naphthalen-2-yl]-3-methylocta-2,4,6-trienoic acid (129) as a yellow solid: $^1$H-NMR (400MHz, CDCl$_3$) δ 7.30 (d of ABq, J=7.9 Hz, 4H, Ar-H), 7.10 (s, 1H, ArH), 7.02 (dd, J=11.2, 15.1 Hz, 1H, olefinic), 6.87 (s, 1H, ArH), 6.11 (appp br t, 1H, olefinic), 5.80 (s, 1H, olefinic), 5.00 (s, 2H, OCH$_2$), 2.38 (s, 3H, CH$_3$), 2.37 (s, 3H, CH$_3$), 2.23 (s, 3H, CH$_3$), 1.67 (s, 4H, 2CH$_2$), 1.27 (s, 6H, 2CH$_3$), 1.26 (s, 6H, 2CH$_3$).

EXAMPLE 30

(2E, 4E, 6Z)-7-[3(4-Methylbenzyloxy-5,6,7,8-Tetrahydro-5,5,8,8-Tetramethyl-2-Naphthalen-2-yl]-3-Methylocta-2,4,6-Trienoic Acid (Compound 130, Prepared as Illustrated and Described in Scheme 7)

The final product mixture from Example 29 was purified by reverse phase HPLC (90% MeOH/10% 1 mM NH$_4$OAc with 0.5% AcOH) to give the title compound (2E, 4E, 6Z)-7-[3(4-methylbenzyloxy-5,6,7,8-tetrahydro-5,5,8,8-tetramethyl-2-naphthalen-2-yl]-3-methylocta-2,4,6-trienoic acid (130 as a yellow solid: $^1$H-NMR (400 MHz, CDCl$_3$) δ 7.27 and 7.15 (d of ABq, J=7.9 Hz, 4H, Ar-H), 6.96 (s, 1H, ArH), 6.87 (s, 1H, ArH), 6.60 (dd, J=11.0, 14.9 Hz, 1H, olefinic), 6.23 (appp br d, 1H, olefinic), 5.80 (s, 1H, olefinic), 5.00 (s, 2H, OCH$_2$), 2.34 (s, 3H, CH$_3$), 2.19 (s, 3H, CH$_3$), 2.13 (s, 3H, CH$_3$), 1.67 (s, 4H, 2CH$_2$), 1.27 (s, 6H, 2CH$_3$), 1.23 (s, 6H, 2CH$_3$).

EXAMPLE 31

4-3,4,5,6,7,8-Hexahydro-(1-Anthracen-1ylmethyl)-benzoic Acid (Compound 131, Prepared as Illustrated and Described in Scheme 9)

To a solution of 1,2,3,4,6,7,8,9-octahydro-6,6,9,9-tetramethylanthracene (prepared by Friedel-Crafts alkylation/annulation of 1,2,3,4-tetrahydronaphthalene with 2,5-dichloro-2,3-dimethylhexane in the presence of aluminum trichloride at 0° C. in dichloromethane, 2.0 g, 8.3 mmol) in CH$_2$Cl$_2$ (100 mL) and pyridine (15 mL) at 0° C. was added CrO$_3$ (8.26 g, 82.6 mmol) in several portions. The reaction mixture was stirred at 0° C. for 30 min, then allowed to warm to room temperature and stirred for 10 h. The reaction mixture was poured over an ice-acid mixture (1N HCl, 100 mL), extracted with Et$_2$O (200 mL), dried (MgSO$_4$), concentrated, and purified by column chromatography (25% ether in hexane) to give 3,4,5,6,7,8-hexahydro-5,5,8,8-tetramethyl-2H-anthracen-1-one (740 mg, 35%): $^1$H NMR(400 MHz, CDCl$_3$) δ 8.0 (s, 1H, ArH), 7.17 (s, 1H, ArH), 2.90 (t, J=6.5 Hz, 2H, CH$_2$), 2.60 (t, J=6.3 Hz, 2H, CH$_2$), 2.10 (m, 2H, CH$_2$), 1.68 (s, 4H, 2CH$_2$), 1.30 (s, $_6$H, 2CH$_3$), 1.29 (s, 6H, 2CH$_3$).

To solution of 3,4,5,6,7,8-hexahydro-5,5,8,8-tetramethyl-2H-anthracen-1-one (512 mg, 2 mmol) in MeOH (10 mL) was added NaBH$_4$ (76 mg, 2 mmol) at 0° C. The reaction mixture was stirred at 0° C. for 30 min, quenched with saturated aqueous NH$_4$Cl (5 mL), extracted with ether (50 mL), dried (MgSO$_4$). The organic layers were concentrated under reduced pressure to give the corresponding tricyclic alcohol, which was used without further purification. To above alcohol (516 mg, 2 mmol) in MeOH (5 mL) was added Ph$_3$P-HBr (686 mg, 2 mmol) at rt. The mixture was heated at 85° C. for 5 h. Removal of the solvent, followed by addition of hexane (100 mL) gave a white solid, which was then filtered to give pure 3,4,5,6,7,8-hexahydro-5,5,8,8-tetramethyl-2H-anthracen-1-triphenylphosphonium bromide (697 mg, 60%). To a solution of the above phosphonium salt (581 mg, 1 mmol) in THF (8 mL) was added n-BuLi (0.4 mL, 2.5 M, 1 mmol) at 0° C. and the resulting dark-red solution was stirred at the temperature for 30 min to afford the ylide. To this freshly prepared ylide was added methyl 4-formyl-benzoate (1.2 mmol) in THF (3 mL) at −78° C. The solution was allowed to warm to ambient temperature and stirred for 6 h. The reaction was quenched with saturated aqueous NH$_4$Cl. The aqueous solution was extracted with EtOAc, 3×. The organic layers were combined and washed with water (2×) and brine. The organic solution was dried (Na$_2$SO$_4$), filtered, and concentrated to give the crude exocyclic ester product as a yellow solid (86%): m.p. 161–163° C.

The ester (220 mg, 0.56 mmol) in methanol (10 mL) was treated with concentrated HCl (0.05 mL) and the solution was allowed to stir at 85° C. for 8 h. The solution was quenched with water and extracted with EtOAc (3×). The organic solution was washed with saturated aqueous NaHCO$_3$, water (2×), and brine. The organic solution was dried (Na$_2$SO$_4$), filtered, and concentrated to give the endocylcic ester product (95%) as a yellow oil: $^1$H NMR (400 MHz, CDCl$_3$) δ 7.92 (½ABq, J=8.2 Hz, 2H, ArH), 7.33 (½ABq, J=8.2 Hz, 2H, ArH), 7.03 (s, 1H, ArH), 7.00 (s, 1H, ArH), 5.77 (broad t, 1H, olefinic), 3.90 (s, 3H, OCH$_3$), 3.78 (s, 2H, CH$_2$), 2.72 (t, J=7.9 Hz, 2H, CH$_2$), 2.30 (m, 2H, CH$_2$), 1.61 (s, 4H, 2CH$_2$), 1.22 (s, 6H, 2CH$_3$), 1.10 (s, 6H, 2CH$_3$).

The ester (80 mg) was hydrolyzed in excess KOH/MeOH at ambient temperature for 24 h. The methanol was removed in vacuo. The residue was taken-up in water and the aqueous layer was adjusted to pH=4–5 with 1 M aqueous HCl. The aqueous solution was extracted with EtOAc, 3×. The organic layers were combined and washed with water (2×) and brine. The organic solution was dried (Na$_2$SO$_4$), filtered, and concentrated to give 4-(3,4,5,6,7,8-hexahydro-5,5,8,8-tetramethyl-anthracen-1-ylmethyl)-bezoic acid (131) 76 mg (96%) as a white solid: m.p. 212–214° C.; $^1$H NMR (400 MHz, CDCl$_3$) δ 7.99 (½ABq, J=8.2 Hz, 2H, ArH), 7.36 (½ABq, J=8.2 Hz, 2H, ArH), 7.03 (s, 1H, ArH), 7.02 (s, 1H, ArH), 5.76 (broad t, 1H, olefinic), 3.81 (s, 2H, CH$_2$) t, J=7.9 Hz, 2H, CH$_2$), 2.31 (m, 2H, CH$_2$), 1.60 (s, 4H, 2CH$_2$), 1.23 (s, 6H, 2CH$_3$), 1.10 (s, 6H, 2CH$_3$).

EXAMPLE 32

4-(5,6,7,8-Tetrahydro-5,5,8,8-Tetramethyl-3H-Cyclopenta[b]naphthalen-1-ylmethyl)-benzoic Acid (Compound 132, Prepared as Illustrated and Described in Scheme 9)

The title compound was prepared in a manner similar to that of Example 30 using 2.3,5,6,7,8-hexahydro-5,5,8,8-tetramethylcyclopental[b]-1-one [U.S. Pat. No. 2,815,382 (1957)] in place of the anthracen-1-one for the NaBH$_4$ reduction step. 4-(5,6,7,8-tetrahydro-5,5,8,8-tetramethyl-3H-cyclopenta[b]naphthalen-1-ylmethyl)-benzoic acid (132) (38%) was obtained as a white, foamy solid: $^1$H NMR (400 MHz, CDCl$_3$) δ 8.01 (½ABq, J=8.2 Hz, 2H, ArH), 7.39 (½ABq, J=8.2 Hz, 2H, ArH), 7.37 (s, 1H, ArH), 7.19 (s, 1H, ArH), 6.00 (broad t, 1H, olefinic), 3.92 (broad s, 2H, CH$_2$), 3.29 (broad s, 2H, CH$_2$), 1.67 (s, 4H, 2CH$_2$), 1.28 (s, 6H, 2CH$_3$), 1.24 (s, 6H, 2CH$_3$).

EXAMPLE 33

4-(6,7,8,9-Tetrahydro-6,6,9,9-Tetramethyl-2H-Benzo[g]chromen-4-ylmethyl)-Benzoic Acid (Compound 133, Prepared as Illustrated and Described in Scheme 9)

Aluminum trichloride (25 g, 0.18 mol) was added portions to a solution of phenol (49.5 g, 0.52 mol) and 2,5- dichloro-2,5-dimethylhexane (101.0 g, 0.55 mol) in dichloromethane (700 mL). The reaction mixture was allowed to stir at 25–40° C. for 2 h, then the dark red mixture was poured onto ice water. Aqueous work up (EtOAc extraction) gave 5,6,7,8-tetrahydro-5,5,8,8-tetramethylnaphthalen-2-ol 84.8 g (80%) as a white solid, which was recrystallized from hexane to give the product as colorless needles: $^1$H NMR (400 MHz, CDCl$_3$) δ 7.17 (d, 1H, ArH), 6.78 (d, 1H, ArH), 6.62 (dd, 1H, ArH), 4.55 (s, 1H, OH), 1.65 (s, 4H, 2CH$_2$), 1.25 (s, 12H, 4CH$_3$).

The hydroxynaphthalene (19.1 g, 93.6 mmol) was treated dropwise with acetyl chloride (7.7 g, 98.2 mmol) in 1,2-dichloroethane (250 ml) at 0° C. After completion of the addition, aluminum chloride (10 g, 75.2 mmol) was added in portions over 5 min. The mixture was heated at reflux for 10 h, then stirred at 25° C. for 8 h. GC analysis indicated the desired keto-phenol was present in 98.6% purity. The reaction mixture was poured onto ice water and aqueous work-up (EtOAc extraction) gave a brown-black solid, which was dissolved in hot methanol, filtered, and concentrated to give a brown viscous semi-solid. Flash chromatography (15% EtOAc/hexane) gave 1-(3-hydroxy-5,5,8,8-tetramethyl-5,6,7,8-tetrahydro-naphthalen-2-yl)ethanone as a light yellow solid. Recrystallization from hexane afforded the product as white crystals 15.2 g (66%): $^1$H NMR (400 MHz, CDCl$_3$) δ 7.63 (s, 1H, ArH), 6.9 (s, 1H, ArH), 2.61 (s, 3H, CH$_3$), 1.67 (s, 4H, 2CH$_2$), 1.29 (s, 6H, 2CH$_3$), 1.27 (s, 6H, 2CH$_3$).

A 200-mL round bottom flask was flame dried under nitrogen and charged with sodium metal (3.2 g, 140 mmol). A solution of 1-(3-hydroxy-5,5,8,8-tetramethyl-5,6,7,8-tetrahydro-naphthalen-2-yl)ethanone (15 g, 61.0 mmol) in ethyl formate (350 mL) was added dropwise over 1 h. The resulting yellow solution was stirred at 35° C. for 4 h. The mixture was cooled to 25° C. solution, diluted with 1N HCl (20 mL) and extracted with ether. The extracts were washed with water, brine, and dried over MgSO$_4$. The extracts were concentrated under vacuum to give 2-hydroxy-6,6,9,9-tetramethyl-2,3,6,7,8,9-hexahydrobenzo[g]chromen-4-one: $^1$H NMR (400 MHz, CDCl$_3$) δ 7.85 (s, 1H, ArH), 6.9 (s, 1H, ArH), 5,85 (t, 1H, CH), 3.32 (br s, 1H, OH), 2.9 (dd, 2H, CH$_2$), 1.67 (s, 4H, 2CH$_2$), 1.27 (s, 12H, 4CH$_3$).

To a solution of above benzochromen-4-one (19.6 g, 71.5 mmol) in methanol (250 mL) was added concentrated HCl (0.5 mL) dropwise. The mixture stirred at 60° C. for 2.5 h. TLC analysis indicated the reaction was complete. The mixture was cooled to 25° C. and diluted with water (200 mL). A light brown solid precipitate was collected by filtration and dissolved in ether, washed with water, brine and dried over sodium sulfate. Concentration under vacuum gave 6,6,9,9-tetramethyl-6,7,8,9-tetrahydro-benzo[g]chromen-4-one 13.3 g (73%) as a light brown solid: m.p. 201–202° C.; $^1$H NMR (400 MHz, CDCl$_3$) δ 8.15 (s, 1H, ArH), 7.8 (d, 1H, olefinic), 7.4 (s, 1H, ArH), 6.25 (d, 1H, olefinic), 1.75 (s, 4H, 2CH$_2$), 1.35 (s, 12H, 4CH$_3$).

A solution of 6,6,9,9-tetramethyl-6,7,8,9-tetrahydro-benzo[g]chromen-4-one (400 mg, 1.56 mmol) in EtOAc (30 mL) was hydrogenated (1 atm H$_2$) over 10% palladium on carbon for 3 h. The mixture was filtered through Celite and the filter pad was rinsed with EtOAc (400 mL) and concentrated to afford 6,6,9,9-tetramethyl-2,3,5,6,7,8,9-hexahydro-benzo[g]chromen-4-one, 379 mg (94%): $^1$H NMR (400 MHz, CDCl$_3$) δ 7.85 ( s, 1H, ArH), 6.89 ( s, 1H, ArH), 4.49 (t, 2H, J=6.4 Hz, ring CH$_2$), 2.77 (t, 2H, J=6.4 Hz, ring CH$_2$), 1.56 (s, 4H, 2CH$_2$), 1.27 (s, 12H, 4CH$_3$).

To the ketone (379 mg, 1.47 mmol) in methanonal (20 mL) at 0° C. was added NaBH$_4$ (82 mg, 2.2 mmol) and the mixture was allowed to stir for 30 min. The reaction was poured into 10% HCl aqueous solution (100 mL), extracted with EtOAc (100 mL), separated, and concentrated to give 6,6,9,9-tetramethyl-2,3,5,6,7,8,9-hexahydro-2H-benzo[g] chromen-4-ol 320 mg (84%): $^1$H NMR (400 MHz, CDCl$_3$) δ 7.26 ( s, 1H, ArH), 6.79 ( s, 1H, ArH), 4.76 (m, 1H, CH-OH), 2.10 (m, 2H, ring CH$_2$), 2.00 (m, 2H, ring CH$_2$), 1.66 (s, 4H, 2CH$_2$), 1.27 (s, 6H, 2CH$_3$), 1.25 (s, 6H, 2CH$_3$).

To a solution of triphenyl phoshine hydrobromide (424 mg, 1.2 mmol) in 25 mL of methanol was added the alcohol (320 mg, 1.2 mmol) in methanol (25 mL) and the solution was stirred at room temperature for 4 h. The reaction was concentrated in vacuo to give a white foam. Trituration with 20% ether/hexane solution (3×10 mL) gave the phosphonium salt as a yellow solid. The phosphonium bromide in THF (10 mL) was treated with a solution of n-BuLi (0.43 mL of a 2.5 M, 1.08 mmol) at −78° C. and allowed to stir for 30 minutes A solution of methyl-4-formyl benzoate (177 mg, 1.08 mmol) in THF (20 mL) was added at −78° C. The reaction was warmed to ambient temperature then quenched with aqueous, saturated NH$_4$Cl. The solution was estracted with ether (100 mL), concentrated, and dried (MgSO$_4$) to afford 4-(6,6,9,9-tetramethyl-6,7,8,9-tetrahydro-2H-benzo [g]chromen-4-ylidenemethyl)-benzoic acid methyl ester (240 mg, 52%): $^1$H NMR (400 MHz, CDCl$_3$) δ 8.02 (½ ABq, 2H, J=8.3 Hz, ArH), 7.58 ( s, 1H, ArH), 7.38 (½ ABq, 2H, J=8.3 Hz, ArH) 7.06 (s, 1H, olefinic) 6.80 (s, 1H, ArH), 4.15 (t, 2H, J=5.6 Hz, ring CH$_2$), 2.89 (t, 2H, J=5.6 Hz, ring CH$_2$), 3.93 (s, 3H, CH$_3$), 1.68 (s, 4H, 2CH$_2$), 1.32 (s, 6H, 2CH$_3$), 1.24 (s, 6H, 2CH$_3$).

To a mixture of 4-(6,6,9,9-tetramethyl-6,7,8,9-tetrahydro-2H-benzo[g]chromen-4-ylidenemethyl)-benzoic acid methyl ester (220 mg, 0.56 mmol) in methanol (10 mL) was added concentrated HCl (0.05 mL) and the solution was allowed to stir at 85° C. for 12 h. The solution was quenched with aqueous saturated NaHCO$_3$ solution (100 mL), extracted with EtOAc, dried (Na$_2$SO$_4$), and concentrated. The acid was obtained by hydrolysis according to the standard conditions and was purified by silica gel preparative TLC (50% EtOAc/Hexane) to afford 4-(6,7,8,9-tetrahydro-6,6,9,9-tetramethyl2H-benzo[g]chromen-4-ylmethyl)-benzoic acid (133) (89%) as a white solid: m.p. 200–201° C.; IR (neat) 2969 s, 2958 s, 2922 s, 2361 m, 1689 s, 1608 m, 1419 s, 1408 s, 1286 m, 1174 s, 1018 s cm$^{-1}$; $^1$H NMR (400 MHz, CDCl$_3$) δ 8.04 (½ ABq, 2H, J=8.0 Hz, ArH), 7.37 (½ ABq, 2H, J=8.0 Hz, ArH), 6.98 (s, 1H, ArH), 6,74 (s, 1H, ArH), 5.43 (broad t, 1H, olefinic), 4.75 (m, 2H, ring CH$_2$), 3.79 (s, 2H, benzylic CH$_2$), 1.59 (s, 4H, 2CH$_2$), 1.22 (s, 6H, 2CH$_3$), 1.13 (s, 6H, 2CH$_3$).

EXAMPLE 34

4-(3,4,6,7,8,9-Hexahydro-2-oxo-6,6,9,9-Tetramethyl-2H-Benzo[g]quinolin-1-ylmethyl)-Benzoic Acid (Compound 134, Prepared as illustrated and Described in Scheme 10)

To a solution of 6,6,9,9-tetramethyl-3,4,6,7,8,9-hexahydro-1H-benzo[g]quinolin-2-one (130 mg, 0.50 mmol) in THF (4 mL) was added NaH (18 mg, 0.76 mmol) in one portion at ambient temperature. To this solution was added methyl 4-(bromomethyl)-benzoate (229 mg, 1.01 mmol) in THF (8 mL). The mixture was then heated at 60° C. for 8 h, cooled to ambient temperature, quenched with aqueous saturated NH$_4$Cl (20 mL), extracted with EtOAc (100 mL), dried with (MgSO$_4$), concentrated, and purified by column chromatography (10% ether in hexane) to afford 4-(6,6,9,9-tetramethyl-3,4,6,7,8,9-hexahydro-1H-benzo[g]quinolin-1-ylmethyl)benzoic acid methyl ester (120 mg, 58%): $^1$H NMR (400 MHz, CDCl$_3$) δ 8.10 (½ ABq, 2H, J=8.0 Hz, ArH), 7.48 (½ ABq, 2H, J=8.0 Hz, ArH), 7.08 (s, 1H, ArH), 6.70 (s, 1H, ArH), 5.20 (s, 2H, CH$_2$), 4.51 (s, 3H, CH$_3$), 2.91 (t, 2H, J=7.0 Hz, ring CH$_2$), 2.81 (broad m, 2H, ring CH$_2$), 1.60 (s, 4H, 2CH$_2$), 1.23 (s, 12H, 4CH$_3$).

The acid was obtained by hydrolysis according to the standard conditions to yield 4-(3,4,6,7,8,9-hexahydro-2-oxo-6,6,9,9-tetramethyl-2H-benzo[g]quinolin-1ylmethyl)-benzoic acid (134) 8.7 mg (10%) as a yellow oil, IR (neat) 3398 m, 2928 m, 2914 m, 2870 m, 1682 m, 1670 m, 1651 s, 1612 s, 1423 s, 1363 s cm$^{-1}$; $^1$H NMR (400 MHz, CDCl$_3$) δ 8.04 (½ ABq, 2H, J=8 Hz, ArH), 7.35 (½ ABq, 2H, J=8 Hz, ArH), 7.07 (s, 1H, ArH), 6.68 (s, 1H, ArH), 5.22 (s, 2H, CH$_2$), 2.94 (t, 2H, J=7 Hz, ring CH$_2$), 2.80 (broad m, 2H, J=8, ring CH$_2$), 1.23 (s, 4H, 2CH$_2$), 1.04 (s, 12H, 4CH$_3$).

EXAMPLE 35

4-(3,4,6,7,8,9-Hexahydro-6,6,9,9-tetramethyl-2H-benxo[g]quinolin-1-ylmethyl)benzoic Acid (Compound 135, prepared as illustrated and described in Scheme 10)

To a solution of 6,6,9,9-tetramethyl-3,4,6,7-hexahydro-1H-benzo[g]quinolin-2-one (1.0 g, 3.9 mmol, prepared by Friedel-Crafts alkylation/annulation of 2-oxo-1,2,3,4-tetrahydroquinoline with 2,5-dichloro-2,5-dimethylhexane in the presence of aluminum trichloride at ambient temperature in dichloromethane) in THF (10 mL) at ambient temperature was added LiAlH$_4$ (11.7 mmol). The reaction mixture was heated to 80° C. and allowed to stir for 30 minutes. The reaction mixture was poured into aqueous saturated sodium potassium tartrate (100 mL), extracted with EtOAc (100 mL), dried (MgSO$_4$), and concentrated to give 6,6,9,9-tetramethyl-1,2,3,4,6,7,8,9-octahydrobenzo[g]quinoline 978 mg (99%): $^1$H NMR (400 MHz, CDCl$_3$) δ 6.88(s, 1H ArH), 6.41(s, 1H, ArH), 3.26(t, 2H, J=6.2 Hz, ring CH$_2$), 2.71(t, 2H, J=4.0 Hz, ring CH$_2$), 1.92(m, 2H, ring CH$_2$), 1.63(s, 4H, 2CH$_2$), 1.23(s, 12H, 4CH$_3$).

To a solution of 6,6,9,9-tetramethyl-1,2,3,4,6,7,8,9-octahydrobenzo[g]quinoline (200 mg, 0.823 mmol) in THF (4 mL) was added NaH (30 mg, 1.2 mmol) in one portion at ambient temperature. To this solution was added methyl 4-(bromomethyl)-benzoate (377 mg, 1.6 mmol) in THF (8 mL). The mixture was then heated at 60° C. for 8 h, cooled to ambient temperature, quenched with aqueous saturated NH$_4$Cl (20 mL), extracted with EtOAc (100 mL), dried (MgSO$_4$), concentrated, and purified by column chromatography (10% ether in hexanes) to afford 4-(6,6,9,9-tetramethyl-3,4,6,7,8,9-hexahydro-2H-benzo[g]quinolin-1-ylmethyl)-benzoic acid methyl ester 130 mg (40%): $^1$H NMR (400 MHz, CDCl$_3$) δ 7.98(½ ABq, 2H, J=9.0 Hz, ArH), 7.38(½ ABq, 2H, J=9.0 Hz, ArH), 6.91(s, 1H, ArH), 6.3(s, 1H, ArH) 4.45(s, 2H, CH$_2$), 3.90(s, 3H, CH$_3$), 3.2(t, 2H, J=5.4 Hz, ring CH$_2$), 2.79(t, 2H, J=6.4 Hz, ring CH$_2$), 2.02(m, 2H, ring CH$_2$), 1.59(s, 4H, 2CH$_2$), 1.22(s, 6H, 2CH$_3$), 1.06(s, 6H, 2CH$_3$).

The acid was prepared by hydrolysis according to the standard conditions to yield 4-(3,4,6,7,8,9-hexahydro-6,6,9,9-tetramethyl-2H-benzo[g]quinolin-1-ylmethyl)benzoic acid (135) 117 mg (40%) as a yellow solid: m.p. 173–175° C.; IR (neat) 2965 s, 2910 s, 2850 s, 1695 s, 1592 s, 1503 s, 1483 m, 1410 s cm$^{-1}$; $^1$H NMR (400 MHz, CDCl$_3$) δ 8.04(½ ABq, 2H, J=8.0 Hz, ArH), 7.42 (½ ABq, 2H, J=8.0 Hz, ArH); 6.91(s, 1H, ArH), 6.33(s, 1H, ArH), 4.46(s, 2H CH$_2$), 3.35(t, J=7.0 Hz, 2H, ring CH$_2$), 2.78(t, 2H, J=6.0, CH$_2$), 2.03 (m, 2H ring CH$_2$), 1.60(s, 4H, 2CH$_2$), 1.26(s, 6H, 2CH$_3$), 1.07(s, 6H, 2CH$_3$).

EXAMPLE 36

4-(2,3,6,7,8,9-Hexahydro-6,6,9,9-tetramethyl-naphtha[2,3-b][1,4]oxazin-4-ylmethyl)-benzoic Acid (Compound 136, prepared as illustrated and described in Scheme 10)

To a solution of 6,6,9,9-tetramethyl-6,7,8,9-tetrahydro-4H-naphtho[2,3-b][1,4] oxazine-3-one (400 mg, 1.5 mmol; prepared by Friedel Crafts acylation/annulation of 2H-1,4-benzoxazin-3[4H]-one with 2,5-dichloro-2,5-dimethylhexane in the presence of aluminum trichloride in dichloromethane) in THF (20 mL) at 0° C. was added LiAlH$_4$ (4.6 mmol). The reaction was warmed to ambient temperature then heated to 80° C. for 1 h. The reaction was then allowed to cool to ambient temperature, was quenched in aqueous saturated sodium potassium tartrate (100 mL), extracted with EtOAc, dried (MgSO$_4$), and concentrated. The product was washed with hexane and purified by column chromatography (30% EtOAc/Hexane) to give 6,6,9,9-tetramethyl-3,4,6,7,8,9-hexahydro-2H-naphtha[2,3-b][1,4]oxazine 300 mg (70%): $^1$H NMR (400 MHz, CDCl$_3$) δ 6.71(s, 1H, ArH), 6.52(s, 1H, ArH), 4.22(t, 2H, J=4.6 Hz, ring CH$_2$), 3.39(t, 2H, J=4.6 Hz, ring CH$_2$), 1.63(s, 4H, 2CH$_2$), 1.22(s, 12H, 4CH$_3$).

To a pressure tube containing a solution of methyl 4-bromomethyl benzoate (187 mg, 0.82 mmol) in THF (20 mL) and NaH (15 mg, 0.61 mmol) was added 6,6,9,9-tetramethyl-3,4,6,7,8,9-hexahydro-2H-naphtha[2,3-b][1,4] oxazine (100 mg, 0.41 mmol) in THF (5 mL). The reaction was heated at 60° C. for 12 h. The reaction was then cooled to ambient temperature, quenched with aqueous saturated NH$_4$Cl, extracted with EtOAc (100 mL), concentrated, and purified by silica gel preparative TLC (12% EtOAc/hexane) to give 4-(6,6,9,9-tetramethyl-2,3,6,7,8,9-hexahydro-naphtha[2,3-b][1,4]oxazin-4-ylmethyl)-benzoic acid methyl ester 104 mg (65%): $^1$H NMR (400 MHz, CDCl$_3$) δ 8.01 (½ABq, J=7.7 Hz, 2H, ArH), 7.4 0(½ABq, J=7.7 Hz, 2H, ArH), 6.74(s, 1H, ArH), 6.47(s, 1H, ArH), 4.42 (s, 2H, CH$_2$), 4.28(t, 2H, J=4.5 Hz, ring CH$_2$), 3.91(s, 3H; CH$_3$), 3.31(t, 2H, J=4.5 Hz, ring CH$_2$), 1.60(s, 4H, 2CH$_2$), 1.22(s, 6H, 2CH$_3$), 1.09(s, 6H, 2CH$_3$).

The acid was obtained by hydrolysis according to the standard conditions to afford 4-(2,3,6,7,8,9-hexahydro-6,6,9,9-tetramethyl-naphtha[2,3-b][1,4]oxazin-4-ylmethyl)-benzoic acid (136) 35 mg (35%) as an off white solid: m.p. 187° C.; IR (neat) 2657 m, 2924 m, 2856 m, 1691 m, 1651 m, 1612 m, 1510 s, 1290 s, 1253 s cm$^{-1}$; $^1$H NMR (400 MHz, CDCl$_3$) δ 8.09(½ ABq, 2H, J=8.0 Hz, ArH), 7.47(½ ABq, 2H, J=8.0 Hz, ArH), 6.76 (s, 1H, ArH), 6.50(s, 1H, ArH), 4.51(broad t, 2H, ring CH$_2$), 4.32(s, 2H, CH$_2$), 3.43(broad t, 2H, ring CH$_2$), 1.60(s, 4H, 2CH$_2$), 1.22(s, 6H, 2CH$_3$), 1.08(s, 6H, 2CH$_3$).

EXAMPLE 37

4-(3-Hydroxy-5,6,7,8-tetrahydro-5,5,8,8-tetramethyl-anthracene-1-carbonyl)benzoic Acid (Compound 137, prepared as illustrated and described in Scheme 11)

A solution of 3,4,5,6,7,8-hexahydro-5,5,8,8-tetramethyl-2H-anthracen-1-one (from Example 30, 1.0 g, 3.9 mmol) in EtOH (10 mL) was combined with 4-toluenesulfonhydrazide (731 mg, 3.9 mmol). A catalytic amount of concentrated HCl (100 mL) was added and the solution was heated at reflux for 3 h. The mixture was cooled to ambient temperature and the solid was collected by filtration. The solid was recrystallized (EtOH) to yield the tricyclic hydrazone 2.18 g (87%). The hydrazone (626 mg, 1.5 mmol) in THF (10 mL) was treated directly with n-BuLi (2.5 M in hexanes, 2.36 mL, 6.0 mmol) at 0° C. and the orange solution was allowed to warm to ambient temperature and subsequently cooled at −78° C. A solution of methyl 4-formylbenzoate (366 mg, 2.25 mmol) in THF (3 mL) was added dropwise to the solution of the vinyl anion. The resulting yellow solution was allowed to warm to ambient temperature over 2 h and then quenched with aqueous saturated $NH_4Cl$. The aqueous solution was extracted with EtOAc (3x). The organic layers were combined, and washed with water (2x) and brine. The organic solution was dried ($Na_2SO_4$), filtered, and concentrated. The crude product was purified by silica gel chromatography (10.1= hexanes:EtOAc) to give 4-(3,4,5,6,7,8-hexahydro-5,5,8,8-tetramethyl-anthracen-1-yl hydroxymethyl)-benzoic acid methyl ester 350 mg (84%): $^1H$ NMR (400 MHz, $CDCl_3$) δ 8.00(½ABq, J=8.2 Hz, 2H, ArH), 7.55(½ABq, J=8.2 Hz, 2H, ArH), 7.12(s, 1H, ArH), 7.01(s, 1H, ArH), 6.05(broad t, 1H, olefinic), 6.33(broad s, 1H, CH), 3.90(s, 3H, $OCH_3$), 2.72(t, J=7.9 Hz, 2H, $CH_2$), 2.34(m, 2H, $CH_2$), 1.63(s, 4H, $2CH_2$), 1.22(s, 6H, $2CH_3$), 1.15(s, 3H, $CH_3$), 1.05(s, 3H, $CH_3$).

The hydroxy ester (350 mg, 0.84 mmol) was oxidized directly with $MnO_2$(350 mg=2) in dichloromethane (20 mL) at ambient temperature for 3 h. The reaction mixture was filtered through a pad of Celite and the pad was rinsed with EtOAc. The organic solution was concentrated to give 4-(3,4,5,6,7,8-hexahydro-5,5,8,8-tetramethyl-anthracene-1-carbonyl-benzoic acid methyl ester 306 mg (88%): $^1H$ NMR (400 MHz, $CDCl_3$) δ 8.09(½ABq, J=8.2 Hz. 2H, ArH), 7.83(½ABq, J=8.2 Hz, 2H, ArH), 7.28(s, 1H, ArH), 7.08(s, 1H, ArH), 6.48(broad t, 1H, olefinic), 3.93(s, 3H, $OCH_3$), 2.72(t, J=7.9 Hz, 2H, $CH_2$), 2.50(m, 2H, $CH_2$), 1.65(m, 4H, $2CH_2$), 1.30(s, 6H, $2CH_3$), 1.13(s, 6H, $2CH_3$).

Hydrolysis of the ester has described in Example 30 afforded two products. 4-(3-hydroxy-5,6,7,8-tetrahydro-5,5,8,8-tetramethyl-anthracene-1-carbonyl)benzoic acid (137) 6 mg (8%): IR (neat) 3500–3000 broad m, 2960 m, 2926 m, 1726 s, 1633 m, 1597 s, 1568 m, 1253 s, 1215 s cm-1; $^1H$ NMR (400 MHz, $d_6$-acetone) δ 8.19(½ABq, J=8.2 Hz, 2H, ArH), 7.92(½ABq, J=8.2 Hz, 2H, ArH), 7.81(s, 2H; ArH), 7.37(app d, J=2.2 Hz, 1H, ArH), 7.22(app d, J=2.2 Hz, 1H, ArH), 1.74(m, 4H, $2CH_2$), 1.39(s, 6H, $2CH_3$), 1.19 (s, 6H, $2CH_3$).

The other product isolated from the hydrolysis was 4-(5,6,7,8-tetrahydro-5,5,8,8-tetramethyl-anthracene-1-carbonyl)-benzoic acid 51 mg (68%): m.p. 190–193° C.; $^1H$ NMR (400 MHz, $CDCl_3$) δ 8.18(m, 3H, ArH), 7.93(m, 3H, ArH), 7.84(s, 1H, ArH), 7.52(m, 1H, ArH), 7.38(m, 1H, ArH), 1.74(m, 4H, $2CH_2$), 1.39(s, 6H, $2CH_3$), 1.24(s, 6H, $2CH_3$).

EXAMPLE 38

4-[(5,6,7,8-Tetrahydro-5,5,8,8-tetramethyl-anthracen-1-yl)hydrorymethyl]-benzoic Acid (Compound 138, prepared as illustrated and described in Scheme 12)

A solution of 4-(5,6,7,8-tetrahydro-5,5,8,8-tetramethyl-anthracene-1-carbonyl)-benzoic acid (from Example 36, 10 mg, 0.03 mmol) in MeOH (2 mL) was treated with $NaBH_4$ (5 mg) at ambient temperature and the mixture was allowed to stir for 5 min. The reaction was quenched with aqueous saturated $NH_4Cl$. The aqueous solution was extracted with EtOAc (3x). The organic layers were combined and washed with water (2x) and brine. The organic solution was dried ($Na_2SO_4$), filtered, and concentrated to afford 4-[(5,6,7,8-tetrahydro-5,5,8,8-tetramethyl-anthracen-1-yl) hydrorymethyl]-benzoic acid (138) 9.2 mg (92%) as a colorless oil: $^1H$ NMR (400 MHz, $CDCl_3$) δ 8.04(½ABq, J=8.3 Hz, 2H, ArH), 7.95(s, 1H ArH), 7.76(s, 1H, ArH), 7.71(d, J=8.2 Hz, 1H, ArH), 7.56(½ABq, J=8.3 Hz, 2H, ArH), 7.43(d, J=6.9 Hz, 1H, ArH), 7.34(dd, J=6.9, 8.2 Hz, 1H, ArH), 6.48(s, 1H, CH), 1.70(broad s, 4H, $2CH_2$), 1.35(s, 3H, $CH_3$), 1.34(s, 3H, $CH_3$), 1.24(s, 3H, $CH_3$), 1.19(s, 3H, $CH_3$).

EXAMPLE 39

4-(5,6,7,8-Tetrahydro-5,5,8,8-tetramethyl-anthracen-1-ylmethyl)-benzoic Acid (Compound 139, prepared as illustrated and described in Scheme 12)

A solution of 4-[(5,6,7,8-tetrahydro-5,5,8,8-tetramethyl-anthracen-1-yl)-hydroxymethyl]-benzoic acid (from Example 37, 30 mg, 0.07 mmol) in dichloromethane (5 mL) was treated with excess triethylsilane (0.2 mL) and $BF_3$-$Et_2O$ (0.16 mL) at 0° C. The solution was allowed to stir for 10 min and then EtOH was added. The mixture was diluted with water and EtOAc. The organic solution was washed with water and brine, dried ($Na_2SO_4$), filtered, and concentrated to yield 4-(5,6,7,8-tetrahydro-5,5,8,8-tetramethyl-anthracen-1-ylmethyl)-benzoic acid (139) 15 mg (55%) as a colorless oil: $^1H$ NMR (400 MHz, $CDCl_3$) δ 8.01(½ABq, J=8.2 Hz, 2H, ArH), 7.81(s, 1H, ArH), 7,77(s, 1H, ArH), 7.66(d, J=8.2 Hz, 1H, ArH), 7.32(m, 3H, ArH), 7.24(s, 1H, ArH), 7.19(d, J=6.7 Hz, 1H, ArH), 4.45(s, 2H, $CH_2$), 1.72 (m, 4H, $2CH_2$), 1.35(s, 6H, $2CH_3$), 1.24(s, 6H, $2CH_3$).

EXAMPLE 40

4-[1-Hydroxy-1-(5,6,7,8-Tetrahydro-5,5,8,8-tetramethyl-anthracen-1-yl)-ethyl)]-benzoic Acid (Compound 140, prepared as illustrated and described in Scheme 13)

A solution of 4-(5,6,7,8-tetrahydro-5,5,8,8-tetramethyl-anthracene-1-carbonyl)-benzoic acid (from Example 36, 10 mg, 0.03 mmol) in $CH_2Cl_2$(2 mL) was treated with trimethylaluminum (0.4 mL) at 0° C. and the solution was allowed to stir for 1 h. The reaction was quenched with aqueous saturated potassium sodium tartrate. The aqueous solution was extracted with EtOAc (3x). The organic layers were combined and washed with water (2x) and brine. The organic solution was dried ($Na_2SO_4$), filtered, and concentrated to afford 4-[1-hydroxy-1-(5,6,7,8-tetrahydro-5,5,8,8-tetramethyl-anthracen-1-yl)-ethyl)]-benzoic acid (140) 5.0 mg (55%) as a colorless oil: $^1H$ NMR (400 MHz, $CDCl_3$) δ 8.01(½ABq, J=8.2 Hz, 2H, ArH), 7.74(m, 3H, ArH), 7.53 (½ABq, J=8.2 Hz, 2H, ArH), 7.39(t, J=7.7 Hz, 1H, ArH), 7.26(s, 1H, ArH), 2.05(s, 3H, $CH_3$), 1.64(m, 4H, $2CH_2$), 1.26(s, 6H, $2CH_3$), 1.15(s, 3H, $CH_3$), 0.77(s, 3H, $CH_3$).

EXAMPLE 41

4-[1-Methoxy-1-(5,6,7,8-Tetrahydro-5,5,8,8-tetramethyl-anthracen-1-yl)-ethyl)]-benzoic Acid (Compound 141, prepared as illustrated and described in Scheme 13)

A solution of 4-[1-hydroxy-1-(5,6,7,8-tetrahydro-5,5,8,8-tetramethyl-anthracen-1-yl)-ethyl)-benzoic acid (from Example 39; 5 mg, 0.01 mmol) in MeOH (2 mL) was treated with concentrated HCl (0.25 mL) at ambient temperature The solution was heated to 85° C. and allowed to stir for 1 h. The reaction was quenched with aqueous saturated $NH_4Cl$. The aqueous solution was extracted with EtOAc (3x). The organic layers were combined and washed with water (2x) and brine. The organic solution was dried ($Na_2SO_4$), filtered, and concentrated to afford after silica gel flash chromatography (70.30=EtOAc:hexanes), 4-[1-methoxy-1-(5,6,7,8-tetrahydro-5,5,8,8-tetramethyl-anthracen-1-yl)-ethyl)]-benzoic acid (141) 0.6 mg (12%) as a colorless oil: $^1$H NMR (400 MHz, $CDCl_3$) δ 8.02(½ABq, J=8.2 Hz, 2H, ArH), 7.77(m, 3H, ArH), 7.54(½ABq, J=8.2 Hz, 2H, ArH), 7.36(t, J=7.7 Hz, 1H, ArH), 7.25(s, 1H, ArH), 3.90(s, 3H, $OCH_3$), 2.03(s, 3H, $CH_3$), 1.69(m, 4H, $2CH_2$), 1.29(s, 6H, $2CH_3$), 1.10(s, 3H, $CH_3$), 0.83(s, 3H, $CH_3$).

EXAMPLE 42

4-[1-(5,6,7,8-Tetrahydro-5,5,8,8-tetramethyl-anthracen-1-yl)vinyl)]-benzoic Acid (Compound 142, prepared as illustrated and described in Scheme 13)

The final product mixture from Example 40 was further purified by preparative silica gel TLC (70:30=EtOAc:hexanes), to afford 4-[1-(5,6,7,8-tetrahydro-5,5,8,8-tetramethyl-anthracen-1-yl)vinyl)]-benzoic acid (142) 1 mg (20%) as a colorless oil: $^1$H NMR (400 MHz, $CDCl_3$) δ 7.97(½ABq, J=8.4 Hz, 2H, ArH), 7.75(s, 1H, ArH), 7.73(m, 1H, ArH), 7.50(s, 1H, ArH), 7.40(½ABq, J=8.4 Hz, 2H, ArH), 7.35(m, 2H, ArH), 5.98 (d, J=1.0 Hz, 1H, olefinic), 5.53(app s, 1H, olefinic), 1.65(m, 4H. $2CH_2$), 1.35(s, 6H, $2CH_3$), 1.03(s, 6H, $2CH_3$).

EXAMPLE 43

(traps)4-(5,6,7,8-Tetrahydro-5,5,8,8-tetramethyl-anthracene-1-carbonyl oxime)-benzoic Acid (Compound 143, prepared as illustrated and described in Scheme 14)

A solution of 4-(5,6,7,8-tetrahydro-5,5,8,8-tetramethyl-anthracene-1-carbonyl)-benzoic acid (from Example 36, 18 mg, 0.04 mmol) in EtOH (2 mL) and pyridine (0.05 mL) was treated with hydroxylamine hydrochloride (5 mg, 0.07 mmol), and the mixture was heated at reflex. After 6 h, the mixture was cooled to room temperature and ethanol was removed in vacuo. The residue was taken-up in water and the aqueous layer was adjusted to pH=4–5 with 1 M aqueous HCl. The aqueous solution was extracted with EtOAc (3x). The organic layers were combined and washed with water (2x) and brine. The organic solution was dried ($Na_2SO_4$), filtered, and concentrated to give a foamy white solid. Purification by silica gel chromatography (1:1= hexanes:$Et_2O$ ) (trans)-4-(5,6,7,8-tetrahydro-5,5,8,8-tetramethyl-anthracene-1-carbonyl oxime)-benzoic acid (143), 2.5 mg (16%) as a colorless film: $^1$H-NMR (400 MHz, $CDCl_3$) δ 8.04(½ABq, J=8.5 Hz, 2H, ArH), 7.85(d, J=8.3 Hz, 1H, ArH), 7.83(s, 1H, ArH), 7.60(½ABq, J=8.5 Hz, 2H, ArH), 7.51(s, 1H, ArH), 7.44(dd, J=8.3, 7.2 Hz, 1H, .ArH), 7.26(d, J=7.2 Hz, 1H, ArH), 1.70(m, 4H, $2CH_2$), 1.38(s, 12H, $4CH_3$).

EXAMPLE 44

(cis)-4-(5,6,7,8-Tetrahydro-5,5,8,8-tetramethyl-anthracene-1-carbonyl oxime)-benzoic Acid (Compound 144, prepared as illustrated and described in Scheme 14)

The product mixture from Example 42 was purified by preparative silica gel chromatography ($Et_2O$) to afford (cis)-4-(5,6,7,8-tetrahydro-5,5,8,8-tetramethyl-anthracene-1-carbonyl oxime)-benzoic acid (144) 0.5 mg (3%) as a colorless film: $^1$H NMR (400 MHz, $CDCl_3$) δ8.05(½ABq, J=8.4 Hz, 2H, ArH), 7.99(d, J=8.5 Hz, 1H, ArH), 7.75(s, 1H, ArH), 7.70(½ABq, J=8.4 Hz, 2H, ArH), 7.65(s, 1H, ArH), 7.59(d, J=8.0 Hz, 1H, ArH), 7.38(dd, J=8.5, 8.0 Hz, 1H, ArH), 1.68(m, 4H, $2CH_2$), 1.33(s, 3H, $CH_3$), 1.23(s, 6H, $2CH_3$), 1.06(s, 3H, $CH_3$).

EXAMPLE 45

(trans)-4-(5,6,7,8-Tetrahydro-5,5,8,8-tetramethyl-anthracene-1-carbonyl O-methyloxime-benzoic Acid (Compound 145, prepared as illustrated and described is Scheme 14)

A solution of 4-(5,6,7,8-tetrahydro-5,5,8,8-tetramethyl-anthracene-1-carbonyl)-benzoic acid (from Example 36, 21 mg, 0.04 mmol) in EtOH (2 mL) was treated with methoxyl amine hydrochloride (12 mg, 0.15 mmol) and pyridine (0.05 mL), and the mixture was heated at reflux for 5 h. The reaction was worked-up in a manner identical to that described for Example 42 to give, after silica gel chromatography (1:1=hexanes:$Et_2O$) (trans)-4-(5,6,7,8-tetrahydro-5,5,8,8-tetramethyl-anthracene-1-carbonyl O-methyloxime)-benzoic acid (145) 8.2 mg (49%) as a colorless oil: $^1$H NMR (400 MHz, $CDCl_3$) δ 8.04 (½ABq, J=8.5 Hz, 2H, ArH), 7.85(d, J=8.3 Hz, 1H, ArH), 7.83(s, 1H, ArH), 7.63(½ ABq, J=8.5 Hz, 2H, ArH), 7.51(s, 1H, ArH), 7.44(dd, J=8.3, 7.2 Hz, 1H, ArH), 7.20(d, J=7.2 Hz, 1H, ArH), 3.98(s, 3H, $OCH_3$), 1.70(m, 4H, $2CH_2$), 1.38(s, 12H, $4CH_3$).

EXAMPLE 46

(2E, 4E, 6E)-7-(3,5-Diisopropyl-2-n-heptyloxyphenyl)-3-methylocta-2,4,6-trienoic Acid (Compound 146, prepared as illustrated and described in Scheme 15).

A solution of 3,5-diisopropyl-2-hydroxybenzoic acid (20.0 g, 90.1 mmol) in THF (100 mL) at −78° C. was treated dropwise with a solution of methyllithium (1.4 M in ether, 193 mL, 270 mmol). The reaction solution was allowed to warm to room temperature and stirred for 30 min. The solution was poured into saturated aqueous $NH_4Cl$ (200 mL), and the organic product was extracted with 1:1= EtOAc:hexanes (2×100 mL), dried ($MgSO_4$), filtered, and concentrated. Distillation (1 mm Hg, 120° C.) gave 3,5-diisopropyl-2-hydroxyacetophenone 12.0 g (61%): TLC (5% EtOAc-95% hexanes) $R_f$=0.4; $^1$H-NMR ($CDCl_3$) δ 7.39(s, 1H, ArH), 7.29(s, 1H, ArH), 3.38(m, 1H, CH), 2.87(m, 1H, CH), 2.63(s, 3H $CH_3$), 1.24(d, J=14.0 Hz, 12H, $4CH_3$).

A solution of 3,5-diisopropyl-2-hydroxy-acetophenone (1.0 g, 4.54 mmol) DMSO (1 mL was treated with n-heptylbromide (1 mL, excess) and KOH (solid, 600 mg, 10.7 mmol) at ambient temperature. The mixture was heated at 50° C. for 12 h, cooled to room temperature and diluted with water (5 mL) and hexanes (10 mL). The organic layer was separated and washed with water (2×5 mL) and brine (5 mL), dried ($MgSO_4$), and concentrated to give 3,5-diisopropyl-2-n-heptyloxyacetophenone 1.3 g (90%): $^1$H-NMR ($CDCl_3$) δ 7.23(s, 1H, ArH), 7.21(s, 1H, ArH), 3.71(t, J=7.4 Hz, 2H, $OCH_2$), 3.32(m, 1H, CH), 2.87(m, 1H, CH), 2.63(s, 3H, $CH_3$), 1.78(m, 2H, $CH_2$), 1.31(m, 8H, $4CH_2$), 1.27 (d, J=14.0 Hz, 6H, $2CH_3$), 1.24(d, J=14.0 Hz, 6H, $2CH_3$), 0.89(t, J=7.5 Hz, 3H, $CH_3$), A solution of diethylcyanomethyl phosphonate (2.00 g, 11.18 mmol) in THF (10 mL) at −78° C. was treated dropwise with n-BuLi (2.5 M in hexanes, 4.4 mL, 11.0 mmol). The reaction solution was allowed to warm to ambient temperature and stirred for 30 min. A solution of the unpurified 3,5-diisopropyl-2-n-heptyloxyacetophenone (1.0 g, 3.14 mmol) in THF (5 mL) was added dropwise to the ylide solution. After stirring for 1 h at ambient temperature, the reaction solution was diluted with saturated aqueous $NH_4Cl$ (20 mL) and extracted with hexanes (2×20 mL). The organic extracts were combined and washed with water (2×5 mL) and brine (5 mL), dried ($MgSO_4$), filtered, and concentrated to give 3-(3,5-diisopropyl-2-n-heptyloxyphenyl)-but-2-enenitrile 900 mg (32%), predominantly as the traps isomer: TLC (5% EtOAc-95% hexanes) $R_f$=0.9; $^1$H-NMR ($CDCl_3$) δ 7.11(s, 1H, ArH), 6.81 (s, 1H, ArH), 5.57(s, 1H, olefinic), 3.61(t, J=7.4 Hz, 2H, $OCH_2$), 3.32(m, 1H, CH), 2.84 (m, 1H, CH), 2.46(s, 3H, $CH_3$), 1.73(m, 2H, $CH_2$), 1.31(m, 8H, $4CH_2$), 1.27(d, J=14.0 Hz, 6H, $2CH_3$), 1.24(d, J=14.0 Hz, 6H, $2CH_3$), 0.89(t, J=7.5 Hz, 3H, $CH_3$).

A solution of 3-(3,5-diisopropyl-2-n-heptyloxyphenyl)-but-2-enenitrile (900 mg, 2.64 mmol) in hexanes (8 mL) was treated with DIBAL (1.5 M in toluene, 2.0 mL, 7.95 mmol) at −78° C. After stirring for 15 min at −78° C., the reaction solution was quenched with a saturated aqueous sodium-potassium tartrate solution (20 mL) and allowed to warm to room temperature over 30 min. The product was extracted with ether (2×40 mL), and the organic solution was washed with water (2×5 mL) and brine (5 mL); dried ($MgSO_4$), filtered, concentrated. Purification by silica gel flash chromatography (3% EtOAc-hexanes) gave the unsaturated aldehyde 3-(3,5-diisopropyl-2 n-heptyloxyphenyl)-but-2-enal 800 mg (90%): TLC (10% EtOAc-90% hexanes) $R_f$=0.7; $^1$H NMR ($CDCl_3$) δ 10.17(d, J=8.0 Hz, 1H, CHO), 7.11(s, 1H, ArH), 6.82(s, 1H, ArH), 6.17(d, J=8 Hz, 1H, olefinic), 3.65(t, J=7.4 Hz, 2H, $OCH_2$), 3.32(m, 1H, CH), 2.84(m, 1H, CH), 2.57(s, 3H, $CH_3$), 1.73(m, 2H, $CH_2$), 1.31(m, 8H, $4CH_2$), 1.27(d, J=14.0 Hz, 6H, $2CH_3$), 1.24(d, J=14.0 Hz, 6H, $2CH_3$), 0.89(t, J=7.5 Hz, 3H, $CH_3$).

A solution of diethyl 3-ethoxycarbonyl-2-methyl prop-2-enylphosphonate (1.0 g, 3.79 mmol) and DMPU (4 mL) in THF (4 mL) was cooled in a −78° C. bath and treated with n-BuLi (2.5 M solution in hexanes, 1.5 mL, 3.75 mmol). The reaction solution was allowed to warm to room temperature and stirred for 15 min. A solution of 3-(3,5-diisopropyl-2-n-heptyloxyphenyl)-but-2-enal (820 mg, 2.38 mmol) in THF (10 mL) was added and the resulting solution was allowed to stir for 1 h at room temperature. The reaction was quenched with saturated aqueous $NH_4Cl$ (20 mL) and extracted with ether (2×20 mL). The combined organic extracts were washed with water (2×5 mL) and brine (5 mL), dried ($MgSO_4$), filtered, concentrated and purified by silica gel flash column chromatography (5% EtOAc-hexanes) to give ethyl-(2E, 4E, 6E)-7-(3,5-diisopropyl-2-n-heptyloxyphenyl)-3-methylocta-2,4,6-trienoate 1.0 g (92%): TLC (5% EtOAc-95% hexanes) $R_f$=0.8; $^1$H-NMR ($CDCl_3$) δ 7.01(s, 1H, ArH), 6.99(m, 1H, olefinic), 6.84(s, 1H, Ar), 6.35(d, J=11.0 Hz, 1H, olefinic), 6.30(d, J=15.0 Hz, 1H, olefinic), 5.79(s, 1H, olefinic), 4.18(m, 2H, $OCH_2$), 3.65 (t, J=7.4 Hz, 2H, $OCH_2$), 3.32(m, 1H, CH), 2.84(m, 1H, CH), 2.37(s, 3H, $CH_3$), 2.19(s, 3H, $CH_3$), 1.66(m, 2H, $CH_2$), 1.31(m, 8H, $4CH_2$), 1.29(t, J=14.0 Hz, 3H, $CH_3$), 1.27(d, J=14.0 Hz, 6H, $2CH_3$), 1.24(d, J=14.0 Hz, 6H, $2CH_3$), 0.89(t, J=7, 5 Hz, 3H, $CH_3$).

A solution of the crude ethyl-(2E, 4E, 6E)-7-(3,5-diisopropyl-2-n-heptyloxyphenyl)-3-methylocta-2,4,6-trienoate (500 mg, 1.10 mmol) in methanol (5 mL) was hydrolyzed with NaOH (1 mL of 5N aqueous solution) at reflux temperature. After 10 min, the mixture was cooled to room temperature and acidified with a 20% aqueous HCl solution. The solution was concentrated and the aqueous residue was extracted with EtOAc (2×10 mL). The EtOAc layer was washed with water (2×5 mL) and brine (5 mL), dried ($MgSO_4$), filtered and concentrated. The major product (highest running spot by TLC) was isolated by preparative TLC (20% EtOAC-80% hexanes) to give (2E, 4E, 6E)-7-(3,5-diisopropyl-2-n-heptyloxyphenyl)-3-methylocta-2,4,6-trienoic acid (146) 220 mg (47%): TLC (10% MeOH-90% $CHCl_3$) $R_f$=0.6; $^1$H NMR ($CDCl_3$) δ 7.04(m, 1H, olefinic), 7.01(s, 1H, ArH), 6.84(s, 1H, ArH), 6.35(d, J=11.0 Hz, 1H, olefinic), 6.30(d, J=15.0 Hz, 1H, olefinic), 5.79(s, 1H, olefinic), 3.65(t, J=7.4 Hz, 2H, $OCH_2$), 3.32(m, 1H, CH), 2.84(m, 1H, CH), 2.37(s, 3H, $CH_3$), 2.19(s, 3H, $CH_3$), 1.66(m, 2H, $CH_2$), 1.31(m, 8H, $4CH_2$), 1.27(d, J=14.0 Hz, 6H, $2CH_3$), 1.24(d, J=14.0 Hz, 6H, $2CH_3$), 0.89(t, J=7.5 Hz, 3H, $CH_3$).

EXAMPLE 47

(2E, 4E, 6E)-7-(3,5-Diisopropyl-2-n-heptyloxyphenyl)-3-methylocta-2,4,6-trienoic Acid (Compound 147, prepared as illustrated and described in Scheme 15).

The final product mixture from Example 46 was purified by preparative silica gel thin layer chromatography (20% EtOAc:hexanes) to give the title compound (2E, 4E, 6Z)-7-(3,5-diisopropyl-2-n-heptyloxyphenyl)-3-methylocta-2,4,6-trienoic, acid (147) as a colorless oil: TLC (10% MeOH-90% $CHCl_3$) $R_f$=0.6; $^1$H-NMR ($CDCl_3$) δ 7.26 (d, J=2.3 Hz, 1H, Ar—H), 7.03(d, J=2.3 Hz; 1H, Ar—H), 6.73(m, 1H, olefinic), 6.24(d, J=15.2 Hz, 1H, olefinic), 6.21(d, J=10.2 Hz, 1H, olefinic), 5.72(s, 1H, olefinic), 3.61(t, J=6.5 Hz, 2H, $OCH_2$), 3.34(m, 1H, CH), 2.85(m, 1H, CH), 2.21(s, 3H, $CH_3$), 2.14(s, 3H, $CH_3$), 1.64(m, 2H; $CH_2$), 1.50(m, 2H, $CH_2$), 1.37(m; 6H, $3CH_3$), 1.27(d, J=4.7 Hz, 6H, $2CH_3$), 1.21(d, J=4.7 Hz, 6H, $2CH_3$); 0.88(t, J=6.5 Hz, 3H; $CH_3$).

EXAMPLE 48

(2E, 4E,)-7-(3,5-Diisopropyl-2-n-heptyloxyphenyl)-3-methylocta-2,4-dienoic Acid (Compound 148, prepared as illustrated and described in Scheme 16).

To a solution of 3-(3,5-di-t-butyl-2-n-heptyloxyphenyl)-but-2-enenitrile (900 mg, 2.64 mmol) in EtOAc (5 mL) was added 10% Pd on carbon (20 mg, catalytic amount). The mixture was placed under vacuum for 1 min followed by addition of $H_2$. After stirring for 24 h under an atmosphere of $H_2$, the solution was filtered through celite. The celite washed with EtOAc (3×5 mL) and the solution was concentrated to give the reduced product 3-(3,5-di-t-butyl-2-n-heptyloxyphenyl)-butyronitrile 880 mg (97%): TLC (5% EtOAc-95% hexanes) $R_f$ 0.8; $^1$H-NMR ($CDCl_3$) δ 7.00(d, J=2.2 Hz, 1H, Ar—H) 6.89(d, J=2.2 Hz, 1H Ar—H), 3.73 (t, J=6.5 Hz, 2H, $OCH_2$), 3.52(m, 1H, CH), 3.27(m, 1H, CH), 2.86(m, 1H, CH), 2.63(m, 2H, $CH_2CN$), 1.79(m, 2H, $CH_2$), 1.50(m, 2H, $CH_2$), 1.44(m, 6H, $3CH_2$), 1.39(d, J=13.2 Hz, 3H, $CH_3$), 1.27(d, J=4.7 Hz, $2CH_3$), 1.21(d, J=4.7 Hz, $2CH_3$), 0.89(t, J=6.6 Hz, 3H, $CH_3$).

To a solution of the (3,5-di-t-butyl-2-n-heptyloxyphenyl) butyronitrile (200 mg, 0.58 mmol) in hexanes (5 mL) at −78° C. was added DIBAL (1.5 M solution in toluene, 1.20 mL, 1.80 mmol). The reaction was stirred for 5 min, quenched with saturated aqueous NH$_4$Cl(10 mL), extracted with ether (2×20 mL), dried (MgSO$_4$); filtered, concentrated and purified by chromatography (SiO$_2$, 5% EtOAc-hexanes) to give the aldehyde 3-(3,5-di-t-butyl-2-n-heptyloxyphenyl) butyroacetal 60 mg (30%): TLC (5% EtOAc-95% hexanes) R$_f$0.8; $^1$H-NMR (CDCl$_3$) δ 9.70(t, J=2.3 Hz, 1H, CHO), 6.96(d, J=2.2 Hz, 1H, Ar—H), 6.86(d, J=2.2 Hz, 1H, Ar—H), 3.74(t, J=6.5 Hz, 2H, OCH$_2$), 3.39(m, 1H, CH), 3.26(m, 1H, CH), 2.82(m, 1H, CH), 2.64(m, 2H, CH$_2$), 1.50(m, 2H, CH$_2$), 1.40(m, 6H, 3CH$_2$), 1.32(d, J=13.2 Hz, 3H, CH$_3$), 1.27(d, J=4.7 Hz, 2CH$_3$), 1.21(d, J=4.7 Hz, 2CH$_3$), 0.88(t, J=6.6 Hz, 3H, CH$_3$).

In a manner similar to that described in Example 46, the intermediate aldehyde was converted to ethyl (2E, 4E)—[7-(3,5-di-t-butyl-2-n-heptyloxyphenyl)-3-methyl]-octa-2,4-dienoate: TLC (5% EtOAc-95% hexanes) R$_f$0.9; $^1$H-NMR (CDCl$_3$) δ 6.93(d, J=2.2 Hz, 1H, Ar—H), 6.86(d, J=2.2 Hz, 1H, Ar—H), 6.06(m, 2H, 2x olefinic), 5.65(s, 1H, olefinic), 4.16(m, 2H, —CH$_2$ CH$_3$), 3.68(t, J=6.5 Hz, 2H, OCH$_3$), 3.32(m, 1H, CH), 2.84(m, 1H, CH), 2,46(m, 1H, CH), 2.37(m, 2H, CH$_2$), 2.22(s, 3H, CH$_3$), 1.79(m, 2H, CH$_2$), 1.47(m, 2H, CH$_2$), 1.32(d, J=13.2 Hz, 3H, CH$_3$), 1.31(m, 6H, 3CH$_2$), 1.29(t, J=7.0 Hz, 3H, CH$_3$), 1.27(d, J=4.7 Hz, 6H, 2CH$_3$), 1.21(d, J=4.7 Hz, 6H, 2CH$_3$), 0.89(t, J=7.0 Hz, 3H, CH$_3$).

The ester was hydrolyzed as described in Example 46 to give (2E, 4E)-7-(3,5-di-t-butyl-2-n-heptyloxyphenyl)-3-methylocta-2,4-dienoic acid (148): TLC (10% MeOH-90% CHCl$_3$) R$_f$0.5; $^1$H-NMR (CDCl$_3$) δ 6.94(d, J=2.2 Hz, 1H, Ar—H), 6.86(d, J=2.2 Hz, 1H, Ar—H), 6.11(m, 2H, 2x olefinic), 5.68(s, 1H, olefinic), 3.68(t, J=6.5 Hz, 2H, OCH$_3$), 3.28 (m, 1H, CH), 2.82(m, 1H, CH), 2.43(m, 1H, CH), 2.38(m, 2H, CH$_2$), 2.23(s, 3H, CH$_3$), 1.77(m, 2H, CH$_2$), 1.43(m, 2H, CH$_2$), 1.34(m, 6H, 3CH$_2$), 7.32(d, J=13.2 Hz, 3H, CH$_3$), 1.27(t, J=4.7 Hz, 3H, CH$_3$), 1.21(d, J=4.7 Hz, 6H 2CH$_3$), 0.88(t, J=6.6 Hz, 3H, CH$_3$).

EXAMPLE 49

(2Z, 4E,)-7-(3,5-Diisopropyl-2-n-heptyloxyphenyl)-3-methylocta-2,4,dienoic Acid (Compound 149, prepared as illustrated and described in Scheme 16).

The final product mixture from Example 48 was purified by preparative silica gel thin layer chromatography (20% EtOAc-hexanes) to give the title compound (2Z, 4E,)-7-(3, 5-diisopropyl-2-n-heptyloxyphenyl)-3-methylocta-2,4, dienoic acid (149) as a colorless oil: TLC (10% MeOH-90% CHCl$_3$) R$_f$0.6; $^1$H-NMR (CDCl$_3$) δ 7.52(d, J=15.8 Hz, 1H, olefinic), 6.93(d, J=2.2 Hz, 1H, Ar—H), 6.89(d, J=2.2 Hz, 1H, Ar—H), 6.10(s, 1H, olefinic), 5.60(s, 1H, olefinic), 3.68(t, J=6.5 Hz, 2H, OCH$_3$), 3.28(m, 1H, CH), 3.28(m, 1H, CH), 2.85(m, 1H, CH), 2.49(m, 3H, CH-CH$_3$), 1.97(s, 3H, CH$_3$), 1.77(m, 2H, CH$_2$), 1.47(m, 2H, CH$_2$), 1.31(m, 6H; 3CH$_2$), 1.27(d, J=13.2 Hz, 3H, CH$_3$), 1.24(t, J=4.7 Hz, 3H, CH$_3$), 1.21(d, J=4.7 Hz, 6H, 2CH$_3$), 0.88(t, J=6.6 Hz, 3H, CH$_3$).

EXAMPLE 50

(2E, 4E, 6E)-7-(3,3-Diisopropyl-2-benzyloxyphenyl-3-methylocta-2,4,6-trienoic Acid (Compound 150, prepared as illustrated and described in Scheme 15).

The title compound was prepared in an analogous manner as described in Example 46 using 3,5-diisopropyl-2-benzyloxyacetophenone instead of 3,5-diisopropyl-2-n-heptyloxyacetophenone to give (2E, 4E, 6E)-7-(3,5-diisopropyl-2-benzyloxyphenyl)-3-methylocta-2,4,6-trienoic acid (150): TLC (10% MeOH-90% CHCl$_3$) R$_f$=0.5; $^1$H-NMR (CDCl$_3$) δ 7.74(m, 5H, Ar—H), 7.05(m, 1H, olefinic), 7.03(s, 1H, ArH ), 6.90(s, 1H, ArH ), 6.43(d, J=11.0 Hz, 1H, olefinic), 6.34(d, J=15.0 Hz, 1H, olefinic), 5.83(s, 1H, olefinic), 4.71(s, 2H, OCH$_2$), 3.39(m, 1H, CH), 2.88(m, 1H, CH); 2.40(s, 3H, CH$_3$), 2.26(s, 3H, CH$_3$), 1.26(m, 12H, 4CH$_3$).

EXAMPLE 51

(2E, 4E, 6E)-7-(3,5-Diisopropyl-2-n-butyloxyphenyl)-3-methylocta 2,4,6-trienoic Acid (Compound 151, prepared as illustrated and described in Scheme 1).

The title compound was prepared in an analogous manner as described in Example 46 using 3,5-diisopropyl-2-butyloxyacetophenone instead of 3,5-diisopropyl-2-n-heptyloxyacetophenone to give (2E, 4E, 6E)-7-(3,5-diisopropyl-2-n-butyloxyphenyl)-3-methylocta-2,4,6-trienoic acid (151): TLC (10% MeOH-90% CHCl$_3$) R$_f$=0.6; $^1$H-NMR (CDCl$_3$) δ 7.05(m, 1H, olefinic), 7.03(s, 1H, ArH ), 6.85(s, 1H, ArH), 6.36(d, J=11.0 Hz, 1H, olefinic), 6.30(d, J=15.0 Hz, 1H, olefinic), 5.83(s, 1H, olefinic), 3.66(t, J=7.4 Hz, 2H, OCH$_2$), 3.32(m, 1H, CH), 2.84(m, 1H, CH), 2.40(s, 3H, CH$_3$), 2.26(s, 3H, CH$_3$), 1.67(m, 2H, CH$_2$), 1.44(m, 8H, 4CH$_2$), 1.25(d, J=14.0 Hz, 6H, 2CH$_3$), 1.23(d, J=14.0 Hz, 6H, 2CH$_3$), 0.92(t, J=7.5 Hz, 3H, CH$_3$).

EXAMPLE 52

(2E, 4E)-6-[2-(5,5,8,8-Tetramethyl-3-propyloxy-5,6, 7,8-tetrahydronaphthalen-2-yl) cyclopropan-1-yl]-3-methyl hexadienoic Acid (Compound 152, prepared as illustrated and described in Scheme 17)

To a solution of 2-bromophenol (10 g, 57.8 mmol) and 2,5-dichloro-dimethyl hexane (13.04 g, 69.36 mmol) in 160 mL anhydrous CH$_2$Cl$_2$ at 5° C. was added, portionwise, AlCl$_3$ (2.31 g, 17.34 mmol). Upon addition of AlCl$_3$, HCl gas evolution was observed. The solution changed from yellow to reddish orange. The reaction solution was kept at 5–20° C. for two hours and then allowed to stir at room temperature overnight. The reaction mixture was poured into 160 g of ice and extracted with 160 mL CHCl$_3$). The organic phase was washed with water, aqueous, saturated NaHCO$_3$, saturated NaCl and dried (Na$_2$SO$_4$). The organic solution was then concentrated in vacuo and chromatographed (5 to 10% EtOAc/hexane) to provide 12.83 g of 2-bromo-3-hydroxy-5,5,8,8-tetramethyl-5,6,7,8-tetrahydronaphthalene as a white solid in 80% yield. $^1$H NMR (400 MHz, CDCl$_3$) δ 7.34(s, 1H, aromatic), 6.93(s, 1H, aromatic), 5.24(s, 1H, phenolic OH), 1.64(s; 4H, 2CH$_2$), 1.23(s, 6H, 2CH$_3$), 1.22(s, 6H, 2CH$_3$).

A mixture of tetrahydrobromonaphthol (3.0 g, 10.38 mmol), iodopropane (1.42 mL, 14.53 mmol), and K$_2$CO$_3$ (2.3 g, 16.61 mmol) were mixed together in 100 mL of acetone and allowed to reflux overnight. The solvent was removed in vacuo and then 100 mL of water was added. The aqueous phase was extracted with EtOAc (3×50 mL), washed with brine, and dried (Na$_2$SO$_4$). The organic phase was concentrated in vacuo to afford 3.29 g of 2-bromo-3-propyloxy-5,5,8,8-tetramethyl-5,6,7,8- tetrahydronaphthalene as a brownish oil (97%). The crude material was carried on to the next step without further purification. $^1$H NMR (400 MHz, CDCl$_3$) δ 7.41(s, 1H, aromatic), 6.78(s, 1H, aromatic), 3.97(t, J=6.4 Hz, 2H, CH$_2$), 1.86(m, 2H, CH$_2$), 1.67(s, 4H, 2CH$_2$), 1.25(s, 6H, 2CH$_3$), 1.23(s, 6H, 2CH$_3$), 1.08(t, J=7.4 Hz, 3H, CH$_3$).

To a solution of the above aryl bromide (12 g, 36.89 mmol) in 200 mL of anhydrous THF at −78° C., was added n-BuLi (16.23 mL, 40.58 mmol), generating a pale yellow solution. This reaction solution was stirred at −78° C. for 15–20 minutes. Trimethyl borate (4.19 mL, 36.89 mmol) was then added via a syringe. The reaction mixture was allowed to warm to room temperature and stirred overnight. It was then cooled to 0° C. and acidified with 5% HCl to pH=6. The organic phase was concentrated in vacuo and the residue was diluted with 200 mL of water and extracted with CH$_2$Cl$_2$(3×100 mL). The organic phase was washed with brine and dried (MgSO$_4$). After removal of the solvent, 9.5 g of the boronic acid was isolated as an off white solid in 82% yield. To a solution of tetrakistriphenylphosphine palladium (0,032 g, 0.03 mmol) in 2 mL of toluene under N$_2$ was added 2-bromopropene (0.82 mL, 0.92 mmol) at room temperature. The mixture was allowed to stir for 10 min. The above boronic acid (0.399 g, 1.37 mmol) in 1 mL of ethanol was added, followed by 1.38 mL of an aqueous 2M solution of Na$_2$CO$_3$. The reaction mixture was then refluxed for three hours after which the solvent was removed in vacuo to give an oil. The residue was then dissolved in 15 mL of EtOAc and 15 mL of water. The aqueous phase was extracted with EtOAc (2×10 mL). The combined organic solution was washed with water and saturated NaCl, dried (Na$_2$SO$_4$) and concentrated in vacuo to an oil that was subjected to chromatography (5% EtOAC/95% hexane) to give 0.366 g (93%) of 2-(5,5,8,8-tetramethyl-3-propyloxy-5,6,7,8-tetrahydronaphthalen-2-yl)-propene. $^1$H NMR (400 MHz, CDCl$_3$) δ 7.11 (s, 1H, aromatic), 6.73(s, 1H, aromatic), 5.07(s, 2H, olefinic), 3.90(t, J=6.5 Hz, 2H, CH$_2$), 2.14(s, 3H, allylic CH$_3$), 1.81(sx, J=6.8 Hz, 2H, CH$_2$), 1.66(s, 4H, 2CH$_2$), 1.28(s, 6H, 2X CH$_3$), 1.26(s, 6H, 2CH$_2$) and 1.03(t, J=7.4 Hz, 3H, CH$_3$).

Into a 5 mL round-bottom flask was introduced selenium dioxide (71 mg, 0.64 mmol), 1 mL of dichloromethane, and 90% t-butyl hydroperoxide (0.284 mL, 2.56 mmol). After the mixture had been stirred for 30 min. at room temperature, 2-(5,5,8,8-tetramethyl-3-propyloxy-5,6,7,8-tetrahydronaphthalen-2-yl)-propene (366 mg, 1.28 mmol), in 1 mL of dichloromethane was slowly added. The mixture was stirred at room temperature for 3 h. Then quenched with aqueous saturated NaHCO$_3$. The mixture was extracted with dichloromethane (2×10 mL), washed with water (10 mL) and brine (10 mL), and the combined organic phase dried (Na$_2$SO$_4$). Concentrated in vacuo to give an oil which was subjected to chromatography (10% EtOAC/90% hexane) to give 149 mg (40%) of 2-(5,5,8,8-tetramethyl-3-propyloxy-5,6,7,8-tetrahydro naphthalen-2-yl)-propen-1-ol. $^1$H NMR (400 MHz, (CDCl$_3$) δ 7.14(s, 1H, aromatic), 6.76(s, 1H, aromatic), 5.36(s, 1H, vinylic), 5.22(s, 1H, vinylic), 4.44(d, J=6.1 Hz, CH$_2$OH), 3.93(t, J=6.5 Hz, 2H, CH$_2$), 2.19(t, J=6.1 Hz, 1H, OH), 1.82(sx, J=6.8 Hz, 2H, CH$_2$), 1.66(s, 4H, 2CH$_2$), 1.28(s, 6H, 2CH$_3$), 1.26(s, 3H, CH$_3$), 1.25(s, 3H, CH$_3$) and 1.03(t, J=7.3 Hz, 3H, CH$_3$).

A 15 mL round bottom flask (oven dried and under argon) was charged with 1 mL anhydrous dichloroethane and diethyl zinc ) 1M is hexane, 0.660 mL, 0.66 mmol). The mixture was cooled to 0° C. and chloroiodomethane (0.096 mL, 1.32 mmol), was slowly added via a syringe. The reaction mixture was stirred at 0° C. for 5 min. and a solution of the above allylic alcohol (0.100 g, Hz, 0.33 mmol) in 1 mL dichloroethane was slowly added. The reaction mixture was stirred at 0° C. for 20 min. and quenched with aqueous saturated NH$_4$Cl and the aqueous phase was extracted with EtOAc (2×10 mL). The organic phase was then washed with saturated NaCl, dried (Na$_2$SO$_4$). and concentrated in vacuo. The resulting oil was subjected to chromatography (10% EtOAc/90% hexane) to provide 56 mg (54%) of [1-(5,5,8,8-tetramethyl-3-propyloxy-5,6,7,8-tetrahydronaphthalen-2-yl)-cyclopropyl] methanol. $^1$H NMR (400 MHz, CDCl$_3$) δ 7.17(s, 1H, aromatic), 6.72(s, 1H, aromatic), 3.94(t, J=6.3 Hz, 2H, CH$_2$), 3.56(d, J=5.2 Hz, 2H, CH$_2$), 2.63(t, J=5.3 Hz, 1 H, OH), 1.84(sx, J=6.5 Hz, 2H, CH$_2$), 1.65(s, 4H, 2CH$_2$), 1.26(s, 6H, 2CH$_3$), 1.24(s, 6H, 2CH$_3$), 1.08(t, J=7.4 Hz, 3H, CH$_3$) and 0.82(m, 4H, cyclpropyl CH$_2$).

To a solution of the above cyclopropyl alcohol (56 mg, 0.177 mmol) in 3 mL CH$_2$Cl$_2$ at room temperature was added celite (0.13 g, 2×wt. PCC) and PCC (60 mg, 0.282 mmol). The reaction mixture was stirred for 4 hours and then filtered and rinsed with 15%). EtOAc/hexane through a pad of celite/silica gel. The solvent was removed in vacuo to provide 49 mg of 1-(5,5,8,8-tetramethyl-3-propyloxy-5,6,7,8-tetrahydronaphthalen-2-yl)-cyclopropane carboxaldehyde as a white solid in 95% yield. $^1$H NMR (400 MHz, (CDCl$_3$) δ 9.39(s, 1H, aldehyde), 7.06(s, 1H, aromatic), 6.77(s, 1H, aromatic), 3.91(t, J=6.2 Hz, 2H; CH$_2$), 1.75(sx, J=6.4 Hz, 2H, CH$_2$), 1.66(s, 4H, 2CH$_2$), 1.53(m, 2H, cyclopropyl CH$_2$), 1.29(s, 6H, 2CH$_3$), 1.26(m, 2H, cyclopropyl CH$_2$), 1.23(s, 6H, 2CH$_3$) and 0.99(t, J=7.4 Hz, 3H, CH$_3$).

A solution 3-ethoxycarbonyl-2-methylprop-2-enylphosphonate (123 mg, 0.47 mmol), in THF/DMPU (1:1; 2 mL) was treated with n-BuLi (2.5 M in hexane; 0.190 mL, 0.47 mmol) at −78° C. The reaction mixture was stirred for ten minutes. The above cyclopropane carboxaldehyde (49 mg, 0.155 mmol) in THF/DMPU (2 mL of 1:1 mixture) was added. The reaction mixture was warmed to 0° C. and monitored by TLC. The reaction was complete in 30 minutes and was quenched with saturated aqueous NH$_4$Cl. The aqueous layer was extracted with EtOAc (2×10 mL). The combined organic solution was washed with saturated NaCl and dried (Na$_2$SO$_4$). The recovered oil was then filtered through a short plug of silica gel and further rinsed with 5% ethyl acetate/hexane to remove DMPU. A mixture of isomers (52 mg) of ethyl-6-[(5,5,8,8-tetramethyl-3-propyloxy-5,6,7,8-tetrahydronaphthalen-2-yl)cyclopropan-1-yl]-3-methyl-2,4-hexadienoate was recovered in 82% yield.

To a solution of the above ester (52 mg, 0.127 mmol) in 2 mL of MeOH was added 12 drops of 6.4M KOH (excess). The reaction mixture was allowed to reflux for three hours. The MeOH was then evaporate in vacuo and the residue was diluted in 3 mL of water. The aqueous phase was neutralized with 5% HCl to pH=6. The aqueous phase was then extracted with EtOAc (2×15 mL). The organic phase was washed with brine, dried (Na$_2$SO$_4$), and concentrated in vacuo. The final product was recrystallized from Et$_2$O/hexane (1:2) to give 23 mg (46%) of (2E, 4E)-6-[2-(5,5,8,8-tetramethyl-3-propyloxy-5,6,7,8-tetrahydronaphthalen-2-yl)-cyclopropan-1-yl]-3-methylhexadienoic acid (152) as a white solid. $^1$H NMR (400 MHz, CDCl$_3$) δ 7.09(s, 1H, aromatic), 6.71(s, 1H, aromatic) 5.98(d, J=15.6 Hz, 1H, vinylic), 5.63(d, J=15.5 Hz, 1H, vinylic), 5.54(s, 1H, vinylic), 3.88(t, J=6.2 Hz, CH$_2$), 2.23(s, 3H, CH$_3$), 1.74(sx, J=6.2 Hz, 2H, CH$_2$), 1.67(s, 4H, 2CH$_2$), 1.29(s, 6H, 2CH$_3$), 1.24(s, 6H, 2CH$_3$), 1.17(m, 2H, cyclopropyl CH$_2$), 1.06(m, 2H, cyclopropyl CH$_2$), 0.98(t; J=7.4 Hz, 3H, CH$_3$).

EXAMPLE 53

(2E, 4E)-6-[2-(5,5,8,8-Tetramethyl-3-heptyloxy-5,6, 7,8-tetrahydronaphthalen-2-yl) cyclopropan-1-yl]-3-methyl Hexadienoic Acid (Compound 153, prepared as illustrated and described is Scheme 17)

The heptyloxy boronic acid (prepared as described in Example 52, 2.92 g, 8.03 mmol), was coupled with 2-bromopropene as described in Example 52 to give 1.65 g of 2-(5,5,8,8-tetramethyl-3-heptyloxy-5,6,7,8-tetrahydronaphthalen-2-yl)-propane as a colorless oil in 57% yield after column chromatography (hexane). $^1$H (400 MHz, CDCl$_3$) δ 7.11(s, 1H, aromatic), 6.74(s, 1H, aromatic), 5.47(s, 3H, olefinic CH$_2$), 3.94(t, J=6.5 Hz, 2H, CH$_2$), 2.13(s, 3H, CH$_3$), 1.77(m, 2H, CH$_2$), 1.66(m, 4H, 2CH$_2$), 1.45(m, 2H, CH$_2$), 1.33(m, 6H, 3CH$_2$), 1.28 (s, 6H, 2CH$_3$), 1.26(s, 6H, CH$_3$), 0.89(t, J=6.7 Hz, 3H, CH$_3$).

The above 2-propene derivative (1.0 g, 3.0 mmol) was oxidize as described in Example 52 to give 2-(5,5,8,8-tetramethyl-3-heptyloxy-5,6,7,8-tetrahydronaphthalen-2-yl)-2-proper-1-ol as a white solid in 53% yield after column chromatography (15% EtOAc/hexane). $^1$H NMR (400 MHz, CDCl$_3$) δ 7.13(s, 1H, aromatic), 6.75(s, 1H, aromatic), 5.35(s, 1H, vinylic), 5.23(s, 1H, vinylic), 4.43(d, J=6.5 Hz, 2H, CH$_2$), 3.96(t, J=6.6 Hz, 2H, CH$_2$), 2.20(t, J=6.6 Hz, 1H, OH), 1.79(m, 2H, CH$_2$), 1.66(m, 4H, 2CH$_2$), 1.45(m, 2H, CH$_2$), 1.35(m, 6H, 3CH$_2$), 1.28(s, 6H, 2CH$_3$), 1.26(s, 6H, CH$_3$), 0.89(t, J=6.9 Hz, 3H, CH$_3$).

The above alcohol (0.57 g, 1.59 mmol) was cyclopropanated as described in Example 52 to give [1-(5,5,8;8-tetramethyl-3-heptyloxy-5,6,7,8-tetrahydronaphthalen-2-yl)-cyclopropyl]-methanol as a pale yellow oil in 73% yield. The cyclopropyl alcohol (0.43 g, 1.20 mmol) was oxidized as described in Example 52 to give 1-(5,5,8,8-tetramethyl-3-heptyloxy-5,6,7,8-tetrahydronaphthalen-2-yl)-cyclopropanecarboxaldehyde as a colorless oil in 87% yield. $^1$H NMR (400 MHz, (CDCl$_3$) δ 9.37(s, 1H, CHO), 7.06(s, 1H, aromatic), 6.77(s, 1H, aromatic), 3.94(t, J=6.4 Hz, 2H, CH$_2$), 1.74(m, 2H, CH$_2$), 1.67(s, 4H, 2 CH$_2$), 1.53 (m, 2H, CH$_2$), 1.40(m, 2H, CH$_2$), 1.34(m, 8H, 4CH$_2$), 1.29(s, 6H,. 2CH$_3$), 1.24(s, 6H, 2CH$_3$), 0.89(t, J=6.5 Hz, 3H, CH$_3$).

The above cyclopropyl aldehyde (0.40 g, 1.10 mmol) and 3-ethoxycarbonyl-2-methylprop-2-enylphosphonate (912 mg, 3.3 mmol) were condensed as described for Example 52 to give ethyl-6-[(5,5,8,8-tetramethyl-3-heptyloxy-5,6,7,8-tetrahydronaphthalen-2-yl) cyclopropan-1-yl]-3-methyl-2,4-hexanedienoate as a pale yellow oil in 78% yield. The resulting ethyl ester (0.41 g, 0.846 mmol) in 9 mL MeOH was hydrolyzed as described in Example 52 to give the crude acid. The crude mixture was recrystallized from Et$_2$O/hexane (1:2) to give 205 mg (53%) of (2E, 4E)-6-[2-(5,5, 8,8-tetramethyl-3-heptyloxy-5,6,7;8-tetrahydronaphthalen-2-yl)cyclopropan-1-yl]-3-methyl-2,4-heptadienoic (153) mp=152–153° C. $^1$H NMR (400 MHz, (CDCl$_3$) δ 7.09(s, 1H, aromatic), 6.71(s, 1H, aromatic), 5.97(d, J=15.6 Hz, 1H, olefinic CH), 5.63(d, J=15.6 Hz, 1H, olefinic CH), 5.52(s, 1H, olefinic CH), 3.91(t, J=6.2 Hz, 2H, CH$_2$), 2.23(s, 3H, CH$_3$), 1.71(m, 2H, CH$_2$), 1.66(s, 4H, 2CH$_2$), 1.40(m, 2H, CH$_2$), 1.29(s, 6H, 2CH$_3$), 1.27(m, 6H, 3 CH$_2$), 1.24(s, 6H 2CH$_3$), 1.16(m, 2H, CH$_2$), 1.05(m, 2H, CH$_2$), 0.87(t, J=6.5 Hz, 3H, CH$_3$).

EXAMPLE 54

(2E, 4E)-6-[2-(5,5,8,8-Tetramethyl-3-benzyloxy-5,6, 7,8-tetrahydronaphthalen-2-yl) Cyclopropan-1-yl]-3-methyl Hexadienoic Acid (Compound 154 prepared as illustrated and described in Scheme 17)

The benzyloxy boronic acid (prepared as described in Example 52, 1.31 g, 3.95 mmol), was coupled with 2-bromopropene as described in Example 52 to give 400 mg of 2-(5,5,8,8-tetramethyl-3-benzyloxy-5,6,7,8-tetrahydronaphthalen-2-yl)-propene as a colorless oil in 39% yield after column chromatography (hexane). $^1$H NMR NMR (400 MHz, CDCl$_3$) δ 7.45–7.18 (m, 5H, aromatic), 7.14(s, 1H, aromatic), 6.81(s, 1H, aromatic), 5.10(s, 2H, benzylic CH$_2$), 5.06(s, 2H, olefinic CH$_2$), 2.15(s, 3H, CH$_3$), 1.66(s, 4H, 2CH$_2$), 1.27(s, 6H, 2CH$_3$), 1.24(s, 6H, 2CH$_3$).

The above 2-propene derivative (0.34 g, 0.96 mmol), was oxidize as described in Example 52 to give 130 mg of 2-(5,5,8,8-tetramethyl-3-benzyloxy-5,6,7,8-tetrahydronaphthalen-2-yl)-2-proper-1-ol as a white solid in 36% yield after column chromatography (15% EtOAc/hexane). $^1$H NMR (400 MHz, CDCl$_3$) δ 7.43–7.31(m, 5H, aromatic), 7.15(s, 1H, aromatic), 6.84(s, 1H, aromatic), 5.37(d, J=1.5 Hz, 1H, olefinic CH), 5.25(d, J=1.5 Hz, 1H, olefinic CH), 5.06(s, 2H, benzylic CH$_2$), 4.43(d, J=6.5 Hz, 2H, CH$_2$), 1.97(t, J=6.5 Hz, 1H, alcohol), 1.67(s, 4H, 2CH$_2$), 1.26(s, 6H, 2CH$_3$), 1.25(s, 6H, 2CH$_3$).

The above alcohol (0.13 g, 0.35 mmol) was cyclopropanated as described in Example 52 to give [1-(5,5,8,8-tetramethyl-3-benzyloxy-5,6,7,8-tetrahydronaphthalen-2-yl) cyclopropyl]-methanol as a pale yellow oil in 73% yield. The cyclopropyl alcohol (50 mg, 0.131 mmol) was oxidized as described in Example 52 to give 1-(5,5,8,8-tetramethyl-3-benzyloxy-5,6,7,8-tetrahydronaphthalen-2-yl)-cyclopropanecarboxaldehyde as a colorless oil in 92% yield 1H NMR (400 MHz, CDCl$_3$) b 9.35(s, 1H, aldehyde), 7.52–7.29(m, 5H, aromatic), 7.09(s, 1H, aromatic), 6.84(s, 1H, aromatic), 5.07(s, 2H, benzylic CH$_2$), 1.66(s, 4H, 2CH$_2$), 1.56(dd, J=4.0, 3.1 Hz, 2H, CH$_2$), 1.30(dd, J=4.0, 3.1 Hz, 2H, 2CH$_2$), 1.25(s, 6H, 2CH$_3$), 1.24(s, 6H, 2CH$_3$).

The above cyclopropyl aldehyde (45 mg, 0.12 mmol), and 3-ethoxycarbonyl-2-methylprop-2-enylphosphonate (190 mg, 0.72 mmol) were condended as described for Example 52 to give ethyl-6-[(5,5,8,8-tetramethyl-3-benzyloxy-5,6,7, 8-tetrahydronaphthalen-2-yl)-cyclopropan-1-yl]-3-methyl-2,4-hexanedienoate as a pale yellow oil in 77% yield. The resulting ethyl ester (36 mg, 0.10 mmol) in 2 mL MeOH was hydrolyzed as described in Example 52 to give the crude acid. The crude mixture was recrystallized from Et$_2$O/hexane (1:2) to give 18 mg (52%) of (2E, 4E)-6-[2-(5,5,8, 8-tetramethyl-3-benzyloxy-5,6,7,8-tetrahydronaphthalen-2-yl)-cyclopropan-1-yl]-3-methyl-2,4-heptadienoic (154). mp=210° C. (dec.) $^1$H NMR (400 MHz, CDCl$_3$) δ 7.40–7.27 (m, 5H, aromatic), 7.13(s, 1H, aromatic), 6.78(s, 1H, aromatic), 5.99(d, J=15. 5 Hz, 1H, olefinic CH), 5.66(d, J=15.5 Hz, 1H, olefinic CH), 5.53(s, 1H, olefinic CH), 5.06(s, 2H, benzylic CH$_2$), 2.24(s, 3H, CH$_3$), 1.66(s, 4H, 2CH$_2$), 1.24(s, 12H, 4CH$_3$), 1.21(dd, J=4.0, 3.1 Hz, 2H, CH$_2$), 1.10(dd, J=4.0, 3.1 Hz, 2H, CH$_2$).

EXAMPLE 55

(2E, 4E)-7-[(5,5,8,8-Tetramethyl-3-propyloxy-5,6,7, 8-tetrahydronaphtha-len-2-yl) cyclopropan-1-yl]-3-methyl heptadienoic Acid (Compound 155, prepared as illustrated and described in Scheme 18)

The propyloxy boronic acid (prepared as described in Example 52, 0.70 g, 2.39 mmol) in toluene (6 mL) was coupled to 3-bromo-3-buten-1-ol (0.16 mL, 1.59 mmol) as described in Example 52 to provide, after column chromatography (10 to 15% EtOAc/hexane), 0.16 g of 2-(5,5,8,8-tetramethyl-3-propyloxy-5,6,7,8-tetrahydronaphthalen-2-yl)-3-buten-1-ol as a pale yellow oil in 31% yield. $^1$H NMR (400 MHz, CDCl$_3$) δ 7.03(s, 1H, aromatic), 6.74(s 1H, aromatic), 5.22(d, J=1.1 Hz, 1H, olefinic CH), 5.13(d, J=1.9 Hz, 1H, olefinic CH), 3.91 (t, J=6.6 Hz, 2H, CH$_2$), 3.61(dd, J=6.1, 6.0 Hz, 2H, CH$_2$), 2.71(dd, J=5.9, 5.8 Hz, 2H, CH$_2$), 1.88(t, J=6.2 Hz, 1H, alcohol), 1.79(m, 2H, CH$_2$), 1.66(s, 4H, 2CH$_2$), 1.28(s, 6H, 2CH$_3$), 1.24(s, 6H, 2CH$_3$), 1.02(t, J=7.5 Hz, 3H, CH$_3$).

In a 15 mL round-bottom flask (oven dried and under argon) was added anhydrous dichloroethane (2 mL) and diethyl zinc (0.11 ml 1.08 mmol). The mixture was cooled to 0° C. and chloroiodomethane (0.14 mL, 1.96 mmol) was slowly added via syringe. The reaction mixture was stirred at 0° C. for 5 min. and a solution of the above homoallylic alcohol (0.16 g, 0.49 mmol) in dichloroethane (2 mL) was slowly added. The mixture was allowed to warm to room temperature and stirred for one hour. The reaction mixture was then quenched with saturated NH$_4$Cl and the aqueous phase was extracted with EtOAc (2×15 mL). The organic solution was washed with saturated NaCl, dried (Na$_2$SO$_4$) and concentrated in vacuo. Crude [1-(5,5,8,8-tetramethyl-3-propyloxy-5,6,7,8-tetrahydronaphthalen-2-yl)-cyclopropyl] ethanol was recovered in 89% yield (0.15 g) and carried directly on to the next step. To a solution of the above cyclopropyl alcohol (0.06 g, 0.19 mmol) in 5 mL CH$_2$Cl$_2$ at room temperature was added celite (0.13 g, 2×wt. PCC) and PCC (0.07 g, 0.30 mmol). The reaction mixture was stirred for 4 hours and then filtered and rinsed with 15% EtOAc/hexane through a pad of celite/silica gel. Solvent was removed in vacuo to provide 60 mg of 1-(5,5,8,8-tetramethyl-3-propyloxy-5,6,7,8-tetrahydronaphthalen-2-yl)-cyclopropaneacetaldehyde as a white solid in 95% yield. $^1$H NMR (400 MHz, CDCl$_3$) δ 9.75 (t, J=2.9 Hz, 1H, aldehyde), 7.17 (s, 1H, aromatic), 6.67 (s, 1H, aromatic), 3.91 (t, J=6.3 Hz, 2H, CH$_2$), 2.50 (d, J=2.9 Hz, 2H, CH$_2$), 1.83 (m, 2H, CH$_2$), 1.64 (s, 4H, 2CH$_2$), 1.26 (s, 6H, 2CH$_3$), 1.08 (t, J=7.4 Hz, 3H, CH$_3$), 0.89 (dd, J=6.4, 4.3 Hz, 2H, CH$_2$), 0.80 (dd, J=6.4, 4.3 Hz, 2H, CH$_2$).

The above propyloxy cyclopropyl aldehyde (0.06 g, 0.18 mmol) and 3-ethoxycarbonyl-2-methylprop-2-enylphosphonate (285 mg, 1.08 mmol) were condensed as described in Example 52 to give 70 mg of ethyl-7-[2-(5,5,8,8-tetramethyl-3-propyloxy-5,6,7,8-tetrahydronaphthalen-2-yl)-cyclopropyl]-3-methyl-2,4-heptadienoate as a pale yellow oil in 97% yield. The resulting ethyl ester (70 mg, 0.17 mmol) in 2.5 mL MeOH was hydrolyzed as described in Example 52 to give the crude acid. The crude material was recrystallized from Et$_2$O/hexane (1:2) to give 31 mg (45%) of (2E, 4E)-6-[2-(5,5,8,8-tetramethyl-3-propyloxy-5,6,7,8-tetrahydronaphthalen-2-yl)-cyclopropyl]-3-methyl-2,4-heptadienoic acid (155). $^1$H NMR (400 MHz, CDCl$_3$) δ 7.03 (s, 1H, aromatic), 6.68 (s, 1H, aromatic), 6.11 (m, 1H, olefinic CH), 5,96 (d, J=15.6 Hz, 1H, olefinic CH), 5.65 (s, 1H, olefinic CH), 3.92 (t, J=6.3 Hz, 2H, CH$_2$), 2.38 (d, J=7.1 Hz, 2H, CH$_2$), 2.20 (s, 3H, CH$_3$), 1.83 (m, 2H, CH$_2$), 1.64 (s, 4H, 2CH$_2$), 1.26 (s, 6H, 2CH$_3$), 1.21 (s, 6H, 2CH$_3$), 1.09 (t, J=7.5 Hz, 3H, CH$_3$), 0.74 (dd, J=6.4, 4.3 Hz, 2H, CH$_2$), 0.66 (dd, J=6.4, 4.3 Hz, 2H, CH$_2$).

EXAMPLE 56

(2E, 4E)-7-[(5,5,8,8-Tetramethyl-3-heptyloxy-5,6,7,8-tetrahydronaphtha-len-2-yl) cyclopropan-1-yl]-3-methyl Heptadienoic Acid (Compound 156, Prepared as Illustrated and Described in Scheme 18)

The tetrahydrobromonaphthol (Example 52, 1.5 g, 5.19 mmol) was alkylated with heptyl bromide (1.14 mL, 7.27 mmol) as described for Example 52 to provide 2.1 g of 2-bromo-3-heptyloxy-5,5,8,8-tetramethyl-5,6,7,8-tetrahydronaphthalene as a clear oil in quantitative yield. $^1$H NMR (400 MHz, CDCl$_3$) δ 7.41 (s, 1H, aromatic), 6.77 (s, 1H, aromatic), 3.98 (t, J=6.5 Hz, 2H, CH$_2$), 1.85–1.78 (m, 2H, CH$_2$), 1.65 (s, 4H, 2CH$_2$), 1.53–1.29 (m, 10H, aliphatic CH$_2$), 1.26 (s, 6H, 2CH$_3$), 1.24 (s, 6H, 2CH$_3$), 0.89 (t, J=6.0 Hz, 3H, CH$_3$).

The 2-bromo-3-heptyloxy-5,5,8,8-tetramethyl-5,6,7,8-tetrahydro naphthalene (2.1 g, 5.42 mmol) was converted to the corresponding boronic acid as described for Example 52 to give 1.74 g of a brown residue in 79% yield. The crude mixture was carried out to the next step.

The above heptyloxy boronic acid (0.90 g, 2.18 mmol) was coupled with 3-bromo-3-butenol as described in Example 55 to give 270 mg of 2-(5,5,8,8-tetramethyl-3-heptyloxy-5,6,7,8-tetrahydronaphthalen-2-yl)-3-buten-1-ol as a white solid in 42% yield after column chromatography (10 to 15% EtOAc/hexane). $^1$H NMR (400 MHz, CDCl$_3$) δ 7.02 (s, 1H, aromatic), 6.74 (s, 1H, aromatic), 5.23 (d, J=2.2 Hz, 1H, olefinic CH), 5.12 (d, J=2.2 Hz, 1H, olefinic CH), 3.93 (t, J=6.5 Hz, 2H, CH$_2$), 3.60 (q, J=6.1 Hz, 2H, CH$_2$), 2.70 (t, J=5.9 Hz, 2H, CH$_2$), 1.84 (t, J=6.3 Hz, 1H, alcohol), 1.76 (m, 2H, CH$_2$), 1.66 (s, 4H, 2CH$_2$), 1.54–1.30 (m, 8H, aliphatic CH$_2$), 1.28 (s, 6H, 2CH$_3$), 1.24 (s, 6H, 2CH$_3$), 0.88 (t, J=6.7 Hz, 3H, CH$_3$).

The above unsaturated alcohol (0.27 g, 0.61 mmol) was converted to the cyclopropyl alcohol as described in Example 55 to give 190 mg of [1-(5,5,8,8-tetramethyl-3-heptyloxy-5,6,7,8-tetrahydronaphthalen-2-yl)-cyclopropyl]-ethanol as a pale yellow oil in 69% yield. The above cyclopropyl alcohol (0.19 g, 0.41 mmol) was oxidized as described in Example 55 to give 170 mg of 1-(5,5,8,8-tetramethyl-3-heptyloxy-5,6,7,8-tetrahydronaphthalen-2-yl)-cyclopropaneacetaldehyde as a white solid in 92% yield. $^1$H NMR (400 MHz, CDCl$_3$) δ 9.75 (t, J=2.9 Hz, 1H, CHO), 7.17 (s, 1H, aromatic), 6.67 (s, 1H, aromatic), 3.94 (t, J=6.3 Hz, 2H, CH$_2$), 2.49 (d, J=2.9 Hz, 2H, CH$_2$), 1.80 (m, 2H, CH$_2$), 1.53 (s, 4H, 2CH$_2$), 1.50–1.32 (m, 8H, aliphatic CH$_2$), 1.26 (s, 6H, 2CH$_3$), 1.23 (s, 6H, 2CH$_3$), 0.91 (t, J=6.7 Hz, 3H, CH$_3$), 0.88 (dd, J=6.3, 4.2 Hz, 2H, CH$_2$), 0.79 (dd, J=6.3, 4.2 Hz, 2H, CH$_2$).

The above cyclopropyl aldehyde (0.17 g, 0.38 mmol) and 3-ethoxycarbonyl-2-methylprop-2-enylphosphonate (285 mg, 1.08 mmol) were condensed as described for Example 52 to give 220 mg of ethyl-7-[2-(5,5,8,8-tetramethyl-3-heptyloxy-5,6,7,8-tetrahydronaphthalen-2-yl)-cyclopropyl]-3-methyl-2,4-heptadienoate as a pale yellow oil in quantitative yield.

The above ethyl ester (0.22 g, 0.44 mmol) in 8 mL MeOH was hydrolyzed as described for Example 52 to give the crude acid. The crude mixture was recrystallized from Et$_2$O/Hex (1:2) to give 130 mg (63%) of (2E, 4E)-6-[2-(5,5,8,8-tetramethyl-3-heptyloxy-5,6,7,8-tetrahydro naphthalen-2-yl)-cyclopropyl]-3-methyl-2,4-heptadienoic acid (156). $^1$H NMR NMR (400 MHz, CDCl$_3$) δ 7.03 (s, 1H, aromatic), 6.68 (s, 1H, aromatic), 6.11 (m, 1H, olefinic CH), 5.96 (d, J=15.6 Hz, 1H, olefinic CH), 5.64 (s, 1H, olefinic CH), 3.94 (t, J=6.2 Hz, 2H, CH$_2$), 2.37 (d, J=7.1 Hz, 2H, CH$_2$), 2.20 (s, 3H, CH$_3$), 1.82 (m, 2H, CH2), 1.64 (s, 4H, 2CH2), 1.54–1.29 (m, 8H, aliphatic CH2), 1.26 (s, 6H, 2CH$_3$), 1.21 (s, 6H, 2CH$_3$), 0.90 (t, J=6.8 Hz, 3H, CH$_3$), 0.74 (dd, J=6.3, 4.0 Hz, 2H, CH$_2$), 0.66 (dd, J=6.3, 4.0 Hz, 2H, CH$_2$).

EXAMPLE 57

(2E, 4E)-7-[(5,5,8,8-Tetramethyl-3-benzyloxy-5,6,7,
8-tetrahydronaphtha-len-2-yl) cyclopropan-1-yl]-3-
methyl Heptadienoic Acid (Compound 157, Prepared as Illustrated and
Described in Scheme 18)

The tetrahydrobromonaphthol (Example 52, 3.0 g, 10.38 mmol) was alkylated with benzyl bromide (1.73 mL, 14.53 mmol) as described for Example 52 to provide 4.21 g of 2-bromo-3-benzyloxy-5,5,8,8-tetramethyl-5,6,7,8-tetrahydronaphthalene as a clear oil in quantitative yield. $^1$H NMR (400 MHz, CDCl$_3$) d7.48 (d, J=7.48 Hz, 2H, aromatic), 7.44 (s, 1H, aromatic), 7.38 (dd, J=8.6, 1.6 Hz, 2H, aromatic), 7.31 (dd, J=7.1, 2.2 Hz, 1H, aromatic), 6.82 (s, 1H, aromatic), 5.12 (s, 2H, benzylic CH$_2$), 1.64 (s, 4H, 2CH$_2$), 1.24 (s, 6H, 2CH$_3$), 1.20 (s, 6H, 2CH$_3$).

The 2-bromo-3-benzyloxy-5,5,8,8-tetramethyl-5,6,7,8-tetrahydro naphthalene (1.57 g, 4.14 mmol) was converted to the corresponding boronic acid as described for Example 52 to give 1.31 g of a brown residue in 79% yield. The crude mixture was carried on to the next step.

The above benzyloxy boronic acid (1.04 g, 2.93 mmol) was coupled with 3-bromo-3-butenol as described in Example 55 to give 370 mg of 2-(5,5,8,8-tetramethyl-3-heptyloxy-5,6,7,8-tetrahydronaphthalen-2-yl)-3-buten-1-ol as a white solid in 49% yield after column chromatography (10 to 15% EtOAc/hexane). $^1$H NMR (400 MHz, CDCl$_3$) δ 7.42–7.35 (m, 5H, aromatic), 7.05 (s, 1H, aromatic), 6.81 (s, 1H, aromatic), 5.23 (d, J=1.5 Hz, 1H, olefinic CH), 5.16 (d, J=2.0 Hz, 1H, olefinic CH), 5.04 (s, 2H, benzylic CH$_2$), 3.59 (q, J=6.1 Hz, 2H, CH$_2$), 2.71 (t, J=6.0 Hz, 2H, CH$_2$), 1.66 (s, 4H, 2CH$_2$), 1.25 (s, 6H, 2CH$_3$), 1.24 (s, 6H, 2CH$_3$).

The above unsaturated alcohol (0.37 g, 0.96 mmol) was converted to the cyclopropyl alcohol as described in Example 55 to give 190 mg of [1-(5,5,8,8-tetramethyl-3-heptyloxy-5,6,7,8-tetrahydronaphthalen-2-yl)-cyclopropyl]-ethanol as a pale yellow oil in 52% yield. The above cyclopropyl alcohol (0.19 g, 0.48 mmol) was oxidized as described in Example 55 to give 180 mg of 1-(5,5,8,8-tetramethyl-3-benzyloxy-5,6,7,8-tetrahydronaphthalen-2-yl)-cyclopropaneacetaldehyde as a white solid in 95% yield. $^1$H NMR (400 MHz, CDCl$_3$) δ 9.72 (d, J=3.2 Hz, 1H, CHO), 7.47 (d, J=7.2 Hz, 2H, aromatic), 7.40 (dd, J=8.6, 1.6 Hz, 2H, aromatic), 7.32 (dd, J=7.1, 2.2 Hz, 1H, aromatic), 7.20 (s, 1H, aromatic), 6.76 (s, 1H, aromatic), 5.07 (s, 2H, benzylic CH$_2$), 1.64 (s, 4H, 2CH$_2$), 1.23 (s, 12H, 4CH$_3$), 0.94 (dd, J=6.4, 4.2 Hz, 2H, CH$_2$), 0.82 (dd, J=6.4, 4.2 Hz, 2H, CH$_2$).

The above cyclopropyl aldehyde (0.18 g, 0.46 mmol) and 3-ethoxycarbonyl-2-methylprop-2-enylphosphonate (322 mg, 1.43 mmol) were condensed as described for Example 52 to give 230 mg of ethyl-7-[2-(5,5,8,8-tetramethyl-3-benzyloxy-5,6,7,8-tetrahydronaphthalen-2-yl)-cyclopropyl]-3-methyl-2,4-heptadienoate as a pale yellow oil in quantitative yield.

The above ethyl ester (0.23 g, 0.46 mmol) in 8 mL MeOH was hydrolyzed as described for Example 52 to give the crude acid. The crude mixture was recrystallized from Et$_2$O/Hex (1:2) to give 91 mg (43%) of (2E, 4E)-6-[2-(5,5,8,8-tetramethyl-3-benzyloxy-5,6,7,8-tetrahydronaphthalen-2-yl)-cyclopropyl]-3-methyl-2,4-heptadienoic acid (157). $^1$H NMR NMR (400 MHz, CDCl$_3$) δ 7.50 (d, J=7.3 Hz, 2H, aromatic), 7.39 (dd, J=6.8, 1.3 Hz, 2H, aromatic), 7.32 (dd, J=7.4, 2.3 Hz, 1H, aromatic), 7.07 (s, 1H, aromatic), 6.77 (s, 1H, aromatic), 6.11 (m, 1H, olefinic CH), 5.94 (d, J=15.7 Hz, 1H, olefinic CH), 5.64 (s, 1H, olefinic CH), 5.09 (s, 2H, benzylic CH$_2$), 2.41 (d, J=7.2 Hz, 2H, CH$_2$), 2.16 (s, 3H, CH$_3$), 1.64 (s, 4H, 2CH$_2$), 1.25 (s, 6H, 2CH$_3$), 1.22 (s, 6H, 2CH$_3$), 0.80 (dd, J=6.5, 3.8 Hz, 2H, CH$_2$), 0.71 (dd, J=6.4, 4.0 Hz, 2H, CH$_2$).

EXAMPLE 58

(2E, 4E)-5-[2-(5,5,8,8-Tetramethyl-3-propyloxy-5,6,
7,8-tetrahydronaphthalen-2-yl) cyclopent-1-en-1-yl]-
3-methyl Pentadienoic Acid (Compound 158, Prepared as Illustrated and
Described in Scheme 19)

To a solution of tetrakistriphenylphosphine palladium (0.035 gm, 0.03 mmol) in 4 mL of toluene under N$_2$ was added 1,2-dibromocyclopentene (0.66 mL, 5.55 mmol) at room temperature. The mixture was allowed to stir for 10 min. Then boronic acid (see Example 52, 0.28 g, 1.11 mmol) in 1 mL of ethanol was added, followed by an aqueous 2M solution of Na$_2$CO$_3$. The reaction mixture was then refluxed for three hours after which the solvent was removed in vacuo to give an oil. The residue was then dissolved in 15 mL of EtOAc and 15 mL of water. The aqueous phase was extracted with EtOAc (2×10 mL). The combined organic solution was washed with water and saturated NaCl, dried (Na$_2$SO$_4$) and concentrated in vacuo to give 0.255 g (59% of 1-[2-(5,5,8,8-tetramethyl-3-propyloxy-5,6,7,8-tetrahydronaphth-2-yl]-2-bromocyclopentene as an oil that was used directly in the next step.

To a solution of the above cyclopentyl bromide (0.255 g, 0.65 mmol) in 6 mL of anhydrous ether, at −78° C., was added t-BuLi (0.84 mL, 1.43 mmol) dropwise. The mixture was stirred at −78° C. for one hour. The anhydrous DMF (0.055 mL, 0.72 mmol) was added and the reaction mixture was stirred at room temperature 30 min. The reaction mixture was cooled to 0° C. and quenched with 2 mL of water. The aqueous phase was extracted with ether (2×15 mL). The combined organic phase was washed with water and satd NaCl, dried (Na$_2$SO$_4$), and concentrated in vacuo. The desired product was purified by chromatography (5% EA/Hex) to give 0.168 g (76%) of the 1-[2-(5,5,8,8-tetramethyl-3-propyloxy-5,6,7,8-tetrahydronaphthalen-2-yl]cyclopentene-2-carboxaldehyde. $^1$H NMR (400 MHz, CDCl$_3$) δ 9.66 (s, 1H, CHO), 7.06 (s, 1H, aromatic), 6.80 (s, 1H, aromatic), 3.90 (t, J=6.4 Hz, 2H, CH$_2$), 2.99 (dd, J=7.4, 2.4 Hz, 2H, CH$_2$), 2.70 (dd, J=7.4, 2.4 Hz, 2H, CH$_2$), 1.98 (m, 2H, CH$_2$), 1.76 (m, 2H, CH$_2$), 1.68 (s, 4H, 2CH$_2$), 1.30 (s, 6H, 2CH$_3$), 1.24 (s, 6H, 2CH$_3$), 1.00 (t, J=7.4 Hz, 3H, CH$_3$).

A solution 3-ethoxycarbonyl-2-methylprop-2-enylphosphonate (0.07 g, 0.26 mmol) in THF/DMPU (1:1, 2 mL) was treated with BuLi (1.6M, 0.163 mL) at −78° C. The reaction mixture was stirred for ten minutes. The above cyclopentene aldehyde (0.03 g, 0.09 mmol) in THF/DMPU (1 mL of 1:1) was added. The reaction mixture was warmed to 0° C. and monitored by TLC. The reaction was complete in 30 minutes and was quenched with saturated aqueous NH$_4$Cl. The aqueous layer was extracted with EtOAc (2×10 mL). The combined organic phase was then washed with saturated NaCl and dried (Na$_2$SO$_4$). Concentration in vacuo provided an oil which was then filtered through a short pad of silica gel and rinsed with 5% ethyl acetate/hexane to remove DMPU. The isolated mixture of isomers (44 mg) of ethyl-5-[2-(5,5,8,8-tetramethyl-3-propyloxy-5,6,7,8-tetrahydronaphthalen-2-yl)cyclopent-1-en-1-yl]-3-methyl 2,4-pentadienoate was recovered in quantitative yield. To a solution of the cyclopentene ethyl ester (0.044 g, 0.01 mmol) in 2 mL of MeOH was added 12 drops of 6.4 M KOH (excess). The reaction mixture was heated at reflux for three hours. The MeOH was then evaporated in vacuo and the residue was diluted in 3 mL of water. The aqueous phase was then neutralized with 5% HCl to pH=6. The aqueous phase was then extracted with EtOAc (2×15 mL). The organic phase was subsequently washed with brine, dried ($Na_2SO_4$) and concentrated in vacuo. The final product was recrystallized from $Et_2O$/hexane (1:2) to give 23 mg (55% of (2E, 4E)-5-[2-(5,5,8,8-Tetramethyl-3-propyloxy-5,6,7,8-tetrahydronaphthalen-2-yl)cyclopent-1-en-1-yl]-3-methyl pentadienoic acid (158). $^1$H NMR (400 MHz, $CDCl_3$) δ (ppm) 7.01 (s, 1H, aromatic), 6.94 (d, J=15.7 Hz, 1H, olefinic CH), 6.79 (s, 1H, aromatic), 6.25 (d, J=15.7 Hz, 1H, olefinic CH), 5.82 (s, 1H, olefinic CH), 3.89 (t, J=6.4 Hz, 2H, $CH_2$), 2.92 (dd, J=7.4, 2.1 Hz, 2H, $CH_2$), 2.65 (dd, J=7.4, 2.1 Hz, 2H, $CH_2$), 2.23 l(s, 3H, $CH_3$), 1.98 (m, 2H, $CH_2$), 1.78 (m, 2H, $CH_2$), 1.68 (s, 4H, $2CH_2$), 1.31 (s, 6H, $2CH_3$), 1.25 (s, 6H, $2CH_3$), 1.01 (t, J=7.5 Hz, 3H, $CH_3$).

EXAMPLE 59 cis (2E, 4E)-5-[2-(5,5,8,8-Tetramethyl-3-propyloxy-5,6,7,8-tetrahydro-2-naphthyl) cyclopentan-1-yl]-3-methyl Pentadienoic Acid (Compound 159, Prepared as Illustrated and Described in Scheme 20)

1-[2-(5,5,8,8-tetramethyl-3-propyloxy-5,6,7,8-tetrahydronaphthalen-2-yl]cyclopentene-2-carboxaldehyde (from Example 58, 0.09 g, 0.27 mmol) and 5% Pd on C (0.01 g) was taken-up in 3 mL of EtOAc. The reaction mixture was kept under an atmosphere of hydrogen. After 16 h of stirring, the reaction mixture was then filtered through a short plug of celite and the solvent was removed in vacuo. Chromatography (5% EtOAc/95% hexane) afforded 78 mg (83%) of the desired 1-[2-(5,5,8,8-tetramethyl-3-propyloxy-5,6,7,8-tetrahydronaphthalen-2-yl]cyclopentane-2-carboxaldehyde. $^1$H NMR (400 MHz, $CDCl_3$) δ 9.20 (d, J=2.1 Hz, 1H, aldehyde), 7.04 (s, 1H, aromatic), 6.68 (s, 1H, aromatic), 3.93 (m, 2H, $CH_2$), 3.65 (m, 1H, CH), 3.21 (m, 1H, CH), 2.15–1.78 (m, 8H, $4CH_2$), 1.62 (s, 4H, $2CH_2$), 1.26 (s, 6H, $2CH_3$), 1.24 (s, 6H, $2CH_3$), 1.06 (t, J=7.4 Hz, 3H, $CH_3$).

A solution 3-ethoxycarbonyl-2-methylprop-2-enylphosphonate (0.67 g, 0.25 mmol) in THF/DMPU (1:1, 2 mL) was treated with BuLi (1.6M, 0.151 mL) at −78° C. The reaction mixture was stirred for ten minutes. The above cyclopentane aldehyde (0.03 g, 0.09 mmol) in THF/DMPU (1 mL of 1:1) was added. The reaction mixture was warmed to 0° C. and monitored by TLC. The reaction was complete in 30 minutes and was quenched with saturated aqueous $NH_4Cl$. The aqueous layer was extracted with EtOAc (2×10 mL). The combined organic phase was then washed with saturated NaCl and dried ($Na_2SO_4$). Cocentration in vacuo provided an oil which was then filtered through a short plug of silica gel and rinsed with 5% ethyl acetate/hexane to remove DMPU. The isolated mixture of isomers (44 mg) of ethyl-5-[2-(5,5,8,8-tetramethyl-3-propyloxy-5,6,7,8-tetrahydronaphthalen-2-yl)cyclopentan-1-yl]-3-methyl 2,4-pentadienoate was recovered in quantitative yield To a solution of the cyclopentane ethyl ester (0.044 g, 0.01 mmol) in 2 mL of MeOH was added 12 drops of 6.4 M KOH (excess). The reaction mixture was heated at reflux for three hours. The MeOH was then evaporated in vacuo and the residue was diluted in 3 mL of water. The aqueous phase was then neutralized with 5% HCl to pH=6. The aqueous phase was then extracted with EtOAc (2×15 mL). The organic phase was subsequently washed with brine, dried ($Na_2SO_4$) and concentrated in vacuo. The final product was recrystallized from $Et_2O$/hexane (1:2) to give 23 mg (55%) ofcis-(2E, 4E)-5-[2-(5,5,8,8-tetramethyl-3-propyloxy-5,6,7,8-tetrahydronaphthalen-2-yl)cyclopentan-1-yl]-3-methylpentadienoic acid (159). $^1$H NMR ($CDCl_3$, 400 MHz) δ 6.99 (s, 1H, aromatic), 6.64 (s, 1H, aromatic), 5.83 (d, J=15.7 Hz, 1H, olefinic CH), 5.74 (dd, J=15.7, 8.1 Hz, 1H, olefinic CH), 5.52 (s, 1H, olefinic CH), 3.85 (t, J=6.6 Hz, 2H, $CH_2$), 3.62 (m, 1H, CH), 3.03 (m, 1H, CH), 1.98–1.78 (m, 6H, $3CH_2$), 1.63 (s, 4H, $2CH_2$), 1.23 (s, 6H, $2CH_3$), 1.22 (s, 6H, $2CH_3$), 1.05 (t, J=7.4 Hz, 3H, $CH_3$).

EXAMPLE 60

4-[(3-(4-t-Butylbenzyloxy)-5,6,7,8-tetrahydro-5,5,8,8-tetramethyl-2-naphthyl)carbonyl]benzoic Acid Oxime (Compound 160, Prepared as Illustrated and Described in Scheme 1 and Scheme 3)

A solution of the 4-[(3-hydroxy-5,6,7,8-tetrahydro-5,5,8,8-tetramethyl-2-naphthyl)carbonyl]benzoic acid methyl ester (from Example 7; 225 mg, 0.61 mmol) in acetone (3 mL) was stirred with $K_2CO_3$ (1.0 mmol) at room temperature for one hour. The yellow solution was treated with a solution of 4-t-butylbenzylbromide (168 mg, 0.74 mmol) and allowed to stir for 10 h. The reaction was quenched with saturated aqueous $NH_4Cl$. The aqueous solution was extracted 3 times with EtOAc; the organic layers were combined, and washed with water (2×) and brine. The organic solution was dried ($NaSO_4$), filtered, and concentrated. Purification by cyrstallization ($CH_2Cl_2$/hexanes) gave 4-[(3-(4-t-butylbenzyloxy)-5,6,7,8-tetrahydro-5,5,8,8-tetramethyl-2-naphthyl)carbonyl]benzoic acid methyl ester 298 mg (95%) as a white solid: mp 168–169.5° C; $^1$H NMR (400 MHz, $CDCl_3$) δ 8.04 (1/2ABq, J=8.5 Hz, 2H, ArH), 7.81 (1/2ABq, J=8.5 Hz, 2H, ArH), 7.44 (s, 1H, ArH), 7.19 (1/2ABq, J=8.2 Hz, 2H, ArH), 6.89 (s, 1H, ArH), 6.87 (1/2ABq, J=8.4 Hz, 2H, ArH), 4.89 (s, 2H, $OCH_2$), 3.94 (s, 3H, $OCH_3$), 1.69 (m, 4H, $2CH_2$), 1.28 (s, 6H, $2CH_3$), 1.26 (s, 6H, $2CH_3$), 1.25 (s, 9H, $3CH_3$).

The above 4-t-butylbenzyloxy keto ester was hydrolyzed as described for Example 1 to give 4-[(3-(4-t-butylbenzyloxy)-5,6,7,8-tetrahydro-5,5,8,8-tetramethyl-2-naphthyl)carbonyl]benzoic acid as a white solid (90%): mp 218–219° C.; $^1$H NMR (400 MHz, $CDCl_3$) δ 8.11 (1/2ABq, J=8.4 Hz, 2H, ArH), 7.84 (1/2ABq, J=8.4 Hz, 2H, ArH), 7.47 (s, 1H, ArH), 7.20 (1/2ABq, J=8.2 Hz, 2H, ArH), 6.90 (s, 1H, ArH), 6.88 (1/2ABq, J=8.3 Hz, 2H, ArH), 4.89 (s, 2H, $OCH_2$), 1.70 (m, 4H, $2CH_2$), 1.29 (s, 6H, $2CH_3$), 1.28 (s, 6H, $2CH_3$), 1.26 (s, 9H, $3CH_3$); $^{13}$C NMR (100 MHz, $CDCl_3$) δ 196.4, 170.6, 155.0, 151.0, 150.9, 143.8, 138.1, 133.6, 132.1, 130.1, 129.6, 129.3, 126.9, 126.4, 125.4, 111.1, 70.4, 35.2, 35.1, 35.0, 34.7, 34.1, 32.1, 31.9, 31.5.

The above acid was condensed with hydroxylamine hydrochloride as described for Example 4 to give 4-[(3-(4-t-butylbenzyloxy)-5,6,7,8-tetrahydro-5,5,8,8-tetramethyl-2-naphthyl)carbonyl]benzoic acid oxime (160) as a white solid (97%): mp 223–336° C. d; $^1$H NMR (400 MHz, $CDCl_3$) δ 8.11 (1/2ABq, J=8.4 Hz, 2H, ArH), 7.59 (1/2ABq, J=8.4 Hz, 2H, ArH), 7.24 (s, 1H, ArH), 7.20 (1/2ABq, J=8.1 Hz, 2H, ArH), 7.00 (1/2ABq, J=8.2 Hz, 2H, ArH), 6.93 (s, 1H, ArH), 4.93 (s, 2H, $OCH_2$), 1.69 (m, 4H, $2CH_2$), 1.28 (s, 6H, $2CH_3$), 1.25 (s, 6H, $2CH_3$), 1.24 (s, 9H, $3CH_3$).

EXAMPLE 61

4-[(3-(4-Bromobenzyloxy)-5,6,7,8-tetrahydro-5,5,8,8-tetramethyl-2-naphthyl)carbonyl]benzoic Acid Oxime (Compound 161, Prepared as Illustrated and Described in Scheme 1 and Scheme 3)

The 4-[(3-hydroxy-5,6,7,8-tetrahydro-5,5,8,8-tetramethyl-2-naphthyl)carbonyl]benzoic acid methyl ester (from Example 7) was alkylated with 4-bromobenzylbromide as described for Example 60 to give 4-[(3-(4-bromobenzyloxy)-5,6,7,8-tetrahydro-5,5,8,8-tetramethyl-2-naphthyl)carbonyl]benzoic acid methyl ester (60%): $^1$H NMR (400 MHz, CDCl$_3$) δ 8.03 (1/2ABq, 2H, J=8.4 Hz, ArH), 7.80 (1/2ABq, 2H, J=8.4 Hz, ArH), 7.46 (s, 1H, ArH), 7.29 (1/2ABq, 2H, J=8.4 Hz, ArH), 6.87 (s, 1H, ArH), 6.81 (1/2ABq, 2H, J=8.4 Hz, ArH), 4.87 (s, 2H, OCH$_2$), 3.97 (s, 3H, OCH$_3$), 1.70 (m, 4H, 2CH$_2$), 1.30 (s, 6H, 2CH$_3$), 1.27 (s, 6H, 2CH$_3$).

The above 4-bromobenzyloxy keto ester was hydrolyzed as described for Example 1 to give 4-[(3-(4-t-butylbenzyloxy)-5,6,7,8-tetrahydro-5,5,8,8-tetramethyl-2-naphthyl)carbonyl]benzoic acid as a white solid (90%): mp 218–219° C.; $^1$H NMR (400 MHz, CDCl$_3$) δ 8.08 (1/2ABq, 2H, J=8.1 Hz, ArH), 7.82 (1/2ABq, 2H, J=8.1 Hz, ArH), 7.44 (s, 1H, ArH), 7.31 (1/2ABq, 2H, J=8.3 Hz, ArH), 6.88 (s, 1H, ArH), 6.82 (1/2ABq, 2H, J=8.3 Hz, ArH), 4.89 (s, 2H, OCH$_2$), 1.70 (m, 4H, 2CH$_2$), 1.30 (s, 6H, 2CH$_3$), 1.27 (s, 6H, 2CH$_3$).

The above acid was condensed with hydroxylamine hydrochloride as described for Example 4 to give 4-[(3-(4-bromobenzyloxy)-5,6,7,8-tetrahydro-5,5,8,8-tetramethyl-2-naphthyl)carbonyl]benzoic acid oxime (161) as a white solid (97%): mp 221–223.5° C.; $^1$H NMR (400 MHz, CDCl$_3$) δ 7.99 (1/2ABq, 2H, J=8.4 Hz, ArH), 7.55 (1/2ABq, 2H, J=8.4 Hz, ArH), 7.33 (1/2ABq, 2H, J=8.4 Hz, ArH), 7.15 (s, 1H, ArH), 6.95 (1/2ABq, 2H, J=8.4 Hz, ArH), 6.88 (s, 1H, ArH), 4.91 (s, 2H, OCH$_2$), 1.70 (s, 4H, 2CH$_2$), 1.28 (s, 6H, 2CH$_3$), 1.25 (s, 6H, 2CH$_3$).

EXAMPLE 62 cis-4-[(3-Benzyloxy-5,6,7,8-tetrahydro-5,5,8,8-tetramethyl-2-naphthyl)carbonyl]benzoic Acid O-methyloxime (Compound 162, Prepared as Illustrated and Described in Scheme 1 and Scheme 4)

A solution of the 4-[3-benzyloxy-5,6,7,8-tetrahydro-5,5,8,8-tetramethyl-2-naphthyl)carbonyl]benzoic acid methyl ester in MeOH was hydrolyzed as described for Example 1 to give 4-[(3-(benzyloxy)-5,6,7,8-tetrahydro-5,5,8,8-tetramethyl-2-naphthyl)carbonyl]benzoic acid as a white solid: mp 211.5–213° C; IR (thin film) 2961, 2926, 1696, 1661, 1602, 1240, 735 cm$^{-1}$; $^1$H NMR (400 MHz, CDCl$_3$) δ 8.11 (1/2ABq, J=8.4 Hz, 2H, aromatic), 7.85 (1/2ABq, J=8.4 Hz, 2H, aromatic), 7.48 (s, 1H, aromatic), 7.19 (m, 3H, aromatic), 6.94 (m, 2H, aromatic), 6.90 (s, 1H, aromatic), 4.93 (s, 2H, OCH$_2$), 1.70 (m, 4H, 2CH$_2$), 1.29 (s, 6H, 2CH$_3$), 1.28 (s, 6H, 2CH$_3$); 13C NMR (100 Mhz, CDCl$_3$) δ 196.1, 170.5, 154.6, 150.8, 143.6, 138.0, 136.3, 129.9, 129.3, 129.1, 128.2, 127.7, 126.8, 126.2, 110.7, 70.3, 35.0, 34.9, 34.8, 33.8, 31.8, 31.7. HRMS (EI, 70 eV) calcd for C$_{29}$H$_{30}$O$_4$ (M$^-$): 442.2144. Found: 442.2126.

The above benzyloxy ketoacid (45 mg, 0.10 mmol) was converted to the O-methyloxime derivative as described for Example 8 (87%). Purification by reverse phase HPLC (90% MeOH/10% NH$_4$OAc with 0.5% AcOH) gave cis-4-[(3-benzyloxy-5,6,7,8-tetrahydro-5,5,8,8-tetramethyl-2-naphthyl)carbonyl]benzoic acid O-methyloxime (162) as a white solid: $^1$H NMR (400 MHz, CDCl$_3$) δ 7.93 (m, 2H, ArH), 7.46 (m, 2H, ArH), 7.34 (s, 1H, ArH), 7.17 (, 3H, ArH), 6.83 (m, 2H, ArH), 6.74 (s, 1H, ArH), 4.74 (s, 2H, OCH$_2$), 3.93 (s, 3H, OCH$_3$), 1.65 (s, 4H, 2CH$_2$), 1.27 (s, 6H, 2CH$_3$), 1.20 (s, 6H, 2CH$_3$); $^{13}$C NMR (100 MHz, CDCl$_3$) δ 155.6, 154.6, 148.1, 138.9, 137.6, 136.8, 129.4, 129.3, 128.3, 127.8, 127.4, 123.7, 110.7, 70.3, 62.4, 35.3, 35.2, 34.9, 33.9, 32.1, 32.0.

EXAMPLE 63 trans-4-[(3-Benzyloxy-5,6,7,8-tetrahydro-5,5,8,8-tetramethyl-2-naphthyl)carbonyl]benzoic Acid O-methyloxime (Compound 163, Prepared as Illustrated and Described in Scheme 1 and Scheme 4)

HPLC purification (reverse phase; 90% MeOH/10% NH$_4$OAc with 0.5% AcOH) of the crude product mixture from Example 62 yielded trans-4-[(3-benzyloxy-5,6,7,8-tetrahydro-5,5,8,8-tetramethyl-2-naphthyl)carbonyl]benzoic acid O-methyloxime (163) as a white solid: $^1$H NMR (400 MHz, CDCl$_3$) δ 7.96 (br s, 2H, ArH), 7.56 (br s, 2H, ArH), 7.19 (m, 3H, ArH), 7.08 (s, 1H, ArH), 7.06 (m, 2H, ArH), 6.87 (s, 1H, ArH), 4.93 (s, 2H, OCH$_2$), 3.97 (s, 3H, OCH$_3$), 1.67 (m, 4H, 2CH$_2$), 1.26 (s, 6H, 2CH$_3$), 1.22 (s, 6H, 2CH$_3$); $^{13}$C NMR (100 MHz, CDCl$_3$) δ 154.3, 153.4, 147.4, 137.6, 137.4, 128.7, 128.5, 127.8, 127.5, 127.2, 120.1, 110.9, 70.4, 62.8, 35.3, 34.9, 34.0, 32.2, 32.0, 29.9.

EXAMPLE 64

4-[2-(3-Benzyloxy-5,6,7,8-tetrahydro-5,5,8,8-tetramethyl-2-naphthyl)-[1,3]dioxolan-2-yl]benzoic Acid (Compound 164, Prepared as Illustrated and Described in Scheme 5)

A solution of 4-[3-benzyloxy-5,6,7,8-tetrahydro-5,5,8,8-tetramethyl-2-naphthyl)carbonyl]benzoic acid (from Example 62; 102 mg, 0.23 mmol) in benzene (2 mL) was treated with ethylene glycol (0.7 mmol) and p-toluenesulfonic acid (20 mg). The solution was heated at reflux with azeotropic distillation for 12 h. The solution was cooled to ambient temperature, water was added, and the mixture was extracted with EtOAc. The organic solution was washed with water and brine, dried (MgSO$_4$), filtered, and concentrated. The crude product was purified by silica gel chromatography to give 4-[2-(3-benzyloxy-5,6,7,8-tetrahydro-5,5,8,8-tetramethyl-2-naphthyl)-[1,3]dioxolan-2-yl]benzoic acid as a white solid (40%): mp 222–228° C. d; $^1$H NMR (400 MHz, CDCl$_3$) δ 7.93 (1/2ABq, 2H, J=8.4 Hz, ArH), 1.63 (s, 1H, ArH), 7.50 (1/2ABq, 2H, J=8.4 Hz, ArH), 7.22 (m, 3H, ArH), 6.98 (m, 2H, ArH), 6.72 (s, 1H, ArH), 4.84 (s, 2H, OCH$_2$), 4.06 (m, 4H, 2OCH$_2$), 1.65 (s, 4H, 2CH$_2$), 1.28 (s, 6H, 2CH$_3$), 1.18 (s, 6H, 2CH$_3$).

EXAMPLE 65

4-[2-Methyl-1-(3-benzyloxy-5,6,7,8-tetrahydro-5,5,8,8-tetramethyl-2-naphthyl)propenyl]benzoic Acid (Compound 165, Prepared as Illustrated and Described in Scheme 6)

A solution of 4-[3-benzyloxy-5,6,7,8-tetrahydro-5,5,8,8-tetramethyl-2-naphthyl)carbonyl]benzoic acid methyl ester (201 mg, 0.44 mmol) in THF (1 mL) was cooled with an ice/water bath and treated dropwise with isopropylmagnesium bromide (0.53 mmol). The mixture was allowed to warm to room temperature and stirred for 2 h. Concentrated sulfuric acid (0.2 mL) was added and the mixture was stirred for an additional 2 h. Water was added and the mixture was extracted with EtOAc. The organic solution was washed with water and brine, dried (MgSO$_4$), filtered, and concentrated. The crude product was purified by silica gel chromatography to give 4-[2-methyl-1-(3-benzyloxy-5,6,7,8-tetrahydro-5,5,8,8-tetramethyl-2-naphthyl)propenyl] benzoic acid methyl ester (37%): $^1$H NMR (400 MHz, CDCl$_3$) δ 7.89 (1/2ABq, 2H, J=8.3 Hz, ArH), 7.25 (m, 3H, ArH), 7.22 (1/2ABq, 2H, J=8.3 Hz, ArH), 7.07 (m, 2H, ArH), 7.05 (s, 1H, ArH), 6.72 (s, 1H, ArH), 4.84 (s, 2H, OCH$_2$), 3.89 (s, 3H, OCH$_3$), 1.81 (s, 3H, CH$_3$), 1.72 (s, 3H, CH$_3$), 1.65 (s, 4H, 2CH$_2$), 1.24 (s, 6H, 2CH$_3$), 1.21 (s, 6H, 2CH$_3$).

The above ester was hydrolyzed as described for Example 1 to give 4-[2-methyl-1-(3-benzyloxy-5,6,7,8-tetrahydro-5, 5,8,8-tetramethyl-2-naphthyl)propenyl]benzoic acid (165) as a white solid (91%): $^1$H NMR (400 MHz, CDCl$_3$) δ 7.94 (1/2ABq, 2H, J=8.3 Hz, ArH), 7.25 (m, 3H, ArH), 7.22 (1/2ABq, 2H, J=8.3 Hz, ArH), 7.06 (m, 3H, ArH), 6.72 (s, 1H, ArH), 4.84 (s, 2H, OCH$_2$), 1.82 (s, 3H, CH$_3$), 1.73 (s, 3H, CH$_3$), 1.65 (s, 4H, 2CH$_2$), 1.25 (s, 6H, 2CH$_3$), 1.21 (s, 6H, 2CH$_3$).

EXAMPLE 66

(2E, 4E, 6E)-7-[3-(4-tert-butylbenzyloxy)-5,6,7,8-tetrahydro-5,5,8,8-tetramethyl-2-naphthalen-2-yl]-3-methyl-octa-2,4,6-trienoic Acid (Compound 166, Prepared as Illustrated and Described in Scheme 7)

1-(3-Hydroxy-5,6,7,8-tetrahydro-5,5,8,8-tetramethyl-naphthalen-2-yl)-ethanone (0.285 g, 1.16 mmol) was alkylated with t-butylbenzylbromide (0.368 g, 1.62 mmol, 0.30 mL) as described in Example 21. Aqueous workup gave 1-[3-(4-t-butylbenzyloxy)-5,6,7,8-tetrahydro-5,5,8,8-tetramethyl-naphthalen-2-yl]-ethanone 0.452 g (99%) as a brown/orange oil: $^1$H NMR (400 MHz, CDCl$_3$) δ 7.74 (s, 1H, Ar—H), 7.43 (d of ABq, J=8.4 Hz, 2H), 7.38 (d of ABq, J=8.4 Hz, 2H), 6.91 (s, 1H, Ar—H), 5.11 (s, 2H, OCH$_2$), 2.60 (s, 3H, CH$_3$), 1.67 (m, 4H, 2CH$_2$), 1.33 (s, 9H, 3CH$_3$), 1.27 (s, 6H, 2CH$_3$), 1.26 (s, 6H, 2CH$_3$).

The above 3-(4-t-butylbenzyloxy)-2-acyltetrahydronapthalene (0.440 g, 1.12 mmol) was condensed with diethyl cyanomethylphosphonate (0.417 g, 2.35 mmol, 0.381 mL) as described for Example 19. Aqueous work-up afforded the crude product 3-[3-(4-t-butylbenzyloxy)-5,6,7,8-tetrahydro-5,5,8,8-tetramethyl-naphthalen-2-yl]-but-2-enenitrile 0.391 g (84%) as a pale orange oil: $^1$H-NMR (400 MHz, CDCl$_3$) δ 7.42 (d of ABq, J=8.4 Hz, 2H), 7.32 (d of ABq, J=8.4 Hz, 2H), 7.13 (s, 1H, Ar—H), 6.90 (s, 1H, Ar—H), 5.59 (s, 1H, olefinic), 5.02 (s, 2H, OCH$_2$), 2.44 (s, 3H, CH$_3$), 1.66 (s, 4H, 2CH$_2$), 1.33 (s, 9H, 3CH$_3$), 1.32 (s, 6H, 2CH$_3$), 1.27 (s, 6H, 2CH$_3$).

The cyano(4-t-butylbenzyloxy)naphthalene adduct (0.525 g, 1.26 mmol) was reduced with DIBAL (2.65 mL of a 1.0 M solution in hexanes, 2.65 mmol) as described for Example 19. Aqueous work-up gave the aldehyde 3-[3-(4-t-butylbenzyloxy)-5,6,7,8-tetrahydro-5,5,8,8-tetramethyl-naphthalen-2-yl]-but-2-enal 0.347 g (66%) as a yellow oil: $^1$H-NMR (trans isomer, CDCl$_3$) δ 10.13 (d, J=8.1 Hz, 1H, CHO), 7.41 (d of ABq, J=8.4 Hz, 2H), 7.33 (d of ABq, J=8.4 Hz, 2H), 7.10 (s, 1H, Ar—H), 6.86 (s, 1H, Ar—H), 6.14 (d, J=8.1 Hz, 1H, olefinic), 5.03 (s, 2H, OCH$_2$), 2.55 (s, 3H, CH$_3$), 1.67 (s, 4H, 2CH$_2$), 1.33 (s, 9H, 3CH$_3$), 1.26 (s, 6H, 2CH$_3$), 1.25 (s, 6H, 2CH$_3$).

The above aldehyde (0.347 g, 0.829 mmol) and diethyl-3-ethoxycarbonyl-2-methylprop-2-enylphosphonate (0.350 g, 1.33 mmol, 0.325 mL) were condensed as described for Example 19. Aqueous work-up afforded the ester (0.381 g, 87%) as a yellow oil. Standard hydrolysis of the crude ester (0.117 g, 0.256 mmol) followed by the typical aqueous work-up gave the acid as a mixture of geometric isomers (0.222 g, 62%). The product mixture was crystallized with hexanes to give (2E, 4E, 6E)-7-[3-(4-tert-butylbenzyloxy)-5,6,7,8-tetrahydro-5,5,8,8-tetramethyl-2-naphthalen-2-yl]-3-methyl-octa-2,4,6-trienoic acid (166) as a yellow solid: mp=188–190° C.; $^1$H NMR (400 MHz, CDCl$_3$) δ 7.40 (d of ABq, J=8.4 Hz, 2H), 7.35 (d of ABq, J=8.4 Hz, 2H), 7.11 (s, 1H, Ar—H), 7.05 (dd, J=15.3, 11.3 Hz, 1H, CH), 6.83 (s, 1H, Ar—H), 6.33 (app br t, 2H, 2×olefinic), 5.81 (s, 1H, olefinic), 5.01 (s, 2H, OCH$_2$), 2.39 (s, 3H, CH$_3$), 2.26 (s, 3H, CH$_3$), 1.67 (s, 4H, 2CH$_2$), 1.33 (s, 9H, 3CH$_3$), 1.27 (s, 6H, 2CH$_3$), 1.26 (s, 6H, 2CH$_3$); $^{13}$C-NMR (400 MHz, CDCl$_3$) δ 171.2, 155.7, 154.0, 151.0, 145.8, 142.5, 137.5, 135.0, 134.6, 132.4, 131.8, 128.8, 127.5, 127.4, 125.6, 117.4, 110.8, 70.6, 35.4, 35.3, 34.8, 34.7, 34.0, 32.1, 32.0, 31.6, 18.4, 14.3.

EXAMPLE 67

(2E, 4E, 6Z)-7-[3-(4-tert-butylbenzyloxy)-5,6,7,8-tetrahydro-5,5,8,8-tetramethyl-2-naphthalen-2-yl]-3-methyl-octa-2,4,6-trienoic Acid (Compound 167, Prepared as Illustrated and Described in Scheme 7)

The final product mixture from Example 66 was purified by reverse phase HPLC (90% MeOH/10% NH$_4$OAc with 0.3% AcOH) to give the title compound (2E, 4E, 6Z)-7-[3-(4-tert-butylbenzyloxy)-5,6,7,8-tetrahydro-5,5,8,8-tetramethyl-2-naphthalen-2-yl]-3-methyl-octa-2,4,6-trienoic acid (167) as a pale yellow solid: $^1$H-NMR (400 MHz, CDCl$_3$) δ 7.38 (d of ABq, J=8.4 Hz, 2H), 7.32 (d of ABq, J=8.4 Hz, 2H), 6.97 (s, 1H, Ar—H), 6.86 (s, 1H, Ar—H), 7.05 (dd, J=15.3, 11.3 Hz, 1H, CH), 6.23 (app br t, 2H, 2×olefinic), 5.76 (s, 1H, olefinic), 5.01 (s, 2H, OCH$_2$), 2.21 (s, 3H, CH$_3$), 2.14 (s, 3H, CH$_3$), 1.67 (s, 4H, 2CH$_2$), 1.31 (s, 9H, 3CH$_3$), 1.26 (s, 6H, 2CH$_3$), 1.24 (s, 6H, 2CH$_3$).

EXAMPLE 68

(2E, 4E, 6E)-7-[3-isobutyloxy-5,6,7,8-tetrahydro-5, 5,8,8-tetramethyl-2-naphthalen-2-yl]-3-methyl-octa-2,4,6-trienoic Acid (Compound 168, Prepared as Illustrated and Described in Scheme 7)

1-(3-Hydroxy-5,6,7,8-tetrahydro-5,5,8,8-tetramethyl-naphthalen-2-yl)-ethanone (0.250 g, 1.01 mmol) was alkylated with isobutylbromide (0.195 g, 1.42 mmol, 0.154 mL) as described in Example 21. Aqueous workup gave 1-[3-isobutyloxy-5,6,7,8-tetrahydro-5,5,8,8-tetramethyl-naphthalen-2-yl]-ethanone 0.322 g (crude) as an orange oil: $^1$H-NMR (400 MHz, CDCl$_3$) δ 7.74 (s, 1H, Ar—H), 6.81 (s, 1H, Ar—H), 4.13 (d, J=6.2 Hz, 2H, OCH$_2$), 2.62 (s, 3H, CH$_3$), 2.16 (m, 1H, CH), 1.68 (app br d, 4H, 2CH$_2$), 1.30 (s, 6H, 2CH$_3$), 1.28 (s, 6H, 2CH$_3$), 1.08 (d, J=6.7 Hz, 6H, 2CH$_3$).

The above 3-isobutyloxy-2-acyltetrahydronapthalene (0.307 g, 1.01 mmol) and diethyl cyanomethylphosphonate (0.378 g, 2.13 mmol, 0.345 mL) were condensed as described for Example 19. Aqueous work-up afforded the crude product 3-[3-isobutyloxy-5,6,7,8-tetrahydro-5,5,8,8-tetramethyl-naphthalen-2-yl]-but-2-enenitrile 0.569 g (crude) as an orange oil: $^1$H-NMR (400 MHz, CDCl$_3$) δ 7.10 (s, 1H, Ar—H), 6.77 (s, 1H, Ar—H), 5.61 (s, 1H, olefinic), 3.73 (d, J=6.3 Hz, 2H, OCH$_2$), 2.45 (s, 3H, CH$_3$), 2.09 (m, 1H, CH), 1.68 (app br s, 4H, 2CH$_2$), 1.29 (s, 6H, 2CH$_3$), 1.26 (s, 6H, 2CH$_3$), 1.02 (d, J=6.7 Hz, 6H, 2CH$_3$).

The cyanoisobutyloxynaphthalene adduct (0.560 g, 1.72 mmol) was reduced with DIBAL (3.44 mL of a 1.0 M solution in hexanes, 3.44 mmol) as described for Example 19. Aqueous work-up gave the aldehyde 3-[3-isobutyloxy-5,6,7,8-tetrahydro-5,5,8,8-tetramethyl-naphthalen-2-yl]-but-2-enal 0.255 g (45%) as a brown oil: $^1$H-NMR (trans isomer, CDCl$_3$) δ 10.15 (d, J=8.3 Hz, 1H, CHO), 7.09 (s, 1H, Ar—H), 6.76 (s, 1H, Ar—H), 6.14 (d, J=8.3 Hz, 1H, olefinic), 3.73 (d, J=6.4 Hz, 2H, OCH$_2$), 2.57 (s, 3H, CH$_3$), 2.09 (m, 1H, CH), 1.66 (app br s, 4H, 2CH$_2$), 1.30 (s, 6H, 2CH$_3$), 1.25 (s, 6H, 2CH$_3$), 1.01 (d, J=6.7 Hz, 6H, 2CH$_3$).

The above aldehyde (0.255 g, 0.776 mmol) and diethyl-3-ethoxycarbonyl-2-methylprop-2-enylphosphonate (0.328 g, 1.24 mmol, 0.304 mL) were condensed as described for Example 19. Aqueous work-up afforded the crude ester as an orange oil. Standard hydrolysis of the ester (0.280 g) and aqueous work-up gave the acid as a mixture of geometric isomers. The product mixture was recrystallized with EtOAc/hexanes to give (2E, 4E, 6E)-7-[3-isobutyloxy-5,6,7,8-tetrahydro-5,5,8,8-tetramethyl-2-naphthalen-2-yl]-3-methyl-octa-2,4,6-trienoic acid (168) as a yellow solid: mp=179–181° C.; $^1$H NMR (400 MHz, CDCl$_3$) δ 7.09 (s, 1H, Ar—H), 7.06 (dd, J=15.3, 11.1 Hz, 1H, olefinic), 6.74 (s, 1H, Ar—H), 6.32 (app br d, J=14.6 Hz, 2H, 2×olefinic), 5.81 (s, 1H, olefinic), 3.70 (d, J=6.3 Hz, 2H, OCH$_2$), 2.40 (s, 3H, CH$_3$), 2.25 (s, 3H, CH$_3$), 2.07 (m, 1H, CH), 1.67 (s, 4H, 2CH$_2$), 1.29 (s, 6H, 2CH$_3$), 1.27 (s, 6H, 2CH$_3$), 1.02 (d, J=6.7 Hz, 6H, 2CH$_3$).

EXAMPLE 69

(2E, 4E, 6Z)-7-[3-isobutyloxy-5,6,7,8-tetrahydro-5,5,8,8-tetramethyl-2-naphthalen-2-yl]-3-methyl-octa-2,4,6-trienoic Acid (Compound 169, Prepared as Illustrated and Described in Scheme 7)

A sample of the product mixture from Example 68 was purified by reverse phase HPLC (90% MeOH/10% ammonium acetate with 0.3% AcOH) to give (2E, 4E, 6Z)-7-[3-isobutyloxy-5,6,7,8-tetrahydro-5,5,8,8-tetramethyl-2-naphthalen-2-yl]-3-methyl-octa-2,4,6-trienoic acid (169) as a pale yellow solid: $^1$H-NMR (400 MHz, CDCl$_3$) δ 6.95 (s, 1H, Ar—H), 6.77 (s, 1H, Ar—H), 6.64 (dd, J=15.3, 10.9 Hz, 1H, olefinic), 6.23 (app br d, J=14.6 Hz, 2H, 2×olefinic), 5.75 (s, 1H, olefinic), 3.69 (d, J=6.3 Hz, 2H, OCH$_2$), 2.20 (s, 3H, CH$_3$), 2.14 (s, 3H, CH$_3$), 2.04 (m, 1H, CH), 1.67 (s, 4H, 2CH$_2$), 1.31 (s, 6H, 2CH$_3$), 1.23 (s, 6H, 2CH$_3$), 1.00 (d, J=6.7 Hz, 6H, 2CH$_3$).

EXAMPLE 70

(2E, 4E, 6E)-7-[3-pentyloxy-5,6,7,8-tetrahydro-5,5,8,8-tetramethyl-2-naphthalen-2-yl]-3-methyl-octa-2,4,6-trienoic Acid (Compound 170, Prepared as Illustrated and Described in Scheme 7)

1-(3-Hydroxy-5,6,7,8-tetrahydro-5,5,8,8-tetramethyl-naphthalen-2-yl)-ethanone (0.316 g, 1.28 mmol) was alkylated with n-bromopentane (0.271 g, 1.80 mmol, 0.223 mL) as described in Example 21. Aqueous workup gave 1-[3-pentyloxy-5,6,7,8-tetrahydro-5,5,8,8-tetramethyl-naphthalen-2-yl]-ethanone 0.461 g (crude) as an orange oil: $^1$H-NMR (400 MHz, CDCl$_3$) δ 7.74 (s, 1H, Ar—H), 6.82 (s, 1H, Ar—H), 4.03 (t, J=6.3 Hz, 2H, OCH$_2$), 2.61 (s, 3H, CH$_3$), 1.84 (m, 2H, CH$_2$), 1.67 (app br d, 4H, 2CH$_2$), 1.39 (m, 4H, 2CH$_2$), 1.29 (s, 6H, 2CH$_3$), 1.26 (s, 6H, 2CH$_3$), 0.94 (t, J=7.1 Hz, 3H, CH$_3$).

The above 3-pentyloxy-2-acyltetrahydronapthalene (0.450 g, 1.42 mmol) and diethyl cyanomethylphosphonate (0.529 g, 2.98 mmol, 0.483 mL) were condensed as described for Example 19. Aqueous work-up afforded the product 3-[3-pentyloxy-5,6,7,8-tetrahydro-5,5,8,8-tetramethyl-naphthalen-2-yl]-but-2-enenitrile 0.595 g (crude) as an orange oil: $^1$H-NMR (400 MHz, CDCl$_3$) δ 7.10 (s, 1H, Ar—H), 6.78 (s, 1H, Ar—H), 5.61 (s, 1H, olefinic), 3.95 (t, J=6.4 Hz, 2H, OCH$_2$), 2.44 (s, 3H, CH$_3$), 1.78 (m, 2H, CH$_2$), 1.67 (app br s, 4H, 2CH$_2$), 1.39 (m, 4H, 2CH$_2$), 1.28 (s, 6H, 2CH$_3$), 1.25 (s, 6H, 2CH$_3$), 0.94 (t, J=6.9 Hz, 3H, CH$_3$).

The above cyanopentyloxynaphthalene adduct (0.148 g, 0.436 mmol) was reduced with DIBAL (0.872 mL of a 1.0 M solution in hexanes, 0.872 mmol) as described for Example 1. Aqueous work-up gave the aldehyde 3-[3-pentyloxy-5,6,7,8-tetrahydro-5,5,8,8-tetramethyl-naphthalen-2-yl]-but-2-enal 0.136 g (91%) as a yellow oil: $^1$H-NMR (trans isomer, CDCl$_3$) δ 10.16 (d, J=8.0 Hz, 1H, CHO), 7.09 (s, 1H, Ar—H), 6.78 (s, 1H, Ar—H), 6.14 (d, J=6.8 Hz, 1H, olefinic), 3.95 (t, J=6.4 Hz, 2H, OCH$_2$), 2.44 (s, 3H, CH$_3$), 1.78 (m, 2H, CH$_2$), 1.67 (app br s, 4H, 2CH$_2$), 1.39 (m, 4H, 2CH$_2$), 1.28 (s, 6H, 2CH$_3$), 1.25 (s, 6H, 2CH$_3$), 0.94 (t, J=6.9 Hz, 3H, CH$_3$).

The above aldehyde (0.090 g, 0.263 mmol) and diethyl-3-ethoxycarbonyl-2-methylprop-2-enylphosphonate (0.111 g, 0.420 mmol, 0.103 mL) were condensed as described for Example 19. Aqueous work-up afforded the crude ester (0.100 g, 83%). Standard hydrolysis of the ester (0.100 g, 0.221 mmol) and aqueous work-up gave the acid as a mixture of geometric isomers (0.093 g, 87%). A sample of the product mixture was purified by reverse phase HPLC (92% MeOH/8% ammonium acetate with 0.3% AcOH) to give (2E, 4E, 6E)-7-[3-pentyloxy-5,6,7,8-tetrahydro-5,5,8,8-tetramethyl-2-naphthalen-2-yl]-3-methyl-octa-2,4,6-trienoic acid (170) as a pale yellow oil: $^1$H-NMR (400 MHz, CDCl$_3$) δ 7.08 (s, 1H, Ar—H), 7.06 (dd, J=15.1, 11.5 Hz, 1H, olefinic), 6.75 (s, 1H, Ar—H), 6.33 (d, J=5.3 Hz, 1H, olefinic), 6.30 (s, 1H, olefinic), 5.87 (s, 1H, olefinic), 3.93 (t, J=6.5 Hz, 2H, OCH$_2$), 2.40 (s, 3H, CH$_3$), 2.24 (s, 3H, CH$_3$), 1.75 (m, 2H, CH$_2$), 1.67 (s, 4H, 2CH$_2$), 1.39 (m, 4H, 2CH$_2$), 1.29 (s, 6H, 2CH$_3$), 1.26 (s, 6H, 2CH$_3$), 0.92 (t, J=7.2 Hz, 3H, CH$_3$).

EXAMPLE 71

(2E, 4E, 6Z)-7-[3-pentyloxy-5,6,7,8-tetrahydro-5,5,8,8-tetramethyl-2-naphthalen-2-yl]-3-methyl-octa-2,4,6-trienoic Acid (Compound 171, Prepared as Illustrated and Described in Scheme 7.)

A sample of the product mixture from Example 70 was purified by reverse phase HPLC (92% MeOH/8% ammonium acetate with 0.3% AcOH) to give (2E, 4E, 6Z)-7-[3-pentyloxy-5,6,7,8-tetrahydro-5,5,8,8-tetramethyl-2-naphthalen-2-yl]-3-methyl-octa-2,4,6-trienoic acid (171) as a pale yellow solid: $^1$H-NMR (400 MHz, CDCl$_3$) δ 7.08 (s, 1H, Ar—H), 6.95 (s, 1H, Ar—H), 6.64 (dd, J=15.5, 10.8 Hz, 1H, olefinic), 6.23 (app br d, 2H, 2×olefinic), 5.75 (s, 1H, olefinic), 3.93 (t, J=6.6 Hz, 2H, OCH$_2$), 2.19 (s, 3H, CH$_3$), 2.14 (s, 3H, CH$_3$), 1.75 (m, 2H, CH$_2$), 1.68 (s, 4H, 2CH$_2$), 1.39 (m, 4H, 2CH$_2$), 1.30 (s, 6H, 2CH$_3$), 1.23 (s, 6H, 2CH$_3$), 0.90 (t, J=7.2 Hz, 3H, CH$_3$).

EXAMPLE 72

(2E, 4E, 6E)-7-[3-heptyloxy-5,6,7,8-tetrahydro-5,5,8,8-tetramethyl-2-naphthalen-2-yl]-3-methyl-octa-2,4,6-trienoic Acid (Compound 172, Prepared as Illustrated and Described in Scheme 7)

1-(3-Hydroxy-5,6,7,8-tetrahydro-5,5,8,8-tetramethyl-naphthalen-2-yl)-ethanone (0.410 g, 01.66 mmol) was alkylated with n-bromopentane (0.417 g, 2.33 mmol, 0.366 mL) as described in Example 21. Aqueous workup gave 1-[3-heptyloxy-5,6,7,8-tetrahydro-5,5,8,8-tetramethyl-naphthalen-2-yl]-ethanone 0.629 g (crude) as an orange oil which was used without further purification. The 3-n-heptyloxy-2-acyltetrahydronapthalene (0.625 g, 1.81 mmol) and diethyl cyanomethylphosphonate (0.705 g, 3.98 mmol, 0.644 mL) were condensed as described for Example 19. Aqueous work-upu afforded the crude product 3-[3-heptyloxy-5,6,7,8-tetrahydro-5,5,8,8-tetramethyl-naphthalen-2-yl]-but-2-enenitrile 0.915 g as an orange oil: $^1$H-NMR (400 MHz, CDCl$_3$) δ 7.10 (s, 1H, Ar—H), 6.78 (s, 1H, Ar—H), 5.61 (s, 1H, olefinic), 3.95 (t, J=6.4 Hz, 2H, OCH$_2$), 2.44 (s, 3H, CH$_3$), 1.78 (m, 4H, 2CH$_2$), 1.67 (app br s, 4H, 2CH$_2$), 1.39 (m, 2H, CH$_2$), 1.30 (m, 4H, 2CH$_2$), 1.28 (s, 6H, 2CH$_3$), 1.25 (s, 6H, 2CH$_3$), 0.94 (t, 3H, CH$_3$).

The above cyanoheptyloxynaphthalene adduct (0.915 g, 2.48 mmol) was reduced with DIBAL (5.21 mL of a 1.0 M solution in hexanes, 5.21 mmol) as described for Example 19. Aqueous work-up gave the aldehyde 3-[3-isobutyloxy-5,6,7,8-tetrahydro-5,5,8,8-tetramethyl-naphthalen-2-yl]-but-2-enal 0.452 g (49%) as an orange oil which was used without further purification. The aldehyde (0.452 g, 1.22 mmol) and diethyl-3-ethoxycarbonyl-2-methylprop-2-enylphosphonate (0.514 g, 1.95 mmol, 0.477 mL) were condensed as described for Example 19. Aqueous work-up afforded the crude ester (0.458, 78%) as a yellow oil. Standard hydrolysis of the ester (0.458 g, 0.952 mmol) and aqueous work-up gave the crude acid as a mixture of geometric isomers. A sample of the product mixture was purified by preparative TLC to give (2E, 4E, 6E)-7-[3-heptyloxy-5,6,7,8-tetrahydro-5,5,8,8-tetramethyl-2-naphthalen-2-yl]-3-methyl-octa-2,4,6-trienoic acid (172) as a yellow oil: $^1$H-NMR (400 MHz, CDCl$_3$) δ 7.08 (s, 1H, Ar—H), 7.06 (dd, J=15.2, 11.4 Hz, 1H, olefinic), 6.75 (s, 1H, Ar—H), 6.33 (broad t, 2H, 2×olefinic), 5.81 (s, 1H, olefinic), 3.92 (t, J=6.5 Hz, 2H, OCH$_2$), 2.39 (s, 3H, CH$_3$), 2.23 (s, 3H, CH$_3$), 1.68 (m, 4H, 2CH$_2$), 1.67 (s, 4H, 2CH$_2$), 1.41 (m, 2H, CH$_2$), 1.30 (m, 4H, 2CH$_2$), 1.28 (s, 6H, 2CH$_3$), 1.26 (s, 6H, 2CH$_3$), 0.88 (t, 3H, CH$_3$).

The above aldehyde (0.090 g, 0.263 mmol) and diethyl-3-ethoxycarbonyl-2-methylprop-2-enylphosphonate (0.111 g, 0.420 mmol, 0.103 mL) were condensed as described for Example 19. Aqueous work-up afforded the crude ester (0.100 g, 83%). Standard hydrolysis of the ester (0.100 g, 0.221 mmol) and aqueous work-up gave the acid as a mixture of geometric isomers (0.093 g, 87%). A sample of the product mixture was purified by reverse phase HPLC (92% MeOH/8% ammonium acetate with 0.3% AcOH) to give (2E, 4E, 6E)-7-[3-pentyloxy-5,6,7,8-tetrahydro-5,5,8,8-tetramethyl-2-naphthalen-2-yl]-3-methyl-octa-2,4,6-trienoic acid (170) as a pale yellow oil: $^1$H-NMR (400 MHz, CDCl$_3$) δ 7.08 (s, 1H, Ar—H), 7.06 (dd, J=15.1, 11.5 Hz, 1H, olefinic), 6.75 (s, 1H, Ar—H), 6.33 (d, J=5.3 Hz, 1H, olefinic), 6.30 (s, 1H, olefinic), 5.87 (s, 1H, olefinic), 3.93 (t, J=6.5 Hz, 2H, OCH$_2$), 2.40 (s, 3H, CH$_3$), 2.24 (s, 3H, CH$_3$), 1.75 (m, 2H, CH$_2$), 1.67 (s, 4H, 2CH$_2$), 1.39 (m, 4H, 2CH$_2$), 1.29 (s, 6H, 2CH$_3$), 1.26 (s, 6H, 2CH$_3$), 0.92 (t, J=7.2 Hz, 3H, CH$_3$).

EXAMPLE 73

(2E, 4E, 6Z)-7-[3-heptyloxy-5,6,7,8-tetrahydro-5,5,8,8-tetramethyl-2-naphthalen-2-yl]-3-methyl-octa-2,4,6-trienoic Acid (Compound 173, Prepared as Illustrated and Described in Scheme 7)

A sample of the product mixture from Example 72 was purified by reverse phase HPLC (92% MeOH/8% ammonium acetate with 0.3% AcOH) to give (2E, 4E, 6Z)-7-[3-heptyloxy-5,6,7,8-tetrahydro-5,5,8,8-tetramethyl-2-naphthalen-2-yl]-3-methyl-octa-2,4,6-trienoic acid (173) as a yellow oil: $^1$H-NMR (400 MHz, CDCl$_3$) δ 6.95 (s, 1H, Ar—H), 6.79 (s, 1H, Ar—H), 6.64 (dd, J=15.5, 10.8 Hz, 1H, olefinic), 6.23 (app br d, 2H, 2×olefinic), 5.74 (s, 1H, olefinic), 3.92 (t, J=6.6 Hz, 2H, OCH$_2$), 2.19 (s, 3H, CH$_3$), 2.14 (s, 3H, CH$_3$), 1.75 (m, 2H, CH$_2$), 1.70 (s, 4H, 2CH$_2$), 1.39 (m, 4H, 2CH$_2$), 1.30 (s, 6H, 2CH$_3$), 1.23 (s, 6H, 2CH$_3$), 0.89 (t, J=6.6 Hz, 3H, CH$_3$).

EXAMPLE 74

(2E, 4E, 6E)-7-[3-(4-methoxybenzyloxy)-5,6,7,8-tetrahydro-5,5,8,8-tetramethyl-2-naphthalen-2-yl]-3-methyl-octa-2,4,6-trienoic Acid (Compound 174, Prepared as Illustrated and Described in Scheme 7)

1-(3-Hydroxy-5,6,7,8-tetrahydro-5,5,8,8-tetramethyl-naphthalen-2-yl)-ethanone (0.315 g, 1.28 mmol) was alkylated with 4-methoxybenzylchloride (0.280 g, 1.79 mmol, 0.24 mL) as described in Example 21. Aqueous workup gave 1-[3-(4-methoxybenzyloxy)-5,6,7,8-tetrahydro-5,5,8,8-tetramethyl-naphthalen-2-yl]-ethanone 0.606 g (crude) as an orange oil: $^1$H-NMR (400 MHz, CDCl$_3$) δ 7.74 (s, 1H, Ar—H), 7.39 (d of ABq, J=8.6 Hz, 2H), 6.92 (d of ABq, J=8.6 Hz, 2H), 6.91 (s, 1H, Ar—H), 5.06 (s, 2H, OCH$_2$), 3.82 (s, 3H, OCH$_3$), 2.55 (s, 3H, CH$_3$), 1.67 (m, 4H, 2CH$_2$), 1.27 (s, 6H, 2CH$_3$), 1.26 (s, 6H, 2CH$_3$).

The above 4-methoxybenzyloxy-2-acyltetrahydronaphthalene (0.606 g, 1.65 mmol) was condensed with diethyl cyanomethylphosphonate (0.644 g, 3.64 mmol, 0.588 mL) as described for Example 19. Aqueous work-up and flash chromatography (10:1=hexanes:EtOAc) afforded the product 3-[3-(4-methoxybenzyloxy)-5,6,7,8-tetrahydro-5,5,8,8-tetramethyl-naphthalen-2-yl]-but-2-enenitrile 0.218 g (34%) as a clear oil: $^1$H-NMR (400 MHz, CDCl$_3$) δ 7.32 (d of ABq, J=8.6 Hz, 2H), 7.11 (s, 1H, Ar—H), 6.93 (d of ABq, J=8.6 Hz, 2H), 6.88 (s, 1H, Ar—H), 5.59 (s, 1H, olefinic), 4.99 (s, 2H, OCH$_2$), 3.83 (s, 3H, OCH$_3$), 2.42 (s, 3H, CH$_3$), 1.68 (s, 4H, 2CH$_2$), 1.27 (s, 6H, 2CH$_3$), 1.26 (s, 6H, 2CH$_3$).

The cyano(4-methoxybenzyloxy)naphthalene adduct (0.525 g, 1.26 mmol) was reduced with DIBAL (2.65 mL of a 1.0 M solution in hexanes, 2.65 mmol) as described for Example 19. Aqueous work-up gave the crude aldehyde 3-(3-hexyloxy-5,6,7,8-tetrahydro-5,5,8,8-tetramethyl-naphthalen-2-yl)-but-2-enal 0.203 g (92%) as a yellow oil: $^1$H-NMR (trans isomer, CDCl$_3$) δ 10.11 (d, J=8.2 Hz, 1H, CHO), 7.32 (d of ABq, J=8.5 Hz, 2H), 7.09 (s, 1H, Ar—H), 6.90 (d of ABq, J=8.5 Hz, 2H), 6.88 (s, 1H, Ar—H), 6.13 (d, J=8.2 Hz, 1H, olefinic), 4.99 (s, 2H, OCH$_2$), 3.82 (s, 3H, OCH$_3$), 2.52 (s, 3H, CH$_3$), 1.67 (s, 4H, 2CH$_2$), 1.27 (s, 6H, 2CH$_3$), 1.26 (s, 6H, 2CH$_3$).

The above aldehyde (0.203 g, 0.517 mmol) and diethyl-3-ethoxycarbonyl-2-methylprop-2-enylphosphonate (0.218 g, 0.828 mmol, 0.203 mL) were condensed as described for Example 19. Aqueous work-up and flash chromatography (10:1=hexanes:EtOAc) afforded the ester (0.078, 30%) as a yellow oil. Standard hydrolysis of the crude ester (0.078 g, 0.155 mmol) followed by the typical aqueous work-up gave the acid as a mixture of geometric isomers. The product mixture was crystallized with hexanes to give (2E, 4E, 6E)-7-[3-(4-methoxybenzyloxy)-5,6,7,8-tetrahydro-5,5,8,8-tetramethyl-2-naphthalen-2-yl]-3-methyl-octa-2,4,6-trienoic acid (174) as a pale yellow solid: $^1$H-NMR (400 MHz, CDCl$_3$) δ 7.30 (d of Abq, J=8.6 Hz, 2H), 6.96 (s, 1H, Ar—H), 6.88 (d of ABq, J=8.6 Hz, 2H), 6.88 (s, 1H, Ar—H), 6.62 (dd, J=15.5, 10.9 Hz, 1H, CH), 6.22 (app br d, J=14.6 Hz, 2H, 2×olefinic), 5.74 (s, 1H, olefinic), 4.97 (s, 2H, OCH$_2$), 3.80 (s, 3H, OCH$_3$), 2.19 (s, 3H, CH$_3$), 2.13 (s, 3H, CH$_3$), 1.67 (s, 4H, 2CH$_2$), 1.28 (s, 6H, 2CH$_3$), 1.23 (s, 6H, 2CH$_3$).

EXAMPLE 75

(2E, 4E)-7-[3-propoxy-5,6,7,8-tetrahydro-5,5,8,8-tetramethyl-2-naphthalen-2-yl]-3-methyl-octa-2,4-dienoic Acid (Compound 175, Prepared as Illustrated and Described in Scheme 7 and Scheme 16)

The propoxy nitrile (prepared as described in Example 19) (0.503 g, 1.61 mmol) was stirred at room temperature in a EtOAc:EtOH (1:1) solution. 10% Pd/C was added and the black mixture was stirred under atmospheric H$_2$ for 36 h. The reaction solution was filtered through Celite, and the pad was rinsed with EtOAc. Concentration of the filtrate gave 3-[3-propoxy-5,6,7,8-tetrahydro-5,5,8,8-tetramethyl-naphthalen-2-yl]-butyronitrile 0.478 g (95%) as a turbid oil: $^1$H-NMR (400 MHz, CDCl$_3$) δ 7.09 (s, 1H, Ar—H), 6.63 (s, 1H, Ar—H), 3.42 (m, 1H, benzylic), 2.72 (dd, J=16.7, 5.4 Hz, 1H, CHCN), 2.62 (dd, J=16.7, 8.0 Hz, 1H, CHCN), 1.65 (s, 4H, 2CH$_2$), 1.46 (d, J=7.1 Hz, 3H, CH$_3$), 1.25 (s, 6H, 2CH$_3$), 1.24 (d, J=1.9 Hz, 6H, 2CH$_3$).

The above cyanopropoxynaphthalene adduct (0.475 g, 1.39 mmol) was reduced with DIBAL (2.78 mL of a 1.0 M solution in hexanes, 2.78 mmol) as described for Example 19. Aqueous work-up gave the aldehyde 3-[3-propoxy-5,6,7,8-tetrahydro-5,5,8,8-tetramethyl-naphthalen-2-yl]-butyraldehyde 0.341 g (71%) as a pale yellow turbid oil: $^1$H-NMR (400 MHz, CDCl$_3$) δ 9.70 (app d, 1H, CHO), 7.05 (s, 1H, Ar-H), 6.71 (s, 1H, Ar-H), 3.90 (m, 2H, OCH$_2$), 3.65 (m, 1H, benzylic), 2.75 (dd, J=16.7, 5.2 Hz, 1H, CHCHO), 2.62 (d, J=16.7, 8.4 Hz, 1H, CHCHO), 1.80 (m, 2H, CH$_2$), 1.65 (s, 4H, 2CH$_2$), 1.30 (d, J=7.0 Hz, 3H, CH$_3$), 1.28 (s, 6H, 2CH$_3$), 1.27 (s, 6H, 2CH$_3$), 1.05 (t, J=7.4 Hz, 3H, CH$_3$).

The above aldehyde (0.341 g, 1.08 mmol) and diethyl-3-ethoxycarbonyl-2-methylprop-2-enylphosphonate (0.455 g, 1.72 mmol, 0.422 mL) were condensed as described for Example 21. Aqueous work-up afforded the crude ester as a clear oil. Standard hydrolysis of the ester (0.302 g, 0.682 mmol) and aqueous work-up gave the acid as a mixture of geometric isomers. A sample of the product mixture was purified by prep TLC (10:1=hexanes:EtOAc) to give (2E, 4E)-7-[3-propoxy-5,6,7,8-tetrahydro-5,5,8,8-tetramethyl-2-naphthalen-2yl]-3-methyl-octa-2,4-dienoic acid (175) as a yellow oil: $^1$H-NMR (400 MHz, CDCl$_3$) δ 7.51 (d, J=15.9 Hz, 1H, olefinic), 7.01 (s, 1H, Ar-H), 6.67 (s, 1H, Ar-H), 6.10 (m, 1H, olefinic), 5.59 (s, 1H, olefinic), 3.87 (t, J=6.6 Hz, 2H, OCH$_2$), 3.21 (m, 1H, benzylic), 2.55 (m, 1H, CH), 2.40 (m, 1H, CH), 1.94 (s, 3H, CH$_3$), 1.78 (m, 2H, CH$_2$), 1.62 (s, 4H, 2CH$_2$), 1.24 (s, 6H, 2CH$_3$), 1.21 (m, 9H, 3CH$_3$), 1.03 (t, J=7.4 Hz, 3H, CH$_3$).

Evaluation of Retinoid Receptor Subfamily Activity

Utilizing the "cis-trans" or "co-transfection" assay described by Evans et al., Science, 240:889–95 (May 13, 1988), the disclosure of which is herein incorporated by reference, the dimer-selective RXR modulator compounds of the present invention were tested and found to have strong, specific activity as selective RXR modulators, including activity as full agonists, partial agonists and/or full antagonists of RXR homodimers and/or heterodimers. This assay is described in further detail in U.S. Pat. Nos. 4,981,784 and 5,071,773, the disclosures of which are incorporated herein by reference.

The co-transfection assay provides a method for identifying functional agonists which mimic, or antagonists which inhibit, the effect of native hormones, and quantifying their activity for responsive IR proteins. In this regard, the co-transfection assay mimics an in vivo system in the laboratory. Importantly, activity in the co-transfection assay correlates very well with known in vivo activity, such that the co-transfection assy functions as a qualitative and quantitative predictor of a tested compounds in vivo pharmacology. See, e.g., T. Berger et al. 41 *J. Steroid Biochem. Molec. Biol.* 773 (1992), the disclosure of which is herein incorporated by reference.

In the co-transfection assay, cloned cDNA for one or more IRs (e.g., human, murine or rat RXRα, RXRβ, RXRγ, PPARα, VDR, LXR), alone or in combination (i.e. for heterodimer assays) under hte control of a constitutive promoter (e.g., the SV 40, RSV or CMV promoter) is introduced by transfection (a procedure to introduce exogenous genes into cells) into a background cell substantially devoid of endogenous IRs. These introduced gene(s) direct the recipient cells to make the IR protein(s) of interest. A further gene is also introduced (co-transfected) into the same cells in conjunction with the IR gene(s). This further gene, comprising the cDNA for a reporter protein, such as firefly luciferase (LUC), controlled by an appropriate hormone responsive promoter containing a hormone response element (HRE). This reporter plasmid functions as a reporter for the transcriptional-modulating activity of the target IR(s). Thus, the reporter acts as a surrogate for the products (mRNA then protein) normally expressed by a gene under control of the target receptor(s) and their native hormone(s).

The co-transfection assay can detect small molecule agonists or antagonists, including partial agonists and antagonist, of target IRs. Exposing the transfected cells to an agonist ligand compound increases reporter activity in the transfected cells. This activity can be conveniently measured, e.g., by increasing luciferase production and enzymatic activity, which reflects compound-dependent, IR-mediated increases in reporter transcription. To detect antagonists, the co-transfection assay is carried out in the presence of a constant concentration of an known agnoists to the target IR (e.g., 4-[(3,5,5,8,8-Pentamethyl-5,6,7,8-tetrahydro-2-naphthyl)ethenyl]benzoic acid (LGD1069, Ligand Pharmaceuticals, Inc.) for RXRα) known to induce a defined reporter signal. Increasing concentrations of a suspected antagonist will decrease the reporter signal (e.g., luciferase production). The co-transfection assay is therefore useful to detect both agonists and antagonists of specific IRs. Furthermore, it determines not only whether a compound interacts with a particular IR, but whether this interaction mimics (agonizes) or blocks (antagonizes) the effects of native or synthetic regulatory molecules on target gene expression, as well as the specificity and strength of ths interaction.

The activity of the dimer-selective RXR retinoid modulator compounds of the present invention were evaluated utilizing the co-transfection assay according to the following illustrative Examples.

EXAMPLE 76

RXR Homodimer Co-Transfection Assay

CV-1 cells (African green monkey kidney fibroblasts) were cultured in the presence of Dulbecco's Modified Eagle Medium (DMEM) supplemented with 10% charcoal resin-stripped fetal bovine serum then transferred to 96-well microtiter plates one day prior to transfection.

To determine agonist and antagonist activity of the modulator compounds of the present invention, the CV-1 cells or Schneider cells were transiently transfected by calcium phosphate coprecipitation according to the procedure of Berger et al., 41 *J.Steroid Biochem. Mol. Biol.*, 733 (1992) with one or more of the following receptor expressing plasmids: pRShRARα: Giguere et al., 330 *Nature*, 624 (1987); pRShRARβ and pRShRARγ, Ishikawa et al., 4 *Mol. Endocrin.*, 837 (1990); pRShRXRα, Mangelsdorf et al., 345 *Nature*, 224 (1990); and pRSmRXRβ and pRSmRXRγ, Mangelsdorf et al., 6 *Genes & Devel.*, 329 (1992), the disclosures of which are herein incorporated by reference. Each of these receptor expressing plasmids was co-transfected at a concentration of 5 ng/well, along with a basal reporter plasmid at 100 ng/well, the internal control plasmid pRS-β-Gal at 50 ng/well and filler DNA, pGEM at 45 ng/well.

The basal reporter plasmid Δ-MTV-LUC (Hollenberg and Evans, 55 *Cell*, 899 (1988), the disclosure of which is herein incorporated by reference) containing an RARE which is referred to as two copies of the TRE-palindromic response element described in Umensono et al., 336 *Nature*, 262 (1988), the disclosure of which is herein incorporated by reference, was used in transfections for the RARs, and the reporter plasmid CRBPIITKLUC, which contains an RXRE (retinoid X receptor response element, as described in Mangelsdorf et al., 66 *Cell*, 555 (1991), the disclosure of which is herein incorporated by reference), was used in transfections for the RXRs. Each of these reporter plasmids contains the cDNA for firefly luciferase (LUC) under the control of a promoter containing the appropriate RAR or RXR response element. As noted above, pRS-β-Gal, coding for consitutive expression of *E. coli* β-galactosidase (β-Gal), was included as an internal control for evaluation of transfection efficiency and compound toxicity.

Six hours after transfection, media was removed and the cells were washed with phosphate-buffered saline (PBS). Media containing compounds of the present invention in concentrations ranging from $10^{-12}$ to $10^{-5}$ M were added to the cells. Similarly, the reference compounds all-trans retinoic acid (ATRA)(Sigma Chemical), a known RAR selective agonist compound, and 9-cis retinoic acid (9-cis) (as described in Heyman et al., *Cell*, 68:397–406 (1992)), a compound with known agonist activity on RXRs, were added at similar concentrations to provide a reference point for analysis of the agonist activity of the compounds of the present invention. When determining the antagonist activity of the compounds of the present invention, the compounds were added to the cells in the presence of a fixed concentration ($3.2 \times 10^{-8}$ M) of the known RXR agonist LGD1069 (4-[(3,5,5,8,8-Pentamethyl-5,6,7,8-tetrahydro-2-naphthyl) ethenyl]benzoic acid: Ligand Pharmaceuticals, Inc.) or the known RAR/RXR panagonist compound (2E,4E,6Z)-7-[5, 6,7,8-tetrahydro-5,5,8,8-tetramethyl-2-naphthalen-2-yl]-3-methyl-octa-2,4,6-trienoic acid (Hoffmann LaRoche, Inc.). Retinoid purity was established as greater than 99% by reverse phase high-performance liquid chromatography. Retinoids were dissolved in dimethylsulfoxide for use in the transcriptional activation assays. Three to four replicates were used for each sample. Transfections and subsequent procedures were performed on a Biomek 1000 automated work station.

After 40 hours, the cells were washed with PBS, lysed with a Triton X-100-based buffer and assayed for LUC and β-Gal activities using a luminometer or spectrophotometer, respectively. For each replicate, the normalized response (NR) was calculated as:

LUC resonse/β-Gal rate where β-Gal rate=β-Gal·$1 \times 10^{-5}$/β-Gal incubation time.

The mean and standard error of the mean (SEM) of the NR were calculated. Data was plotted as the response of the compound compared to the reference compounds over the range of the dose-response curve. For the agonist activity of the compounds of the present invention, the effective concentration that produced 50% of the maximum response ($EC_{50}$) was quantified. Antagonist activity was determined by testing the amount of LUC expression in the presence of the RAR and/or RXR agonists described above at the $EC_{50}$ concentration for such known compounds. The concentration of compounds of the present invention that inhibited 50% of LUC expression induced by the reference agonist was quantified ($IC_{50}$). In addition, the efficacy of antagonists was determined as a function (%) maximal inhibition.

RXR and RAR Binding

In addition to the cotransfection data, the binding of selected compounds of the present invention to the RAR and RXR receptors was also investigated according to the methodology described in M. F., Boehm, et al., "Synthesis and Structure-Activity Relationships of Novel Retinoid X Receptor Selective Retinoids", 37 *J. Med. Chem.*, 2930 (1994); M. F. Boehm, et al., "Synthesis of High Specific Activity [$^3$H]-9-cis Retinoic Acid and Its Application for Identifying Retinoids with Unusual Binding Properties", 37 *J. Med. Chem.*, 408 (1994), and E. A. Allegretto, et al., "Characterization and Comparison of Hormone-Binding and Transactivation Properties of Retinoic Acid and Retinoid X Receptors Expressed in Mammalian Cells and Yeast", 268 *J. Biol. Chem.*, 22625 (1993), the disclosures of which are herein incorporated by reference.

Non-specific binding was defined as that binding remaining in the presence of 500 nM of the appropriate unlabelled compound. At the end of the incubation period, bound from free ligand were separated. The amount of bound tritiated retinoids was determined by liquid scintillation counting of an aliquot (700 μL) of the supernatant fluid or the hydroxylapatite pellet.

After correcting for non-specific binding, $IC_{50}$ values were determined. The $IC_{50}$ value is defined as the concentration of competing ligand needed to reduce specific binding by 50%. The $IC_{50}$ value was determined graphically from a log-logit plot of the data. The $K_d$ values were determined by application of the Cheng-Prussof equation to the $IC_{50}$ values, the labeled ligand concentration and the $K_d$ of the labeled ligand.

The $IC_{50}$ antagonist potency (nM) and binding activity (Kd in nM) of selected retinoid modulator compounds of the present invention in RXRα,β,γ are shown in Table 1 below. In this regard, all of the dimer-selective RXR modulator compounds of the present invention displayed occasionally weak, but most often negligible, if any, agonist activity (i.e., $EC_{50}$) on all of the RAR and RXR receptors. Accordingly, only RXR antagonist co-transfection data and RXR binding data is provided in Table 1.

TABLE 1

Antagonist potency ($IC_{50}$ in nM) in the presence of the known RXR agonist LGD1069, and binding (Kd in nM -v- tritiated LGD1069 and tritiated 9-cis retinoic acid) of selected dimer-selective RXR modulator compounds of the present invention

| Cmpd. No. | RXRα Potency $IC_{50}$ in nM | RXRα Binding Kd in nM | RXRβ Potency $IC_{50}$ in nM | RXRβ Binding Kd in nM | RXRγ Potency $IC_{50}$ in nM | RXRγ Binding Kd in nM |
|---|---|---|---|---|---|---|
| 102 | 386 | 282 | 659 | 426 | 1668 | 683 |
| 103 | 498 | 389 | 701 | 846 | 1669 | 936 |
| 109 | 210 | 37 | 193 | 33 | 394 | 47 |
| 110 | 80 | 40 | 217 | 77 | 211 | 66 |
| 114 | 126 | 9 | 197 | 12 | 206 | 38 |
| 117 | 81 | 3 | 234 | 17 | 155 | 17 |
| 122 | 21 | 11 | 101 | 29 | 29 | 33 |
| 125 | 188 | 56 | 276 | 145 | 265 | 186 |
| 128 | 50 | 9 | 67 | 23 | 120 | 27 |
| 131 | 528 | 140 | 1409 | 105 | 1264 | 107 |
| 135 | 334 | 163 | 236 | 155 | 620 | 181 |
| 141 | 258 | 49 | 184 | 13 | 234 | 70 |
| 142 | 673 | 27 | 1828 | 90 | 1764 | 50 |
| 146 | 85 | 46 | 29 | 100 | 98 | 116 |
| 147 | 5 | 3 | 4 | 8 | 8 | 6 |
| 148 | 89 | 53 | 66 | 87 | 122 | 84 |
| 149 | 88 | 16 | 129 | 37 | 149 | 42 |
| 152 | 195 | 8 | 337 | 45 | 428 | 21 |
| 155 | 24 | 9 | 53 | 9 | 37 | 8 |
| 156 | 18 | 11 | 62 | 7 | 47 | 9 |
| 158 | 38 | 21 | 136 | 53 | 144 | 106 |
| 163 | 22 | 2 | 162 | 6 | 50 | 6 |
| 169 | 29 | 5 | 93 | 14 | 45 | 31 |
| 170 | 23 | 11 | 40 | 41 | 42 | 78 |
| 173 | 34 | 4 | 111 | 12 | 43 | 21 |
| 174 | 50 | 5 | 166 | 43 | 40 | 46 |
| 175 | 39 | 11 | 79 | 21 | 60 | 31 |

As can be seen in Table 1, the RXR modulator compounds of the present invention act as antagonists in the context of an RXR:RXR homodimer, with Compound 147 being an especially potent antagonist, both in terms of binding and repression of transactivation of hte RXR:RXR homodimer.

Figure 1B:
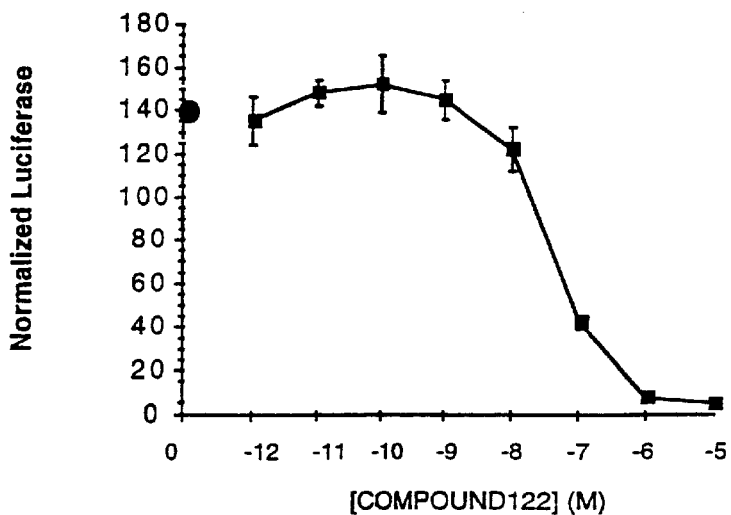
FIG. 1B is a dose response curve showing that Compound 122 of the present invention (■) functions as an RXR homodimer antagonist of a fixed concentration of LGD1069 (●, 100 nM)
Figure 1C:
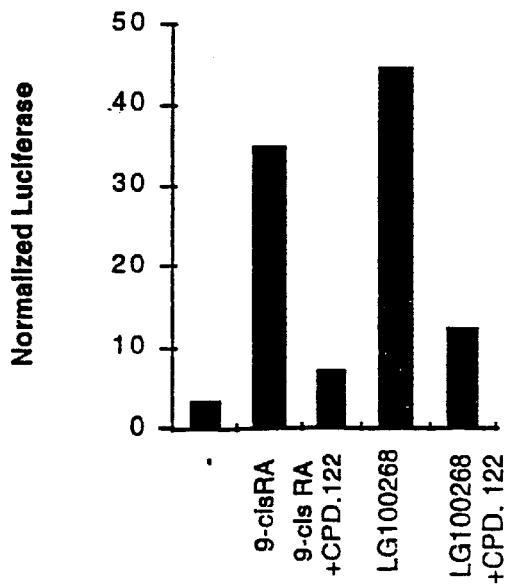
FIG. 1C is a bar graph showing that 1 mM of Compound 122 of the present invention also antagonizes the RXR activators 9-cis retinoic acid (100 nM) and LG100268 (100 nM)

Furthermore, as can be seen in FIG. 1A, Compound 122 binds RXR (See Table 1) but is unable to activate RXR homodimers. In contrast, the known RXR agonist, LG100268, is a potent activator and produces a concentration dependent activation ($EC_{50}$ value=4 nM) which is consistent with its ligand binding affinity. In addition, Compound 122 antagonizes the transcriptional activation of an RXR homodimer produced with a known RXR activator, LGD1069 (FIG. 1B), producing a concentration dependent inhibition of transactivation ($IC_{50}$ value=20 nM). Further, Compound 122 also antagonizes transactivation of RXR homodimers in the presence of other known RXR activators, i.e., LG100268 and 9-cis retinoic acid (9-cis RA) (FIG. 1C). Thus, Compound 122 of the present invention has properties that are distinct from LG100268, in that it is transcriptionally neutral by itself and functions as a competitive RXR antagonist in the context of RXR homodimers.

EXAMPLE 77
RXR Heterodimer Co-Transfection Assay

The cotransfection assay was utilized with CV-1 cells as described in Example 76. Additional IR expression plasmids and reporter plasmids employed included: pCMVhPPARα expression plasmid with the pPREA3-tk-LUC reporter plasmid: Kliewer et al., 358 *Nature*, 771–774 (1992) and Jow & Mukherjee, 270 *Journ. Biol. Chem.*, 3836–3840 (1994) and references cited therein, the disclosures of which are herein incorporated by reference. Co-transfections were performed as described in Mukherjee et al. 51 *Journ. Steroid Biochem. Molec. Biol.*, 157–166 (1994), the disclosure of which is herein incorpoated by reference. Reference agonists employed included clofibric acid (Sigma Chemical) for PPARα and LGD1069 (Ligand Pharmaceuticals, Inc.) for RXRα.

Table 2 below shows the relative normalized response of reporter activity, both in terms in $EC_{50}$ and fold induction values generated in response to the added compounds in a CV-1 cell transfected with both RXRα and PPARα and a reporter containing the PPARα response element indicated above.

TABLE 2

Agonist potency ($EC_{50}$ in nM) and fold induction of dimer-selective RXR modulator compounds of the present invention in comparison to the known RXRα agonist LGD 1069 and known PPARα agonist clofibric acid. Fold Activation = Normalized luciferase values at 10–5M (for RXR modulators and LGD 1069) or at 10–4M (for clofibric acid) divided by normalized luciferase values with vehicle. $EC_{50}$ values were calculated as described in example 76.

| Compound | $EC_{50}$ [M] | Fold activation |
|---|---|---|
| 131 | 8 × 10–7 | 7 |
| 135 | 10–6 | 5 |
| 114 | 2 × 10–7 | 4 |
| 117 | 9 × 10–7 | 9 |
| 122 | 3 × 10–7 | 7.5 |
| 128 | 2 × 10–7 | 4 |
| LGD1069 | 3 × 10–7 | 9 |
| Clofibric acid | 4 × 10–5 | 6.5 |

As can be seen in Table 2, the known RXR agonist LGD 1069 induces transactivation of the RXRα:PPARα heterodimer as does the fibrate derivative clofibric acid. In addition, the dimer-selective RXR modulator compounds of the present invention also all induce transcription of hte RXRα:PPARα heterodimer. Thus, in the context of this heterodimer, these compounds functions as RXRα:PPARα agonists in a cotransfection assay in a similar manner to LGD1069, however, as noted above in Table 1, Example 76, Compounds 114, 117, 122, 131 and 135 in the context of an RXRα:RXRα homodimer function as antagonists.

Figure 2A:
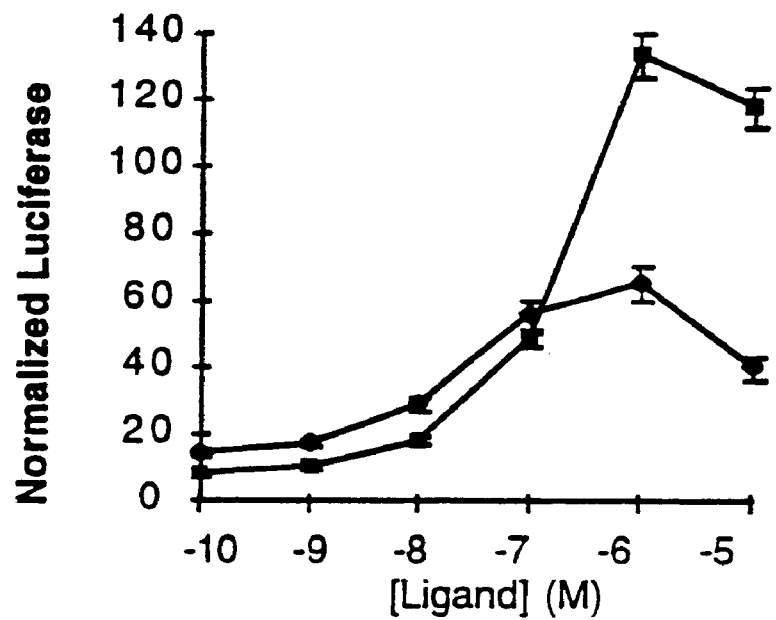
FIG. 2A is a dose response curve showing that Compound 122 of the present invention (■) activates RXRα:PPARα heterodimers to a greater extent than the known RXR agonist LG100268 (♦)

This result is further supported by a comparison of the activities of Compound 122 of the present invention and the known RXR agonist, LG100268, in the context of PPARα:RXRα and RARα:RXRα heterodimer pairs. RXR-:PPAR heterodimers have previously been shown to be responsive to both RXR and PPAR ligands. Kliewer, et al., *Nature* 358, 771–774 (1992). Accordingly, as shown in FIG. 2A, LG100268 (◆) activates the RXRα:PPARα heterodimer, producing a maximal induction of 4.5 fold at 1 mM. Unexpectedly, Compound 122 (■) activates the heterodimer and, in fact, is a stronger and more efficacious activator than LG100268 producing a 13 fold induction at 1 mM. Thus, Compound 122, along with other compounds of the present invention, have the unique properties of functioning as antagonists of RXR homodimers and a transcriptionally active agonist of RXRα:PPARα heterdimers.

Although ligands with mixed agonist/antagonist function have been reported for estrogen receptors, See Danielian, P. S., et al. *Mol Endocrinol.* 7, 232–240 (1993), the compounds of the present invention, including Compound 122, are the first examples of mixed function retinoids whose activity is dimer selective.

Figure 2B:
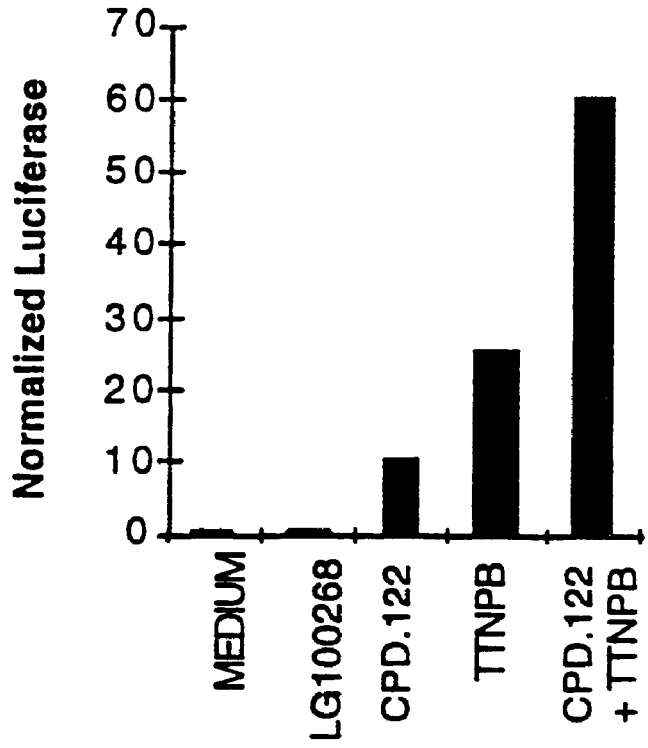
FIG. 2B is a bar graph showing that 1 mM of Compound 122 of the present invention and the known RAR agonist TTNPB (100 nM; Hoffman La-Roche, Inc.) activate RXRα:RARα heterodimers, whereas the known RXR agonist LG100268 (100 nM; Ligand Pharmaceuticals, Inc.) is inactive, and further that TTNPB added with Compound 122 leads to a grater than additive response than either compound added alone.

In contrast to PPAR, RAR suppresses RXR ligand binding and transactivation of typical RXR agonists (e.g., LGD1069, LG100268) via allosteric interactions. Forman, B. M., Umesono, K., Chem, J., & Evans, R. M., *Cell* 81, 541–550 (1995) and Kurokawa, R., et al., *Nature* 371, 528–531 (1994). However, when RAR is occupied, typical RXR agonists activate the heterodimer. Forman, B. M., Umesono, K., Chen, J., & Evans, R. M., *Cell* 81, 541–550 (1995) and Roy, B., Taneja, R., & Chambon, P., *Mol. Cell. Biol.* 15, 6481–6487 (1995). To examine the effects of LG100268 and Compound 122 on the transcriptional properties of the RXRα:RARα a heterodimer cotransfection assays as described above was employed. As shown in FIG. 2B, whereas RXR agonists, such as LG100268 by themseleves, do not activate the wild-type RXRα:RARα heterodimer, Compound 122 or the RAR selective agonist, TTNPB, strongly transactivate this heterodimer pair. Interestingly, the addition of both Compound 122 and TTNPB further enhance the transactivation in a greater than additive manner (FIG. 2B). This suggests that Compound 122 is active on RXR:RAR heterodimers, and either receptor within this dimer can be activated by its ligand while the partner remains unoccupied.

EXAMPLE 78

The activity of the dimer-selective RXR modulator compounds of the present invention was further tested in an RXRα:RARα heterodimer assay. A slightly modified assay to the one described in Example 76 was employed by using Gal4-receptor chimeras in which the DNA binding domain of the receptor was replaced by that of Gal4 to generate a fusion protein according to Nagpal et al, 12 EMBO Journal, 2349 (1993), the disclosure of which is herein incorporated by reference. Briefly, CV-1 cells were transfected in 12 well multi-well plates using 0.1 μg of each receptor and 0.5 μg of reporter per well. Each well was also transfected with 0.5 μg of the β-Gal expression plasmid as an internal control for transfection efficiency. Total plasmid per well was 2 μg made up using the plasmid pGEM. In this regard, the Gal4 plasmids contained 1–147 amino acids of Gal4 driven by the CMV (cytomegalovirus) promoter. Receptor ligand binding domains (LBDs) were fused in-frame downstream to the Gal4 cDNA to produce Gal4-receptor fusion proteins. To express only the receptor LBDs, the LBD was cloned directly downstream to the CMV promoter.

Cells were plated in the morning at a density of ~6×10$^4$ cells/well and allowed to attach for ~5–6 hours. Cell were then transfected using the calcium phosphate method and precipitates as described in Example 76 and allowed to incubate with the cells for 12–14 hours following which cells were washed 2X with phosphate buffered saline (PBS) and incubated with the tested compounds at either 100 nM for LGD1057 (9-cis retinoic acid: Ligand Pharmaceuticals, Inc.), LG100268 (6-[1-(3,5,5,8,8-pentamethyl-5,6,7,8-tetrahydronaphthalen-2-yl)cyclopropyl]nicotinic acid: Ligand Pharmaceuticals, Inc.) and LGD1069(Ligand Pharmaceuticals, Inc.), 500 nM for Compounds 117, 122 and 130 or 1 mM for Compound 131 in charcoal stripped medium for 20–24 hours. Cells were then washed 2X with PBS and lysed using Promega lysis buffer and assayed for luciferase activity and β-galactosidase activity. All results were normalized against β-Gal. Each set was done in triplicates and each experiment was carried out at least 3 separate times with similar results.

The above assay system was used because reporter activity is dependent upon the binding of the Gal4 DNA binding domain to copies of its binding site, the UAS (upstream activation sequence), located upstream of the luciferase cDNA. Nagpal et al (1993). Since endogenous receptors lack the Gal4 DNA binding domain, no background activation of the reporter is observed, however, Gal4-receptor LBD fusion proteins can bind the Gal4 site and be activated in a receptor ligand dependent manner. This system, therefore, completely eliminates the low background activity of endogenous receptors in CV-1 cells making it possible to test compound activity on exogenously added receptors.

Although all of the compounds tested, directly and specifically bind RXR, they manifest distinct properties in the RXR:RAR heterodimer assay as compared to the RXR:RXR homodimer assay. The distinct properties appear to be regulated through the binding of the RXR partner. Specifically, when tested on RXRα:PPARα heterodimers, Compounds 130, 122, 117 and 131 displayed similar agonist activity to LGD1069, albeit to different degrees (See Example 77, Table 2). A summary of the effects of the various modulator compounds on RXRα:RARα heterodimers and RXR homodimers in the present transactivation assay is shown below in Table 3 and Table 4.

TABLE 3

Agonist potency and antagonist potency in terms of fold induction and fold repression respectively for dimer-selective RXR modulator compounds of the present invention in comparison to the known RXRα agonists LGD1069 and LG100268 on an RXRα::RARα heterodimer.

| Compound | Fold Activation | Compound | Fold Activation | Compound | Fold Repression |
|---|---|---|---|---|---|
| 122 | 50 | LG100268 | n.e. | 117 | 1.4 |
| 130 | 25 | 117 | n.e. | | |
| 131 | 25 | | | | |
| LG1069 | 5 | | | | | n.e. = no effect

TABLE 4

Agonist potency and antagonist potency in terms of fold induction and fold repression respectively for dimer-selective RXR modulator compounds of the present invention in comparison to the known RXRα agonists LGD1069 and LG100268 on an RXRα:RXRα homodimer.

| Compound | Fold Activation | Compound | Fold Activation | Compound | Fold Repression |
|---|---|---|---|---|---|
| LG100268 | 50–75 | 130 | n.e. | 130 | 25–75 |
| LGD1069 | 50–75 | 117 | n.e. | 117 | 1.5 |
| | | 131 | n.e. | 131 | 1.3 |
| | | 122 | n.e. | 122 | 75 | n.e. = no effect

As noted above in Table 3, when tested on RXRα:RARα heterodimers, Compounds 130, 131 and 122 were potent agonists, whereas the known RXR agonist LGD1069 functioned as a weaker agonist, and LG100268 and Compound 117 appeared to be inactive. The RAR selective activator TTNPB ((E)-4-[2-(5,6,7,8-tetrahydro-5,5,8,8-tetramethyl-2-naphthalenyl)-1-propenyl]benzoic acid: Hoffman LaRoche, Inc.) activates the RXRα:RARα heterodimer. (Data not shown). When the dimer-selective RXR modulator compound of the present invention were combined with the RXR:RAR activator, TTNPB, there was a slight increase in activation with Compounds 130, 122 and 131, further suggesting that in the context of a RXRα:RARα heterodimer, all three function as agonists. (Data not shown). However, in combination with TTNPB, Compound 117 acted as a weak repressor, indicating that is could antagonize the properties associated with a RXRα:RARα heterodimer. Thus, there appears to be a continuum of activities from the dimer-selective RXR modulator compounds of the present invention, such that: (a) Compounds 117, 122, 130, and 131 function as agonists, (b) LGD1069 functions as a partial agonist, (c) LG100268 is inactive, and (d) Compound 117 is also inactive but, can display some partial antagonist activity.

Finally, we tested the same RXR modulator compunds on RXR homodimers in the GAL4 transfection assay. As can be seen in Table 4, only LGD1069 and LG100268 were agonists, whereas Compounds 130, 117, 122 and 131 were inactive. When tested in combination with either LGD1069 or LG100268, Compounds 130 and 122 functioned as strong antagonists (repressors) of RXR homodimer activity. Additionally, Compound 117 was a moderate antagonist and Compound 131 was a weak antagonist. These data employing the Gal4RXR chimeric receptors are entirely consistent with the assays employing the wild type receptors shown in Table 1. Thus, the various RXR modulator compounds of the present invention have a range of distinct activities when compared with each other, such that their actual function as either agonist, partial agonist and/or antagonists change depending upon the RXR partner.

EXAMPLE 79

Compounds of the present invention, including Compound 122 were tested for their ablity to induce NM4 myeloid leukemic cells to differeniate according to the procedure described by Lanotte et al., *Blood* 77, 1080–1086 (1991), the disclousre of which is herein incorporated by reference. All points were performed in triplicate for each experiment and varied less than 20%. Each experiment was repeated at least three times with similar results.

Figure 3:
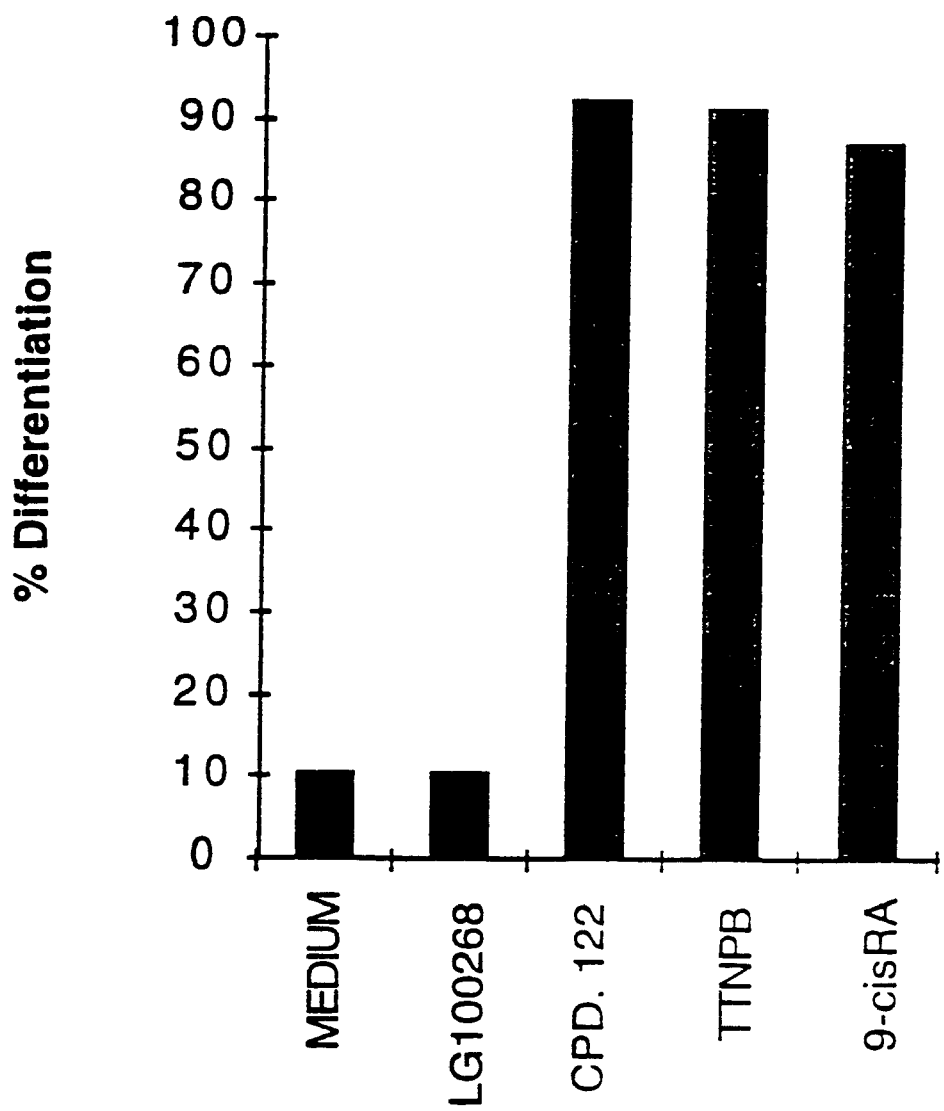
FIG. 3 is a bar graph showing that a concentration of 1 mM of Compound 122 of the present invention, as well as TTNBP (100 nM) and 9-cis retinoic acid (100 nM) stimulate NB4 cells to differentiate, whereas LB100268 (100 nM) does not.

As can be seen in FIG. 3, Compound 122 was equally, if not more effective in promoting differentiation of NB4 cells than the known RAR activator TTNPB and the known RAR/RXR panagonist compound, 9-cis retinoic acid. Suprisingly, RXR in a complex with Compound 122 escapes suppression by RAR, and promotes cellular differentiation in a similar manner to compounds that exert their activity through the RAR side of the heterodimer. In contrast, the known RXR agonist, LG100268, does not promote NB4 differentiation, and in fact cannot interact with the RXR side of the heterodimer unless jointly administered with an RAR active compound (Data not shown). Thus, this data further supports the novel activity of these dimer-selective RXR modulators.

EXAMPLE 80

The following examples provide illustrative pharmacological composition formulations:

Hard gelatin capsules are prepared using the following ingredients:

|  | Quantity (mg/capsule) |
|---|---|
| Compound 101 | 140 |
| Starch, dried | 100 |
| Magnesium stearate | 10 |
| Total | 250 mg |

The above ingredients are mixed and filled into hard gelatin capsules in 250 mg quantities.

A tablet is prepared using the ingredients below:

|  | Quantity (mg/tablet) |
|---|---|
| Compound 101 | 140 |
| Cellulose, microcrystalline | 200 |
| Silicon dioxide, fumed | 10 |
| Stearic acid | 10 |
| Total | 360 mg |

The components are blended and compressed to form tablets each viewing 360 mg.

Tablets, each containing 60 mg of active ingredient, are made as follows:

|  | Quantity (mg/tablet) |
|---|---|
| Compound 101 | 60 |
| Starch | 45 |
| Cellulose, microcrystalline | 35 |
| Polyvinylpyrrolidone (PVP) (as 10% solution in water) | 4 |
| Sodium carboxymethyl starch (SCMS) | 4.5 |
| Magnesium stearate | 0.5 |
| Talc | 1.0 |
| Total | 150 mg |

The active ingredient, starch, and cellulose are passed through a No. 45 mesh U.S. sieve and mixed thoroughly. The solution of PVP is mixed with the resultant powders, which are then passed through a No. 14 mesh U.S. sieve. The granules so produced are dried at 50° C. and passed through a No. 18 mesh U.S. sieve. The SCMS, magnesium stearate, and talc, previously passed through a No. 60 mesh U.S. sieve, are then added to the granules which, after mixing, are compressed on a tablet machine to yield tablets each weighing 150 mg.

Suppositories, each containing 225 mg of active ingredient, may be made as follows:

|  |  |
|---|---|
| Compound 101 | 225 mg |
| Saturated fatty acid glycerides | 2000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of normal 2 g capacity and allowed to cool.

An intravenous formulation may be prepared as follows:

| | |
|---|---|
| Compound 101 | 100 mg |
| Isotonic saline | 1,000 ml |
| Glycerol | 100 ml |

The compound is dissolved in the glycerol and then the solution is slowly diluted with isotonic saline. The solution of the above ingredients is then administered intravenously at a rate of 1 ml per minute to a patient.

While in accordance with the patent statutes, description of the preferred embodiments and processing conditions have been provided, the scope of the invention is not to be limited thereto or thereby. Various modifications and alterations of the present invention will be apparent to those skilled in teh art without departing from the scope and spirit of the present invention.

Consequently, for an understanding of the scope of the present invention, reference is made to the following claims.

What is claimed is:

1. A compound of the formula:

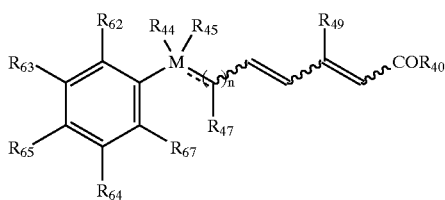

(IV)

wherein, $R_{40}$ is $OR_{41}$ or $NR_{42}R_{43}$, with $R_{41}$ being hydrogen, a $C_1$–$C_6$ alkyl or a $C_7$–$C_{15}$ arylalkyl or heteroarylalkyl, and with $R_{42}$ and $R_{43}$ each independently being hydrogen, a $C_1$–$C_6$ alkyl, a $C_7$–$C_{15}$ arylalkyl or heteroarylalkyl, aryl, ortho-, meta-, or para-substituted hydroxyaryl, or taken together are a $C_3$–$C_6$ cycloalkyl;

$R_{44}$ and $R_{45}$ each independently are hydrogen, a $C_1$–$C_4$ alkyl or $CH_2OR_{46}$, where $R_{46}$ is hydrogen or a $C_1$–$C_6$ alkyl, or $R_{44}$ and $R_{45}$ taken together are a $C_3$–$C_6$ cycloalkyl or cycloheteroalkyl;

$R_{47}$ is hydrogen, a $C_1$–$C_4$ alkyl, or when n=1, $R_{47}$ taken together with $R_{44}$ or $R_{45}$ are a $C_3$–$C_6$ cycloalkyl or cycloheteroalkyl;

$R_{49}$ is $C_1$–$C_4$ alkyl;

$R_{62}$ is hydrogen, aryl, heteroaryl, $CF_3$, a $C_2$–$C_6$ alkyl, $C_2$–$C_6$ heteroalkyl or $NR_{51}R_{52}$, where $R_{51}$ and $R_{52}$ each independently are a $C_2$–$C_{10}$ alkyl, heteroalkyl, a $C_7$–$C_{15}$ arylaklyl or heteroarylalkyl, or a $C_3$–$C_{10}$ acyl, provided that only one of $R_{51}$ or $R_{52}$ can be acyl, or $R_{51}$ and $R_{52}$ taken together are $C_3$–$C_6$ cycloalkyl;

$R_{63}$ and $R_{64}$ each independently are aryl, heteroaryl, $CF_3$, a $C_2$–$C_6$ alkyl, $C_2$–$C_6$ heteroalkyl or $NR_{51}R_{52}$, where $R_{51}$ and $R_{52}$ each independently are a $C_2$–$C_{10}$ alkyl, heteroalkyl, a $C_7$–$C_{15}$ arylalkyl or heteroarylalkyl, or a $C_3$–$C_{10}$ acyl, provided that only one of $R_{51}$ or $R_{52}$ can be acyl, or $R_{51}$ and $R_{52}$ taken together are $C_3$–$C_6$ cycloalkyl;

$R_{65}$ is hydrogen, a $C_1$–$C_2$ alkyl or $OR_{66}$, where $R_{66}$ is a $C_1$–$C_2$ alkyl;

$R_{67}$ is a $C_4$–$C_{10}$ alkyl, heteroalkyl, aryl, heteraryl, a $C_7$–$C_{15}$ arylalkyl or heteroarylalkyl, $NR_{51}R_{52}$, or $OR_{68}$, where $R_{51}$ and $R_{52}$ have the definitions given above;

$R_{68}$ is a $C_3$–$C_{10}$ alkyl, heteroalkyl, aryl, heteroaryl, or a $C_7$–$C_{15}$ arylalklyl or heteroarylalkyl;

M is N or C;

n is 0 or 1 carbon atoms;

the dashed lines in the structures represent optional double bonds, provided, however, that the double bonds cannot be adjacent to each other, and further provided that when such optional double bonds exist then the substitution patterns around such bonds cannot violate double bond valency; and the wavy lines represent olefin geometry that is either cis (Z) or trans (E).

2. A compound according to claim 1, wherein the compound is a dimer-selective RXR modulator.

3. A compound according to claim 2, wherein the compound is effective in modulating RXR homodimer interactions.

4. A compound according to claim 3, wherein the compound is a RXR homodimer antagonist.

5. A compound according to claim 2, wherein the compound is effective in modulating RXR heterodimer interactions, and wherein the RXR heterodimer comprises an RXR complexed with another intracellular receptor that forms a heterodimer with RXR.

6. A compound according to claim 5, wherein the compound is a RXR heterodimer antagonist.

7. A compound according to claim 5, wherein the RXR is selected from the group consisting of RXRα, RXRβ and RXRγ.

8. A compound according to claim 5, wherein the other intracellular receptor is selected form the group consisting of PPARα, PPARβ, PPARγ1, PPARγ2, TRα, TRβ, VDRs, RARα, RARβ, RARγ, NGFIBs, NURR1s, LXRα, LXRβ and DAXs.

9. A pharmaceutical composition comprising a pharmaceutically effective amount of a compound according to claim 2 and a pharmaceutically acceptable carrier.

10. A pharmaceutical composition according to claim 9, wherein the composition is formulated for oral, topical, intravenous, suppository or parental administration.

11. A pharmaceutical composition according to claim 9, wherein the composition is administered to a patient as a dosage unit at from about 1 µg/kg of body weight to about 500 mg/kg of body weight.

12. A pharmaceutical composition according to claim 9, wherein the composition is administered to a patient as a dosage unit at from about 10 µg/kg of body weight to about 250 mg/kg of body weight.

13. A pharmaceutical composition according to claim 9, wherein the composition is administered to a patient as a dosage unit at from about 20 µg/kg of body weight to about 100 mg/kg of body weight.

14. A method of modulating processes mediated by RXR homodimers and/or RXR heterodimres comprising administering to a patient an effective amount of a dimer-selective RXR modulator compound of the formula:

(IV)

[Chemical structure showing substituted aromatic ring with substituents $R_{62}$, $R_{63}$, $R_{64}$, $R_{65}$, $R_{67}$, M, $R_{44}$, $R_{45}$, $R_{47}$, $R_{49}$, and $COR_{40}$]

wherein, $R_{40}$ is $OR_{41}$ or $NR_{42}R_{43}$, with $R_{41}$ being hydrogen, a $C_1$–$C_6$ alkyl or a $C_7$–$C_{15}$ arylalkyl or heteroarylalkyl, and with $R_{42}$ and $R_{43}$ each independently being hydrogen, a $C_1$–$C_6$ alkyl, a $C_7$–$C_{15}$ arylalkyl or heteroarylalkyl, aryl, ortho-, meta-, or para-substituted hydroxyaryl, or taken together are a $C_3$–$C_6$ cycloalkyl;

$R_{44}$ and $R_{45}$ each independently are hydrogen, a $C_1$–$C_4$ alkyl or $CH_2OR_{46}$, where $R_{46}$ is hydrogen or a $C_1$–$C_6$ alkyl, or $R_{44}$ and $R_{45}$ taken together are a $C_3$–$C_6$ cycloalkyl or cycloheteroalkyl;

$R_{47}$ is hydrogen, a $C_1$–$C_4$ alkyl, or when n=1, $R_{47}$ taken together with $R_{44}$ or $R_{45}$ are a $C_3$–$C_6$ cycloalkyl or cycloheteroalkyl;

$R_{49}$ is $C_1$–$C_4$ alkyl;

$R_{62}$ is hydrogen, aryl, heteroaryl, $CF_3$, a $C_2$–$C_6$ alkyl, $C_2$–$C_6$ heteroalkyl or $NR_{51}R_{52}$, where $R_{51}$ and $R_{52}$ each independently are a $C_2$–$C_{10}$ alkyl, heteroalkyl, a $C_7$–$C_{15}$ arylalkyl or heteroarylalkyl, or a $C_3$–$C_{10}$ acyl, provided that only one of $R_{51}$ or $R_{52}$ can be acyl, or $R_{51}$ and $R_{52}$ taken together are $C_3$–$C_6$ cycloalkyl;

$R_{63}$ and $R_{64}$ each independently are aryl, heteroaryl, $CF_3$, a $C_2$–$C_6$ alkyl, $C_2$–$C_6$ heteroalkyl or $NR_{51}R_{52}$, where $R_{51}$ and $R_{52}$ each independently are a $C_2$–$C_{10}$ alkyl, heteroalkyl, a $C_7$–$C_{15}$ arylalkyl or heteroarylalkyl, or a $C_3$–$C_{10}$ acyl, provided that only one of $R_{51}$ or $R_{52}$ can be acyl, or $R_{51}$ and $R_{52}$ taken together are $C_3$–$C_6$ cycloalkyl;

$R_{65}$ is hydrogen, a $C_1$–$C_2$ alkyl or $OR_{66}$, where $R_{66}$ is a $C_1$–$C_2$ alkyl;

$R_{67}$ is a $C_4$–$C_{10}$ alkyl, heteroalkyl, aryl, heteroaryl, a $C_7$–$C_{15}$ arylalkyl or heteroarylalkyl, $NR_{51}R_{52}$, or $OR_{68}$, where $R_{51}$ and $R_{52}$ each independently are a $C_2$–$C_{10}$ alkyl, heteroalkyl, a $C_7$–$C_{15}$ arylalkyl or heteroarylalkyl, a $C_3$–$C_{10}$ acyl, provided that only one of $R_{51}$ or $R_{52}$ can be acyl, or $R_{51}$ and $R_{52}$ taken together are $C_3$–$C_6$ cycloalkyl;

$R_{68}$ is a $C_3$–$C_{10}$ alkyl, heteroalkyl, aryl, heteroaryl, or a $C_7$–$C_{15}$ arylalkyl or heteroarylalkyl;

M is N or C;

n is 0 or 1 carbon atoms;

the dashed lines in the structures, other than at $R_{14}$ and $R_{15}$, represent optional double bonds, provided, however, that the double bonds cannot be adjacent to each other, and further provided that when such optional double bonds exist then the substitution patterns around such bonds cannot violate double bond valency; and the wavy lines represnt olefin geometry that is either cis (Z) or trans (E).

15. A method of modulating according to claim 14, wherein the process is mediated by RXR homodimers.

16. A method of modulating according to claim 14, wherein the process is mediated by RXR heterodimers.

17. A method of modulating according to claim 14, wherein the dimer-selective RXR modulator compound is combined with a pharmaceutically acceptable carrier to form a pharmaceutical composition.

18. A method of modulating according to claim 17, wherein the pharmaceutical composition is formulated for oral, topical, intravenous, suppository or parental administration.

19. A method of modulating according to claim 17, wherein the composition is administered to a patient as a dosage unit at from about 1 µg/kg of body weight to about 500 mg/kg of body weight.

20. A method of modulating according to claim 17, wherein the composition is administered to a patient as a dosage unit at from about 10 µg/kg of body weight to about 250 mg/kg of body weight.

21. A method of modulating according to claim 17, wherein the composition is administered to a patient as a dosage unit at from about 20 µg/kg of body weight to about 100 mg/kg of body weight.

22. A dimer-selective RXR modulator of the formula:

(IV)

[Chemical structure showing substituted aromatic ring with substituents $R_{62}$, $R_{63}$, $R_{64}$, $R_{65}$, $R_{67}$, M, $R_{44}$, $R_{45}$, $R_{47}$, $R_{49}$, and $COR_{40}$]

wherein, $R_{40}$ is $OR_{41}$ or $NR_{42}R_{43}$, with $R_{41}$ being hydrogen, a $C_1$–$C_6$ alkyl or a $C_7$–$C_{15}$ arylalkyl or heteroarylalkyl, and with $R_{42}$ and $R_{43}$ each independently being hydrogen, a $C_1$–$C_6$ alkyl, a $C_7$–$C_{15}$ arylalkyl or heteroarylalkyl, aryl, ortho-, meta-, or para-substituted hydroxyaryl, or taken together are a $C_3$–$C_6$ cycloalkyl;

$R_{44}$ and $R_{45}$ each independently are hydrogen, a $C_1$–$C_4$ alkyl or $CH_2OR_{46}$, where $R_{46}$ is hydrogen or a $C_1$–$C_6$ alkyl, or $R_{44}$ and $R_{45}$ taken together are a $C_3$–$C_6$ cycloalkyl or cycloheteroalkyl;

$R_{47}$ is hydrogen, a $C_1$–$C_4$ alkyl, or when n=1, $R_{47}$ taken together with $R_{44}$ or $R_{45}$ are a $C_3$–$C_6$ cycloalkyl or cycloheteroalkyl;

$R_{49}$ is $C_1$–$C_4$ alkyl;

$R_{62}$ is hydrogen, aryl, heteroaryl, $CF_3$, a $C_2$–$C_6$ alkyl, $C_2$–$C_6$ heteroalkyl or $NR_{51}R_{52}$, where $R_{51}$ and $R_{52}$ each independently are a $C_2$–$C_{10}$ alkyl, heteroalkyl, a $C_7$–$C_{15}$ arylalkyl or heteroarylalkyl, or a $C_3$–$C_{10}$ acyl, provided that only one of $R_{51}$ or $R_{52}$ can be acyl, or $R_{51}$ and $R_{52}$ taken together are $C_3$–$C_6$ cycloalkyl;

$R_{63}$ and $R_{64}$ each independently are aryl, heteroaryl, $CF_3$, a $C_2$–$C_6$ alkyl, $C_2$–$C_6$ heteroalkyl or $NR_{51}R_{52}$, where $R_{51}$ and $R_{52}$ each independently are a $C_2$–$C_{10}$ alkyl, heteroalkyl, a $C_7$–$C_{15}$ arylalkyl or heteroarylalkyl, or a $C_3$–$C_{10}$ acyl, provided that only one of $R_{51}$ or $R_{52}$ can be acyl, or $R_{51}$ and $R_{52}$ taken together are $C_3$–$C_6$ cycloalkyl;

$R_{65}$ is hydrogen, a $C_1$–$C_2$ alkyl or $OR_{66}$, where $R_{66}$ is a $C_1$–$C_2$ alkyl;

$R_{67}$ is a $C_4$–$C_{10}$ alkyl, heteroalkyl, aryl, heteroaryl, a $C_7$–$C_{15}$ arylalkyl or heteroarylalkyl, $NR_{51}R_{52}$, or $OR_{68}$, where $R_{51}$ and $R_{52}$ have the definitions given above;

$R_{68}$ is a $C_3$–$C_{10}$ alkyl, heteroalkyl, aryl, heteroaryl, or a $C_7$–$C_{15}$ arylalkyl or heteroarylalkyl;

M is N or C;

n is 0 or 1 carbon atoms;

the dashed lines in the structures represent optional double bonds, provided, however, that the double bonds cannot be adjacent to each other, and further provided that when such optional double bonds exist then the substitution patterns around such bonds cannot violate double bond valency; and the wavy lines represent olefin geometry that is either cis (Z) or trans (E);

wherein the compound is selected from the group consisting of (2E, 4E, 6E)-7-(3,5-diisopropyl-2-n-heptyloxyphenyl)-3-methylocta-2,4,6-trienoic acid (Compound 146); (2E, 4E, 6Z)-7-(3,5-diisopropyl-2-n-heptyloxyphenyl)-3-methylocta-2,4,6-trienoic acid (Compound 147); (2E, 4E)-7-(3,5-diisopropyl-2-n-heptyloxyphenyl)-3-methylocta-2,4-dienoic acid (Compound 148); (2Z, 4E)-7-(3,5-diisopropyl-2-n-heptyloxyphenyl)-3-methylocta-2,4-dienoic acid (Compound 149); (2E, 4E, 6E)-7-(3,5-diisopropyl-2-benzyloxyphenyl)-3-methylocta-2,4,6-trienoic acid (Compound 150); and (2E, 4E, 6E)-7-(3,5-diisopropyl-2-n-butyloxyphenyl)-3-methylocta-2,4,6-trienoic acid (Compound 151).

23. A compound according to claim 1, wherein:

$R_{44}$ and $R_{45}$ each independently are $C_1$–$C_4$ alkyl.

24. A compound according to claim 1, wherein:

M is carbon.

25. A compound according to claim 1, wherein:

$R_{47}$ is hydrogen.

26. A compound according to claim 1, wherein:

$R_{49}$ is methyl.

27. A compound according to claim 1, wherein:

$R_{44}$ and $R_{45}$ each independently are $C_1$–$C_4$ alkyl; and

M is carbon.

28. A compound according to claim 27, wherein:

$R_{47}$ is hydrogen; and $R_{49}$ is methyl.

29. A compound according to claim 1, wherein:

$R_{44}$ and $R_{45}$ each independently are $C_1$–$C_3$ alkyl;

M is carbon;

$R_{47}$ is hydrogen; and $R_{49}$ is methyl.

30. A method according to claim 14, wherein:

$R_{44}$ and $R_{45}$ each independently are $C_1$–$C_4$ alkyl.

31. A method according to claim 14, wherein:

M is carbon.

32. A method according to claim 14, wherein:

$R_{47}$ is hydrogen.

33. A method according to claim 14, wherein:

$R_{49}$ is methyl.

34. A method according to claim 14, wherein:

$R_{44}$ and $R_{45}$ each independently are $C_1$–$C_4$ alkyl; and

M is carbon.

35. A method according to claim 34, wherein:

$R_{47}$ is hydrogen; and $R_{49}$ is methyl.

36. A method according to claim 14, wherein:

$R_{44}$ and $R_{45}$ each independently are $C_1$–$C_3$ alkyl;

M is carbon;

$R_{47}$ is hydrogen; and $R_{49}$ is methyl.

* * * * *